(12) United States Patent
Barlow et al.

(10) Patent No.: US 7,998,971 B2
(45) Date of Patent: Aug. 16, 2011

(54) COMBINATIONS CONTAINING A 4-ACYLAMINOPYRIDINE DERIVATIVE

(75) Inventors: Carrolee Barlow, Del Mar, CA (US); Todd A. Carter, San Diego, CA (US); Andrew Morse, San Diego, CA (US); Kai Treuner, San Diego, CA (US); Kym I. Lorrain, San Diego, CA (US)

(73) Assignee: BrainCells Inc., San Diego, CA (US)

( * ) Notice: Subject to any disclaimer, the term of this patent is extended or adjusted under 35 U.S.C. 154(b) by 230 days.

(21) Appl. No.: 11/766,721

(22) Filed: Jun. 21, 2007

(65) Prior Publication Data

US 2008/0064671 A1 Mar. 13, 2008

Related U.S. Application Data

(60) Provisional application No. 60/825,080, filed on Sep. 8, 2006, provisional application No. 60/868,510, filed on Dec. 4, 2006, provisional application No. 60/884,584, filed on Jan. 11, 2007.

(51) Int. Cl.
*A61K 31/44* (2006.01)
*A61K 31/165* (2006.01)
*A61K 31/47* (2006.01)

(52) U.S. Cl. ............... 514/292; 514/618; 514/314

(58) Field of Classification Search ............... None
See application file for complete search history.

(56) References Cited

U.S. PATENT DOCUMENTS

| | | |
|---|---|---|
| 1,873,732 A | 8/1932 | Adams |
| 3,019,843 A | 2/1962 | Powell |
| 3,077,854 A | 2/1963 | Pall |
| 3,116,203 A | 12/1963 | Kariss et al. |
| 3,121,076 A | 2/1964 | Keller et al. |
| 3,136,815 A | 6/1964 | Reeder et al. |
| 3,242,190 A | 3/1966 | Hafliger et al. |
| 3,296,249 A | 1/1967 | Bell |
| 3,371,085 A | 2/1968 | Reeder et al. |
| 3,471,548 A | 10/1969 | Keberle et al. |
| 3,534,041 A | 10/1970 | Van der Burg et al. |
| 3,758,528 A | 9/1973 | Malen et al. |
| 3,814,812 A | 6/1974 | Eynard |
| 3,819,631 A | 6/1974 | Broughton et al. |
| 3,819,706 A | 6/1974 | Mehta et al. |
| 3,821,249 A | 6/1974 | Malen et al. |
| 3,862,149 A | 1/1975 | Cotrel et al. |
| 3,885,046 A | 5/1975 | Mehta |
| 3,912,743 A | 10/1975 | Christensen et al. |
| 3,932,407 A | 1/1976 | Beverung, Jr. et al. |
| 3,941,785 A | 3/1976 | Clarke et al. |
| 3,960,927 A | 6/1976 | Metcalf et al. |
| 4,007,196 A | 2/1977 | Christensen et al. |
| 4,024,175 A | 5/1977 | Satzinger et al. |
| 4,036,840 A | 7/1977 | O'Brien et al. |
| 4,051,236 A | 9/1977 | Harris et al. |
| 4,062,848 A | 12/1977 | Van der Burg |
| 4,085,225 A | 4/1978 | Welle et al. |
| 4,093,617 A | 6/1978 | Robins et al. |
| 4,094,992 A | 6/1978 | Kaplan et al. |
| 4,096,257 A | 6/1978 | Menschik et al. |
| 4,107,307 A | 8/1978 | Paul et al. |
| 4,107,309 A | 8/1978 | Paul et al. |
| 4,123,534 A | 10/1978 | Credner et al. |
| 4,136,193 A | 1/1979 | Bogeso et al. |
| 4,146,718 A | 3/1979 | Jenks et al. |
| 4,188,391 A | 2/1980 | Campbell et al. |
| 4,220,646 A | 9/1980 | Cotrel et al. |
| 4,229,449 A | 10/1980 | Melloni et al. |
| RE30,511 E | 2/1981 | Paul et al. |
| 4,278,676 A | 7/1981 | Krogsgaard-LarsenPovl |
| 4,280,957 A | 7/1981 | Walser et al. |
| 4,289,772 A | 9/1981 | Campbell et al. |
| 4,298,734 A | 11/1981 | Temple, Jr. |
| 4,301,176 A | 11/1981 | Grabowski et al. |
| 4,314,081 A | 2/1982 | Molloy et al. |
| 4,316,839 A | 2/1982 | Gerecke et al. |
| 4,338,317 A | 7/1982 | Temple, Jr. et al. |
| 4,361,583 A | 11/1982 | Kapan |
| 4,366,156 A | 12/1982 | Temple, Jr. |
| 4,370,328 A | 1/1983 | Campbell et al. |
| 4,370,338 A | 1/1983 | Mizoule |
| 4,383,999 A | 5/1983 | Bondinell et al. |
| 4,404,380 A | 9/1983 | Temple, Jr. |
| RE31,617 E | 6/1984 | Beverung, Jr. et al. |

(Continued)

FOREIGN PATENT DOCUMENTS

EP 0050551 4/1982

(Continued)

OTHER PUBLICATIONS

Turner et al., "Modafinil Improves Cognition and Attentional Set Shifting in Patients with Chronic Schizophrenia" Neuropsychopharmacology (2004) 29, pp. 163-1373.*

(Continued)

*Primary Examiner* — Yong Chong
*Assistant Examiner* — Jody Karol
(74) *Attorney, Agent, or Firm* — Sughrue Mion, PLLC

(57) ABSTRACT

The instant disclosure describes compositions and methods for treating diseases and conditions of the central and peripheral nervous system. The disclosure includes compositions and methods based on use of a 4-acylaminopyridine derivative in combination with one or more other neurogenic agents. One 4-acylaminopyridine derivative is MKC-231.

5 Claims, 10 Drawing Sheets

U.S. PATENT DOCUMENTS

| | | |
|---|---|---|
| 4,460,765 A | 7/1984 | Naito et al. |
| 4,478,836 A | 10/1984 | Mouzin et al. |
| 4,489,078 A | 12/1984 | Temple, Jr. |
| 4,490,371 A | 12/1984 | Jones et al. |
| 4,513,006 A | 4/1985 | Maryanoff et al. |
| 4,521,422 A | 6/1985 | Dusza et al. |
| 4,536,518 A | 8/1985 | Welch, Jr. et al. |
| 4,564,619 A | 1/1986 | Tanaka et al. |
| 4,593,029 A | 6/1986 | Venuti et al. |
| 4,626,538 A | 12/1986 | Dusza et al. |
| 4,642,345 A | 2/1987 | Temple, Jr. |
| 4,656,298 A | 4/1987 | Dingwall et al. |
| 4,663,320 A | 5/1987 | Jones et al. |
| 4,670,434 A | 6/1987 | Venuti |
| 4,699,927 A | 10/1987 | Deboeck |
| 4,701,459 A | 10/1987 | Meanwell et al. |
| 4,709,094 A | 11/1987 | Weber et al. |
| 4,710,508 A | 12/1987 | Bergmeier et al. |
| 4,721,784 A | 1/1988 | Combs |
| 4,739,056 A | 4/1988 | Venuti |
| 4,761,416 A | 8/1988 | Fried et al. |
| 4,761,501 A | 8/1988 | Husbands et al. |
| 4,766,118 A | 8/1988 | Combs |
| 4,775,674 A | 10/1988 | Meanwell et al. |
| 4,786,648 A | 11/1988 | Bergmeier et al. |
| 4,794,185 A | 12/1988 | Rossey et al. |
| 4,831,031 A | 5/1989 | Lowe, III et al. |
| 4,855,290 A | 8/1989 | Fisher et al. |
| 4,861,891 A | 8/1989 | Saccomano et al. |
| 4,866,077 A | 9/1989 | Bogeso et al. |
| 4,870,081 A | 9/1989 | Orlek et al. |
| 4,900,836 A | 2/1990 | Tomcufcik et al. |
| 4,906,628 A | 3/1990 | Coates |
| 4,925,858 A | 5/1990 | Bogeso et al. |
| 4,929,734 A | 5/1990 | Coughenour et al. |
| 4,940,795 A | 7/1990 | Tsukamoto et al. |
| 4,943,573 A | 7/1990 | Meanwell |
| 4,956,368 A | 9/1990 | Cipollina et al. |
| 4,956,388 A | 9/1990 | Robertson et al. |
| 4,957,916 A | 9/1990 | Kennis et al. |
| 4,963,561 A | 10/1990 | Lesher et al. |
| 4,968,691 A | 11/1990 | Orlek et al. |
| 4,971,972 A | 11/1990 | Doll et al. |
| 4,971,975 A | 11/1990 | Hadley et al. |
| 4,981,858 A | 1/1991 | Fisher et al. |
| 4,992,457 A | 2/1991 | Schulman et al. |
| 4,996,210 A | 2/1991 | Tsukamoto et al. |
| 5,010,086 A | 4/1991 | Lesher et al. |
| 5,010,090 A | 4/1991 | Gronvald et al. |
| 5,041,455 A | 8/1991 | Sauerberg et al. |
| 5,041,549 A | 8/1991 | Tsukamoto et al. |
| 5,043,345 A | 8/1991 | Sauerberg et al. |
| 5,061,728 A | 10/1991 | Koe |
| 5,066,653 A | 11/1991 | Coates |
| 5,081,242 A | 1/1992 | Combs |
| 5,086,054 A | 2/1992 | Parish |
| 5,091,242 A | 2/1992 | Chung |
| 5,091,431 A | 2/1992 | Tulshian et al. |
| 5,093,333 A | 3/1992 | Saab |
| 5,093,525 A | 3/1992 | Weber et al. |
| 5,095,015 A | 3/1992 | Albaugh |
| 5,109,002 A | 4/1992 | Cain et al. |
| 5,110,828 A | 5/1992 | Bromidge et al. |
| 5,116,837 A | 5/1992 | Combs |
| 5,116,995 A | 5/1992 | Nakazato et al. |
| 5,124,460 A | 6/1992 | Humphrey |
| 5,130,154 A | 7/1992 | Liu et al. |
| 5,130,430 A | 7/1992 | Shaw |
| 5,132,316 A | 7/1992 | Hadley et al. |
| 5,137,895 A | 8/1992 | Munson, Jr. et al. |
| 5,139,802 A | 8/1992 | Liu et al. |
| 5,149,817 A | 9/1992 | Matsumura et al. |
| 5,158,947 A | 10/1992 | Tatsuoka et al. |
| 5,162,341 A | 11/1992 | Cook |
| 5,166,357 A | 11/1992 | Orlek et al. |
| 5,169,855 A | 12/1992 | Cain et al. |
| 5,182,290 A | 1/1993 | Albaugh |
| 5,185,446 A | 2/1993 | Shaw et al. |
| 5,212,310 A | 5/1993 | Thurkauf et al. |
| 5,216,159 A | 6/1993 | Thurkauf et al. |
| 5,232,917 A | 8/1993 | Bolger et al. |
| 5,243,049 A | 9/1993 | Shaw et al. |
| 5,250,534 A | 10/1993 | Bell et al. |
| 5,260,314 A | 11/1993 | Sauerberg et al. |
| 5,262,427 A | 11/1993 | Nielson et al. |
| 5,266,698 A | 11/1993 | Shaw et al. |
| 5,278,170 A | 1/1994 | Orlek et al. |
| 5,286,860 A | 2/1994 | Blum et al. |
| 5,286,864 A | 2/1994 | Walther et al. |
| 5,294,612 A | 3/1994 | Bacon et al. |
| 5,298,657 A | 3/1994 | Durant et al. |
| 5,306,819 A | 4/1994 | Albaugh et al. |
| 5,312,822 A | 5/1994 | Albaugh |
| 5,312,840 A | 5/1994 | Keana et al. |
| 5,314,901 A | 5/1994 | Bromidge et al. |
| 5,324,724 A | 6/1994 | Orlek et al. |
| RE34,653 E | 7/1994 | Tsukamoto et al. |
| 5,326,868 A | 7/1994 | Thurkauf et al. |
| 5,328,912 A | 7/1994 | Albaugh |
| 5,340,821 A | 8/1994 | Abe et al. |
| 5,340,827 A | 8/1994 | Beeley et al. |
| 5,346,901 A | 9/1994 | Bell et al. |
| 5,356,912 A | 10/1994 | Nielsen et al. |
| 5,356,914 A | 10/1994 | Bromidge et al. |
| 5,362,739 A | 11/1994 | Orlek et al. |
| 5,362,860 A | 11/1994 | Huang et al. |
| 5,367,077 A | 11/1994 | Blum et al. |
| 5,369,108 A | 11/1994 | Breslow et al. |
| 5,384,408 A | 1/1995 | Baker et al. |
| 5,385,946 A | 1/1995 | Keana et al. |
| 5,395,841 A | 3/1995 | Foguet et al. |
| 5,397,785 A | 3/1995 | Ninomiya et al. |
| 5,403,931 A | 4/1995 | Tsukamoto et al. |
| 5,407,938 A | 4/1995 | Fisher et al. |
| 5,412,096 A | 5/1995 | Tsukamoto et al. |
| 5,424,301 A | 6/1995 | Huang et al. |
| 5,426,186 A | 6/1995 | Shaw et al. |
| 5,451,585 A | 9/1995 | Albaugh |
| 5,451,587 A | 9/1995 | Walther et al. |
| 5,463,054 A | 10/1995 | Thurkauf et al. |
| 5,468,875 A | 11/1995 | Saab et al. |
| 5,473,073 A | 12/1995 | Albaugh et al. |
| 5,473,077 A | 12/1995 | Monn et al. |
| 5,478,963 A | 12/1995 | Pfirmann et al. |
| 5,484,944 A | 1/1996 | Albaugh et al. |
| 5,488,055 A | 1/1996 | Kumar et al. |
| 5,491,147 A | 2/1996 | Boyd et al. |
| 5,500,420 A | 3/1996 | Maiese |
| 5,502,072 A | 3/1996 | Masamune |
| 5,502,255 A | 3/1996 | Keana et al. |
| 5,508,405 A | 4/1996 | Walther et al. |
| 5,510,478 A | 4/1996 | Sabb |
| 5,510,480 A | 4/1996 | Albaugh |
| 5,512,574 A | 4/1996 | Husbands et al. |
| 5,527,813 A | 6/1996 | Sauerberg et al. |
| 5,534,520 A | 7/1996 | Fisher et al. |
| 5,534,522 A | 7/1996 | Ando et al. |
| 5,536,721 A | 7/1996 | Jakobsen et al. |
| 5,536,728 A | 7/1996 | Ninomiya et al. |
| 5,541,194 A | 7/1996 | Orlek et al. |
| 5,545,740 A | 8/1996 | Hughes et al. |
| 5,550,137 A | 8/1996 | Beeley et al. |
| 5,561,135 A | 10/1996 | Foguet et al. |
| 5,571,819 A | 11/1996 | Sabb et al. |
| 5,571,826 A | 11/1996 | Sauerberg et al. |
| 5,574,043 A | 11/1996 | Sauerberg et al. |
| 5,574,070 A | 11/1996 | Keana et al. |
| 5,578,602 A | 11/1996 | Sauerberg et al. |
| 5,580,880 A | 12/1996 | Handa et al. |
| 5,585,490 A | 12/1996 | Thurkauf et al. |
| 5,591,733 A | 1/1997 | Bolger et al. |
| 5,599,937 A | 2/1997 | Glas et al. |
| 5,604,235 A | 2/1997 | Shaw et al. |
| 5,605,908 A | 2/1997 | Merritt et al. |
| 5,606,059 A | 2/1997 | Blum et al. |
| 5,608,070 A | 3/1997 | Alexander et al. |
| 5,608,079 A | 3/1997 | Albaugh et al. |

| | | | | | |
|---|---|---|---|---|---|
| 5,610,299 A | 3/1997 | Blum et al. | 5,925,770 A | 7/1999 | Albaugh et al. |
| 5,622,977 A | 4/1997 | Warrellow et al. | 5,928,947 A | 7/1999 | Anderson et al. |
| 5,625,063 A | 4/1997 | Thurkauf et al. | 5,929,236 A | 7/1999 | Kuo et al. |
| RE35,517 E | 5/1997 | Gee et al. | 5,936,095 A | 8/1999 | DeSimone et al. |
| 5,633,257 A | 5/1997 | Warrellow et al. | 5,939,545 A | 8/1999 | Upasani et al. |
| 5,637,617 A | 6/1997 | Woodward et al. | 5,945,417 A | 8/1999 | Olesen et al. |
| 5,637,724 A | 6/1997 | DeSimone et al. | 5,958,960 A | 9/1999 | Massey et al. |
| 5,637,725 A | 6/1997 | DeSimone et al. | 5,962,483 A | 10/1999 | Warrellow et al. |
| 5,641,791 A | 6/1997 | Sauerberg et al. | 5,962,492 A | 10/1999 | Warrellow et al. |
| 5,646,289 A | 7/1997 | Alt et al. | 5,972,927 A | 10/1999 | Pascal et al. |
| 5,650,174 A | 7/1997 | Muhammad et al. | RE36,374 E | 11/1999 | Bogeso et al. |
| RE35,593 E | 8/1997 | Orlek et al. | 5,981,527 A | 11/1999 | Daugan et al. |
| 5,665,725 A | 9/1997 | Moltzen et al. | 5,981,545 A | 11/1999 | Jenkins et al. |
| 5,665,745 A | 9/1997 | Alt et al. | 6,011,037 A | 1/2000 | Bar et al. |
| 5,665,754 A | 9/1997 | Feldman et al. | 6,013,799 A | 1/2000 | Shaw et al. |
| 5,668,174 A | 9/1997 | Kawagishi et al. | 6,017,924 A | 1/2000 | Edwards et al. |
| 5,668,283 A | 9/1997 | Blum et al. | 6,043,252 A | 3/2000 | Bombrun |
| 5,672,709 A | 9/1997 | Alt et al. | 6,043,263 A | 3/2000 | Bar et al. |
| 5,674,880 A | 10/1997 | Boyd et al. | 6,051,581 A | 4/2000 | Gordon et al. |
| 5,675,007 A | 10/1997 | Keogh et al. | 6,054,448 A | 4/2000 | Clark et al. |
| 5,677,309 A | 10/1997 | Chen et al. | 6,054,475 A | 4/2000 | Martin et al. |
| 5,686,434 A | 11/1997 | Kleinman | 6,069,151 A | 5/2000 | Dyke et al. |
| 5,688,826 A | 11/1997 | Massey et al. | 6,071,909 A | 6/2000 | Harrison et al. |
| 5,693,659 A | 12/1997 | Head et al. | 6,071,932 A | 6/2000 | Lau et al. |
| 5,693,801 A | 12/1997 | Shaw et al. | 6,080,782 A | 6/2000 | Ulrich et al. |
| 5,696,148 A | 12/1997 | Lundbech et al. | 6,080,790 A | 6/2000 | Boyd et al. |
| 5,696,260 A | 12/1997 | Shaw et al. | 6,080,873 A | 6/2000 | Albaugh et al. |
| 5,710,160 A | 1/1998 | Guay et al. | 6,087,346 A | 7/2000 | Glennon et al. |
| 5,710,170 A | 1/1998 | Guay et al. | 6,090,817 A | 7/2000 | Manley |
| 5,712,298 A | 1/1998 | Amschler | 6,096,887 A | 8/2000 | Albaugh et al. |
| 5,716,967 A | 2/1998 | Kleinman | 6,103,718 A | 8/2000 | Sterk |
| 5,719,283 A | 2/1998 | Bell et al. | 6,103,731 A | 8/2000 | Chen et al. |
| 5,723,460 A | 3/1998 | Warrellow et al. | 6,103,903 A | 8/2000 | Cai et al. |
| 5,723,462 A | 3/1998 | Albaugh et al. | 6,107,295 A | 8/2000 | Rochus et al. |
| 5,731,307 A | 3/1998 | Desai | 6,107,342 A | 8/2000 | Adam et al. |
| 5,739,144 A | 4/1998 | Warrellow et al. | 6,117,881 A | 9/2000 | Bombrun |
| 5,744,602 A | 4/1998 | Whitcome et al. | 6,121,279 A | 9/2000 | Gutterer |
| 5,744,603 A | 4/1998 | Blum et al. | 6,127,363 A | 10/2000 | Doherty, Jr. et al. |
| 5,750,566 A | 5/1998 | Monn et al. | 6,127,378 A | 10/2000 | Gutterer et al. |
| 5,750,702 A | 5/1998 | Albaugh et al. | 6,127,395 A | 10/2000 | DeSimone et al. |
| 5,756,501 A | 5/1998 | Sabb | 6,130,333 A | 10/2000 | Huang et al. |
| 5,773,458 A | 6/1998 | Sabb et al. | 6,133,255 A | 10/2000 | Harrison et al. |
| 5,773,619 A | 6/1998 | Bromidge et al. | 6,136,821 A | 10/2000 | Hersperger |
| 5,776,958 A | 7/1998 | Warrellow et al. | 6,140,329 A | 10/2000 | Daugan |
| 5,780,477 A | 7/1998 | Head et al. | 6,143,736 A | 11/2000 | Upasani et al. |
| 5,780,478 A | 7/1998 | Alexander et al. | 6,143,760 A | 11/2000 | Albaugh et al. |
| 5,783,575 A | 7/1998 | Jakobsen et al. | 6,143,777 A | 11/2000 | Jonas et al. |
| 5,786,354 A | 7/1998 | Warrellow et al. | 6,143,783 A | 11/2000 | Monn et al. |
| 5,792,766 A | 8/1998 | Chen et al. | 6,146,876 A | 11/2000 | Robision et al. |
| 5,798,373 A | 8/1998 | Warrellow | 6,147,063 A | 11/2000 | Durant et al. |
| 5,800,539 A | 9/1998 | Waller | 6,153,618 A | 11/2000 | Schultz et al. |
| 5,804,686 A | 9/1998 | Albaugh et al. | 6,156,753 A | 12/2000 | Doherty, Jr. et al. |
| 5,808,075 A | 9/1998 | Bromidge et al. | 6,156,898 A | 12/2000 | DeSimone et al. |
| 5,814,651 A | 9/1998 | Duplantier et al. | 6,166,041 A | 12/2000 | Cavalla et al. |
| 5,817,670 A | 10/1998 | Takayama et al. | 6,166,203 A | 12/2000 | Cai et al. |
| 5,817,773 A | 10/1998 | Wilson et al. | 6,177,569 B1 | 1/2001 | Rachwal et al. |
| 5,817,813 A | 10/1998 | Thurkauf et al. | 6,191,138 B1 | 2/2001 | Gutterer |
| 5,834,458 A | 11/1998 | Mitch | 6,194,427 B1 | 2/2001 | DeSimone et al. |
| 5,840,888 A | 11/1998 | Shaw et al. | 6,197,792 B1 | 3/2001 | Alexander et al. |
| 5,843,988 A | 12/1998 | Annora et al. | 6,200,975 B1 | 3/2001 | Carling et al. |
| 5,849,770 A | 12/1998 | Head et al. | 6,204,292 B1 | 3/2001 | Kozikowski et al. |
| 5,849,927 A | 12/1998 | DeSimone et al. | 6,211,203 B1 | 4/2001 | Amschler |
| 5,852,029 A | 12/1998 | Fisher et al. | 6,211,365 B1 | 4/2001 | Albaugh et al. |
| 5,859,006 A | 1/1999 | Daugan | 6,218,385 B1 | 4/2001 | Adam et al. |
| 5,859,009 A | 1/1999 | Schaper et al. | 6,218,547 B1 | 4/2001 | Teuber et al. |
| 5,859,034 A | 1/1999 | Warrellow et al. | 6,225,115 B1 | 5/2001 | Smith et al. |
| 5,861,411 A | 1/1999 | Ninomiya et al. | 6,228,859 B1 | 5/2001 | Cavalla et al. |
| 5,866,593 A | 2/1999 | Warrellow et al. | 6,245,774 B1 | 6/2001 | Warrellow et al. |
| 5,869,516 A | 2/1999 | Arlt et al. | 6,251,904 B1 | 6/2001 | Bunnage et al. |
| 5,877,190 A | 3/1999 | Dhainaut et al. | 6,251,923 B1 | 6/2001 | Hofgen et al. |
| 5,891,896 A | 4/1999 | Warrellow et al. | 6,255,305 B1 | 7/2001 | Broughton et al. |
| 5,902,814 A | 5/1999 | Gordon et al. | 6,258,833 B1 | 7/2001 | Martins et al. |
| 5,902,824 A | 5/1999 | Ulrich | 6,258,843 B1 | 7/2001 | Manley |
| 5,908,932 A | 6/1999 | Shaw et al. | 6,268,496 B1 | 7/2001 | Shaw |
| 5,910,590 A | 6/1999 | Blum et al. | 6,268,507 B1 | 7/2001 | Massey et al. |
| 5,912,248 A | 6/1999 | Fernandez et al. | 6,277,838 B1 | 8/2001 | Upasani et al. |
| 5,916,920 A | 6/1999 | Fernandez et al. | 6,284,785 B1 | 9/2001 | Mutel et al. |
| 5,922,724 A | 7/1999 | Teuber et al. | 6,291,460 B1 | 9/2001 | Harrison et al. |
| 5,925,630 A | 7/1999 | Upasani et al. | 6,294,561 B1 | 9/2001 | Fowler et al. |

| | | | | | | |
|---|---|---|---|---|---|---|
| 6,297,248 B1 | 10/2001 | Shimamoto et al. | | 6,541,484 B2 | 4/2003 | Collins et al. |
| 6,297,252 B1 | 10/2001 | Chen et al. | | 6,541,661 B2 | 4/2003 | Delorme et al. |
| 6,297,256 B1 | 10/2001 | Cai et al. | | 6,545,025 B2 | 4/2003 | Hofgen et al. |
| 6,297,257 B1 | 10/2001 | Napoletano et al. | | 6,545,158 B2 | 4/2003 | Hofgen et al. |
| 6,297,262 B1 | 10/2001 | Sams-Dodd et al. | | 6,552,016 B1 | 4/2003 | Baxter et al. |
| 6,297,264 B1 | 10/2001 | Head et al. | | 6,552,065 B2 | 4/2003 | Remiszewski et al. |
| 6,303,597 B1 | 10/2001 | Carling et al. | | 6,559,159 B2 | 5/2003 | Carroll et al. |
| 6,303,605 B1 | 10/2001 | Harrison et al. | | 6,559,168 B2 | 5/2003 | Marfat et al. |
| 6,303,789 B1 | 10/2001 | Bar | | 6,562,995 B1 | 5/2003 | Lan-Hargest et al. |
| 6,306,870 B1 | 10/2001 | Bombrun | | 6,566,360 B1 | 5/2003 | Niewohner et al. |
| 6,310,203 B1 | 10/2001 | Carling et al. | | 6,569,885 B1 | 5/2003 | Martins et al. |
| 6,313,116 B1 | 11/2001 | Dyke et al. | | 6,569,890 B2 | 5/2003 | Martins et al. |
| 6,313,125 B1 | 11/2001 | Carling et al. | | 6,576,644 B2 | 6/2003 | Bi et al. |
| 6,313,156 B1 | 11/2001 | Fowler et al. | | 6,579,875 B1 | 6/2003 | Carling et al. |
| 6,313,159 B1 | 11/2001 | Jackson et al. | | 6,582,351 B1 | 6/2003 | Sawada et al. |
| 6,316,472 B1 | 11/2001 | Frenette et al. | | 6,586,422 B2 | 7/2003 | Binggeli et al. |
| 6,319,924 B1 | 11/2001 | Harrison et al. | | 6,589,978 B2 | 7/2003 | Mutel et al. |
| 6,331,543 B1 | 12/2001 | Garvey et al. | | 6,593,325 B1 | 7/2003 | Carling et al. |
| 6,331,548 B1 | 12/2001 | Shimamoto et al. | | 6,596,869 B2 | 7/2003 | Hughes et al. |
| 6,333,336 B1 | 12/2001 | Blackaby et al. | | 6,602,890 B2 | 8/2003 | Hofgen et al. |
| 6,333,354 B1 | 12/2001 | Schudt | | 6,608,062 B1 | 8/2003 | Carling et al. |
| 6,333,428 B1 | 12/2001 | Nakazato et al. | | 6,610,677 B2 | 8/2003 | Davies et al. |
| 6,337,331 B1 | 1/2002 | Broughton et al. | | 6,613,776 B2 | 9/2003 | Knegtel et al. |
| 6,342,496 B1 | 1/2002 | Jerussi et al. | | 6,613,778 B1 | 9/2003 | Eggenweiler et al. |
| 6,348,602 B1 | 2/2002 | Fowler et al. | | 6,613,794 B2 | 9/2003 | Hofgen et al. |
| 6,353,109 B1 | 3/2002 | Albaugh et al. | | 6,617,326 B2 | 9/2003 | Carling et al. |
| 6,355,798 B1 | 3/2002 | Madin et al. | | 6,617,357 B2 | 9/2003 | Aubart et al. |
| 6,362,178 B1 | 3/2002 | Niewohner et al. | | 6,627,645 B2 | 9/2003 | Andersson et al. |
| 6,362,213 B1 | 3/2002 | Gaudino | | 6,635,638 B2 | 10/2003 | Sui et al. |
| 6,365,585 B1 | 4/2002 | Jacobelli et al. | | 6,638,926 B2 | 10/2003 | Davies et al. |
| 6,372,777 B1 | 4/2002 | Martins et al. | | 6,642,229 B2 | 11/2003 | Blackaby et al. |
| 6,376,485 B1 | 4/2002 | Martin | | 6,642,250 B2 | 11/2003 | Aotsuka et al. |
| 6,376,489 B1 | 4/2002 | Martins et al. | | 6,645,990 B2 | 11/2003 | Askew et al. |
| 6,376,532 B2 | 4/2002 | Kozikowski et al. | | 6,646,124 B2 | 11/2003 | Albaugh et al. |
| 6,376,535 B2 | 4/2002 | Ohshima et al. | | 6,653,300 B2 | 11/2003 | Bebbington et al. |
| 6,380,209 B1 | 4/2002 | Cai et al. | | 6,653,301 B2 | 11/2003 | Bebbington et al. |
| 6,384,236 B1 | 5/2002 | Kleinman | | 6,656,939 B2 | 12/2003 | Bebbington et al. |
| 6,387,673 B1 | 5/2002 | Evans et al. | | 6,660,753 B2 | 12/2003 | Van Wagenen et al. |
| 6,399,604 B1 | 6/2002 | Albaugh et al. | | 6,660,773 B2 | 12/2003 | Mendelovici et al. |
| 6,399,641 B1 | 6/2002 | Jolidon et al. | | 6,664,247 B2 | 12/2003 | Bebbington et al. |
| 6,407,108 B1 | 6/2002 | Gracia Ferrer et al. | | 6,677,335 B1 | 1/2004 | Bunnage et al. |
| 6,410,547 B1 | 6/2002 | Manley | | 6,680,336 B2 | 1/2004 | Martins et al. |
| 6,414,147 B1 | 7/2002 | Currie et al. | | 6,686,349 B2 | 2/2004 | Jiang et al. |
| 6,417,185 B1 | 7/2002 | Goff et al. | | 6,696,444 B2 | 2/2004 | Carling et al. |
| 6,423,710 B1 | 7/2002 | Martins et al. | | 6,696,452 B2 | 2/2004 | Davies et al. |
| 6,423,711 B1 | 7/2002 | Cai et al. | | 6,699,859 B1 | 3/2004 | Carling et al. |
| 6,426,343 B1 | 7/2002 | Dawson | | 6,716,987 B1 | 4/2004 | Ohshima et al. |
| 6,429,207 B1 | 8/2002 | Van Wagenen et al. | | 6,719,520 B2 | 4/2004 | Coghlan et al. |
| 6,444,671 B1 | 9/2002 | Gaudino | | 6,720,445 B2 | 4/2004 | Lan-Hargest et al. |
| 6,448,246 B1 | 9/2002 | Cai et al. | | 6,723,735 B1 | 4/2004 | Hallett et al. |
| 6,448,259 B1 | 9/2002 | DeSimone et al. | | 6,727,251 B2 | 4/2004 | Bebbington et al. |
| 6,451,809 B2 | 9/2002 | Rachwal et al. | | 6,730,676 B2 | 5/2004 | Blackaby et al. |
| 6,455,562 B1 | 9/2002 | Fowler et al. | | 6,730,681 B2 | 5/2004 | Chambers et al. |
| 6,458,787 B1 | 10/2002 | Martins et al. | | 6,737,436 B1 | 5/2004 | Eggenweiler et al. |
| 6,458,951 B1 | 10/2002 | Bunnage et al. | | 6,740,655 B2 | 5/2004 | Magee et al. |
| 6,462,047 B1 | 10/2002 | Bombrun et al. | | 6,740,662 B1 | 5/2004 | Iwata et al. |
| 6,468,560 B2 | 10/2002 | Sauer et al. | | 6,743,802 B2 | 6/2004 | Guay et al. |
| 6,469,012 B1 | 10/2002 | Ellis et al. | | 6,747,035 B2 | 6/2004 | Guadilliere et al. |
| 6,476,030 B1 | 11/2002 | Carling et al. | | 6,762,179 B2 | 7/2004 | Cochran et al. |
| 6,479,470 B1 | 11/2002 | Kozikowski et al. | | 6,777,217 B1 | 8/2004 | Schreiber et al. |
| 6,479,494 B1 | 11/2002 | Rochus et al. | | 6,787,548 B1 | 9/2004 | Jonas et al. |
| 6,479,506 B1 | 11/2002 | Broughton et al. | | 6,787,554 B2 | 9/2004 | Gaudilliere |
| 6,486,186 B2 | 11/2002 | Fowler et al. | | RE38,624 E | 10/2004 | Hofgen et al. |
| 6,489,344 B1 | 12/2002 | Nuss et al. | | 6,800,625 B2 | 10/2004 | Jiang et al. |
| 6,492,358 B2 | 12/2002 | Sui et al. | | 6,800,632 B2 | 10/2004 | Nuss et al. |
| 6,492,554 B2 | 12/2002 | Dalton et al. | | 6,818,646 B2 | 11/2004 | Sui et al. |
| 6,495,700 B1 | 12/2002 | Bruening | | 6,818,651 B2 | 11/2004 | Weinbrenner et al. |
| 6,498,160 B2 | 12/2002 | Napoletano et al. | | 6,821,975 B1 | 11/2004 | Anderson et al. |
| 6,498,176 B1 | 12/2002 | Lackey et al. | | 6,825,197 B2 | 11/2004 | Orme et al. |
| 6,498,180 B1 | 12/2002 | Collado Cano et al. | | 6,825,211 B1 | 11/2004 | Kozikowski et al. |
| 6,500,828 B1 | 12/2002 | Carling et al. | | 6,828,315 B1 | 12/2004 | Gaudilliere et al. |
| 6,500,856 B1 | 12/2002 | Fowler et al. | | 6,828,322 B2 | 12/2004 | Carling et al. |
| 6,503,925 B1 | 1/2003 | Teuber et al. | | 6,828,333 B2 | 12/2004 | Marfat et al. |
| 6,514,996 B2 | 2/2003 | Ohshima et al. | | 6,833,384 B2 | 12/2004 | Remiszewski et al. |
| 6,515,140 B2 | 2/2003 | Albaugh et al. | | 6,838,559 B2 | 1/2005 | Vaccaro et al. |
| 6,528,499 B1 | 3/2003 | Kozikowski et al. | | 6,844,352 B2 | 1/2005 | Mork et al. |
| 6,528,529 B1 | 3/2003 | Brann et al. | | 6,846,823 B2 | 1/2005 | Landau et al. |
| 6,534,505 B2 | 3/2003 | Kaufman et al. | | 6,864,253 B2 | 3/2005 | Sui et al. |
| 6,541,480 B2 | 4/2003 | Shimamoto et al. | | 6,869,945 B2 | 3/2005 | Marfat et al. |

| | | | | | |
|---|---|---|---|---|---|
| 6,872,716 B2 | 3/2005 | Wu et al. | 2003/0212066 A1 | 11/2003 | Mutel et al. |
| 6,872,720 B2 | 3/2005 | Carling et al. | 2003/0212094 A1 | 11/2003 | Yamabe et al. |
| 6,872,731 B2 | 3/2005 | Crawforth et al. | 2004/0002478 A1 | 1/2004 | Kozikowski et al. |
| 6,872,737 B2 | 3/2005 | Gil et al. | 2004/0006114 A1 | 1/2004 | Coleman et al. |
| 6,884,800 B1 | 4/2005 | Eggenweiler et al. | 2004/0010031 A1 | 1/2004 | Coghlan et al. |
| 6,884,805 B2 | 4/2005 | Yamabe et al. | 2004/0023945 A1 | 2/2004 | Martins et al. |
| 6,888,027 B2 | 5/2005 | Watkins et al. | 2004/0053960 A1 | 3/2004 | Georges et al. |
| 6,894,041 B2 | 5/2005 | Marfat et al. | 2004/0064945 A1 | 4/2004 | Howley |
| 6,897,220 B2 | 5/2005 | Delorme et al. | 2004/0067945 A1 | 4/2004 | Niewohner et al. |
| 6,897,305 B2 | 5/2005 | Ji et al. | 2004/0077599 A1 | 4/2004 | Curry |
| 6,900,205 B2 | 5/2005 | Wang et al. | 2004/0077698 A1 | 4/2004 | Georges et al. |
| 6,900,215 B2 | 5/2005 | Chambers et al. | 2004/0077726 A1 | 4/2004 | Watkins et al. |
| 6,900,228 B1 | 5/2005 | Carroll et al. | 2004/0082592 A1 | 4/2004 | Mabire et al. |
| 6,906,061 B2 | 6/2005 | Uehata et al. | 2004/0092598 A1 | 5/2004 | Watkins et al. |
| 6,906,177 B1 | 6/2005 | Kimura et al. | 2004/0102521 A1 | 5/2004 | Collado-Cano et al. |
| 6,911,452 B2 | 6/2005 | Schlienger | 2004/0106599 A1 | 6/2004 | Delorme et al. |
| 6,911,477 B2 | 6/2005 | Villalobos et al. | 2004/0106631 A1 | 6/2004 | Bernardelli et al. |
| 6,914,060 B2 | 7/2005 | Goodacre | 2004/0138249 A1 | 7/2004 | Niewohner et al. |
| 6,914,063 B2 | 7/2005 | Goodacre | 2004/0138273 A1 | 7/2004 | Wagman et al. |
| 6,914,065 B2 | 7/2005 | Hallett et al. | 2004/0138279 A1 | 7/2004 | Eggenweiler et al. |
| 6,924,292 B2 | 8/2005 | Kawano et al. | 2004/0142953 A1 | 7/2004 | Delorme et al. |
| 6,924,311 B2 | 8/2005 | Schulman et al. | 2004/0147482 A1 | 7/2004 | Pajouhesh et al. |
| 6,930,114 B2 | 8/2005 | Niewohner et al. | 2004/0152754 A1 | 8/2004 | Martins et al. |
| 6,936,608 B2 | 8/2005 | Bettati et al. | 2004/0171633 A1 | 9/2004 | Carling et al. |
| 6,943,166 B1 | 9/2005 | Pullman et al. | 2004/0185429 A1 | 9/2004 | Kelleher-Andersson et al. |
| 6,943,253 B2 | 9/2005 | Vidal Juan et al. | 2004/0192692 A1 | 9/2004 | Blackaby et al. |
| 6,949,573 B2 | 9/2005 | Bailey et al. | 2004/0198830 A1 | 10/2004 | Watkins et al. |
| 6,951,849 B2 | 10/2005 | Kelly et al. | 2004/0214843 A1 | 10/2004 | Bernardelli et al. |
| 6,953,810 B2 | 10/2005 | Chambers et al. | 2004/0214928 A1 | 10/2004 | Aronov et al. |
| 6,956,049 B1 | 10/2005 | Cosfod et al. | 2004/0229291 A1 | 11/2004 | Zhou et al. |
| 7,045,636 B2 | 5/2006 | Palani et al. | 2004/0229889 A1 | 11/2004 | Urano et al. |
| 7,060,450 B1 | 6/2006 | Tabin et al. | 2004/0229917 A1 | 11/2004 | Buettelmann et al. |
| 2001/0003588 A1 | 6/2001 | Sauer et al. | 2004/0235884 A1 | 11/2004 | Takashina et al. |
| 2001/0018074 A1 | 8/2001 | Napper et al. | 2004/0236123 A1 | 11/2004 | Romanczyk, Jr. et al. |
| 2001/0034373 A1* | 10/2001 | Miller et al. .................. 514/625 | 2004/0249148 A1 | 12/2004 | Erguden et al. |
| 2001/0039275 A1 | 11/2001 | Bowler et al. | 2004/0254152 A1 | 12/2004 | Monje et al. |
| 2001/0044436 A1 | 11/2001 | Nuss et al. | 2004/0254220 A1 | 12/2004 | Bressi et al. |
| 2002/0004523 A1 | 1/2002 | Romanczyk, Jr. et al. | 2004/0259818 A1 | 12/2004 | Halevy et al. |
| 2002/0018807 A1 | 2/2002 | Schmitz et al. | 2004/0259917 A1 | 12/2004 | Cosford et al. |
| 2002/0065282 A1 | 5/2002 | Georges et al. | 2004/0266769 A1 | 12/2004 | Bressi et al. |
| 2002/0086833 A1 | 7/2002 | Romanczyk, Jr. et al. | 2005/0004046 A1 | 1/2005 | Praag et al. |
| 2002/0103192 A1 | 8/2002 | Curtin et al. | 2005/0004125 A1 | 1/2005 | Freyne et al. |
| 2002/0106731 A1 | 8/2002 | Ruben et al. | 2005/0004130 A1 | 1/2005 | Gyback et al. |
| 2002/0107292 A1 | 8/2002 | Bortlik et al. | 2005/0009742 A1 | 1/2005 | Bertilsson et al. |
| 2002/0115826 A1 | 8/2002 | Delorme et al. | 2005/0009847 A1 | 1/2005 | Bertilsson et al. |
| 2002/0119996 A1 | 8/2002 | Lan-Hargest et al. | 2005/0014839 A1 | 1/2005 | Kozikowski et al. |
| 2002/0127271 A1 | 9/2002 | Van-Schie | 2005/0014939 A1 | 1/2005 | Albaugh et al. |
| 2002/0132754 A1 | 9/2002 | Boss et al. | 2005/0020585 A1 | 1/2005 | Cosford et al. |
| 2002/0132828 A1 | 9/2002 | Carroll et al. | 2005/0026913 A1 | 2/2005 | Techim et al. |
| 2002/0150618 A1 | 10/2002 | Napper et al. | 2005/0026963 A1 | 2/2005 | Cosford et al. |
| 2002/0161045 A1 | 10/2002 | Lan-Hargest et al. | 2005/0031538 A1 | 2/2005 | Steindler et al. |
| 2002/0177594 A1 | 11/2002 | Curtin et al. | 2005/0031762 A1 | 2/2005 | Mc Carthy et al. |
| 2002/0198198 A1 | 12/2002 | Bernardelli et al. | 2005/0032702 A1 | 2/2005 | Eriksson |
| 2003/0008866 A1 | 1/2003 | Nuss et al. | 2005/0032831 A1 | 2/2005 | Kozikowski et al. |
| 2003/0013715 A1 | 1/2003 | Van Wagenen et al. | 2005/0038011 A1 | 2/2005 | Radeke et al. |
| 2003/0045557 A1 | 3/2003 | Vergne et al. | 2005/0049243 A1 | 3/2005 | Ballard et al. |
| 2003/0092721 A1 | 5/2003 | Pitts et al. | 2005/0059686 A1 | 3/2005 | Eggenweiler et al. |
| 2003/0092908 A1 | 5/2003 | Pitts et al. | 2005/0065340 A1 | 3/2005 | Arruda et al. |
| 2003/0100545 A1 | 5/2003 | Kelly et al. | 2005/0070541 A1 | 3/2005 | Niewohner et al. |
| 2003/0100571 A1 | 5/2003 | Vaccaro et al. | 2005/0085514 A1 | 4/2005 | Cosford et al. |
| 2003/0104075 A1 | 6/2003 | Chevaux et al. | 2005/0085515 A1 | 4/2005 | Watkins et al. |
| 2003/0104974 A1 | 6/2003 | Pitts et al. | 2005/0096468 A1 | 5/2005 | Van Emelen et al. |
| 2003/0105075 A1 | 6/2003 | Meijer | 2005/0107384 A1 | 5/2005 | Angibaud et al. |
| 2003/0105079 A1 | 6/2003 | Choi et al. | 2005/0107432 A1 | 5/2005 | Iimura et al. |
| 2003/0109504 A1 | 6/2003 | Brotchie et al. | 2005/0107445 A1 | 5/2005 | Watkins et al. |
| 2003/0129246 A1 | 7/2003 | Napper et al. | 2005/0113357 A1 | 5/2005 | Anderson et al. |
| 2003/0130289 A1 | 7/2003 | Nuss et al. | 2005/0113373 A1 | 5/2005 | Van Emelen et al. |
| 2003/0144285 A1 | 7/2003 | Brann et al. | 2005/0113402 A1 | 5/2005 | Sui et al. |
| 2003/0157169 A1 | 8/2003 | Sauer et al. | 2005/0119225 A1 | 6/2005 | Schumacher et al. |
| 2003/0157647 A1 | 8/2003 | Krapcho et al. | 2005/0119250 A1 | 6/2005 | Angibaud et al. |
| 2003/0162802 A1 | 8/2003 | Guo et al. | 2005/0119345 A1 | 6/2005 | Nakazato et al. |
| 2003/0166641 A1 | 9/2003 | Sui et al. | 2005/0130961 A1 | 6/2005 | Davis et al. |
| 2003/0171355 A1 | 9/2003 | Radeke et al. | 2005/0132429 A1 | 6/2005 | Castanedo et al. |
| 2003/0176418 A1 | 9/2003 | Skjaerback et al. | 2005/0137201 A1 | 6/2005 | Aronov et al. |
| 2003/0180406 A1 | 9/2003 | Sies | 2005/0137232 A1 | 6/2005 | Bressi et al. |
| 2003/0181439 A1 | 9/2003 | Meijer et al. | 2005/0137234 A1 | 6/2005 | Bressi et al. |
| 2003/0187027 A1 | 10/2003 | Schreiber et al. | 2005/0143385 A1 | 6/2005 | Watkins et al. |
| 2003/0195139 A1 | 10/2003 | Corsi et al. | 2005/0148604 A1 | 7/2005 | Inoue et al. |
| 2003/0199533 A1 | 10/2003 | Curry | 2005/0153986 A1 | 7/2005 | Chen et al. |

| | | | |
|---|---|---|---|
| 2005/0154027 A1 | 7/2005 | Wagenen et al. | |
| 2005/0159470 A1 | 7/2005 | Bressi et al. | |
| 2005/0165016 A1 | 7/2005 | Van Emelen | |
| 2005/0165023 A1 | 7/2005 | Bettati et al. | |
| 2005/0165048 A1 | 7/2005 | Goodacre et al. | |
| 2005/0171029 A1 | 8/2005 | Ramljak et al. | |
| 2005/0171094 A1 | 8/2005 | Kataoka et al. | |
| 2005/0171098 A1 | 8/2005 | Clader et al. | |
| 2005/0171135 A1 | 8/2005 | Mork et al. | |
| 2005/0171347 A1 | 8/2005 | Emelen et al. | |
| 2005/0176713 A1 | 8/2005 | Freyne et al. | |
| 2005/0176976 A1 | 8/2005 | Calogeropoulou et al. | |
| 2005/0192268 A1 | 9/2005 | Ek et al. | |
| 2005/0197361 A1 | 9/2005 | Jirgensons et al. | |
| 2005/0209226 A1 | 9/2005 | Skjaerbaek et al. | |
| 2005/0209273 A1 | 9/2005 | Mabire et al. | |
| 2005/0222138 A1 | 10/2005 | Ohhata et al. | |
| 2005/0234048 A1 | 10/2005 | Adam et al. | |
| 2005/0245601 A1 | 11/2005 | Schmitz | |
| 2006/0173031 A1 | 8/2006 | Bessho et al. | |
| 2007/0015138 A1 | 1/2007 | Barlow et al. | |

FOREIGN PATENT DOCUMENTS

| | | |
|---|---|---|
| EP | 0050563 | 4/1982 |
| EP | 311313 | 4/1989 |
| EP | 362001 | 4/1990 |
| EP | 370415 | 5/1990 |
| EP | 384285 | 8/1990 |
| EP | 384288 | 8/1990 |
| EP | 429344 | 5/1991 |
| EP | 461986 | 12/1991 |
| EP | 503411 | 9/1992 |
| EP | 579496 | 1/1994 |
| EP | 647642 | 4/1995 |
| EP | 685479 | 12/1995 |
| EP | 0702555 | 3/1996 |
| EP | 709381 | 5/1996 |
| EP | 723781 | 7/1996 |
| EP | 727208 | 8/1996 |
| EP | 727209 | 8/1996 |
| EP | 0763534 | 9/1996 |
| EP | 805153 | 11/1997 |
| EP | 819688 | 1/1998 |
| EP | 0870760 | 10/1998 |
| EP | 1038880 | 9/2000 |
| EP | 1295884 | 3/2003 |
| EP | 1295885 | 3/2003 |
| EP | 1 415 651 A1 | 5/2004 |
| EP | 01454900 | 9/2004 |
| EP | 01454908 | 9/2004 |
| EP | 01454910 | 9/2004 |
| EP | 01460076 | 9/2004 |
| EP | 1 541 197 A1 | 6/2005 |
| JP | 6298732 | 10/1994 |
| JP | 6305967 | 11/1994 |
| WO | WO 9014067 | 11/1990 |
| WO | WO 9106297 | 5/1991 |
| WO | WO 9116897 | 11/1991 |
| WO | WO 9214464 | 9/1992 |
| WO | WO 9218127 | 10/1992 |
| WO | WO 9222554 | 12/1992 |
| WO | WO 9303732 | 3/1993 |
| WO | WO 9305786 | 4/1993 |
| WO | WO 9307124 | 4/1993 |
| WO | WO 9309094 | 5/1993 |
| WO | WO 9314089 | 7/1993 |
| WO | WO 9318053 | 9/1993 |
| WO | WO 9422852 | 10/1994 |
| WO | WO 9422861 | 10/1994 |
| WO | WO 9427608 | 12/1994 |
| WO | WO 9428902 | 12/1994 |
| WO | WO 9501338 | 1/1995 |
| WO | WO 9515948 | 6/1995 |
| WO | WO 9519978 | 7/1995 |
| WO | WO 9521617 | 8/1995 |
| WO | WO 9531457 | 11/1995 |
| WO | WO 9535283 | 12/1995 |
| WO | WO 9600215 | 1/1996 |
| WO | WO 9603377 | 2/1996 |
| WO | WO 9616076 | 5/1996 |
| WO | WO 9616644 | 6/1996 |
| WO | WO 9616657 | 6/1996 |
| WO | WO 9626196 | 8/1996 |
| WO | WO 9626940 | 9/1996 |
| WO | WO 9640687 | 12/1996 |
| WO | WO 9700894 | 1/1997 |
| WO | WO 9717074 | 5/1997 |
| WO | WO 9719049 | 5/1997 |
| WO | WO 9722585 | 6/1997 |
| WO | WO 9736905 | 10/1997 |
| WO | WO 9740044 | 10/1997 |
| WO | WO 9742174 | 11/1997 |
| WO | WO 9743287 | 11/1997 |
| WO | WO 9744036 | 11/1997 |
| WO | WO 9744322 | 11/1997 |
| WO | WO 9744337 | 11/1997 |
| WO | WO 9748697 | 12/1997 |
| WO | WO 9749702 | 12/1997 |
| WO | WO 9800391 | 1/1998 |
| WO | WO 9800412 | 1/1998 |
| WO | WO 9802440 | 1/1998 |
| WO | WO 9804560 | 2/1998 |
| WO | WO 9805337 | 2/1998 |
| WO | WO 9806704 | 2/1998 |
| WO | WO 9809533 | 3/1998 |
| WO | WO 9814432 | 4/1998 |
| WO | WO 9816528 | 4/1998 |
| WO | WO 9818796 | 5/1998 |
| WO | WO 9820007 | 5/1998 |
| WO | WO 9847900 | 10/1998 |
| WO | WO 9900391 | 1/1999 |
| WO | WO 9907704 | 2/1999 |
| WO | WO 9917771 | 4/1999 |
| WO | WO 9921859 | 5/1999 |
| WO | WO 9924436 | 5/1999 |
| WO | WO 9925353 | 5/1999 |
| WO | WO 9937644 | 7/1999 |
| WO | WO 9937648 | 7/1999 |
| WO | WO 9937649 | 7/1999 |
| WO | WO 9943661 | 9/1999 |
| WO | WO 9945788 | 9/1999 |
| WO | WO 9947522 | 9/1999 |
| WO | WO 9948892 | 9/1999 |
| WO | WO 9950247 | 10/1999 |
| WO | WO 9965880 | 12/1999 |
| WO | WO 9965897 | 12/1999 |
| WO | WO 0017184 | 3/2000 |
| WO | WO 0018758 | 4/2000 |
| WO | WO 0021927 | 4/2000 |
| WO | WO 0026201 | 5/2000 |
| WO | WO 0038675 | 7/2000 |
| WO | WO 0059890 | 10/2000 |
| WO | WO 0102380 | 1/2001 |
| WO | WO 0105763 | 1/2001 |
| WO | WO 0109106 | 2/2001 |
| WO | WO 0116108 | 3/2001 |
| WO | WO 0116133 | 3/2001 |
| WO | WO 0116139 | 3/2001 |
| WO | WO 0119802 | 3/2001 |
| WO | WO 0137819 | 5/2001 |
| WO | WO 0141768 | 6/2001 |
| WO | WO 0142224 | 6/2001 |
| WO | WO 0144206 | 6/2001 |
| WO | WO 0144246 | 6/2001 |
| WO | WO 0156567 | 8/2001 |
| WO | WO 0160374 | 8/2001 |
| WO | WO 0170243 | 9/2001 |
| WO | WO 0170683 | 9/2001 |
| WO | WO 0170725 | 9/2001 |
| WO | WO 0170726 | 9/2001 |
| WO | WO 0170727 | 9/2001 |
| WO | WO 0170728 | 9/2001 |
| WO | WO 0170729 | 9/2001 |
| WO | WO 0174771 | 10/2001 |
| WO | WO 0176507 | 10/2001 |
| WO | WO 0181345 | 11/2001 |
| WO | WO 0183472 | 11/2001 |
| WO | WO 0185685 | 11/2001 |

| | | |
|---|---|---|
| WO | WO 0210141 | 2/2002 |
| WO | WO 0210158 | 2/2002 |
| WO | WO 0218346 | 3/2002 |
| WO | WO 0218385 | 3/2002 |
| WO | WO 0218386 | 3/2002 |
| WO | WO 0220495 | 3/2002 |
| WO | WO 0224002 | 3/2002 |
| WO | WO 0232896 | 4/2002 |
| WO | WO 02053533 | 7/2002 |
| WO | WO 02/085910 A1 | 10/2002 |
| WO | WO 02096423 | 12/2002 |
| WO | WO 02096463 | 12/2002 |
| WO | WO 03004478 | 1/2003 |
| WO | WO 03007073 | 1/2003 |
| WO | WO 03011843 | 2/2003 |
| WO | WO 03027115 | 4/2003 |
| WO | WO 03027116 | 4/2003 |
| WO | WO 03028650 | 4/2003 |
| WO | WO 03029223 | 4/2003 |
| WO | WO 03037869 | 5/2003 |
| WO | WO 03037877 | 5/2003 |
| WO | WO 03037891 | 5/2003 |
| WO | WO 03045949 | 6/2003 |
| WO | WO 03051847 | 6/2003 |
| WO | WO 03053330 | 7/2003 |
| WO | WO 03053444 | 7/2003 |
| WO | WO 03055492 | 7/2003 |
| WO | WO 03055877 | 7/2003 |
| WO | WO 03056128 | 7/2003 |
| WO | WO 03057672 | 7/2003 |
| WO | WO 03057698 | 7/2003 |
| WO | WO 03068773 | 8/2003 |
| WO | WO 03070729 | 8/2003 |
| WO | WO 03070730 | 8/2003 |
| WO | WO 03072579 | 9/2003 |
| WO | WO 03072580 | 9/2003 |
| WO | WO 03076398 | 9/2003 |
| WO | WO 03076437 | 9/2003 |
| WO | WO 03076442 | 9/2003 |
| WO | WO 03080609 | 10/2003 |
| WO | WO 03080616 | 10/2003 |
| WO | WO 03080617 | 10/2003 |
| WO | WO 03082853 | 10/2003 |
| WO | WO 03082859 | 10/2003 |
| WO | WO 03089419 | 10/2003 |
| WO | WO 03095452 | 11/2003 |
| WO | WO 03103663 | 12/2003 |
| WO | WO 03104222 | 12/2003 |
| WO | WO 2004009562 | 1/2004 |
| WO | WO 2004009596 | 1/2004 |
| WO | WO 2004009597 | 1/2004 |
| WO | WO 2004009602 | 1/2004 |
| WO | WO 2004013140 | 2/2004 |
| WO | WO 2004022561 | 3/2004 |
| WO | WO 2004026229 | 4/2004 |
| WO | WO 2004026881 | 4/2004 |
| WO | WO 2004037791 | 5/2004 |
| WO | WO 2004043953 | 5/2004 |
| WO | WO 2004046117 | 6/2004 |
| WO | WO 2004056368 | 7/2004 |
| WO | WO 2004063201 A1 * | 7/2004 |
| WO | WO 2004063969 | 7/2004 |
| WO | WO 2004065370 | 8/2004 |
| WO | WO 2004072062 | 8/2004 |
| WO | WO 2004072063 | 8/2004 |
| WO | WO 2004078760 | 9/2004 |
| WO | WO 2004080977 | 9/2004 |
| WO | WO 2004085439 | 10/2004 |
| WO | WO 2004087158 | 10/2004 |
| WO | WO 2004089942 | 10/2004 |
| WO | WO 2004098607 | 11/2004 |
| WO | WO 2004106343 | 12/2004 |
| WO | WO 2005000303 | 1/2005 |
| WO | WO 2005000304 | 1/2005 |
| WO | WO 2005000836 | 1/2005 |
| WO | WO 2005002552 | 1/2005 |
| WO | WO 2005002576 | 1/2005 |
| WO | WO 2005005438 | 1/2005 |
| WO | WO 2005012256 | 2/2005 |
| WO | WO 2005012262 | 2/2005 |
| WO | WO 2005012298 | 2/2005 |
| WO | WO 2005012304 | 2/2005 |
| WO | WO 2005012307 | 2/2005 |
| WO | WO 2005019218 | 3/2005 |
| WO | WO 2005019219 | 3/2005 |
| WO | WO 2005025567 | 3/2005 |
| WO | WO 2005026155 | 3/2005 |
| WO | WO 2005026159 | 3/2005 |
| WO | WO 2005027823 | 3/2005 |
| WO | WO 2005028475 | 3/2005 |
| WO | WO 2005035532 | 4/2005 |
| WO | WO 2005037800 | 4/2005 |
| WO | WO 2005042525 | 5/2005 |
| WO | WO 2005051919 | 6/2005 |
| WO | WO 2005063254 | 7/2005 |
| WO | WO 2005108367 | 11/2005 |
| WO | WO 2007/092535 A2 | 8/2007 |
| WO | WO 2007/092535 A3 | 8/2007 |

OTHER PUBLICATIONS

Adachi et al., Selective activation of vitamin D receptor by lithocholic acid acetate, a bile acid derivative, J. Lipid Res. 46:46-57, 2005.

Adams et al., Omega-Conotoxin CVID inhibits a pharmacologically distinct voltage-sensitive calcium channel associated with transmitter release from preganglionic nerve terminals, J. Biol. Chem. 278(6):4057-62, 2003.

Ali et al., Orally active and potent inhibitors of γ-aminobutyric acid uptake[1], J. Med. Chem. 28:653-660, 1985.

Allan et al., Therpeutic androgen receptor ligands, Nucl. Recept. Signal. 1:1-4, 2003.

Amat et al., Activation of picrotoxin-resistant GABA receptors by GABA and related compounds induces modulation of cockroach dorsal paired median (DPM) neuron firing, J. Insect. Physiol. 43(12):1125-1131, 1997.

Andersen et al., The synthesis of novel GABA uptake inhibitors. 1. Elucidation of the structure-activity studies leading to the choice of (R)-1[4,4-bis(3-mehty1-2-thienyl)-3-butenyl]-3-piperidinecarboxylic acid (Tiagabine) as an anticonvulsant drug candidate, J. Med. Chem. 36:1716-1725, 1993.

Andersen, The dopamine uptake inhibitor GBR 12909: selectivity and molecular mechanism of action, Eur. J. Pharmacol. 166:493-504, 1989.

Anderson et al., Anesthetic activity of novel water-soluble 2β-morpholinyl steroids and their modulatory effects at GAB receptors, J. Med. Chem. 40:1668-1681, 1997.

Ansar et al., Isomers of substituted 3-benzo[b]furyl and 3-thienylaminobutyric acids as potent ligands of the GABA-B receptor: synthesis and preparative liquid chromatographic separation, Therapie, 54:651-8, 1999.

Aoki et al., A novel phosphodiesterase type 4 inhibitor, YM976 (4-(3-chlorophenyl)-1,7-diethylpyrido[2,3-d]pyrimidin-2(1H)-one), with little emetogenic activity, J. Pharmacol. Exp. Ther. 295(1):255-60, 2000.

Ashton et al., Selective type IV phosphodiesterase inhibitors as antiasthmatic agents. The syntheses and biological activities of 3-(cyclopentyloxy)-4-methoxybenzamides and analogues, J. Med. Chem. 37:1696-1703, 1994.

Aubin et al., SL25.1131 [3(S), 3a(S)-3-methoxymethy1-7[4,4,4-trifluorobutoxy]-3,3a,4,5-tetrahydro-1,3-oxazolo[3,4-a]quinolin-1-one], a new, reversible, and mixed inhibitor of monoamine oxidase-A and monoamine oxidase-B: biochemical and behavioral profile, J. Pharmacol. Exp. Ther. 310(3):1171-82, 2004.

Baker et al., Enzymatic resolution an dpharmacological activity of the enantiomers of 3,5-dihydroxyphenylglycine, a metabotropic glutamate receptor agonist, Bioorg. Med. Chem. Lett., 5(3):223-8, 1995.

Barnette et al., Phosphodiesterase 4: biological underpinnings for the design of improved inhibitors, Pharmacol. Rev. Commun. 8:65-73, 1996.

Becker et al., An integrated in silico 3D model-driven discovery of a novel, potent, and selective amidosulfonamide 5-HT$_{1A}$ agonist (PRX-00023) for the treatment of anxiety and depression, J. Med. Chem. 49:3116-35, 2006.

Becker et al., G. protein-coupled receptors: in silico drug discovery in 3D, PNAS 101(31):11304-9, 2004.

Beer et al., DOV 216,303, a "triple" reuptake inhibitor: safety, tolerability, and pharmacokinetic profile, J. Clin. Pharmacol. 44:1360-7, 2004.

Bennett et al., Identification of arodyn, a novel acetylated dynorphin A-(1-11) analogue, as a κ opioid receptor antagonist, J. Med. Chem. 45:5617-19, 2002.

Bennett et al., Structure-activity relationships of arodyn, a novel acetylated kappa opioid receptor antagonist, J. Pept. Res. 65:322-32, 2005.

Bermack et al., Effects of the potential antidepressant OPC-14523 [1-[3-[4-(3-chlorophenyl)-1-piperazinyl]propyl]-5-methoxy-3,4-dihydro-2-quinolinone monomethanesulfonate] a combined sigma and 5-HT$_{1A}$ ligand: modulation of neuronal activity in the dorsal raphe nucleus, J. Pharmacol. Exp. Ther. 310(2):578-83, 2004.

Bertha et al., (E)-8-benzylidene derivatives of 2-methyl-5-(3-hydroxyphenyl)morphans: highly selective ligands for the ό$_2$ receptor subtype, J. Med. Chem. 38:4776-85, 1995.

Bi et al., The discovery of novel, potent and selective PDE5 inhibitors, Bioorg. Med. Chem. Lett. 11:2461-4, 2001.

Birse et al., Phenylglycine derivatives as new pharmacological tools for investigating the role of metabotropic glutamate receptors in the central nervous system, Neuroscience 52(3):481-8, 1993.

Bisogno et al., Arachidonoylserotonin and other novel inhibitors of fatty acid amide hydrolase, Biochem. Biophys. Res. Commun. 24:515-22, 1998.

Bitran et al., Anxiolytic effects of 3a-hydroxy-5a[β]-pregnan-20-one: endogenous metabolites of progesterone that are active at the GAB receptor, Brain Res. 561:157-161, 1991.

Boess et al., Inhibition of phosphodiesterase 2 increases neuronal cGMP, synaptic plasticity and memory performance, Neuropharmacology 47:1081-92, 2004.

Bohme et al., In vitro and in vivo characterization of TC-1827, a novel brain α4β2 nicotinic receptor agonist with pro-cognitive activity, Drug Development Research 62:26-40, 2004.

Bolser et al., The pharmacology of SCH 50911: a novel, orally-active GABA-B receptor antagonist, J. Pharmacol. Exp. Ther. 274(3):1393, 1996.

Bonanno et al., GABA$_B$ receptors as potential targets for drugs able to prevent excessive excitatory amino acid transmission in the spinal cord, Eur. J. Pharmacol. 362:143-148, 1998.

Bond et al., A novel orally active group 2 metabotropic glutamate receptor agonist: LY354740, Neuroreport 8:1463-66, 1997.

Bonk et al., Novel high-affinity photoactivatable antagonists of corticotrophin-releasing factor (CRF), Eur. J. Biochem. 267:3017-3024, 2000.

Bowen et al., CB-64D and CB-184: ligands with high ό$_2$ receptor affinity and subtype selectivity, Eur. J. Pharmacol. 278:257-260, 1995.

Bowen et al., Characterization of the enantiomers of cis-N-[2-(3,4-dichlorophenyl)ethyl]-N-methyl-2-(1-pyrrolidinyl)cyclohexylamine (BD737 and BD738): novel compounds with high affinity, selectivity and biological efficacy at *sigma* receptors [1], J. Pharmacol. Exp. Ther. 262(1):32-40, 1992.

Bowen et al., Sigma receptors: recent advances and new clinical potentials, Pharmaceutica. Acta Helvetiae 74:211-8, 2000.

Bowery, GABA$_B$ receptors and their significance in mammalian pharmacology, TIPS Reviews, 10:401-7, 1989.

Boxenbaum et al., First-time-in-human dose selection: allometric thoughts and perspectives, J. Clin. Pharmacol. 35:957-966, 1995.

Brabet et al., Comparative effect of L-CCG-I, DCG-IV and γ-carboxy-L-glutamate on all cloned metabotropic glutamate receptor subtypes, Neuropharmacology 37:1043-1051, 1998.

Brabet et al., Phenylglycine derivatives discriminate between mGluR1- and mGluR5-mediated responses, Neuropharmacology 34(8):895-903, 1995.

Bromidge et al., Biarylcarbamoylindolines are novel and selective 5-HT$_{2C}$ receptor inverse agonists: identification of 5-methyl-1-[[2-[(2-methyl-3-pyridyl)oxy]-5-pyridyl]carbamoyl]-6-triflouromethylindoline (SB-243213) as a potential antidepressant/anxioltyic agent, J. Med. Chem. 43:1123-34, 2000.

Bromidge et al., Design of [R-(Z)]-(+)-α-(methoxyimino)-1-azabicydo[2.2.2]octane-3-acetonitrile (SB 202026), a functionally selective azabicyclic muscarinin M1 agonist incorporating the N-methoxy imidoyl nitrile group as a novel ester bioisostere, J. Med. Chem. 40:4265-80, 1997.

Brown et al., Hippocampal remodeling and damage by corticosteroids: implications for mood disorders, Neuropsychopharmacology 21(4):474-84, 1999.

Brown, Enriched environment and physical activity stimulate hippocampal but not olfactory bulb neurogenesis, J. Eur. J. Neurosci. 17(10):2042-6, May 2003.

Brugger et al., The action of new potent GABA$_B$ receptor antagonists in the hemisected spinal cord preparation of the rat, Eur. J. Pharmacol. 235:153-5, 1993.

Buccafusco et al., Multiple central nervous system targets for eliciting beneficial effects on memory and cognition[1], J. of Pharm. Exp. Ther. 295(2):438-446, 2000.

Buchheit et al., The serotonin 5-HT$_4$ receptor. 2. Structure-activity studies of the indole carbazimidamide class of agonists[1], J. Med. Chem. 38:2331-8, 1995.

Cameron, Adult neurogenesis is regulated by adrenal steroids in the dentate gyrus, Neuroscience 61(2):203-9, 1994.

Cao et al., Synthesis and biological characterization of 1-methyl-1,2,5,6-tetrahydropyridyl-1,2,5-thiadiazole derivatives as muscarinic agonists for the treatment of neurological disorders, J. Med. Chem. 46:4273-86, 2003.

Carraz et al., Approc43:1029hes dans la pharmacodynamie biochimique de la structure N-dipropylacetique, Therapie 20:419-26, 1965.

Carruthers et al., Synthesis of a series of sulfinic acid analogs of GABA and evaluation of their GABA$_B$ receptor affinities, Bioorg. Med. Chem. Lett. 8:3059-64, 1998.

Castelli et al., Stereoselectivity of NCS-382 binding to γ-hydroxybuyarate receptor in the rat brain, Eur. J. Pharmacol. 446:1-5, 2002.

Chambers et al., Spiropiperidines as high-affinity, selective ό 6 ligands, J. Med. Chem. 35:2033-9, 1992.

Chebib et al., the 'ABC' of GABA receptors: a brief review, Clin. Exp. Pharmacol. Physiol. 26:937-40, 1999.

Christian et al., Positron emission tomographic analysis of central dopamine D$_1$ receptor binding in normal subjects treated with the atypical neuroleptic, SDZ MAR 327, Int. J. Mol. Med. 1:243-7, 1998.

Coghlan et al., Selective small molecule inhibitors of glycogen synthase kinase-3 modulate glycogen metabolism and gene transcription, Chemistry & Biology 7:793-803, 2000.

Cummings et al., The efficacy of metrifonate in improving the behavioral disturbances of alzheimer's disease patients, Neurology 50(4), Supp. 4, A251, S24.004, American Academy of Neurolgy, 50th Annual Meeting Program 1998.

Curet et al., Preclinical profile of befloxatone, a new reversible MAO-A inhibitor, J. Affect Disord. 51:287-303, 1998.

Curtis et al., Baclofen antagonism by 2-hydroxy-saclofen in the cat spinal cord, Neurosci. Lett. 92:97-101, 1988.

Da Prada et al., Neurochemical profile of moclobemide, a short-acting and reversible inhibitor of monoamine oxidase type , J. Pharmacol. Exp. Ther. 248(1):400-14, 1988.

Dal Piaz et al., Phosphodiesterase 4 inhibitors, structurally unrelated to rolipram, aS promising agents for the treatment of asthma and other pathologies, Eur. J. Med. Chem. 35:463-80, 2000.

Daugan et al., The discovery of tadalafil: a novel and highly selective PDE5 inhibitor. 1:5,6,11,11a-Tetrahydro-1$H$-imidazo[1',5':1,6]pryrido [3,4-$b$]indole-1,3(2$H$)-dione analogues, J. Med. Chem. 46:4525-32, 2003.

Davies et al., CGP 55845A: a potent antagonist of $GABA_B$ receptors in the C region of rat hippocampus, Neuropharmacology 32(10):1071-3, 1993.

De Costa et al., Alterations in the stereochemistry of the κ-selective opioid agonist U50,488 result in high-affinity ó ligands, J. Med. Chem. 32:1996-2002, 1989.

Dehaene et al., Reward-dependent learning in neuronal networks for planning and decision making, Prog. Brain Res. 126:217-29, 2000.

Deisz, The $GABA_B$ receptor antagonist CGP 55845A reduces presynaptic $GABA_B$ actions in neocortical neurons of the rat in vitro, Neuroscience 93(4):1241-9, 1999.

Di Marzo et al., A structure/activity relationship study on arvanil, an endocannabinoid and vanilloid hybrid, J. Pharmacol. Exp. Ther. 300(3):984-91, 2002.

Ding et al., Synthetic small molecules that control stem cell fate, Proc. Natl. Acad. Sci USA, 100(13):7632-7, 2003.

Dunn, Synthesis of commercial phosphodiesterase(V) inhibitors, Org. Proc. Res. Dev. 9:88-97, 2005.

Eaton et al., Competitive antagonism at metabotropic glutamate receptors by (S)-4-carboxyphenylglycine and (RS)-α-methyl-4-carboxyphenylglycine, Eur. J. Pharmacol., Mol. Pharm. Sect. 244:195-7, 1993.

Eddahibi, Effect of DMPPO, a phosphodiesterase type 5 inhibitor, on hypoxic pulmonary hypertension in rats, Br. J. Pharmacol. 125:681-8, 1988.

Edmonds-Alt et al., Biochemical and pharmacological activities of SSR 146977, a new potent nonpeptide tachykinin $NK_3$ receptor antagonist[1], Can. J. Physiol. Pharmacol. 80:482-8, 2002.

Eglen et al., Selective muscarinic receptor agonists and antagonists, Pharmacol. Toxicol. 78:59-68, 1996.

Eisch et al., Drug dependence and addicion, II, Am. J. Psychiatry, 161(3):426, Mar. 2004.

Elliott et al., Peripheral pre and postjunctional alpha 2-adrenoceptors in man: studies with RX781094, a selective alpha 2 antagonist, J. Hypertens. Suppl. 1(2):109-11, 1983.

Foster et al., In vivo pharmacological characterization of indiplon, a novel pyrazolopyrimidine sedative-hypnotic, J. Pharmacol. Exp. Ther. 311(2):547-59, 2004.

Fray et al., CANTAB battery: proposed utility in neurotoxicology, Neurotoxicol. Teratol. 18(4):499-504, 1996.

Freireich et al., Quantitative comparison of toxicity of anticancer agents in mouse, rat, hamster, dog, monkey, and man[1,2], Cancer Chemother. Repts. 50(4): 219, 1966.

Froestl et al., Phosphinic acid analogues of GABA. 1. New potent and selective $GABA_B$ agonists, J. Med. Chem. 38:3297-3312, 1995.

Froestl et al., Potent, orally active $GABA_B$ receptor antagonists, Pharmacol. Rev. Comm. 8:127-33, 1996.

Fuhrmann et al., Synthesis and biological activity of a novel, highly potent progesterone receptor antagonist, J. Med. Chem. 43:5010-6, 2000.

Gee et al., GABA-dependent modulation of the CI ionophore by steroids in rat brain, Eur. J. Pharmacol. 136:419-23, 1987.

Gelmon et al., Phase I trials of the oral histone deacetylase (HDAC) inhibitor MGCD0103 given either daily or 3x weekly for 14 days every 3 weeks in patients (pts) with advanced solid tumors, J. of Clin. Oncology, 2005 ASCO Annual Meeting Proceedings 23(16S, Jun. 1 Supp.) 2005, 3147.

Getting et al., The melanocortin peptide HP228 displays protective effects in acute models of inflammation and organ damage, Eur. J. Pharmacol. 532:138-44, Jan. 2006.

Gould, Neurogenesis in the neocortex of adult primates, Science, 286:548-52, Oct. 15, 1999.

Grillon et al., Anxiolytic effects of a novel group II metabotropic glutamate receptor agonist (LY354740) in the fear-potentiated startle paradigm in humans, Psychopharmacol. 168:446-454, 2003.

Groenewoud et al., Synthesis of bicuculline, J. Chem. Soc. 199-202, 1936.

Hao et al., Intrathecal $_γ$-aminobutyric acid$_B$ ($GABA_B$) receptor antagonist CGP 35348 induces hypersensitivity to mechanical stimuli in the rat, Neurosci. Lett. 182:299-302, 1994.

Harries et al., The profile of sabcomeline (SB-202026), a functionally selective $M_1$ receptor partial agonist, in the marmoset, British J. Pharm. 124:409-415, 1998.

Harrison et al., Structure-activity relationships for steroid interaction with the $_γ$aminobutyric acid$_A$ receptor complex, J. Pharmacol. Exp. Ther. 241(1):346-353, 1987.

Harvey, Alan, Natural products in drug discovery and development, London, UK, Jun. 27-28, 2005.

Hashimoto, Glycine transporter inhibitors as therapeutic agents for schizophrenia, Recent patents on CNS drug discovery 1:43-53, 2006.

Haworth et al., Synthesis of Hydrastine, Nature 165(4196):529, 1950.

Hayashi et al., Agonist analysis of 2-(carboxycyclopropyl)glycine isomers for cloned metabotropic glutamate receptor subtypes expressed in Chinese hamster ovary cells, Br. J. Pharmacol. 107:539-43, 1992.

Hayashi et al., Analysis of agonist and antagonist activities of phenyglycine derivatives for different cloned metabotropic glutamate receptor subtypes, J. Neurosci. 14(5):3370-7, 1994.

Hayashi et al., Role of a metabotropic glutamate receptor in synaptic modulation in the accessory olfactory bulb, Nature 366:687-690, 1993.

Hersperger et al., Palladium-catalyzed cross-coupling reactions for the synthesis of 6,8-disubstituted 1,7-naphthyridines: a novel class of potent and selective phosphodiesterase type 4D inhibitors, J. Med. Chem. 43:675-82, 2000.

Hills et al., Phosphinic acid analogues of GABA are antagonists at the $GABA_B$ receptor in the rat anococcygeus, Br. J. Pharmacol. 102:5-6, 1991.

Hogenkamp et al., Synthesis and in vitro activity of 3β-substituted-3α-hydroxypregnan-20-ones: allosteric modulators of the GAB receptor, J. Med. Chem. 40:61-72, 1997.

Hosford et al., Characterization of the antiabsence effects of SCH 50911, a $GABA_B$ receptor antagonist, in the lethargic mouse, $_γ$-hydroxybutyrate, and pentylenetetrazole models[1], J. Pharmacol. Exp. Ther. 274(3):1399-1403, 1995.

Hoskison et al., $GABA_B$ receptor modulation of short-term synaptic depression at an excitatory input to murine hippocampal CA3 pyramidal neurons, Neurosci. Lett. 365:48-53, 2004.

Howson and Jane, Actions of LY341495 on metabotropic glutamate receptor-mediated responses in the neonatal rat spinal cord, British Journal of Pharmacology, 139:147-55, 2003.

Hu et al., Neurosteroid analogues: structure-activity studies of benz[$e$]indene modulators of GAB receptor function. 1. The effect of 6-methyl substitution on the electrophysiological activity of 7-substituted benz[e]indene-3-carbonitriles, J. Med. Chem. 36:3956-67, 1993.

Ishibashi et al., Pharmacodynamics of S-2150, a simultaneous calcium-blocking and $\alpha_1$-inhibiting antihypertensive drug, in rats, J. Pharm. Pharmacol. 52:273-80, 2000.

Ito et al., 3,5-Dihydroxyphenyl-glycine: a potent agonist of metabotropic glutamate receptors, NeuroReport 3(11):1013-16, 1992.

Iverson et al., Interpreting change on the WAIS-III,WMS-III in clinical samples, Arch. Clin. Neuropsychol. 16:183-91, 2001.

Jackson et al., Design, synthesis, and biological activity of a potent inhibitor of the neuropeptidase N-acetylated $\alpha$-linked acidic dipeptidase, J. Med. Chem. 39:619-22, 1996.

Jacobs et al., Adult brain neurogenesis and psychiatry: a novel theory of depression, Mol. Psychiatry, 5:262-9, 2000.

Jaen et al., In vitro and in vivo evaluation of the subtype-selective muscarinic agonist PD 151832, Life Sci. 56(11/12):845-52, 1995.

Jane et al., New phenylglycine derivatives with potent and selective antagonist activity at presynaptic glutamate receptors in neonatal rat spinal cord, Neuropharmacology 34(8):851-6, 1995.

Jhee et al., Multiple-dose plasma pharmacokinetic and safety study of LY450108 and LY451395 (AMPA receptor potentiators) and their concentration in cerebrospinal fluid in healthy human subjects, J. Clin. Pharmacol. 46:424-32, 2006.

Johnson et al., The disposition, metabolism, and pharmacokinetics of a selective metabotropic glutamate receptor agonist in rats and dogs, Drug Metab. Disposition 30:27-33, 2002.

Joly et al., Molecular, functional, and pharmacological characterization of the metabotropic glutamate receptor type 5 splice variants: comparison with mGluR1, J. Neurosci. 15(5):3970-81, 1995.

Kalita et al., Pharmacoldynamic effect of MGCD0103, an oral isotype-selective histone deacetylase (HDAC) inhibitor, on HDAC enzyme inhibition and histone acetylation induction in Phase I clinical trials in patients (pts) with advanced solid tumors or non-Hodgkin's lymphoma (NHL), J. of Clin. Oncology, 2005 ASCO Annual Meeting Proceedings. 23(16S, Part I of II, Jun. 1 Supp.), 2005, 9631.

Karla et al., Synthesis and pharmacology of the baclofen homologues 5-amino-4-(4-chlorophenyl)pentanoic acid and the $R$- and $S$-enantiomers of 5-amino-3-(4-chlorphenyl) pentanoic acid, J. Med. Chem. 42:2053-9, 1999.

Karlsson et al., Phaclofen: a $GABA_B$ blocker reduces long-duration inhibition in the neocortex, Eur. J. Pharmacol. 148:485-6, 1988.

Kaupmann et al., Expression cloning of $GABA_B$ receptors uncovers similarity to metabotropic glutamate receptors, Nature 386:239-46, 1997.

Kaupmann et al., $GABA_B$-receptor subtypes assemble into functional heteromeric complexes, Nature 396:683-7, 1998.

Kerr et al., 2-hydroxy-saclofen: an improved antagonist at central and peripheral $GABA_B$ receptors, Neurosci. Lett. 92:92-6, 1988.

Kerr et al., Phaclofen: a peripheral and central baclofen antagonist, Brain Res. 405:150-4, 1987.

Kim et al., Identification of substituted 4-aminopiperidines and 3-aminopyrrolidines as potent MCH-R1 antagonists for the treatment of obesity, Bioorganic & Med. Chem. Lett. 16:5445-50, 2006.

Kingston et al., LY341495 is a nanomolar potent and selective antagonist of group II metabotropic glutamate receptors, Neuropharmacology 37:1-12, 1998.

Knockaert et al., Intracellular targets of paullones: Identification following affinity purification on immobilized inhibitor, J. Biol. Chem. 277(28):25493-501, 2002.

Knopfel et al., Metabotropic glutamate receptors: novel targets for drug development, J. Med. Chem. 38(9):1417-26, 1995.

Koe, Molecular geometry of inhibitors of the uptake of catecholamines and serotonin in synaptosomal preparations of rat brain, J. Pharmacol. Exp. Ther. 199(3):649-661, 1976.

Komas et al., Differential sensitivity to cardiotonic drugs of cyclic AMP phosphodiesterases isolated from canine ventricular and sinoatrial-enriched tissues, J. Cardiovasc. Pharmacol. 14:213-20, 1989.

Kozikowski et al., Synthesis and metabotropic receptor activity of the novel rigidified glutamate analogues (+)-and (-31 )-trans-azetidine-2,4-dicarboxylic acid and their $N$-Methyl derivatives, J. Med. Chem. 36:2706-8, 1993.

Krogsgaard-Larsen, Inhibitors of the GABA uptake systems, Molecular & Cellular Biochemistry 31:105-21, 1980.

Krogsgaard-Larsen, Muscimol analogues. II. Synthesis of some bicyclic 3-isoxazolol zwitterions, Acta. Chem. Scand. 31:584-8, 1977.

Kuhn et al., Neurogenesis in the dentate gyrus of the adult rat: age-related decrease of neuronal progenitor proliferation, J. Neurosci. 16(6):2027-33, Mar. 15, 1996.

Kunick et al., 1-Azakenpaullone is a selective inhibitor of glycogen synthase kinase-3β, Biorganic & Medicinal Chemistry Letters 14:413-6, 2004.

Kunick et al., Evaluation and comparison of 3D-QSAR CoMSIA models for CDK1, CDK5, and GSK-3 inhibition by paullones, J. Med. Chem. 47:22-36, 2004.

Lanza et al., CGP 52432: a novel potent and selective $GABA_B$ autoreceptor antagonist in rat cerebral cortex, Eur. J. Pharmacol. 237:191-5, 1993.

Leinekugel et al., Synaptic GAB activation induces Ca2+ rise in pyramidal cells and interneurons from rat neonatal hippocampal slices, J. Physiol. 487:319-29, 1995.

Leost et al., Paullones are potent inhibitors of glycogen synthase kinase-3β and cycln-dependent kinase 5/p25, Eur. J. Biochem. 267:5983-94, 2000.

Libri et al., Blockade of $GABA_B$ receptors facilitates muscarinic agonist-induced epileptiform activity in immature rat piriform cortex in vitro, Naunyn-Schmied. Arch. Pharmacol. 358:168-74, 1998.

Lingenhoehl et al., Blockade of the late inhibitory postsynaptic potention in vivo by the $GABA_B$ antagonist CGP 46 381, Pharmacol. Comm. 3:49-54,1993.

Luddens et al., GABA antagonists differentiate between recombinant GAB / benzodiazepine receptor subtypes, J. Neurosci. 15(10):6957-62, 1995.

Lund et al., Discovery of a potent, orally available, and isoform-selective retinoic acid β2 receptor agonist, J. Med. Chem. 48:7517-9, 2005.

Ma et al., Discovery of novel peptide-receptor interactions: identification of PHM-27 as a potent agonist of the human calcitonin receptor, Biochem. Pharmacol. 67:1279-84, 2004.

Ma et al., Identification and characterization of noncalcemic, tissue-selective, nonsecosteroidal vitamin D receptor modulators, J. Clin. Invest. 116(4):892-904, 2006.

Ma et al., Synthesis and biological activity of cyclic analogues of MPPG and MCPG as metabotropic glutamate receptor antagonists, Bioorg. Med. Chem. Lett. 7(9):1195-8, 1997.

Mai et al., 3-(4-Arolyl-1-methyl-1$H$-2-pyrrol)-$N$-hydroxy-2-alkylamides as a new class of synthetic histone deacetylase inhibitors. 1. Design, synthesis, biological evaluation, and binding mode studies performed through three different docking procedures, J. Med. Chem., 46:512-24, 2003.

Mai et al., 3-(4-Arolyl-1-methyl-1$H$-2-pyrrol)-$N$-hydroxy-2-propenamindes as a new class of synthetic histone deacetylase inhibitors. 2. Effect of pyrrole-$C_2$and/or -C4 substitutions on biological activity, J. Med. Chem., 47:1098-109, 2004.

Mai et al., Binding mode analysis of 3-(4-Benzoyl-1-methyl-1H-2-pyrrolyl)-N-hydroxy-2-propenamide: a new synthetic histone deacetylase inhibitor inducing histone hyperacetylation, growth inhibition, and terminal cell differentiation, J. Med. Chem., 45(9):1778-84, 2002.

Mai et al., Class II (IIa)-selective histone deacetylase inhibitors. 1. Synthesis and biological evaluation of novel (aryloxopropenyl) pyrrolyl hydroxyamides, J. Med. Chem., 48:3344-53, 2005.

Mai et al., Discovery of (aryloxopropenyl) pyrrolyl hydroxyamides as selective inhibitors of class IIa histone deacetylase homologue HD1-A, J. Med. Chem., 46:4826-9, 2003.

Majewska et al., Steroid hormone metabolites are barbiturate-like modulators of the GABA receptor, Science 232:1004-7, 1986.

Malberg, Chronic antidepressant treatment increases neurogenesis in adult rat hippocampus, J. Neurosci. 20(24):9104-10, Dec. 15, 2000.

Maloney et al., Identification of a chemical tool for the orphan nuclear receptor FXR, J. Med. Chem. 43(16):2971-4, 2000.

Manahan-Vaughan et al., Physiological and pharmacological profile of trans-azetidine-2,4-dicarboxylic acid: metabotropic glutamate receptor agonism and effects on long-term potentiation, Neuroscience 72(4):999-1008, 1996.

Markstein et al., Pharmacological characterisation of 5-HT receptors positively coupled to adenylyl cydase in the rat hippocampus, Naunyn-Schmiedebergs Arch. Pharmacol. 359:454-9, 1999.

Massa et al., 3-(4-Aroly1-1$H$-pyrrol-2-yl)-$N$-hydroxy-2-propenamides, a new class of synthetic histone deacetylase inhibitors, J. Med. Chem., 44:2069-72, 2001.

Massillon et al., Identification of the glycogenic compound 5-iodutubercidin as a general protein kinase inhibitor, Biochem. J. 299:123-8, 1994.

Matsuno et al., Binding properties of SA4503, a novel and selective $ó_1$ receptor agonist, Eur. J. Pharmacol. 306:271-9, 1996.

Maw et al., Design, synthesis and biological activity of β-carboline-based type-5 phosphodiesterase inhibitors, Bioorg. Med. Chem. Lett. 13:1425-8, 2003.

Mazurov et al., Selective α7 nicotinic acetylcholine receptor ligands, Curr. Med. Chem. 13:1567-84, 2006.

Merck Index, An Encyclopedia of Chemicals, Drugs, and Biologicals, 12th Ed., 1996 (Table of Contents only).

Mettey, Y. et al., Aloisines, a new family of CDK-GSK-3 inhibitors. SAR study, crystal structure in complex with CDK2, enzyme selectivity, and cellular effects, J. Med. Chem. 46,222-36, 2003.

Middelmiss et al., Do minoxidil sulphate and cromakalim open pharmacologically similar $K^+$ channels in rat isolated aorta? Br. J. Pharm. 102:153, 1991.

Milliken et al., EB1098, a vitamin D receptor agonist, reduces proliferation and decreases tumor growth rate in a mouse model of hormone-induced mammary cancer, Cancer Lett. 229:205-15, 2005.

Miyachi et al., Potent novel nonsteroidal androgen antagonists with a phthalimide skeleton, Bioorg. Med. Chem. Lett. 7(11):1483-88, 1997.

Mizuno et al., The stimulation of $β_3$-adrenoceptor causes phosphorylation of extracellular signal-regulated kinases 1 and 2 through a $G_s$-but not $G_i$-dependent pathway in 3T3-L1 adipocytes, Eur. J. Pharmacol. 404:63-8, 2000.

Molnar et al., Vitamin D receptor agonists specifically modulate the volume of the ligand-binding pocket, J. Biol. Chem. 281(15):10516-26, 2006.

Moltzen et al., Bioisosteres of arecoline: 1,2,3,6-Tetrahydro-5-pyridyl-substituted and 3-piperidyl-substituted derivatives of tetrazoles and 1,2,3-triazoles. Synthesis and muscarinic activity, J. Med. Chem. 37:4085-99, 1994.

Monn et al., Design, synthesis, and pharmacological characterization of (+)-2-aminobicyclo[3.1.0]hexane-2,6-dicarboxylic acid (LY354740): a potent, selective, and orally active group 2 metabotropic glutamate receptor agonist possessing anticonvulsant and anxiolytic properties, J. Med. Chem., 40:528-37, 1997.

Monn et al., Synthesis of the four isomers of 4-aminopyrrolidine-2,4-dicarboxylate: identification of a potent, highly selective, and systemically-active agonist for metabotropic glutamate receptors negatively coupled to adenylate cyclase, J. Med. Chem. 39:2990-3000, 1996.

Monn et al., Synthesis, pharmacological characterization, and molecular modeling of heterobicyclic amino acids related to (+)-2-aminobicyclos[3.1.0]hexane-2,6-dicarboxylic acid (LY354740): identification of two new potent, selective, and systemically active agonists for group II metabotropic glutamate receptors, J. Med. Chem. 42:1027-40, 1999.

Monro et al., Expression of exposure in negative carcinogenicity studies: dose/body weight, dose/body surface area, or plasma concentrations?*, Toxicology pathology 23(2):187-98, 1995.

Murata et al., The first selective antagonist for a $GABA_c$ receptor, Bioorg. Med. Chem. Lett. 6(17):2073-6, 1996.

Naerum, L. et al., Scaffold hopping and optimization towards libraries of glycogen synthase kinase-3 inhibitors, Biorg. Med. Chem. Lett. 12:1525-8, 2002.

Nakagawa et al., Regulation of neurogenesis in adult mouse hippocampus by cAMP and the cAMP response element-binding protein, Eur. J. Pharmacol. 184:205, 1990.

Nakazato et al., Synthesis, in vitro pharmacology, structure-activity relationships, and pharmacokinetics of 3-Alkoxy-2-amino-6-fluorobicyclo[3.1.0]hexane-2,6-dicarboxylic acid derivatives as potent and selective group II metabotropic glutamate receptor antagonists, J. Med. Chem. 47:4570-87, 2004.

Nicoletti et al., Metabotropic glutamate receptors: a new target for the therapy of neurodegenerative disorders? Trends Neurosci. 19:267-71, 1996.

Nielsen et al., Ethyl β-carboline-3-carboxylate shows differential benzodiazepine receptor interaction, Nature 286:7, 1980.

Nielsen et al., [$^3$H]Propyl β-carboline-3-carboxylate binds specifically brain benzodiazepine receptors, J. Neurochem. 36(1):276-85, 1981.

Nordvall et al., Analogues of the muscarinin agent 2'-methylspiro[1-azabicyclo[2.2.2]octane-3,4'-[1,3]dioxolane]: synthesis and pharmacology, J. Med. Chem. 35:1541-50, 1992.

Ohfune et al., Synthesis of L-2-(2,3-dicarboxycyclopropyl)glycines. Novel conformationally restricted glutamate analogues. Bioorg. Med. Chem. Lett. 3(1):15-18, 1993.

Olpe et al., CGP 35348: a centrally active blocker of $GABA_B$ receptors, Eur. J. Pharmacol. 187:27-38, 1990.

Olsen et al., Studies on the neuropharmacological activity of bicuculline and related compounds, Brain Res. 102:283-99, 1976.

O'Neill et al., Group II metabotropic glutamate receptor antagonists LY341495 and LY366457 increase locomotor activity in mice, Neuropharmacology 45:565-74, 2003.

Ong et al., The morpholino-acetic acid analogue Sch 50911 is a selective $GABA_B$ receptor antagonist in rat neocortical slices, Eur. J. Pharmacol. 362:35-41, 1998.

Oshiro et al., 3,4-dihydro-2(1$H$)-quinolinone as a novel antidepressant drug: synthesis and pharmacology of 1-[3-[4-(3-chlorophenyl)-1-piperazinyl]propyl]-3,4-dihydro-5-methoxy-2(1$H$)-quinolinone and its derivatives, J. Med. Chem. 43:177-89, 2000.

Parkinson Study Group, Effect of lazabemide on the progression of disability in early parkinson's disease, Ann. Neurol. 40:99-107, 1996.

Pellicciari et al., Synthesis and pharmacological characterization of all sixteen stereoisomers of 2-(2'-carboxy-3'-phenylcyclopropyl)glycine. Focus on (2S,1'S,2'S,3'R)-2-(2'-

Carboxy-3'-phenylcyclopropyl) glycine, a novel and selective group II metabotropic glutamate receptors antagonist, J. Med. Chem., 39:2259-69, 1996.

Perregard et al., ó Ligands with subnanomolar affinity and preference for the $ó_2$ binding site. 1. 3-(ω-aminoalkyl)-1H-indoles, J. Med. Chem. 38:1998-2008, 1995.

Perrier et al., Substituted furans as inhibitors of the PDE4 enzyme, Bioorg. Med. Chem. Lett. 9:323-6, 1999.

Plumb et al., Pharmacodynamic response and inhibition of growth of human tumor xenografts by the novel histone deacetylase inhibitor PXD101, Mol. Cancer Ther., 2:721-8, Aug. 2003.

Popik et al., Pharmacological profile of the "Triple" monoamine neurotransmitter uptake inhibitor, DOV 102,677, Cell Mol. Neurobiol., vol. 26, Nos. 4-6:857-73 2006.

Porter et al., (S)-homoquisqualate: a potent agonist at the glutamate metabotropic receptor, Br. J. Pharmacol. 106:509-10, 1992.

Quirk et al., [$^3$H]L-655,708, a novel ligand selective for the benzodiazepine site of GAB receptors which contain the α5 subunit, Neuropharmacology 35(9/10):1331-5, 1996.

Ragno et al., 3-(4-Arolyl-1-methyl-1H-pyrrol-2-yl)-N-hydroxy-2-propenamides as a new class of synthetic histone deacetylase inhibitors. 2. Discovery of novel lead compounds through structure-based drug design and docking studies, J. Med. Chem., 47:1351-9, 2004.

Ragozzino et al., Design and in vitro pharmacology of a selective $_{65}$-aminobutyric acid$_C$ receptor antagonist, Mol. Pharmacol. 50:1024-30, 1996.

Rose et al., Efficacy of MEM 1003, a novel calcium channel blocker, in delay and trace eyeblink conditioning in older rabbits, Neurobiol. Aging 28:766-73, 2007.

Rosen et al., Novel, non-steroidal, selective androgen receptor modulators (SARMs) with anabolic activity in bone and muscle and improved safety profile, J. Musculoskel. Neuron. Interact 2(3):222-4, 2002.

Russell et al., Benz[f]isoquinoline analogues as high-affinity ó ligands, J. Med. Chem. 35:2025-33, 1992.

Ryu et al., SK-7041, a new histone deacetylase inhibitor, induces $G_2$-M cell cycle arrest and apoptosis in pancreatic cancer cell lines, Cancer Lett., 2006, 237:143-54.

Santarelli, Requirement of hippocampal neurogenesis for the behavioral effects of antidepressants, Science 301:805-9, Aug. 8, 2003.

Sasaki et al., The novel and specific Rho-kinase inhibitor (S)-(+)-2-methyl-1-[(4-methyl-5-isoquinoline)sulfonyl]-homopiperazine as a probing molecule for Rho-kinase-involved pathway, Pharmacol. Ther. 93:225-32, 2002.

Schapira et al., In silico discovery of novel retinoic acid receptor agonist structures, BMC Struct. Biol. 1:1, 2001.

Schlicker et al., GABA$_c$ receptor mediated inhibition in acutely isolated neurons of the rat dorsal lateral geniculate nucleus, Brain Res. Bull 63(2):91-7, 2004.

Schoepp et al., 3,5-Dihydroxyphenylglycine is a highly selective agonist for phosphoinositide-linked metabotropic glutamate receptors in the rat hippocampus, J. Neurochem., 63:769-772, 1994.

Schoepp et al., LY354740 is a potent and highly selective group II metabotropic glutamate receptor agonist in cells expressing human glutamate receptors, Neuropharmacology, 36(1):1-11, 1997.

Schoepp et al., Novel functions for subtypes of metabotropic glutamate receptors, Neurochem. Int. 24(5):439-49, 1994.

Schoepp et al., Pharmacological agents acting at subtypes of metabotropic glutamate receptors, Neuropharmacology, 38:1431-76, 1999.

Schultz et al., Paullones, a series of cyclin-dependent kinase inhibitors: synthesis evaluation of CDK1/cyclin B inhibition, and in vitro antitumor activity, J. Med. Chem. 42:2909-19, 1999.

Schulz et al., CP-154,526: a potent and selective nonpeptide antagonist of corticotropin releasing factor receptors, Proc. Natl. Acad. Sci. USA 93:10477-82, 1996.

Sekiyama et al., Structure-activity relationships of new agonists and antagonists of different metabotropic glutamate receptor subtypes, Br. J. Pharmacol. 117:1493-1503, 1996.

Shimokawa et al., Rho-kinase-mediated pathway induces enhanced myosin light chain phosphorylations in a swine model of coronary artery spasm, Cardiovascular Research 43:1029-39, 1999.

Simiand et al., Antidepressant profile in rodents of SR 58611A, a new selective agonist for atypical β-adrenoceptors, Eur. J. Pharmacol. 219:193-201, 1992.

Skolnick et al., Antidepressant-like actions of DOV 21,947: a "triple" reuptake inhibitor, Eur. J. Pharmacol. 461:99-104, 2003.

Slusher et al., Selective inhibition of N LADase, which converts N G to glutamate, reduces ischemic brain injury, Nat. Med. 5(12):1396-402, 1999.

Sonda et al., Synthesis and pharmacological properties of benzamide derivatives as selective serotonin 4 receptor agonists, Bioorg. Med. Chem. 12:2737-47, 2004.

Spitz, Progesterone antagonists and progesterone receptor modulators: an overview, Steroids 68:981-93, 2003.

Squires et al., Some properties of brain specific benzodiazepine receptors: new evidence for multiple receptors, Pharmacol. Biochem. Behav. 10:825-30, 1979.

Stell et al., Receptors with different affinities mediate phasic and tonic GAB conductances in hippocampal neurons, J. Neurosci. 22:1-5, RC223, 2002.

Stephens et al., Abecarnil, a metabolically stable, anxioselective β-carboline acting at benzoldiazepine receptors, J. Pharmacol. Exp. Ther. 253(1):334-43, 1990.

Sur et al., Autoradiographic localization of α5 subunit-containing GAB receptors in rat brain, Brain Res. 822:265-70, 1999.

Sur et al., Rat and human hippocampal α5 subunit-containing $_γ$-aminobutyric acid$_A$ receptors have α5β3γ2 pharmacological characteristics, Mol. Pharmacol. 54:928-33, 1998.

Tazawa et al., KDR-5169, a new gastrointestinal prokinetic agent, enhances gastric contractile and emptying activities in dogs and rats, Eur. J. Pharmacol. 434:169-76, 2002.

Thomas et al., (S)-α-ethyl-glutamic acid and (RS)-α-cyclopropyl-4-phosphonophenylglycine as antagonists of L-AP4-and (1S,3S)-ACPD-induced depression of monosynaptic excitation of neonatal rat motoneurones, Br. J. Pharmacol. 117:70P, 1996.

Trifilieff et al., Pharmacological profile of a novel phosphodiesterase 4 inhibitor, 4-(8-benzo[1,2,5]oxadiazol-5-yl-[1,7]naphthyridin-6-yl)-benzoic acid (NVP-ABE171), a 1,7-naphthyridine derivative, with anti=inflammatory activities, J. of Pharm. and Exp. Ther. 301(1):241-248, 2002.

Ukita, 1-arylnaphthalene lignan: a novel scaffold for type 5 phosphodiesterase inhibitor, J. Med. Chem. 42:1293-1305, 1999.

Ulloor et al., Spontaneous REM sleep is modulated by the activation of the pedunculopontine tegmental GABA$_B$ receptors in the freely moving rat, J. Neurophysiol. 91:1822-31, 2004.

Upasani et al., 3α-hydroxy-3β-(phenylethynyl)-5β-pregnan-20-ones: synthesis and pharmocological activity of neuroactive steroids with high affinity for GAB receptors, J. Med. Chem. 40:73-84, 1997.

Van Praag, Running enhances neurogenesis, learning, and long-term potentiation in mice, Proc. Natl. Acad. Sci., 96(23):13427-31, Nov. 9, 1999.

Voisin et al., Extrapolation of animal toxicity to humans: interspecies comparisons in drug development, Reg. Toxicol. Pharmacol., 12:107-16, 1990.

Wanibuchi et al., Pharmacological studies on novel muscarinic agonists, 1-oxa-8-azaspiro[4.5]decane derivatives, YM796 and YM954, Eur. J. Pharmacol. 187:479-86, 1990.

Ward et al., Functionally selective $M_1$ muscarinic agonists. 3. Side chains and azacycles contributing to functional muscarinic selectivity among pyrazinylazacycles, J. Med. Chem. 38:3469-81, 1995.

Watkins and Collingridge, Phenylglycine derivatives as antagonists of metabotropic glutamate receptors, TiPS, 15:333, 1994.

Weaver Cargin et al., Mild memory impairment in healthy older adults is distinct from normal aging, Brain Cog. 60:146-55, 2006.

Wermuth et al., Aminopyridazines-an alternative route to potent muscarinic agonists with no cholinergic syndrome, II Farmaco. 48(2):253-74, 1993.

Wermuth et al., SR 46559 A and related aminopyridazines are potent muscarinic agonists with no cholinergic syndrome, Biorg. Med. Chem. Let. 2(8):833-8, 1992.

Wermuth et al., Synthesis and structure-activity relationships of a series of aminopyridazine derivatives of $_\gamma$-aminobutyric acid acting as selective GABA-A Antagonists, J. Med. Chem. 30:239-49, 1987.

Werstuck et al., Examining the correlations between GSK-3 inhibitory properties and anti-convulsant efficacy of valproate and valproate-related compounds, Bioorg. Med. Chem. Lett., 14:5465-7 (2004).

White et al., Isoguvacine binding, uptake, and release: relation to the GABA system, J. Neurochem. 40:1701-8, 1983.

Wong et al., Effects of clozapine metabolites and chronic clozapine treatment on rat brain GAB receptors, Eur J. Pharmacol. 314:319-23, 1996.

Wroblewska et al., N-Acetylaspartylglutamate selectively activates mGluR3 receptors in transfected cells, J. Neurochem. 69:174-81, 1997.

Xu et al., Electrophysiologic effects of SB-237376: a new antiarrhythmic compound with dual potassium and calcium channel blocking action, J. Cardiovasc. Pharmacol. 41(3):414-21, 2003.

Xu et al., Structural determinants of ligand binding selectivity between the peroxisome proliferator-activated receptors, Proc. Natl. Acad. Sci. USA 98(24):13919-24, 2001.

Yasumatsu et al., The pharmacological properties of Y-23684, a benzodiazepine receptor partial agonist, Br. J. Pharmacol. 111:1170-8, 1994.

Yee et al., Vitamin D receptor modulators for inflammation and cancer, Mini Rev. Med. Chem. 5:761-78, 2005.

Zaki et al., Agonist-, antagonist-, and inverse agonist-regulated trafficking of the σ-opioid receptor correlates with, but does not require, G protein activation, J. Pharmacol. Exp. Therap. 298(3):1015-20, 2001.

Baldessarini R.J., "Drugs and the Treatment of Psychiatric Disorders. Depression and Anxiety Disorders", Chapter 19, pp. 447-477 (Goodman Gilman A. et al., "The pharmacological basis of therapeutics, Passage", Goodman and Gilman's The Pharmacological Basis of Therapeutics, New York: McGraw-Hill, US, 2001, pp. 447-477), XP002458667, ISBN: 0-07-135469-7.

Chen, Y., "MKC-231 Mitsubishi-Tokyo Pharmaceutical Inc", *Current Opinion in CPNS Investigational Drugs*, 2(4):461-466 (2000).

\* cited by examiner

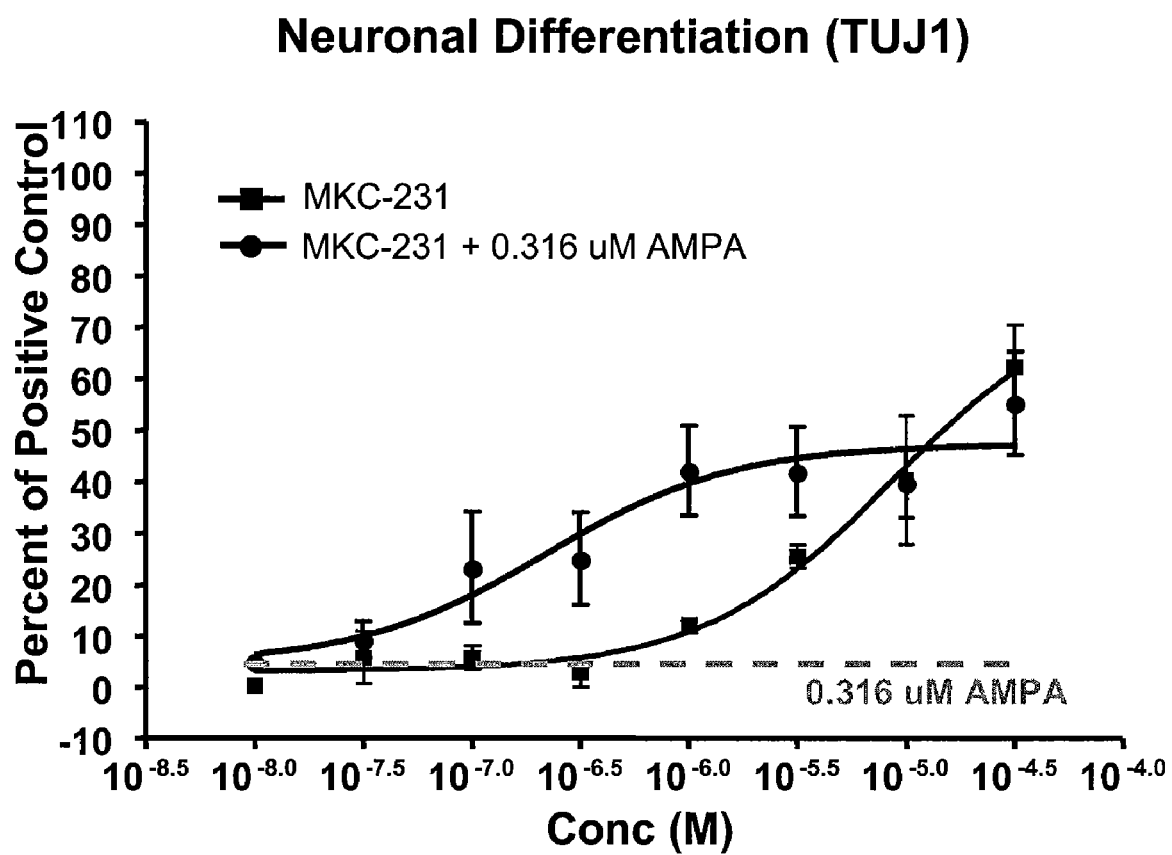
Figure 1: Human Neurogenesis Assay: MKC-231 + AMPA

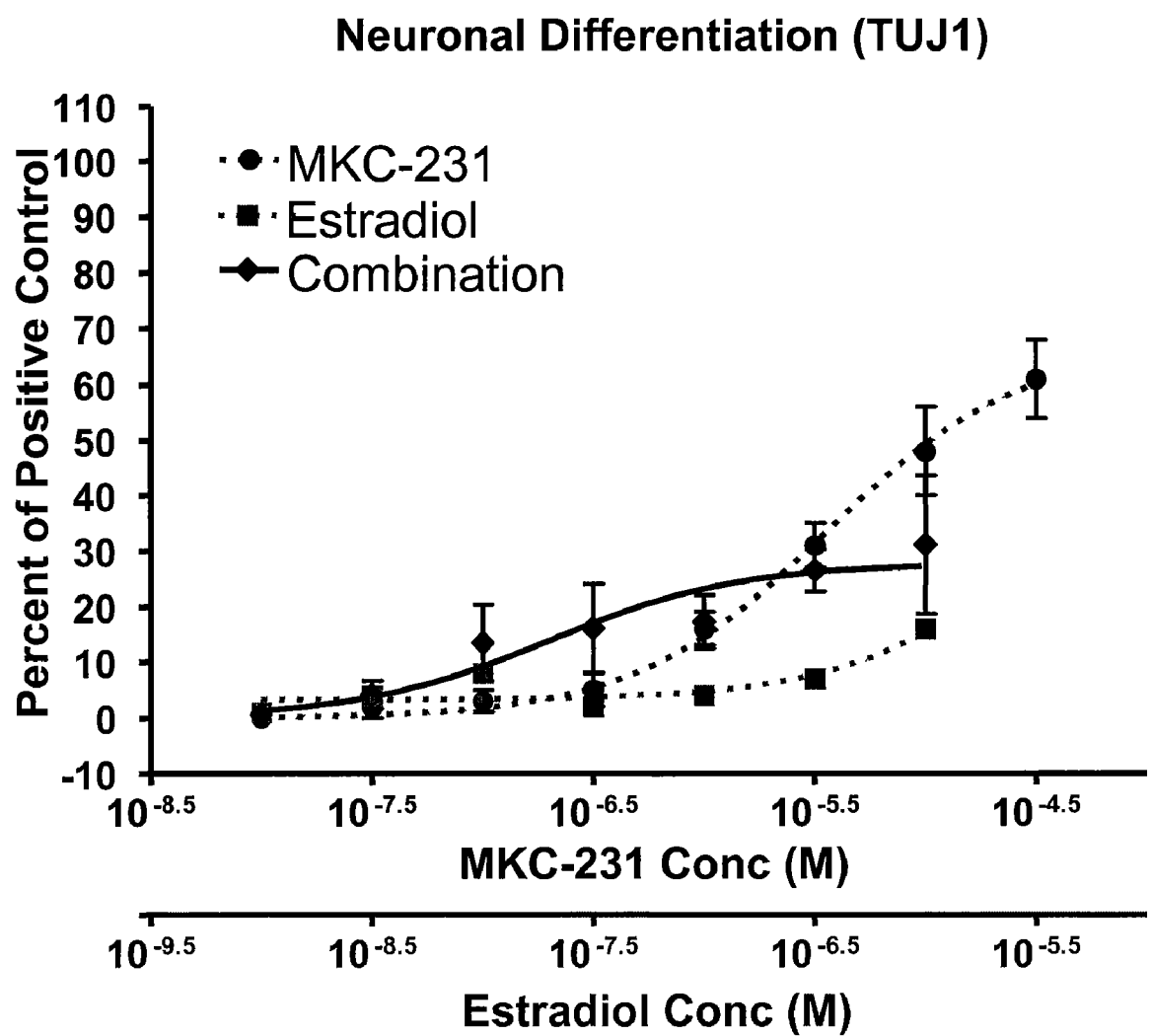
Figure 2: Human Neurogenesis Assay: MKC-231 + Estradiol

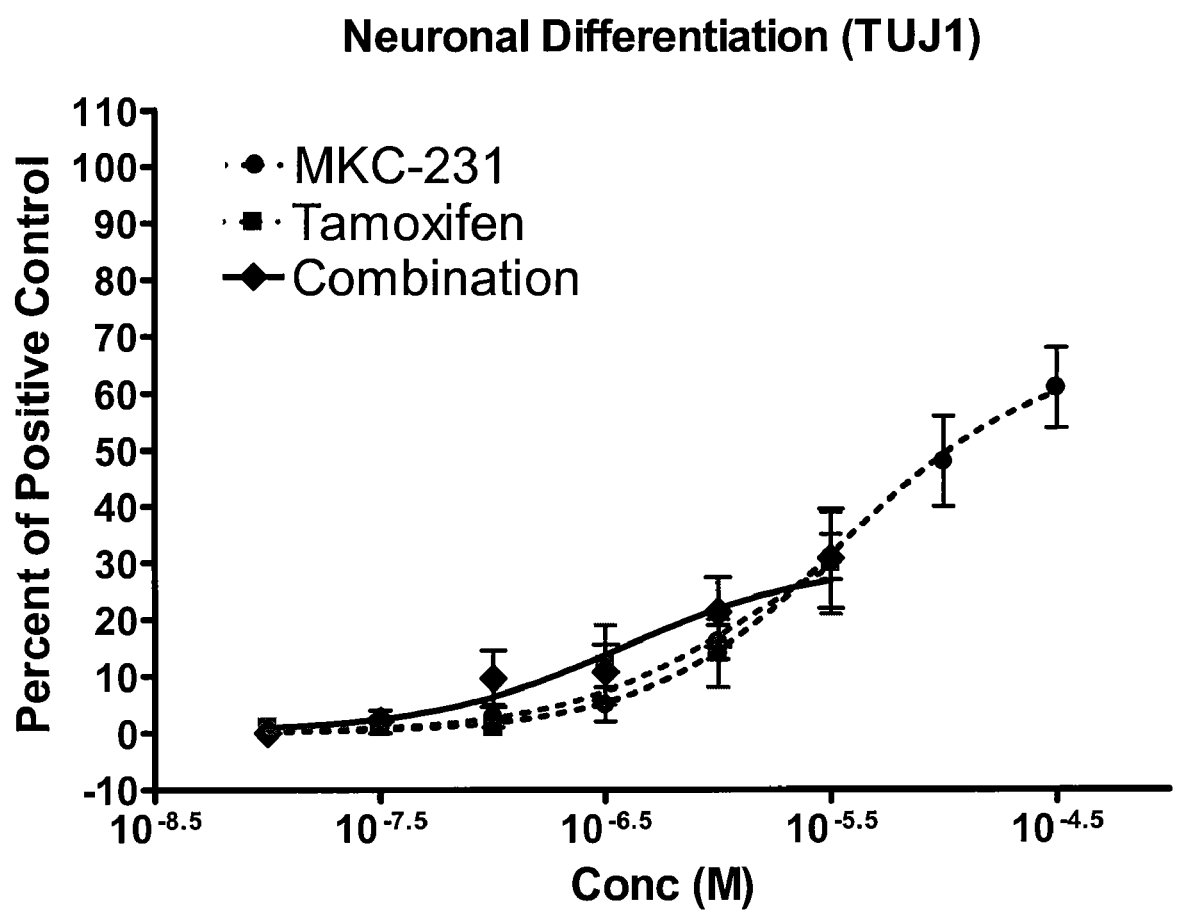
Figure 3: Human Neurogenesis Assay: MKC-231 + Tamoxifen

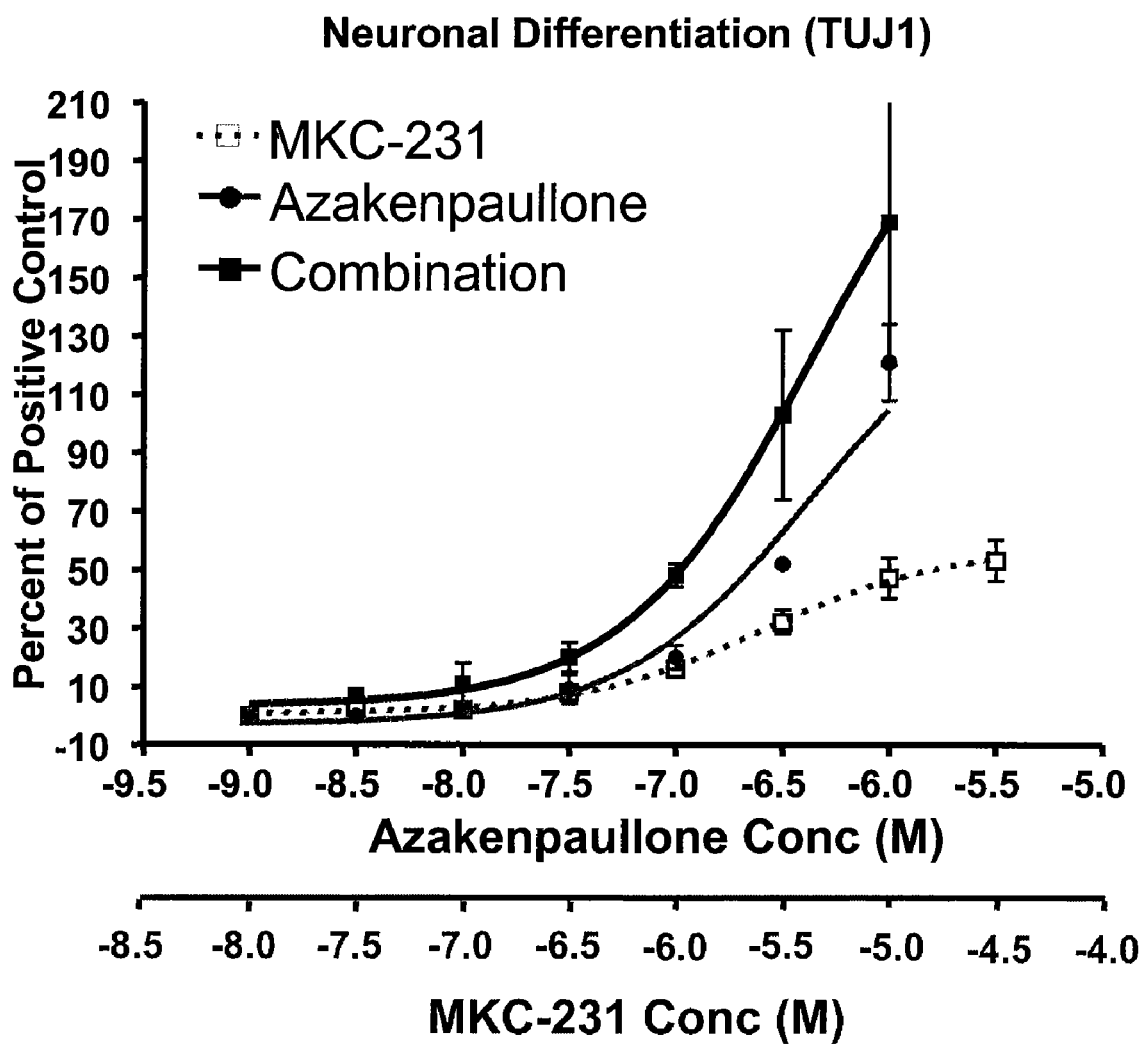
Figure 4: Human Neurogenesis Assay: MKC-231 + Azakenpaullone

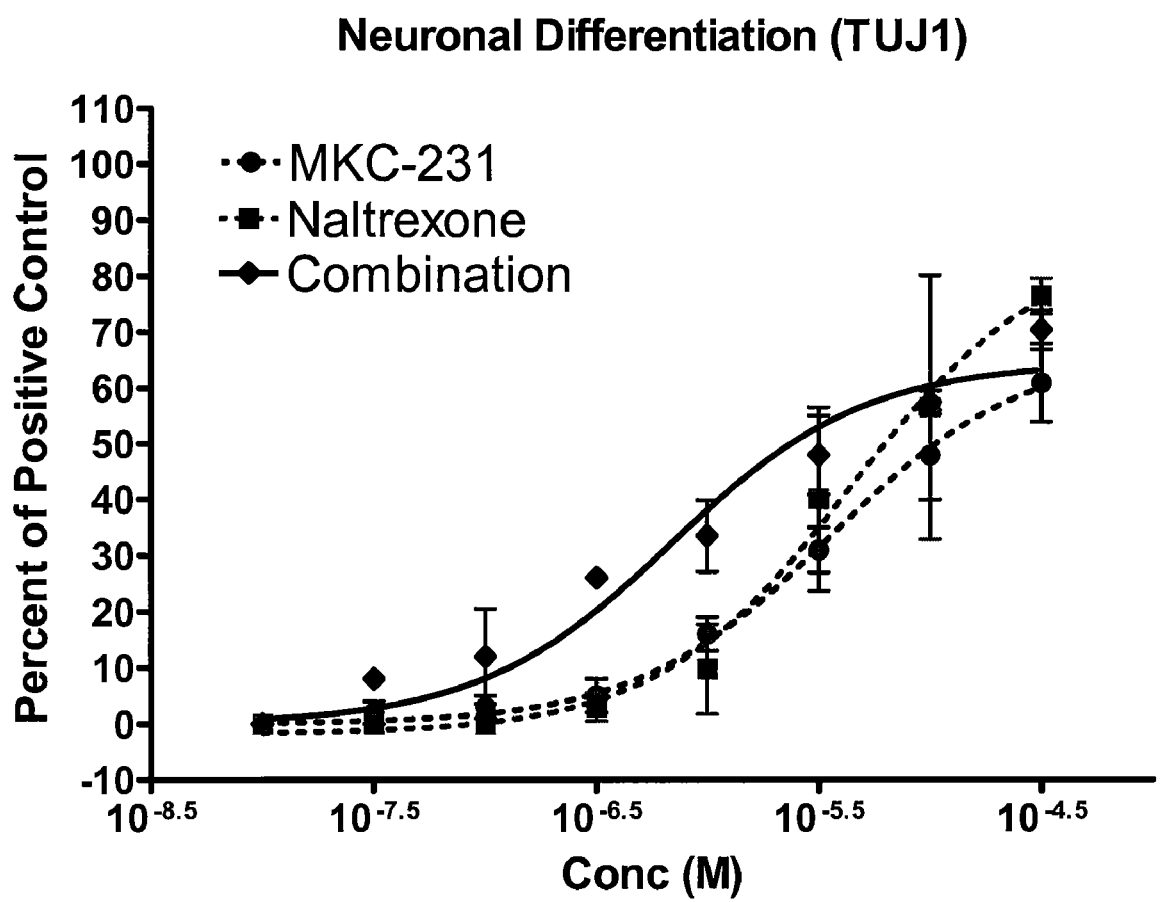
Figure 5: Human Neurogenesis Assay: MKC-231 + Naltrexone

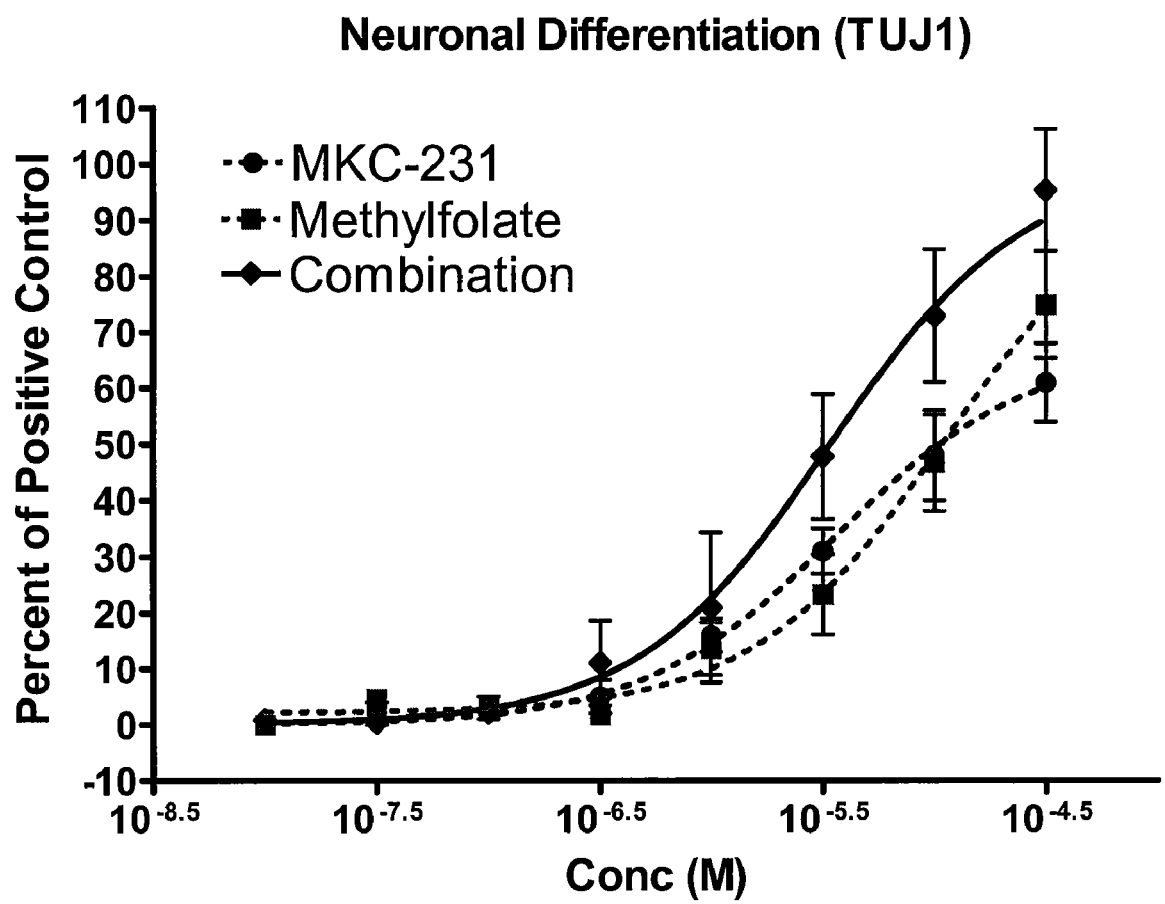
Figure 6: Human Neurogenesis Assay: MKC-231 + Methylfolate

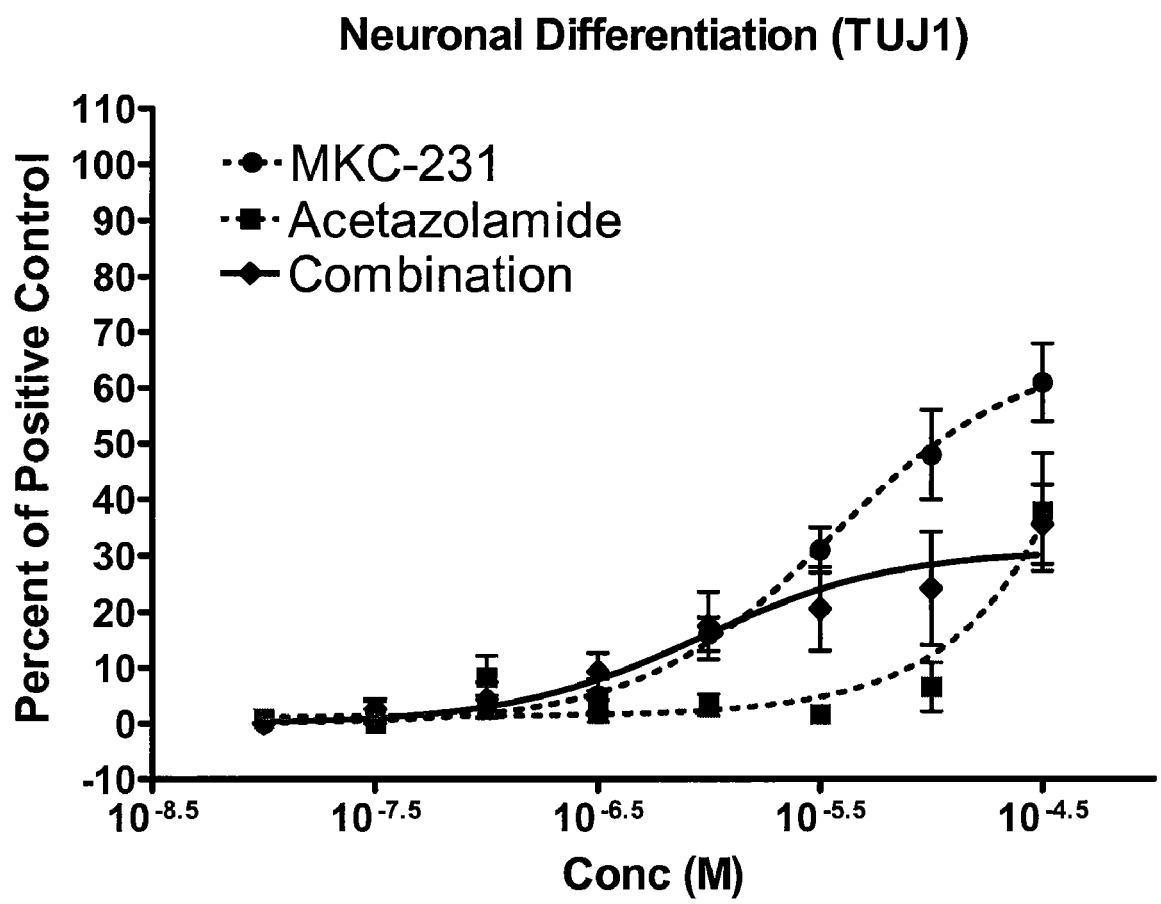
Figure 7: Human Neurogenesis Assay: MKC-231 + Acetazolamide

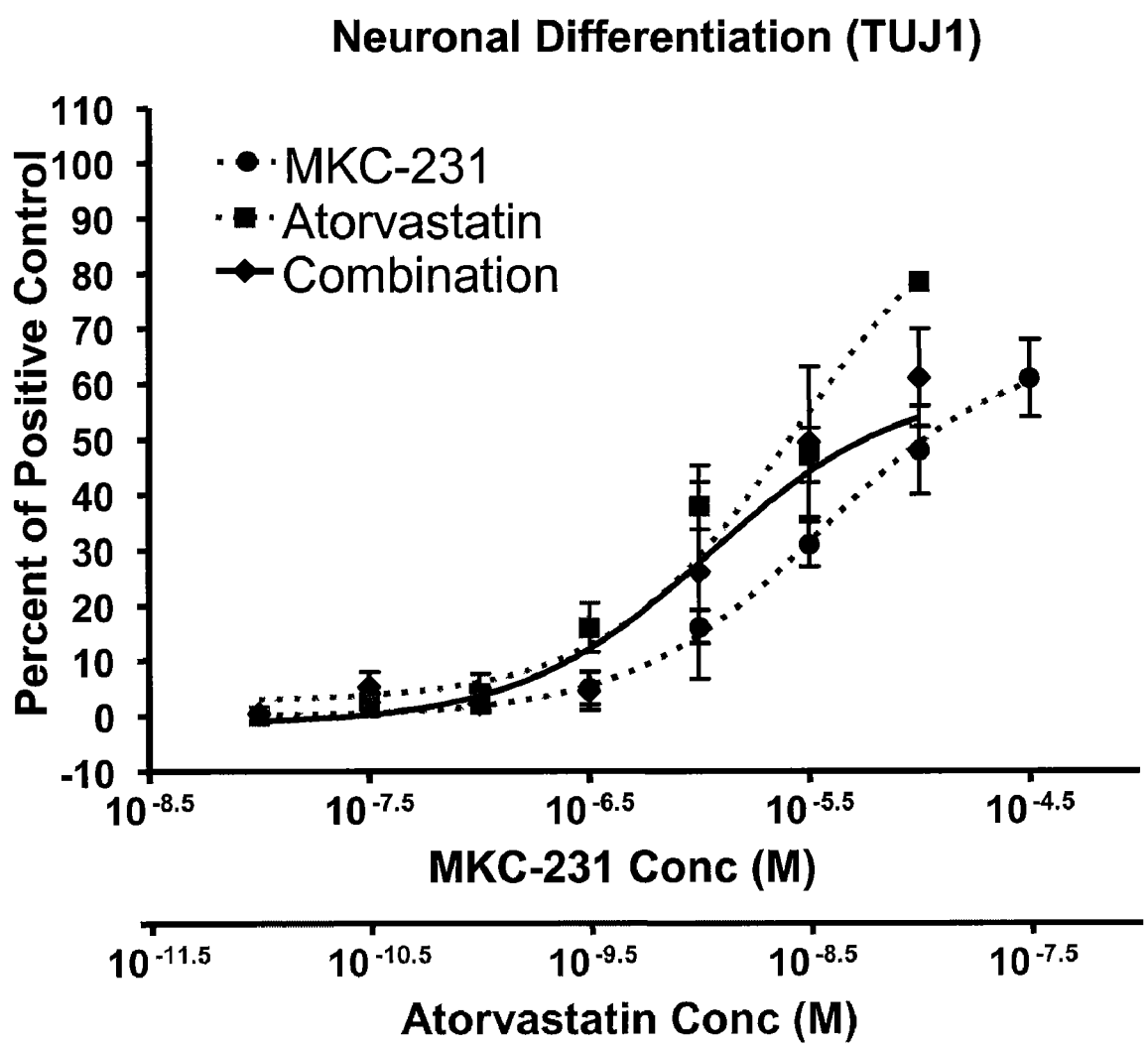

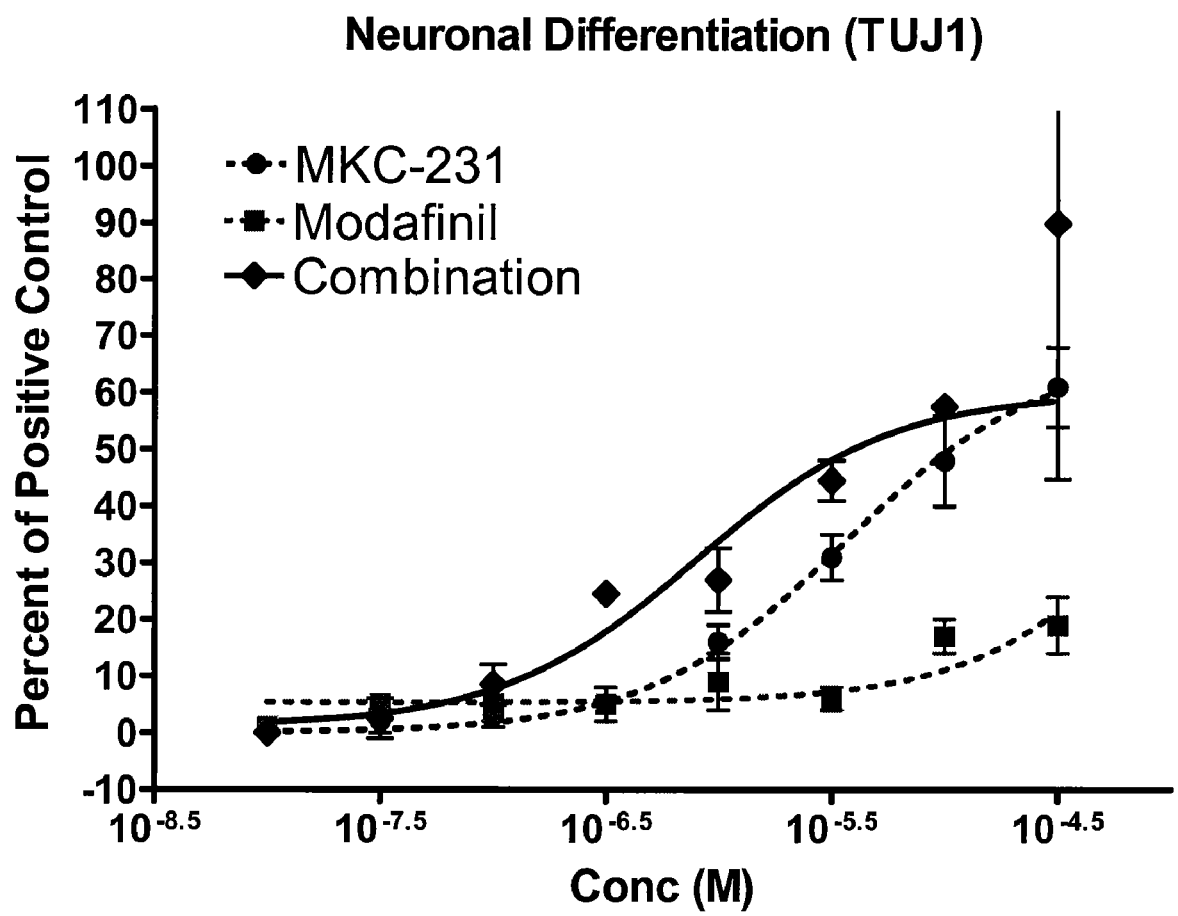
Figure 9: Human Neurogenesis Assay: MKC-231 + Modafinil

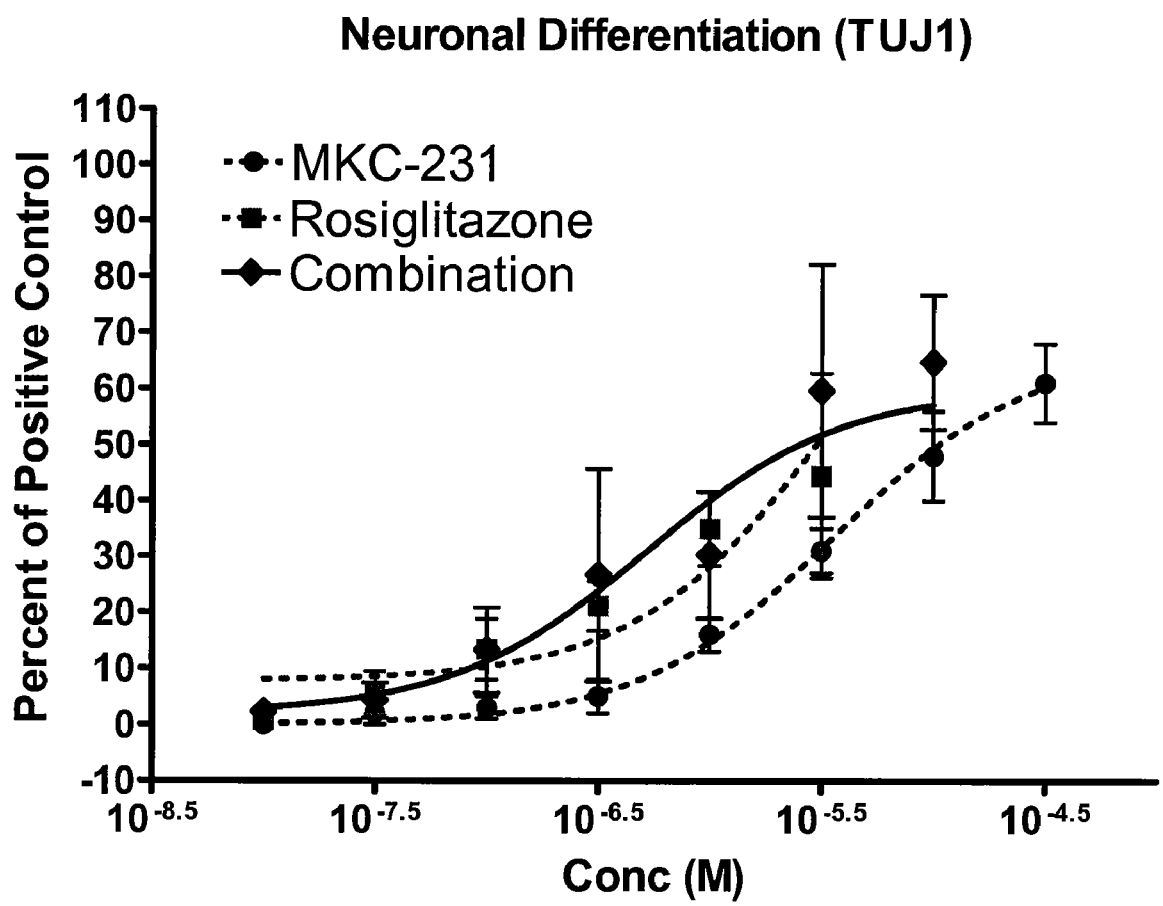
Figure 10: Human Neurogenesis Assay: MKC-231 + Rosiglitazone

US 7,998,971 B2

COMBINATIONS CONTAINING A 4-ACYLAMINOPYRIDINE DERIVATIVE

RELATED APPLICATIONS

This application is related to U.S. Provisional Applications 60/825,080, filed Sep. 8, 2006, which is incorporated by reference as if fully set forth. This application also is related to U.S. Provisional Application 60/868,510, filed Dec. 4, 2006; and U.S. Provisional Application 60/884,584, filed Jan. 11, 2007, both of which are incorporated by reference as if fully set forth.

FIELD OF THE DISCLOSURE

The instant disclosure relates to compositions and methods for treating diseases and conditions of the central and peripheral nervous system by stimulating or increasing neurogenesis via a 4-acylaminopyridine derivative in combination with one or more other neurogenic agents. The disclosure includes methods based on the application of the combination to stimulate or activate the formation of new nerve cells.

BACKGROUND OF THE DISCLOSURE

Neurogenesis is a vital process in the brains of animals and humans, whereby new nerve cells are continuously generated throughout the life span of the organism. The newly born cells are able to differentiate into functional cells of the central nervous system and integrate into existing neural circuits in the brain. Neurogenesis is known to persist throughout adulthood in two regions of the mammalian brain: the subventricular zone (SVZ) of the lateral ventricles and the dentate gyrus of the hippocampus. In these regions, multipotent neural progenitor cells (NPCs) continue to divide and give rise to new functional neurons and glial cells (for review Gage *Mol Psychiatry.* 2000 May;5(3):262-9). It has been shown that a variety of factors can stimulate adult hippocampal neurogenesis, e.g., adrenalectomy, voluntary exercise, enriched environment, hippocampus dependent learning and anti-depressants (Yehuda. *J Neurochem.* 1989 Jul.;53(1):241-8, van Praag. *Proc Natl Acad Sci U S A.* 1999 Nov. 9;96(23):13427-31, Brown. *J Eur J Neurosci.* 2003 May; 17(10):2042-6, Gould. *Science.* 1999 Oct. 15; 286(5439):548-52, Malberg. *J Neurosi.* 2000 Dec. 15; 20(24):9104-10, Santarelli. *Science.* 2003 Aug. 8; 301(5634): 805-9). Other factors, such as adrenal hormones, stress, age and drugs of abuse negatively influence neurogenesis (Cameron. *Neuroscience.* 1994 July; 61(2):203-9, McEwen. *Neuropsychopharmacology.* 1999 Oct.; 21(4):474-84, Kuhn. *J. Neurosci.* 1996 Mar. 15; 16(6):2027-33, Eisch. *Am J Psychiatry.* 2004 March; 161(3):426).

U.S. Pat. No. 5,397,785 describes a number of 4-acylaminopyridine derivatives and compositions as well as their use in the treatment of senile dementia and Alzheimer's Disease. U.S. Pat. No. 6,884,805 describes polymorph crystals of a 4-acylaminopyridine derivative and their use in activating a malfunctioned cholinergic neuron that is associated with memory loss disturbances.

Citation of the above documents is not intended as an admission that any of the foregoing is pertinent prior art. Statements about these documents do not constitute any admission as to the correctness of the dates or contents of these documents.

BRIEF SUMMARY OF THE DISCLOSURE

Disclosed herein are compositions and methods for the prophylaxis and treatment of diseases, conditions and injuries of the central and peripheral nervous systems by stimulating or increasing neurogenesis. Aspects of the methods, and activities of the compositions, include increasing or potentiating neurogenesis in cases of a disease, disorder, or condition of the nervous system. Embodiments of the disclosure include methods of treating a neurodegenerative disorder, neurological trauma including brain or central nervous system trauma and/or recovery therefrom, depression, anxiety, psychosis, learning and memory disorders, and ischemia of the central and/or peripheral nervous systems. In other embodiments, the disclosed methods are used to improve cognitive outcomes.

In one aspect, methods of modulating, such as by stimulating or increasing, neurogenesis are disclosed. The neurogenesis may be at the level of a cell or tissue. The cell or tissue may be present in an animal subject or a human being, or alternatively be in an in vitro or ex vivo setting. In some embodiments, neurogenesis is stimulated or increased in a neural cell or tissue, such as that of the central or peripheral nervous system of an animal or human being. In cases of an animal or human, the methods may be practiced in connection with one or more disease, disorder, or condition of the nervous system as present in the animal or human subject. Thus, embodiments disclosed herein include methods of treating a disease, disorder, or condition by administering a 4-acylaminopyridine derivative in combination with one or more other neurogenic agents. In some embodiments, the 4-acylaminopyridine derivative is MKC-231. (Also known as 2-(2-oxopyrrolidin-1-yl)-N-(2,3-dimethyl-5,6,7,8-tetrahydrofuro [2,3-b]-quinolin-4-yl)acetoamide or N-(2,3-dimethyl-5,6,7, 8-tetrahydrofuro[2,3-b]quinolin-4-yl)-2-(2-oxopyrrolidin-1-yl)acetamide.) There are polymorph and isomer forms of MKC-231.

A 4-acylaminopyridine derivative is used in combination with one or more other neurogenic agents. The additional neurogenic agent may be another 4-acylaminopyridine derivative or a neurogenic agent that acts through a mechanism independent from the 4-acylaminopyridine derivative. An additional neurogenic agent as described herein may be one which acts through a known receptor or one which is known for the treatment of a disease or condition.

Embodiments of the disclosure are based upon a combination of a 4-acylaminopyridine derivative and one or more other neurogenic agents disclosed herein or known to the skilled person. Compositions disclosed herein include such combinations of a 4-acylaminopyridine derivative in combination with one or more other neurogenic agents.

In a second aspect, the disclosure includes a method of lessening and/or reducing a decline or decrease of cognitive function in a subject or patient. In some cases, the method may be applied to maintain and/or stabilize cognitive function in the subject or patient. The method may comprise administering a 4-acylaminopyridine derivative in combination with one or more other neurogenic agents to a subject or patient in an amount effective to lessen or reduce a decline or decrease of cognitive function.

In another aspect, the disclosed methods include identifying a patient suffering from one or more diseases, disorders, or conditions, or a symptom thereof, and administering to the patient a 4-acylaminopyridine derivative in combination with one or more other neurogenic agents as described herein. In some embodiments, a method including identification of a subject as in need of an increase in neurogenesis, and administering to the subject a 4-acylaminopyridine derivative in combination with one or more other neurogenic agents is disclosed herein. In other embodiments, the subject is a patient, such as a human patient.

Additional embodiments describe a method including administering a 4-acylaminopyridine derivative in combination with one or more other neurogenic agents to a subject exhibiting the effects of insufficient amounts of, or inadequate levels of, neurogenesis. In some embodiments, the subject may be one that has been subjected to an agent that decreases or inhibits neurogenesis. Non-limiting examples of an inhibitor of neurogenesis include opioid receptor agonists, such as a mu receptor subtype agonist like morphine. In a related manner, a method provides for administering a 4-acylaminopyridine derivative in combination with one or more other neurogenic agents to a subject or person that will be subjected to an agent that decreases or inhibits neurogenesis. Non-limiting embodiments include those where the subject or person is about to be administered morphine or another opioid receptor agonist, like another opiate, and so about to be subject to a decrease or inhibition of neurogenesis. Non-limiting examples include administering a 4-acylaminopyridine derivative in combination with one or more other neurogenic agents to a subject before, simultaneously with, or after the subject is administered morphine or other opiate in connection with a surgical procedure.

Also disclosed are methods for preparing a population of neural stem cells suitable for transplantation, comprising culturing a population of neural stem cells (NSCs) in vitro, and contacting the cultured neural stem cells with a 4-acylaminopyridine derivative in combination with one or more other neurogenic agents. In some embodiments, the stem cells are prepared and then transferred to a recipient host animal or human. Non-limiting examples of preparation include 1) contact with a 4-acylaminopyridine derivative in combination with one or more other neurogenic agents until the cells have undergone neurogenesis, such as that which is detectable by visual inspection or cell counting, or 2) contact with a 4-acylaminopyridine derivative in combination with one or more other neurogenic agents until the cells have been sufficiently stimulated or induced toward or into neurogenesis. The cells prepared in such a non-limiting manner may be transplanted to a subject, optionally with simultaneous, nearly simultaneous, or subsequent administration of another neurogenic agent to the subject. While the neural stem cells may be in the form of an in vitro culture or cell line, in other embodiments, the cells may be part of a tissue which is subsequently transplanted into a subject.

In yet another aspect, the disclosure includes methods of modulating, such as by stimulating or increasing, neurogenesis in a subject by administering a 4-acylaminopyridine derivative in combination with one or more other neurogenic agents. In some embodiments, the neurogenesis occurs in combination with the stimulation of angiogenesis which provides new cells with access to the circulatory system.

Also included are compositions comprising a 4-acylaminopyridine compound in combination with an antidepressant agent, an estrogen receptor modulator, a folic acid derivative, an opioid inhibitor, a carbonic anhydrase inhibitor, an HMGCR inhibitor, an adrenergic agonist, an AMPA modulator, a PPARgamma activator, an antipsychotic agent, an HDAC inhibitor, a muscarinic modulator, or a 5HT modulator. Optionally, the composition is formulated with a pharmaceutical acceptable carrier and is in a single formulation or in a single unit dosage form. Moreover, the 4-acylaminopyridine compound can be an isomer or polymorph.

Preferably, the compound can be MKC-231 in combination with an AMPA agonist, estradiol, tamoxifen, methylfolate, naltrexone, acetazolamide, atorvastatin, modafinil or rosiglitazone. Often, when the 4-acylaminopyridine compound is used in combination with a neurogenic agent, the effective dosage of either or both actives is less than their effective dose when utilized alone.

The details of additional embodiments are set forth in the accompanying drawings and the description below. Other features, objects, and advantages of the embodiments will be apparent from the drawings and detailed description, and from the claims.

BRIEF DESCRIPTION OF THE DRAWINGS

FIG. 1 is a dose-response curve showing effect of the neurogenic agents MKC-231 (cholinergic uptake inhibitor) in combination with AMPA (α-amino-3-hydroxy-5-methyl-isoxazole-4-propionic acid) (an AMPA receptor agonist) on neuronal differentiation compared to the effect of MKC-231 alone. When run independently, MKC-231 was tested in a concentration response curve ranging from 0.01 µM to 31.6 µM, AMPA had no effect on differentiation at 0.316 µM ($EC_{50}$ ~31.6 µM when run alone). In a combination study, MKC-231 was tested as a concentration response curve (CRC) ranging from 0.01 µM to 31.6 µM in the presence of a fixed 0.316 µM concentration of AMPA. Data is presented as the percentage of the neuronal positive control, with basal media values subtracted. When used alone, $EC_{50}$ was observed at an MKC-231 concentration of 8.6 µM. When run in the presence of 0.316 µM AMPA, $EC_{50}$ was observed at an MKC-231 concentration of 0.22 µM, showing enhanced neurogenesis with a synergistic combination index of 0.04.

FIG. 2 is a dose-response curve showing effect of the neurogenic agents MKC-231 and estradiol (estrogen receptor modulator) in combination on neuronal differentiation of human neural stem cells compared to the effect of either agent alone. When run independently, MKC-231 was tested in a concentration response curve ranging from 0.01 µM to 31.6 µM, and estradiol was tested in a response curve ranging from 0.0001-1.0 µM. In combination, the compounds were combined at a 1:10 ratio at each point (for example, the first point in the combined curve consisted of a test of 0.01 µM MKC-231 and 0.001 µM estradiol). Data is presented as the percentage of the neuronal positive control, with basal media values subtracted. When used alone, $EC_{50}$ was observed at an MKC-231 concentration of 8.6 µM or an estradiol concentration estimated to be 4.4 µM (based on extrapolation of the observed data). When used in combination, neurogenesis is greatly enhanced: $EC_{50}$ was observed at a combination of MKC-231 at a concentration of 0.2 µM and estradiol at a concentration of 0.02 µM, resulting in a synergistic combination index of 0.03.

FIG. 3 is a dose-response curve showing effect of the neurogenic agents MKC-231 and tamoxifen (selective estrogen receptor modulator) in combination on neuronal differentiation of human neural stem cells compared to the effect of either agent alone. When run independently, each compound was tested in a concentration response curve ranging from 0.01 µM to 31.6 µM. In combination, the compounds were combined at equal concentrations at each point (for example, the first point in the combined curve consisted of a test of 0.01 µM MKC-231 and 0.01 µM tamoxifen). Data is presented as the percentage of the neuronal positive control, with basal media values subtracted. When used alone, $EC_{50}$ was observed at an MKC-231 concentration of 8.6 µM or a tamoxifen concentration of 1.5 µM in test cells. When used in combination, neurogenesis is greatly enhanced: $EC_{50}$ was observed at a combination of MKC-231 and tamoxifen at concentrations of 0.37 µM each, resulting in a synergistic combination index of 0.3.

FIG. 4 is a dose-response curve showing effect of the neurogenic agents azakenpaullone (GSK3β inhibitor) and MKC-231 in combination on neuronal differentiation compared to the effect of either agent alone. When run independently or in combination, MKC-231 was tested in a concentration response curve (CRC) ranging from 0.01 uM to 31.6 uM and azakenpaullone in a CRC ranging from 0.001 uM to 3.2 uM (for example, the first point in the combined curve consisted of a test of the combination of 0.01 uM MKC-231 and 0.001 uM azakenpaullone). Data is presented as the percentage of the neuronal positive control, with basal media values subtracted. When used alone, azakenpaullone or MKC-231 showed a maximum neuronal differentiation percent of positive control of 120% or 53%, respectively. When azakenpaullone and MKC-231 were used in combination, the maximum neuronal differentiation percent of positive control observed was 170%.

FIG. 5 is a dose-response curve showing effect of the neurogenic agents MKC-231 and naltrexone (opioid antagonist) in combination on neuronal differentiation of human neural stem cells compared to the effect of either agent alone. When run independently, each compound was tested in a concentration response curve ranging from 0.01 μM to 31.6 μM. In combination, the compounds were combined at equal concentrations at each point (for example, the first point in the combined curve consisted of a test of 0.01 μM MKC-231 and 0.01 μM naltrexone). Data is presented as the percentage of the neuronal positive control, with basal media values subtracted. When used alone, $EC_{50}$ was observed at an MKC-231 concentration of 8.6 μM or a naltrexone concentration of 4.5 μM in test cells. When used in combination, neurogenesis is greatly enhanced: $EC_{50}$ was observed at a combination of MKC-231 and naltrexone at concentrations of 0.93 μM each, resulting in a synergistic combination index of 0.25.

FIG. 6 is a dose-response curve showing effect of the neurogenic agents MKC-231 and methylfolate (folic acid derivative) in combination on neuronal differentiation of human neural stem cells compared to the effect of either agent alone. When run independently, each compound was tested in a concentration response curve ranging from 0.01 μM to 31.6 μM. In combination, the compounds were combined at equal concentrations at each point (for example, the first point in the combined curve consisted of a test of 0.01 μM MKC-231 and 0.01 μM methylfolate). Data is presented as the percentage of the neuronal positive control, with basal media values subtracted. When used alone, $EC_{50}$ was observed at an MKC-231 concentration of 8.6 μM or a methylfolate concentration of 11.3 μM in test cells. When used in combination, neurogenesis is greatly enhanced: $EC_{50}$ was observed at a combination of MKC-231 and methylfolate at concentrations of 3.4 μM each, resulting in a synergistic combination index of 0.82.

FIG. 7 is a dose-response curve showing effect of the neurogenic agents MKC-231 and acetazolamide (carbonic anhydrase inhibitor) in combination on neuronal differentiation of human neural stem cells compared to the effect of either agent alone. When run independently, each compound was tested in a concentration response curve ranging from 0.01 μM to 31.6 μM. In combination, the compounds were combined at equal concentrations at each point (for example, the first point in the combined curve consisted of a test of 0.01 μM MKC-231 and 0.01 μM acetazolamide). Data is presented as the percentage of the neuronal positive control, with basal media values subtracted. When used alone, $EC_{50}$ was observed at an MKC-231 concentration of 8.6 μM or an acetazolamide concentration estimated to be 66 μM (based on extrapolation of the observed data). When used in combination, neurogenesis is greatly enhanced: $EC_{50}$ was observed at a combination of MKC-231 and acetazolamide at concentrations of 0.93 μM each, resulting in a synergistic combination index of 0.12.

FIG. 8 is a dose-response curve showing effect of the neurogenic agents MKC-231 and atorvastatin (HMGCR inhibitor) in combination on neuronal differentiation of human neural stem cells compared to the effect of either agent alone. When run independently, MKC-231 was tested in a concentration response curve ranging from 0.01 μM to 31.6 μM, and atorvastatin was tested in a response curve ranging from 0.00001-0.001 μM. In combination, the compounds were combined at a 1:1000 ratio at each point (for example, the first point in the combined curve consisted of a test of 0.01 μM MKC-231 and 0.00001 μM atorvastatin). Data is presented as the percentage of the neuronal positive control, with basal media values subtracted. When used alone, $EC_{50}$ was observed at an MKC-231 concentration of 8.6 μM or an atorvastatin concentration of 0.003 μM in test cells. When used in combination, neurogenesis is greatly enhanced: $EC_{50}$ was observed at a combination of MKC-231 at a concentration of 1.1 μM and atorvastatin at a concentration of 0.001 μM, resulting in a synergistic combination index of 0.5.

FIG. 9 is a dose-response curve showing effect of the neurogenic agents MKC-231 and modafinil (adrenergic agonist) in combination on neuronal differentiation of human neural stem cells compared to the effect of either agent alone. When run independently, each compound was tested in a concentration response curve ranging from 0.01 μM to 31.6 μM. In combination, the compounds were combined at equal concentrations at each point (for example, the first point in the combined curve consisted of a test of 0.01 μM MKC-231 and 0.01 μM modafinil). Data is presented as the percentage of the neuronal positive control, with basal media values subtracted. When used alone, $EC_{50}$ was observed at an MKC-231 concentration of 8.6 μM or a modafinil concentration estimated to be 83 μM (based on extrapolation of the observed data). When used in combination, neurogenesis is greatly enhanced: $EC_{50}$ was observed at a combination of MKC-231 and modafinil at concentrations of 1.1 μM each, resulting in a synergistic combination index of 0.14.

FIG. 10 is a dose-response curve showing effect of the neurogenic agents MKC-231 and rosiglitazone (PpAR-gamma activator) in combination on neuronal differentiation of human neural stem cells compared to the effect of either agent alone. When run independently, each compound was tested in a concentration response curve ranging from 0.01 μM to 31.6 μM. In combination, the compounds were combined at equal concentrations at each point (for example, the first point in the combined curve consisted of a test of 0.01 μM MKC-231 and 0.01 μM rosiglitazone). Data is presented as the percentage of the neuronal positive control, with basal media values subtracted. When used alone, $EC_{50}$ was observed at an MKC-231 concentration of 8.6 μM or a rosiglitazone concentration of 3.6 μM in test cells. When used in combination, neurogenesis is greatly enhanced: $EC_{50}$ was observed at a combination of MKC-231 and rosiglitazone at concentrations of 0.52 μM each, resulting in a synergistic combination index of 0.21.

DETAILED DESCRIPTION OF MODES OF PRACTICE

"Neurogenesis" is defined herein as proliferation, differentiation, migration and/or survival of a neural cell in vivo or in vitro. In various embodiments, the neural cell is an adult, fetal, or embryonic neural stem cell or population of cells.

The cells may be located in the central nervous system or elsewhere in an animal or human being. The cells may also be in a tissue, such as neural tissue. In some embodiments, the neural cell is an adult, fetal, or embryonic progenitor cell or population of cells, or a population of cells comprising a mixture of stem cells and progenitor cells. Neural cells include all brain stem cells, all brain progenitor cells, and all brain precursor cells. Neurogenesis includes neurogenesis as it occurs during normal development, as well as neural regeneration that occurs following disease, damage or therapeutic intervention, such as by the treatment described herein.

A "neurogenic agent" is defined as a chemical agent or reagent that can promote, stimulate, or otherwise increase the amount or degree or nature of neurogenesis in vivo or ex vivo or in vitro relative to the amount, degree, or nature of neurogenesis in the absence of the agent or reagent. In some embodiments, treatment with a neurogenic agent increases neurogenesis if it promotes neurogenesis by at least about 5%, at least about 10%, at least about 25%, at least about 50%, at least about 100%, at least about 500%, or more in comparison to the amount, degree, and/or nature of neurogenesis in the absence of the agent, under the conditions of the method used to detect or determine neurogenesis.

The term "astrogenic" is defined in relation to "astrogenesis" which refers to the activation, proliferation, differentiation, migration and/or survival of an astrocytic cell in vivo or in vitro. Non-limiting examples of astrocytic cells include astrocytes, activated microglial cells, astrocyte precursors and potentiated cells, and astrocyte progenitor and derived cells. In some embodiments, the astrocyte is an adult, fetal, or embryonic astrocyte or population of astrocytes. The astrocytes may be located in the central nervous system or elsewhere in an animal or human being. The astrocytes may also be in a tissue, such as neural tissue. In some embodiments, the astrocyte is an adult, fetal, or embryonic progenitor cell or population of cells, or a population of cells comprising a mixture of stem and/or progenitor cells, that is/are capable of developing into astrocytes. Astrogenesis includes the proliferation and/or differentiation of astrocytes as it occurs during normal development, as well as astrogenesis that occurs following disease, damage or therapeutic intervention.

The term "stem cell" (or "neural stem cell" (NSC)), as used herein, refers to an undifferentiated cell that is capable of self-renewal and differentiation into neurons, astrocytes, and/or oligodendrocytes.

The term "progenitor cell" (e.g., neural progenitor cell), as used herein, refers to a cell derived from a stem cell that is not itself a stem cell. Some progenitor cells can produce progeny that are capable of differentiating into more than one cell type.

The term "cognitive function" refers to mental processes of an animal or human subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like. In some embodiments, cognitive function may be assessed, and thus optionally defined, via one or more tests or assays for cognitive function. Non-limiting examples of a test or assay for cognitive function include CANTAB (see for example Fray et al. "CANTAB battery: proposed utility in neurotoxicology." *Neurotoxicol Teratol.* 1996; 18(4):499-504), Stroop Test, Trail Making, Wechsler Digit Span, or the CogState computerized cognitive test (see also Dehaene et al. "Reward-dependent learning in neuronal networks for planning and decision making." *Prog Brain Res.* 2000; 126:217-29; Iverson et al. "Interpreting change on the WAIS-III/WMS-III in clinical samples." *Arch Clin Neuropsychol.* 2001; 16(2):183-91; and Weaver et al. "Mild memory impairment in healthy older adults is distinct from normal aging." *Brain Cogn.* 2006; 60(2):146-55).

The terms "neurogenic combination of a 4-acylaminopyridine derivative with one or more other neurogenic agents" or "a 4-acylaminopyridine derivative in combination with one or more other neurogenic agents" refer to a combination of neurogenesis modulating agents. In some embodiments, administering a neurogenic, or neuromodulating, combination according to methods provided herein modulates neurogenesis in a target tissue and/or cell-type by at least about 20%, about 25%, about 30%, about 40%, about 50%, at least about 75%, or at least about 90% or more in comparison to the absence of the combination. In further embodiments, neurogenesis is modulated by at least about 95% or by at least about 99% or more.

A neuromodulating combination may be used to inhibit a neural cell's proliferation, division, or progress through the cell cycle. Alternatively, a neuromodulating combination may be used to stimulate survival and/or differentiation in a neural cell. As an additional alternative, a neuromodulating combination may be used to inhibit, reduce, or prevent astrocyte activation and/or astrogenesis or astrocyte differentiation.

"$IC_{50}$" and "$EC_{50}$" values are concentrations of an agent, in a combination of a 4-acylaminopyridine derivative with one or more other neurogenic agents, that reduce and promote, respectively, neurogenesis or another physiological activity (e.g., the activity of a receptor) to a half-maximal level. $IC_{50}$ and $EC_{50}$ values can be assayed in a variety of environments, including cell-free environments, cellular environments (e.g., cell culture assays), multicellular environments (e.g., in tissues or other multicellular structures), and/or in vivo. In some embodiments, one or more neurogenesis modulating agents in a combination or method disclosed herein individually have $IC_{50}$ or $EC_{50}$ values of less than about 10 µM, less than about 1 µM, or less than about 0.1 µM or lower. In other embodiments, an agent in a combination has an $IC_{50}$ of less than about 50 nM, less than about 10 nM, or less than about 1 nM or lower.

In some embodiments, selectivity of one or more agents, in a combination of a 4-acylaminopyridine derivative with one or more other neurogenic agents, is individually measured as the ratio of the $IC_{50}$ or $EC_{50}$ value for a desired effect (e.g., modulation of neurogenesis) relative to the $IC_{50}/EC_{50}$ value for an undesired effect. In some embodiments, a "selective" agent in a combination has a selectivity of less than about 1:2, less than about 1:10, less than about 1:50, or less than about 1:100. In some embodiments, one or more agents in a combination individually exhibits selective activity in one or more organs, tissues, and/or cell types relative to another organ, tissue, and/or cell type. For example, in some embodiments, an agent in a combination selectively modulates neurogenesis in a neurogenic region of the brain, such as the hippocampus (e.g., the dentate gyrus), the subventricular zone, and/or the olfactory bulb.

In other embodiments, modulation by a combination of agents is in a region containing neural cells affected by disease or injury, region containing neural cells associated with disease effects or processes, or region containing neural cells affect other event injurious to neural cells. Non-limiting examples of such events include stroke or radiation therapy of the region. In additional embodiments, a neuromodulating combination substantially modulates two or more physiological activities or target molecules, while being substantially inactive against one or more other molecules and/or activities.

In some embodiments, a neuromodulating combination as used herein includes a neurogenesis modulating agent, as defined herein, that elicits an observable neurogenic response by producing, generating, stabilizing, or increasing the retention of an intermediate agent which, results in the neurogenic response, optionally when contacted with an agent of the combination. As used herein, "increasing the retention of" or variants of that phrase or the term "retention" refer to decreasing the degradation of, or increasing the stability of, an intermediate agent.

In some cases, a 4-acylaminopyridine derivative in combination with one or more other neurogenic agents results in improved efficacy, fewer side effects, lower effective dosages in one or both actives, less frequent dosing, and/or other desirable effects relative to use of the neurogenesis modulating agents individually (such as at higher doses), due, e.g., to synergistic activities and/or the targeting of molecules and/or activities that are differentially expressed in particular tissues and/or cell-types. Preferably, the neurogenic agent, in combination, has a lower dosage than when used or administered alone.

The disclosed embodiments include methods of modulating neurogenesis by contacting one or more neural cells with a 4-acylaminopyridine derivative in combination with one or more other neurogenic agents. The amount of such a combination may be selected to be effective to produce an improvement in a treated subject, or detectable neurogenesis in vitro. In some embodiments, the amount is one that also minimizes clinical side effects seen with administration of the inhibitor to a subject. The amount of a 4-acylaminopyridine derivative used in vivo may be about 50%, about 45%, about 40%, about 35%, about 30%, about 25%, about 20%, about 18%, about 16%, about 14%, about 12%, about 10%, about 8%, about 6%, about 4%, about 2%, or about 1% or less of the maximum tolerated dose for a subject, given its use in a combination as described herein. This is readily determined for each a 4-acylaminopyridine derivative that has been in clinical use or testing, such as in humans.

Without being bound by theory, and while some 4-acylaminopyridine derivatives have been contemplated in connection to inhibition of acetylcholinesterase (AChE) activity, the instant invention is not believed to be related to AChE inhibition because MKC-231 does not have such inhibitory activity. It is believed, however, that the neurogenic action of MKC-231 may be partially through AMPA or nootropic potentiation or sensitization. These beliefs are offered to improve the understanding of the invention and do not necessarily limit the invention.

In further embodiments, and if compared to a reduced level of cognitive function, a method of the invention may be for enhancing or improving the reduced cognitive function in a subject or patient. The method may comprise administering a 4-acylaminopyridine derivative in combination with one or more other neurogenic agents to a subject or patient to enhance or improve a decline or decrease of cognitive function.

Administration of a 4-acylaminopyridine derivative in combination with one or more other neurogenic agents may be before, after, or concurrent with, another agent, condition, or therapy. In some embodiments, the overall combination may be of a 4-acylaminopyridine derivative in combination with one or more other neurogenic agents.

Methods described herein may also be used to treat a subject or patient of the disclosure for a mood disorder. Various mood disorders are described herein. In some embodiments, a method of treating a mood disorder comprises administering a 4-acylaminopyridine derivative in combination with one or more other neurogenic agents to a subject or patient that is a) under treatment with a cytotoxic anti-cancer therapy or b) diagnosed as having epilepsy, a condition associated with epilepsy, or seizures associated with epilepsy. The administering is of agent(s) in amounts sufficient or effective to produce an improvement in the disorder. Non-limiting examples of mood disorders include depression, anxiety, hypomania, panic attacks, excessive elation, seasonal mood (or affective) disorder, schizophrenia and other psychoses, lissencephaly syndrome, anxiety syndromes, anxiety disorders, phobias, stress and related syndromes, aggression, non-senile dementia, post-pain depression, and combinations thereof.

Where a neural cell is contacted with a 4-acylaminopyridine derivative in combination with one or more other neurogenic agents, the method may be to increase neurodifferentiation. This may be considered a method to potentiate a neural cell for proliferation and thus neurogenesis via the derivative or other agent(s) in the combination. Thus the disclosure includes a method of maintaining, stabilizing, stimulating, or increasing neurodifferentiation in a cell or tissue. The method may comprise contacting a cell or tissue with a 4-acylaminopyridine derivative in combination with one or more other neurogenic agents to maintain, stabilize, stimulate, or increase neurodifferentiation in the cell or tissue.

In some embodiments, the method may comprise contacting the cell or tissue with a 4-acylaminopyridine derivative in combination with one or more other neurogenic agents where the derivative and/or other agent(s) stimulates or increases proliferation or cell division in a neural cell. A method comprising such a combination may be used to produce neurogenesis (in this case both neurodifferentiation and/or proliferation) in a population of neural cells. In some cases, the cell or tissue is in an animal subject or a human patient. In additional embodiments, the cell or tissue is in a human patient treated with chemotherapy and/or radiation; a human patient diagnosed as having cancer; or in a human patient diagnosed as having epilepsy, a condition associated with epilepsy, or seizures associated with epilepsy. Alternatively, the subject or patient is in need of neurogenesis or has been diagnosed with a disease, condition, or injury of the central or peripheral nervous system as described herein.

The amount of a combination of a 4-acylaminopyridine derivative and one or more other neurogenic agents may be an amount that also potentiates or sensitizes, such as by activating or inducing cells to differentiate, a population of neural cells for neurogenesis. The degree of potentiation or sensitization for neurogenesis may be determined with use of the combination in any appropriate neurogenesis assay, including, but not limited to, a neuronal differentiation assay described herein. In some embodiments, the amount of a combination of a 4-acylaminopyridine derivative with one or more other neurogenic agents is based on the highest amount of one agent in a combination, which amount produces no detectable neuroproliferation in vitro but yet produces neurogenesis, or a measurable shift in efficacy in promoting neurogenesis in vitro, when used in the combination. In other embodiments, the amount of a 4-acylaminopyridine derivative and/or other agent(s) in a combination used in vivo may be about 50%, about 45%, about 40%, about 35%, about 30%, about 25%, about 20%, about 18%, about 16%, about 14%, about 12%, about 10%, about 8%, about 6%, about 4%, about 2%, or about 1% or less than the maximum tolerated dose for a subject. Non-limiting examples of subjects include both human beings and animals in assays for behavior linked to neurogenesis. Exemplary animal assays are known to the skilled person in the field.

Alternatively, the amount of a combination of a 4-acylaminopyridine derivative and one or more other neurogenic agents may be an amount selected to be effective to produce an improvement in a treated subject based on detectable neurogenesis in vitro as described above. In some embodiments, such as in the case of a known neurogenic agent in a combination of the disclosure, the amount is one that minimizes clinical side effects seen with administration of the agent to a subject. The amount of an agent used in vivo may be about 50%, about 45%, about 40%, about 35%, about 30%, about 25%, about 20%, about 18%, about 16%, about 14%, about 12%, about 10%, about 8%, about 6%, about 4%, about 2%, or about 1% or less of the maximum tolerated dose in terms of acceptable side effects for a subject. This is readily determined for each 4-acylaminopyridine derivative or other agent(s) of a combination disclosed herein as well as those that have been in clinical use or testing, such as in humans.

In other embodiments, the amount of an additional neurogenic sensitizing agent in a combination of the disclosure is the highest amount which produces no detectable neurogenesis in vitro, including in animal (or non-human) models for behavior linked to neurogenesis, but yet produces neurogenesis, or a measurable shift in efficacy in promoting neurogenesis in the in vitro assay, when used in combination with a 4-acylaminopyridine derivative. Alternative embodiments include amounts which produce about 1%, about 2%, about 4%, about 6%, about 8%, about 10%, about 12%, about 14%, about 16%, about 18%, about 20%, about 25%, about 30%, about 35%, or about 40% or more of the neurogenesis seen with the amount that produces the highest level of neurogenesis in an in vitro assay.

As described herein, the disclosed embodiments include methods of using a 4-acylaminopyridine derivative in combination with one or more other neurogenic agents at a level at which neurogenesis occurs. The amount of a 4-acylaminopyridine derivative in combination with one or more other neurogenic agents may be any that is effective to produce neurogenesis, optionally with reduced or minimized amounts of astrogenesis. In some embodiments, the amount may be the lowest needed to produce a desired, or minimum, level of detectable neurogenesis or beneficial effect.

In methods of increasing neurogenesis by contacting cells with a 4-acylaminopyridine derivative in combination with one or more other neurogenic agents, the cells may be in vitro or in vivo. In some embodiments, the cells are present in a tissue or organ of a subject animal or human being. The cells are those capable of neurogenesis, such as to result, whether by direct differentiation or by proliferation and differentiation, in differentiated neuronal or glial cells.

In applications to an animal or human being, the embodiments relate to a method of bringing cells into contact with a 4-acylaminopyridine derivative in combination with one or more other neurogenic agents in effective amounts to result in an increase in neurogenesis in comparison to the absence of the combination. A non-limiting example is in the administration of the combination to the animal or human being. Such contacting or administration may also be described as exogenously supplying the combination to a cell or tissue.

In some embodiments, the term "animal" or "animal subject" refers to a non-human mammal, such as a primate, canine, or feline. In other embodiments, the terms refer to an animal that is domesticated (e.g. livestock) or otherwise subject to human care and/or maintenance (e.g. zoo animals and other animals for exhibition). In other non-limiting examples, the terms refer to ruminants or carnivores, such as dogs, cats, birds, horses, cattle, sheep, goats, marine animals and mammals, penguins, deer, elk, and foxes.

The disclosed embodiments also relate to methods of treating diseases, disorders, and conditions of the central and/or peripheral nervous systems (CNS and PNS, respectively) by administering a 4-acylaminopyridine derivative in combination with one or more other neurogenic agents. As used herein, "treating" includes prevention, amelioration, alleviation, and/or elimination of the disease, disorder, or condition being treated or one or more symptoms of the disease, disorder, or condition being treated, as well as improvement in the overall well being of a patient, as measured by objective and/or subjective criteria. In some embodiments, treating is used for reversing, attenuating, minimizing, suppressing, or halting undesirable or deleterious effects of, or effects from the progression of, a disease, disorder, or condition of the central and/or peripheral nervous systems. In other embodiments, the method of treating may be advantageously used in cases where additional neurogenesis would replace, replenish, or increase the numbers of cells lost due to injury or disease as non-limiting examples.

The amount of a 4-acylaminopyridine derivative in combination with one or more other neurogenic agents may be any that results in a measurable relief of a disease condition like those described herein. As a non-limiting example, an improvement in the Hamilton depression scale (HAM-D) score for depression may be used to determine (such as quantitatively) or detect (such as qualitatively) a measurable level of improvement in the depression of a subject.

Non-limiting examples of symptoms that may be treated with the methods described herein include abnormal behavior, abnormal movement, hyperactivity, hallucinations, acute delusions, combativeness, hostility, negativism, withdrawal, seclusion, memory defects, sensory defects, cognitive defects, and tension. Non-limiting examples of abnormal behavior include irritability, poor impulse control, distractibility, and aggressiveness. Outcomes from treatment with the disclosed methods include improvements in cognitive function or capability in comparison to the absence of treatment.

In some embodiments, the methods of the disclosure comprise contacting a cell with a 4-acylaminopyridine derivative, or administering such a derivative to a subject, to result in neurogenesis. Some embodiments comprise the use of one derivative, such as MKC-231, in combination with one or more other neurogenic agents. In other embodiments, a combination of two or more derivatives, such as MKC-231 and another derivative, is used in combination with one or more other neurogenic agents.

In some embodiments, the 4-acylaminopyridine derivative used in the methods described herein are substantially inactive with respect to other receptors, such as muscarinic receptors, nicotinic receptors, dopamine receptors, and opioid receptors as non-limiting examples.

In some embodiments, a 4-acylaminopyridine derivative in combination with one or more other neurogenic agents is administered to an animal or human subject to result in neurogenesis. A combination may thus be used to treat a disease, disorder, or condition as described herein. In other embodiments, the combination may be used to increase neurogenesis in vitro.

A 4-acylaminopyridine derivative for use in embodiments of the invention includes MKC-231 as described above. MKC-231 is represented by the following structure:

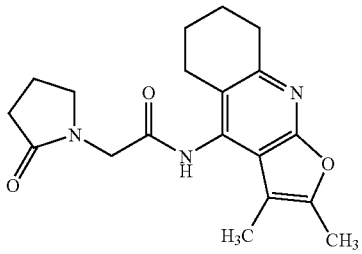

In some embodiments, a 4-acylaminopyridine derivative is one disclosed in U.S. Pat. Nos. 5,536,728 and 5,397,785; or a polymorph crystal form as disclosed in U.S. Pat. No. 6,884,805. Structures, biological activity data, methods for obtaining biological activity data, methods of synthesis, modes of administration and pharmaceutical formulations for such compounds are disclosed therein.

The ability of a substance to crystallize with more than one crystal structure is known as polymorphism, and a particular crystal form is called a polymorph. Different polymorphs of the same compound can have quite different physical properties, such as shelf-life and solubility. Some of these differences in physical properties can lead to differences in efficacy. Two crystal forms of MKC-231 have been identified as shown in U.S. Pat. No. 6,884,805.

The invention provides an essentially pure version of either crystal form. The term "essentially pure" means that either form contains less than 10 weight percent of the other polymorph form, preferably less than 5 weight percent. The percentages refer to any other polymorph form that may exist in addition to the two polymorphs identified.

Methods for assessing the nature and/or degree of neurogenesis in vivo and in vitro, for detecting changes in the nature and/or degree of neurogenesis, for identifying neurogenesis modulating agents, for isolating and culturing neural stem cells, and for preparing neural stem cells for transplantation or other purposes are disclosed, for example, in U.S. Published Application No. 2007/0015138, and U.S. Publication Application Nos. 2005/0009742 and 2005/0009847, 2005/0032702, 2005/0031538, 2005/0004046, 2004/0254152, 2004/0229291, and 2004/0185429, all of which are herein incorporated by reference in their entirety.

As disclosed herein, neurogenesis includes the differentiation of neural cells along different potential lineages. In some embodiments, the differentiation of neural stem or progenitor cells is along a neuronal and/or glial cell lineage, optionally to the exclusion of differentiation along an astrocyte lineage.

A 4-acylaminopyridine derivative as described herein includes pharmaceutically acceptable salts, derivatives, prodrugs, and metabolites of the derivative. Methods for preparing and administering salts, isomers, polymorphs, derivatives, prodrugs, and metabolites of various derivatives are well known in the art.

Compounds described herein that contain a chiral center include all possible stereoisomers of the compound, including compositions comprising the racemic mixture of the two enantiomers, as well as compositions comprising each enantiomer individually, substantially free of the other enantiomer. Thus, for example, contemplated herein is a composition comprising the S enantiomer of a compound substantially free of the R enantiomer, or the R enantiomer substantially free of the S enantiomer. If the named compound comprises more than one chiral center, the scope of the present disclosure also includes compositions comprising mixtures of varying proportions between the diastereomers, as well as compositions comprising one or more diastereomers substantially free of one or more of the other diastereomers. By "substantially free" it is meant that the composition comprises less than 25%, 15%, 10%, 8%, 5%, 3%, or less than 1% of the minor enantiomer or diastereomer(s). Methods for synthesizing, isolating, preparing, and administering various stereoisomers are known in the art.

General

Methods described herein can be used to treat any disease or condition for which it is beneficial to promote or otherwise stimulate or increase neurogenesis. One focus of the methods described herein is to achieve a therapeutic result by increasing neurogenesis. Thus, certain methods described herein can be used to treat any disease or condition susceptible to treatment by increasing neurogenesis.

In some embodiments, a disclosed method is applied to modulating neurogenesis in vivo, in vitro, or ex vivo. In in vivo embodiments, the cells may be present in a tissue or organ of a subject animal or human being. Non-limiting examples of cells include those capable of neurogenesis, such as to result, whether by differentiation or by a combination of differentiation and proliferation, in differentiated neural cells. As described herein, neurogenesis includes the differentiation of neural cells along different potential lineages. In some embodiments, the differentiation of neural stem or progenitor cells is along a neuronal cell lineage to produce neurons. In other embodiments, the differentiation is along both neuronal and glial cell lineages. In additional embodiments, the disclosure further includes differentiation along a neuronal cell lineage to the exclusion of one or more cell types in a glial cell lineage. Non-limiting examples of glial cell types include oligodendrocytes and radial glial cells, as well as astrocytes, which have been reported as being of an "astroglial lineage". Therefore, embodiments of the disclosure include differentiation along a neuronal cell lineage to the exclusion of one or more cell types selected from oligodendrocytes, radial glial cells, and astrocytes.

In other embodiments, the disease or condition being treated is associated with pain and/or addiction, but in contrast to known methods, the disclosed treatments are substantially mediated by increasing neurogenesis. For example, in some embodiments, methods described herein involve increasing neurogenesis ex vivo, such that a composition containing neural stem cells, neural progenitor cells, and/or differentiated neural cells can subsequently be administered to an individual to treat a disease or condition. In some embodiments, methods described herein allow treatment of diseases characterized by pain, addiction, and/or depression to be treated by directly replenishing, replacing, and/or supplementing neurons and/or glial cells. In further embodiments, methods described herein enhance the growth and/or survival of existing neural cells, and/or slow or reverse the loss of such cells in a neurodegenerative condition.

Examples of diseases and conditions treatable by the methods described herein include, but are not limited to, neurodegenerative disorders and neural disease, such as dementias (e.g., senile dementia, memory disturbances/memory loss, dementias caused by neurodegenerative disorders (e.g., Alzheimer's, Parkinson's disease, Parkinson's disorders, Huntington's disease (Huntington's Chorea), Lou Gehrig's disease, multiple sclerosis, Pick's disease, Parkinsonism dementia syndrome), progressive subcortical gliosis, progressive supranuclear palsy, thalmic degeneration syndrome, hereditary aphasia, amyotrophic lateral sclerosis, Shy-Drager syndrome, and Lewy body disease; vascular conditions (e.g., infarcts, hemorrhage, cardiac disorders); mixed vascular and Alzheimer's; bacterial meningitis; Creutzfeld-Jacob Disease; and Cushing's disease.

The disclosed embodiments also provide for the treatment of a nervous system disorder related to neural damage, cellular degeneration, a psychiatric condition, cellular (neurological) trauma and/or injury (e.g., subdural hematoma or traumatic brain injury), toxic chemicals (e.g., heavy metals, alcohol, some medications), CNS hypoxia, or other neurologically related conditions. In practice, the disclosed compositions and methods may be applied to a subject or patient afflicted with, or diagnosed with, one or more central or peripheral nervous system disorders in any combination. Diagnosis may be performed by a skilled person in the applicable fields using known and routine methodologies which identify and/or distinguish these nervous system disorders from other conditions.

Non-limiting examples of nervous system disorders related to cellular degeneration include neurodegenerative disorders, neural stem cell disorders, neural progenitor cell disorders, degenerative diseases of the retina, and ischemic disorders. In some embodiments, an ischemic disorder comprises an insufficiency, or lack, of oxygen or angiogenesis, and non-limiting example include spinal ischemia, ischemic stroke, cerebral infarction, multi-infarct dementia. While these conditions may be present individually in a subject or patient, the disclosed methods also provide for the treatment of a subject or patient afflicted with, or diagnosed with, more than one of these conditions in any combination.

In additional embodiments, the disclosure includes a method of stimulating or increasing neurogenesis in a subject or patient with stimulation of angiogenesis in the subject or patient. The co-stimulation may be used to provide the differentiating and/or proliferating cells with increased access to the circulatory system. The neurogenesis is produced by the 4-acylaminopyridine compound, optionally in combination with one or more other neurogenic agents, as described herein. An increase in angiogenesis may be mediated by a means known to the skilled person, including administration of a angiogenic factor or treatment with an angiogenic therapy. Non-limiting examples of angiogenic factors or conditions include vascular endothelial growth factor (VEGF), angiopoietin-1 or -2, erythropoietin, exercise, or a combination thereof.

So in some embodiments, the disclosure includes a method comprising administering i) a 4-acylaminopyridine, optionally in combination with one or more other neurogenic agents, and ii) one or more angiogenic factors to a subject or patient. In other embodiments, the disclosure includes a method comprising administering i) a 4-acylaminopyridine, optionally in combination with one or more other neurogenic agents, to a subject or patient with ii) treating said subject or patient with one or more angiogenic conditions. The subject or patient may be any as described herein.

The co-treatment of a subject or patient includes simultaneous treatment or sequential treatment as non-limiting examples. In cases of sequential treatment, the administration of a 4-acylaminopyridine, optionally with one or more other neurogenic agents, may be before or after the administration of an angiogenic factor or condition.

Non-limiting embodiments of nervous system disorders related to a psychiatric condition include neuropsychiatric disorders and affective disorders. As used herein, an affective disorder refers to a disorder of mood such as, but not limited to, depression, post-traumatic stress disorder (PTSD), hypo- mania, panic attacks, excessive elation, bipolar depression, bipolar disorder (manic-depression), and seasonal mood (or affective) disorder. Other non-limiting embodiments include schizophrenia and other psychoses, lissencephaly syndrome, anxiety syndromes, anxiety disorders, phobias, stress and related syndromes (e.g., panic disorder, phobias, adjustment disorders, migraines), cognitive function disorders, aggression, drug and alcohol abuse, drug addiction, and drug-induced neurological damage, obsessive compulsive behavior syndromes, borderline personality disorder, non-senile dementia, post-pain depression, postpartum depression, and cerebral palsy.

In other embodiments, and if compared to a reduced level of cognitive function, a method of the invention may be for enhancing or improving the reduced cognitive function in a subject or patient. The method may comprise administering a 4-acylaminopyridine agent, optionally in combination with one or more other neurogenic agents, to a subject or patient to enhance, or improve a decline or decrease, of cognitive function due to a therapy and/or condition that reduces cognitive function. Other methods of the disclosure include treatment to affect or maintain the cognitive function of a subject or patient. In some embodiments, the maintenance or stabilization of cognitive function may be at a level, or thereabouts, present in a subject or patient in the absence of a therapy and/or condition that reduces cognitive function. In alternative embodiments, the maintenance or stabilization may be at a level, or thereabouts, present in a subject or patient as a result of a therapy and/or condition that reduces cognitive function.

In further embodiments, and if compared to a reduced level of cognitive function due to a therapy and/or condition that reduces cognitive function, a method of the invention may be for enhancing or improving the reduced cognitive function in a subject or patient. The method may comprise administering a 4-acylaminopyridine agent, or a combination thereof with one or more other neurogenic agents, to a subject or patient to enhance or improve a decline or decrease of cognitive function due to the therapy or condition. The administering may be in combination with the therapy or condition.

These methods optionally include assessing or measuring cognitive function of the subject or patient before, during, and/or after administration of the treatment to detect or determine the effect thereof on cognitive function. So in one embodiment, a methods may comprise i) treating a subject or patient that has been previously assessed for cognitive function and ii) reassessing cognitive function in the subject or patient during or after the course of treatment. The assessment may measure cognitive function for comparison to a control or standard value (or range) in subjects or patients in the absence of a 4-acylaminopyridine agent, or a combination thereof with one or more other neurogenic agents. This may be used to assess the efficacy of a 4-acylaminopyridine agent, alone or in a combination, in alleviating the reduction in cognitive function.

Examples of nervous system disorders related to cellular or tissue trauma and/or injury include, but are not limited to, neurological traumas and injuries, surgery related trauma and/or injury, retinal injury and trauma, injury related to epilepsy, cord injury, spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxin, and spinal cord injury related to environmental toxin.

Non-limiting examples of nervous system disorders related to other neurologically related conditions include learning disorders, memory disorders, age-associated memory impairment (AAMI) or age-related memory loss, autism, learning or attention deficit disorders (ADD or attention deficit hyperactivity disorder, ADHD), narcolepsy, sleep disorders and sleep deprivation (e.g., insomnia, chronic fatigue syndrome), cognitive disorders, epilepsy, injury related to epilepsy, and temporal lobe epilepsy.

Other non-limiting examples of diseases and conditions treatable by the methods described herein include, but are not limited to, hormonal changes (e.g., depression and other mood disorders associated with puberty, pregnancy, or aging (e.g., menopause)); and lack of exercise (e.g., depression or other mental disorders in elderly, paralyzed, or physically handicapped patients); infections (e.g., HIV); genetic abnormalities (down syndrome); metabolic abnormalities (e.g., vitamin B12 or folate deficiency); hydrocephalus; memory loss separate from dementia, including mild cognitive impairment (MCI), age-related cognitive decline, and memory loss resulting from the use of general anesthetics, chemotherapy, radiation treatment, post-surgical trauma, or therapeutic intervention; and diseases of the of the peripheral nervous system (PNS), including but not limited to, PNS neuropathies (e.g., vascular neuropathies, diabetic neuropathies, amyloid neuropathies, and the like), neuralgias, neoplasms, myelin-related diseases, etc.

Additionally, the disclosed methods provide for the application of a 4-acylaminopyridine derivative in combination with one or more other neurogenic agents to treat a subject or patient for a condition due to the anti-neurogenic effects of an opiate or opioid based analgesic. In some embodiments, the administration of an opiate or opioid based analgesic, such as an opiate like morphine or other opioid receptor agonist, to a subject or patient results in a decrease in, or inhibition of, neurogenesis. The administration of a 4-acylaminopyridine derivative in combination with one or more other neurogenic agents with an opiate or opioid based analgesic would reduce the anti-neurogenic effect. One non-limiting example is administration of such a combination with an opioid receptor agonist after surgery (such as for the treating post-operative pain).

So the disclosed embodiments include a method of treating post operative pain in a subject or patient by combining administration of an opiate or opioid based analgesic with a 4-acylaminopyridine derivative in combination with one or more other neurogenic agents. The analgesic may have been administered before, simultaneously with, or after the combination. In some cases, the analgesic or opioid receptor agonist is morphine or another opiate.

Other disclosed embodiments include a method to treat or prevent decreases in, or inhibition of, neurogenesis in other cases involving use of an opioid receptor agonist. The methods comprise the administration of a 4-acylaminopyridine derivative in combination with one or more other neurogenic agents as described herein. Non-limiting examples include cases involving an opioid receptor agonist, which decreases or inhibits neurogenesis, and drug addiction, drug rehabilitation, and/or prevention of relapse into addiction. In some embodiments, the opioid receptor agonist is morphine, opium or another opiate.

Combinations and compositions disclosed herein can also be used to treat diseases of the peripheral nervous system (PNS), including but not limited to, PNS neuropathies (e.g., vascular neuropathies, diabetic neuropathies, amyloid neuropathies, and the like), neuralgias, neoplasms, myelin-related diseases, etc.

Other conditions that can be beneficially treated by increasing neurogenesis are known in the art (see e.g., U.S. Publication Nos. 2002/0106731, 2005/0009742 and 2005/0009847, 2005/0032702, 2005/0031538, 2005/0004046, 2004/0254152, 2004/0229291, and 2004/0185429).

In some embodiments, a 4-acylaminopyridine derivative in combination with one or more other neurogenic agents used in the methods described herein, is in the form of a composition that includes at least one pharmaceutically acceptable carrier or excipient. As used herein, the term "pharmaceutically acceptable excipient" includes any excipient known in the field as suitable for pharmaceutical application. Suitable pharmaceutical excipients and formulations are known in the art and are described, for example, in Remington's Pharmaceutical Sciences (19th ed.) (Genarro, ed. (1995) Mack Publishing Co., Easton, Pa.). Preferably, pharmaceutical carriers are chosen based upon the intended mode of administration of a 4-acylaminopyridine derivative in combination with one or more other neurogenic agents. The pharmaceutically acceptable carrier may include, for example, disintegrants, binders, lubricants, glidants, emollients, humectants, thickeners, silicones, flavoring agents, and water.

A 4-acylaminopyridine derivative in combination with one or more other neurogenic agents may be incorporated with excipients and administered in the form of ingestible tablets, buccal tablets, troches, capsules, elixirs, suspensions, syrups, wafers, or any other form known in the pharmaceutical arts. The pharmaceutical compositions may also be formulated in a sustained release form. Sustained release compositions, enteric coatings, and the like are known in the art. Alternatively, the compositions may be a quick release formulation.

In some embodiments, methods of treatment disclosed herein comprise the step of administering to a mammal a 4-acylaminopyridine derivative in combination with one or more other neurogenic agents for a time and at a concentration sufficient to treat the condition targeted for treatment. The disclosed methods can be applied to individuals having, or who are likely to develop, disorders relating to neural degeneration, neural damage and/or neural demyelination. In some embodiments, a method comprises selecting a population or sub-population of patients, or selecting an individual patient, that is more amenable to treatment and/or less susceptible to side effects than other patients having the same disease or condition. For example, in some embodiments, a sub-population of patients is identified as being more amenable to neurogenesis with a 4-acylaminopyridine derivative in combination with one or more other neurogenic agents by taking a cell or tissue sample from prospective patients, isolating and culturing neural cells from the sample, and determining the effect of the combination on the degree or nature of neurogenesis, thereby allowing selection of patients for whom the combination has a substantial effect on neurogenesis. Advantageously, the selection step(s) results in more effective treatment for the disease or condition that known methods using the same or similar compounds.

In other embodiments, methods described herein involve modulating neurogenesis ex vivo with a 4-acylaminopyridine derivative in combination with one or more other neurogenic agents such that a composition containing neural stem cells, neural progenitor cells, and/or differentiated neural cells can subsequently be administered to an individual to treat a disease or condition. In some embodiments, the method of treatment comprises the steps of contacting a neural stem cell or progenitor cell with a 4-acylaminopyridine derivative in combination with one or more other neurogenic agents to modulate neurogenesis, and transplanting the cells into a patient in need of treatment. Methods for transplanting stem and progenitor cells are known in the art, and are described, e.g., in U.S. Pat. Nos. 5,928,947; 5,817,773; and 5,800,539, and PCT Publication Nos. WO 01/176507 and WO 01/170243, all of which are incorporated herein by reference in their entirety. In some embodiments, methods described herein allow treatment of diseases or conditions by directly replenishing, replacing, and/or supplementing damaged or dysfunctional neurons. In further embodiments, methods described herein enhance the growth and/or survival of existing neural cells, and/or slow or reverse the loss of such cells in a neurodegenerative or other condition.

In alternative embodiments, the method of treatment comprises identifying, generating, and/or propagating neural cells ex vivo in contact with a 4-acylaminopyridine derivative in combination with one or more other neurogenic agents and transplanting the cells into a subject. In another embodiment, the method of treatment comprises the steps of contacting a neural stem cell of progenitor cell with a 4-acylaminopyridine derivative in combination with one or more other neurogenic agents to stimulate neurogenesis, and transplanting the cells into a patient in need of treatment. Also disclosed are methods for preparing a population of neural stem cells suitable for transplantation, comprising culturing a population of neural stem cells (NSCs) in vitro, and contacting the cultured neural stem cells with a 4-acylaminopyridine derivative in combination with one or more other neurogenic agents described herein. The disclosure further includes methods of treating the diseases, disorders, and conditions described herein by transplanting such cells into a subject or patient.

Methods described herein may comprise administering to the subject an effective amount of a 4-acylaminopyridine derivative in combination with one or more other neurogenic agents, or pharmaceutical composition comprising the combination.

In general, an effective amount of a combination in the disclosed methods is an amount sufficient, when used as described herein, to stimulate or increase neurogenesis in the subject targeted for treatment when compared to the absence of the combination. An effective amount of a combination may vary based on a variety of factors, including but not limited to, the activity of the active compounds, the physiological characteristics of the subject, the nature of the condition to be treated, and the route and/or method of administration. General dosage ranges of certain compounds are provided herein and in the cited references based on animal models of CNS diseases and conditions. Various conversion factors, formulas, and methods for determining human dose equivalents of animal dosages are known in the art, and are described, e.g., in Freireich et al., Cancer Chemother Repts 50(4): 219 (1966), Monro et al., Toxicology Pathology, 23: 187-98 (1995), Boxenbaum and Dilea, J. Clin. Pharmacol. 35: 957-966 (1995), and Voisin et al., Reg. Toxicol. Pharmacol., 12(2): 107-116 (1990), which are herein incorporated by reference.

The disclosed methods typically involve the administration of a 4-acylaminopyridine derivative in combination with one or more other neurogenic agents in a dosage range of 0.001 ng/kg/day to 500 ng/kg/day, or in a dosage range of 0.05 to 200 ng/kg/day. However, as understood by those skilled in the art, the exact dosage of a a 4-acylaminopyridine derivative in combination with one or more other neurogenic agents used to treat a particular condition will vary in practice due to a wide variety of factors. Accordingly, dosage guidelines provided herein are not intended to be inclusive of the range of actual dosages, but rather provide guidance to skilled practitioners in selecting dosages useful in the empirical determination of dosages for individual patients. Advantageously, methods described herein allow treatment of one or more conditions with reductions in side effects, dosage levels, dosage frequency, treatment duration, safety, tolerability, and/or other factors.

In some embodiments, an effective, neurogenesis modulating amount of a combination of a 4-acylaminopyridine derivative with one or more other neurogenic agents is an amount of each agent (in a combination) that achieves a concentration within the target tissue, using the particular mode of administration, at or above the $IC_{50}$ or $EC_{50}$ for activity of target molecule or physiological process. In some cases, a combination of a 4-acylaminopyridine derivative and one or more other neurogenic agents is administered in a manner and dosage that gives a peak concentration of about 1, about 1.5, about 2, about 2.5, about 5, about 10, about 20 or more times the $IC_{50}$ or $EC_{50}$ concentration of one or more of the agents in the combination. $IC_{50}$ and $EC_{50}$ values and bioavailability data for a 4-acylaminopyridine derivative and other agent(s) described herein are known in the art, and are described, e.g., in the references cited herein or can be readily determined using established methods. In addition, methods for determining the concentration of a free compound in plasma and extracellular fluids in the CNS, as well pharmacokinetic properties, are known in the art, and are described, e.g., in de Lange et al., AAPS Journal, 7(3): 532-543 (2005). In some embodiments, a combination of a 4-acylaminopyridine derivative and one or more other neurogenic agents described herein is administered, as a combination or separate agents used together, at a frequency of at least about once daily, or about twice daily, or about three or more times daily, and for a duration of at least about 3 days, about 5 days, about 7 days, about 10 days, about 14 days, or about 21 days, or for about 4 weeks or more.

In other embodiments, an effective, neurogenesis modulating amount is a dose that produces a concentration of a 4-acylaminopyridine derivative and/or other agent(s) of a combination in an organ, tissue, cell, and/or other region of interest that includes the $ED_{50}$ (the pharmacologically effective dose in 50% of subjects) with little or no toxicity. $IC_{50}$ and $EC_{50}$ values for the modulation of neurogenesis can be determined using methods described in U.S. Published Application No. 2007/0015138, incorporated by reference, or by other methods known in the art. In some embodiments, the $IC_{50}$ or $EC_{50}$ concentration for the modulation of neurogenesis is substantially lower than the $IC_{50}$ or $EC_{50}$ concentration for activity of a 4-acylaminopyridine derivative and/or other agent(s) of a combination at non-targeted molecules and/or physiological processes.

In some methods described herein, the application of a 4-acylaminopyridine derivative in combination with one or more other neurogenic agents may allow effective treatment with substantially fewer and/or less severe side effects compared to existing treatments. In some embodiments, combination therapy with a 4-acylaminopyridine derivative and one or more additional neurogenic agents allows the combination to be administered at dosages that would be sub-therapeutic when administered individually or when compared to other treatments. For example, the dosage used in combination could be 50% lower or even 90% lower than the dosage when used alone. In other embodiments, each agent in a combination of agents may be present in an amount that results in fewer and/or less severe side effects than that which occurs with a larger amount. Thus the combined effect of the neurogenic agents will provide a desired neurogenic activity while exhibiting fewer and/or less severe side effects overall. In further embodiments, methods described herein allow treatment of certain conditions for which treatment with the same or similar compounds is ineffective using known methods due, for example, to dose-limiting side effects, toxicity, and/or other factors.

Depending on the desired clinical result, the disclosed combinations of agents or pharmaceutical compositions are administered by any means suitable for achieving a desired effect. Various delivery methods are known in the art and can be used to deliver an agent to a subject or to NSCs or progenitor cells within a tissue of interest. The delivery method will depend on factors such as the tissue of interest, the nature of the compound (e.g., its stability and ability to cross the blood-brain barrier), and the duration of the experiment or treatment, among other factors. For example, an osmotic minipump can be implanted into a neurogenic region, such as the lateral ventricle. Alternatively, compounds can be administered by direct injection into the cerebrospinal fluid of the brain or spinal column, or into the eye. Compounds can also be administered into the periphery (such as by intravenous or subcutaneous injection, or oral delivery), and subsequently cross the blood-brain barrier.

In various embodiments, the disclosed agents or pharmaceutical compositions are administered in a manner that allows them to contact the subventricular zone (SVZ) of the lateral ventricles and/or the dentate gyrus of the hippocampus. Examples of routes of administration include parenteral, e.g., intravenous, intradermal, subcutaneous, oral (e.g., inhalation), transdermal (topical), transmucosal, and rectal administration. Intranasal administration generally includes, but is not limited to, inhalation of aerosol suspensions for delivery of compositions to the nasal mucosa, trachea and bronchioli.

In some embodiments, a combination of a 4-acylaminopyridine derivative and one or more other neurogenic agents is administered so as to either pass through or by-pass the blood-brain barrier. Methods for allowing factors to pass through the blood-brain barrier are known in the art, and include minimizing the size of the factor, providing hydrophobic factors which facilitate passage, and conjugation to a carrier molecule that has substantial permeability across the blood brain barrier. In some instances, the combination of compounds can be administered by a surgical procedure implanting a catheter coupled to a pump device. The pump device can also be implanted or be extracorporally positioned. Administration of a combination of a 4-acylaminopyridine derivative and one or more other neurogenic agents can be in intermittent pulses or as a continuous infusion. Devices for injection to discrete areas of the brain are known in the art. In certain embodiments, the combination is administered locally to the ventricle of the brain, substantia nigra, striatum, locus ceruleous, nucleus basalis Meynert, pedunculopontine nucleus, cerebral cortex, and/or spinal cord by, e.g., injection. Methods, compositions, and devices for delivering therapeutics, including therapeutics for the treatment of diseases and conditions of the CNS and PNS, are known in the art.

In some embodiments, a 4-acylaminopyridine derivative and/or other agent(s) in a combination is modified to facilitate crossing of the gut epithelium. For example, in some embodiments, a derivative or other agent(s) is a prodrug that is actively transported across the intestinal epithelium and metabolized into the active agent in systemic circulation and/or in the CNS.

In some embodiments, the delivery or targeting of a combination of a 4-acylaminopyridine derivative and one or more other neurogenic agents to a neurogenic region, such as the dentate gyrus or the subventricular zone, enhances efficacy and reduces side effects compared to known methods involving administration with the same or similar compounds.

In other embodiments, a 4-acylaminopyridine derivative and/or other agent(s) of a combination is conjugated to a targeting domain to form a chimeric therapeutic, where the targeting domain facilitates passage of the blood-brain barrier (as described above) and/or binds one or more molecular targets in the CNS. In some embodiments, the targeting domain binds a target that is differentially expressed or displayed on, or in close proximity to, tissues, organs, and/or cells of interest. In some cases, the target is preferentially distributed in a neurogenic region of the brain, such as the dentate gyrus and/or the SVZ. For example, in some embodiments, a 4-acylaminopyridine derivative and/or other agent(s) of a combination is conjugated or complexed with the fatty acid docosahexaenoic acid (DHA), which is readily transported across the blood brain barrier and imported into cells of the CNS.

In embodiments to treat subjects and patients, the methods include identifying a patient suffering from one or more disease, disorders, or conditions, or a symptom thereof, and administering to the subject or patient a 4-acylaminopyridine derivative in combination with one or more other neurogenic agents as described herein. The identification of a subject or patient as having one or more disease, disorder or condition, or a symptom thereof, may be made by a skilled practitioner using any appropriate means known in the field.

In some embodiments, identifying a patient in need of neurogenesis modulation comprises identifying a patient who has or will be exposed to a factor or condition known to inhibit neurogenesis, including but not limited to, stress, aging, sleep deprivation, hormonal changes (e.g., those associated with puberty, pregnancy, or aging (e.g., menopause), lack of exercise, lack of environmental stimuli (e.g., social isolation), diabetes and drugs of abuse (e.g., alcohol, especially chronic use; opiates and opioids; psychostimulants). In some embodiments, the patient has been identified as non-responsive to treatment with primary medications for the condition(s) targeted for treatment (e.g., non-responsive to antidepressants for the treatment of depression), and the 4-acylaminopyridine derivative containing combination is administered in a method for enhancing the responsiveness of the patient to a co-existing or pre-existing treatment regimen.

In other embodiments, the method or treatment comprises administering a combination of a primary medications for the condition(s) targeted for treatment and a 4-acylaminopyridine derivative in combination with one or more other neurogenic agents. For example, in the treatment of depression or related neuropsychiatric disorders, a combination may be administered in conjunction with, or in addition to, electroconvulsive shock treatment, a monoamine oxidase modulator, and/or a selective reuptake modulators of serotonin and/or norepinephrine.

In other embodiments, the patient in need of neurogenesis modulation suffers from premenstrual syndrome, post-partum depression, or pregnancy-related fatigue and/or depression, and the treatment comprises administering a therapeutically effective amount of a 4-acylaminopyridine derivative in combination with one or more other neurogenic agents. Without being bound by any particular theory, and offered to improve understanding of the invention, it is believed that levels of steroid hormones, such as estrogen, are increased during the menstrual cycle during and following pregnancy, and that such hormones can exert a modulatory effect on neurogenesis.

In some embodiments, the patient is a user of a recreational drug including but not limited to alcohol, amphetamines, PCP, cocaine, and opiates. Without being bound by any particular theory, and offered to improve understanding of the invention, it is believed that some drugs of abuse have a modulatory effect on neurogenesis, which is associated with depression, anxiety and other mood disorders, as well as deficits in cognition, learning, and memory. Moreover, mood disorders are causative/risk factors for substance abuse, and substance abuse is a common behavioral symptom (e.g., self medicating) of mood disorders. Thus, substance abuse and mood disorders may reinforce each other, rendering patients suffering from both conditions non-responsive to treatment. Thus, in some embodiments, a 4-acylaminopyridine derivative is used in combination with one or more other neurogenic agents to treat patients suffering from substance abuse and/or mood disorders. In various embodiments, the one or more additional agents can be an antidepressant, an antipsychotic, a mood stabilizer, or any other agent known to treat one or more symptoms exhibited by the patient. In some embodiments, a neurogenesis modulating agent exerts a synergistic effect with one or more additional agents on the treatment of substance abuse and/or mood disorders in patients suffering from both conditions.

In further embodiments, the patient is on a co-existing and/or pre-existing treatment regimen involving administration of one or more prescription medications having a modulatory effect on neurogenesis. For example, in some embodiments, the patient suffers from chronic pain and is prescribed one or more opiate/opioid medications; and/or suffers from ADD, ADHD, or a related disorder, and is prescribed a psychostimulant, such as ritalin, dexedrine, adderall, or a similar medication which inhibits neurogenesis. Without being bound by any particular theory, and offered to improve understanding of the invention, it is believed that such medications can exert a modulatory effect on neurogenesis, leading to depression, anxiety and other mood disorders, as well as deficits in cognition, learning, and memory. Thus, in some preferred embodiments, a 4-acylaminopyridine derivative in combination with one or more other neurogenic agents is administered to a patient who is currently or has recently been prescribed a medication that exerts a modulatory effect on neurogenesis, in order to treat depression, anxiety, and/or other mood disorders, and/or to improve cognition.

In additional embodiments, the patient suffers from chronic fatigue syndrome; a sleep disorder; lack of exercise (e.g., elderly, infirm, or physically handicapped patients); and/or lack of environmental stimuli (e.g., social isolation); and the treatment comprises administering a therapeutically effective amount of a 4-acylaminopyridine derivative in combination with one or more other neurogenic agents.

In more embodiments, the patient is an individual having, or who is likely to develop, a disorder relating to neural degeneration, neural damage and/or neural demyelination.

In yet additional embodiments, identifying a patient in need of neurogenesis modulation comprises selecting a population or sub-population of patients, or an individual patient, that is more amenable to treatment and/or less susceptible to side effects than other patients having the same disease or condition. In some embodiments, identifying a patient amenable to treatment with a 4-acylaminopyridine derivative in combination with one or more other neurogenic agents comprises identifying a patient who has been exposed to a factor known to enhance neurogenesis, including but not limited to, exercise, hormones or other endogenous factors, and drugs taken as part of a pre-existing treatment regimen. In some embodiments, a sub-population of patients is identified as being more amenable to neurogenesis modulation with a 4-acylaminopyridine derivative in combination with one or more other neurogenic agents by taking a cell or tissue sample from prospective patients, isolating and culturing neural cells from the sample, and determining the effect of the combination on the degree or nature of neurogenesis of the cells, thereby allowing selection of patients for which the therapeutic agent has a substantial effect on neurogenesis. Advantageously, the selection of a patient or population of patients in need of or amenable to treatment with a combination of the disclosure allows more effective treatment of the disease or condition targeted for treatment than known methods using the same or similar compounds.

In some embodiments, the patient has suffered a CNS insult, such as a CNS lesion, a seizure (e.g., electroconvulsive seizure treatment; epileptic seizures), radiation, chemotherapy and/or stroke or other ischemic injury. Without being bound by any particular theory, and offered to improve understanding of the invention, it is believed that some CNS insults/ injuries leads to increased proliferation of neural stem cells, but that the resulting neural cells form aberrant connections which can lead to impaired CNS function and/or diseases, such as temporal lobe epilepsy. In other embodiments, a 4-acylaminopyridine derivative in combination with one or more other neurogenic agents is administered to a patient who has suffered, or is at risk of suffering, a CNS insult or injury to stimulate neurogenesis. Advantageously, stimulation of the differentiation of neural stem cells with a 4-acylaminopyridine derivative in combination with one or more other neurogenic agents activates signaling pathways necessary for progenitor cells to effectively migrate and incorporate into existing neural networks or to block inappropriate proliferation.

In further embodiments, the methods may be used to treat a cell, tissue, or subject which is exhibiting decreased neurogenesis or increased neurodegeneration. In some cases, the cell, tissue, or subject is, or has been, subjected to, or contacted with, an agent that decreases or inhibits neurogenesis. One non-limiting example is a human subject that has been administered morphine or other agent which decreases or inhibits neurogenesis. Non-limiting examples of other agents include opiates and opioid receptor agonists, such as mu receptor subtype agonists, that inhibit or decrease neurogenesis.

Thus in additional embodiments, the methods may be used to treat subjects having, or diagnosed with, depression or other withdrawal symptoms from morphine or other agents which decrease or inhibit neurogenesis. This is distinct from the treatment of subjects having, or diagnosed with, depression independent of an opiate, such as that of a psychiatric nature, as disclosed herein. In further embodiments, the methods may be used to treat a subject with one or more chemical addiction or dependency, such as with morphine or other opiates, where the addiction or dependency is ameliorated or alleviated by an increase in neurogenesis.

In some embodiments, such as those for treating depression and other neurological diseases and conditions, the methods may comprise use of a combination of a 4-acylaminopyridine derivative and one or more agents reported as anti-depressant agents. Thus a method may comprise treatment with a 4-acylaminopyridine derivative, such as MKC-231, and one or more reported anti-depressant agents as known to the skilled person. Non-limiting examples of such agents include an SSRI (selective serotonin reuptake inhibitor), such as fluoxetine (Prozac®; described, e.g., in U.S. Pat. Nos. 4,314,081 and 4,194,009), citalopram (Celexa; described, e.g., in U.S. Pat. No. 4,136,193), escitalopram (Lexapro; described, e.g., in U.S. Pat. No. 4,136,193), fluvoxamine (described, e.g., in U.S. Pat. No. 4,085,225) or fluvoxamine maleate (CAS RN: 61718-82-9) and Luvox®, paroxetine (Paxil®; described, e.g., in U.S. Pat. Nos. 3,912, 743 and 4,007,196), or sertraline (Zoloft®; described, e.g., in U.S. Pat. No. 4,536,518), or alaproclate; the compound nefazodone (Serozone®; described, e.g., in U.S. Pat. No. 4,338, 317); a selective norepinephrine reuptake inhibitor (SNRI) such as reboxetine (Edronax®), atomoxetine (Strattera®), milnacipran (described, e.g., in U.S. Pat. No. 4,478,836), sibutramine or its primary amine metabolite (BTS 54 505), amoxapine, or maprotiline; a selective serotonin & norepinephrine reuptake inhibitor (SSNR1) such as venlafaxine (Effexor; described, e.g., in U.S. Pat. No. 4,761,501), and its reported metabolite desvenlafaxine, or duloxetine (Cymbalta; described, e.g., in U.S. Pat. No. 4,956,388); a serotonin, noradrenaline, and dopamine "triple uptake inhibitor", such as DOV 102,677 (see Popik et al. "Pharmacological Profile of the "Triple" Monoamine Neurotransmitter Uptake Inhibitor, DOV 102,677." Cell Mol. Neurobiol. 2006 Apr. 25; Epub ahead of print), DOV 216,303 (see Beer et al. "DOV 216,303, a "triple" reuptake inhibitor: safety, tolerability, and pharmacokinetic profile." J Clin Pharmacol. 2004 44(12): 1360-7), DOV 21,947 ((+)-1-(3,4-dichlorophenyl)-3-azabicyclo-(3.1.0)hexane hydrochloride), see Skolnick et al. "Antidepressant-like actions of DOV 21,947: a "triple" reuptake inhibitor." Eur J. Pharmacol. 2003 461(2-3):99-104), NS-2330 or tesofensine (CAS RN 402856-42-2), or NS 2359 (CAS RN 843660-54-8);

and agents like dehydroepiandrosterone (DHEA), and DHEA sulfate (DHEAS), CP-122,721 (CAS RN 145742-28-5).

Additional non-limiting examples of such agents include a tricyclic compound such as clomipramine, dosulepin or dothiepin, lofepramine (described, e.g., in U.S. Pat. No. 4,172,074), trimipramine, protriptyline, amitriptyline, desipramine (described, e.g., in U.S. Pat. No. 3,454,554), doxepin, imipramine, or nortriptyline; a psychostimulant such as dextroamphetamine and methylphenidate; an MAO inhibitor such as selegiline (Emsam®); an ampakine such as CX516 (or Ampalex, CAS RN: 154235-83-3), CX546 (or 1-(1,4-benzodioxan-6-ylcarbonyl)piperidine), and CX614 (CAS RN 191744-13-5) from Cortex Pharmaceuticals; a V1b antagonist such as SSR149415 ((2S,4R)-1-[5-Chloro-1-[(2, 4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide),

[1-(beta-mercapto-beta,beta-cyclopentamethylenepropionic acid), 2-O-ethyltyrosine, 4-valine]arginine vasopressin (d(CH$_2$)$_5$[Tyr(Et$_2$)]VAVP (WK 1-1), 9-desglycine[1-(beta-mercapto-beta,beta-cyclopentamethylenepropionic acid), 2-O-ethyltyrosine, 4-valine]arginine vasopressin desGly9d(CH$_2$)$_5$[Tyr(Et$_2$)]-VAVP (WK 3-6), or 9-desglycine[1-(beta-mercapto-beta,beta-cyclopentamethylenepropionic acid),2-D-(O-ethyl)tyrosine, 4-valine] arginine vasopressin des Gly9d(CH$_2$)$_5$[D-Tyr(Et$_2$)]VAVP (AO 3-21); a corticotropin-releasing factor (CRF) R antagonist such as CP-154,526 (structure disclosed in Schulz et al. "CP-154,526: a potent and selective nonpeptide antagonist of corticotropin releasing factor receptors." Proc Natl Acad Sci USA. 1996 93(19):10477-82), NBI 30775 (also known as R121919 or 2,5-dimethyl-3-(6-dimethyl-4-methylpyridin-3-yl)-7-dipropylaminopyrazolo[1,5-a]pyrimidine), astressin (CAS RN 170809-51-5), or a photoactivatable analog thereof as described in Bonk et al. "Novel high-affinity photoactivatable antagonists of corticotropin-releasing factor (CRF)" Eur. J. Biochem. 267:3017-3024 (2000), or AAG561 (from Novartis); a melanin concentrating hormone (MCH) antagonist such as 3,5-dimethoxy-N-(1-(naphthalen-2-ylmethyl)piperidin-4-yl)benzamide or (R)-3,5-dimethoxy-N-(1-(naphthalen-2-ylmethyl)-pyrrolidin-3-yl)benzamide (see Kim et al. "Identification of substituted 4-aminopiperidines and 3-aminopyrrolidines as potent MCH-R1 antagonists for the treatment of obesity." Bioorg Med Chem. Lett. 2006 Jul. 29; [Epub ahead of print] for both), or any MCH antagonist disclosed in U.S. Pat. No. 7,045,636 or published U.S. Patent Application US2005/0171098.

Further non-limiting examples of such agents include a tetracyclic compound such as mirtazapine (described, e.g., in U.S. Pat. No. 4,062,848; see CAS RN 61337-67-5; also known as Remeron, or CAS RN 85650-52-8), mianserin (described, e.g., in U.S. Pat. No. 3,534,041), or setiptiline.

Further non-limiting examples of such agents include agomelatine (CAS RN 138112-76-2), pindolol (CAS RN 13523-86-9), antalarmin (CAS RN 157284-96-3), mifepristone (CAS RN 84371-65-3), nemifitide (CAS RN 173240-15-8) or nemifitide ditriflutate (CAS RN 204992-09-6), YKP-10A or R228060 (CAS RN 561069-23-6), trazodone (CAS RN 19794-93-5), bupropion (CAS RN 34841-39-9 or 34911-55-2) or bupropion hydrochloride (or Wellbutrin, CAS RN 31677-93-7) and its reported metabolite radafaxine (CAS RN 192374-14-4), NS2359 (CAS RN 843660-54-8), Org 34517 (CAS RN 189035-07-2), Org 34850 (CAS RN 162607-84-3), vilazodone (CAS RN 163521-12-8), CP-122,721 (CAS RN 145742-28-5), gepirone (CAS RN 83928-76-1), SR58611 (see Mizuno et al. "The stimulation of beta(3)-adrenoceptor causes phosphorylation of extracellular signal-regulated kinases 1 and 2 through a G(s)- but not G(i)-dependent pathway in 3T3-L1 adipocytes." Eur J. Pharmacol. 2000 404(1-2):63-8), saredutant or SR 48968 (CAS RN 142001-63-6), PRX-00023 (N-{3-[4-(4-cyclohexylmethanesulfonylaminobutyl)piperazin-1-yl]phenyl}acetamide, see Becker et al. "An integrated in silico 3D model-driven discovery of a novel, potent, and selective amidosulfonamide 5-HT1A agonist (PRX-00023) for the treatment of anxiety and depression." J Med. Chem. 2006 49(11):3116-35), Vestipitant (or GW597599, CAS RN 334476-46-9), OPC-14523 or VPI-013 (see Bermack et al. "Effects of the potential antidepressant OPC-14523 [1-[3-[4-(3-chlorophenyl)-1-piperazinyl]propyl]-5-methoxy-3,4-dihydro-2-quinolinone monomethanesulfonate] a combined sigma and 5-HT1A ligand: modulation of neuronal activity in the dorsal raphe nucleus." J Pharmacol Exp Ther. 2004 310(2):578-83), Casopitant or GW679769 (CAS RN 852393-14-7), Elzasonan or CP-448,187 (CAS RN 361343-19-3), GW823296 (see published U.S. Patent Application US2005/0119248), Delucemine or NPS1506 (CAS RN 186495-49-8), or Ocinaplon (CAS RN 96604-21-6).

Yet additional non-limiting examples of such agents include CX717 from Cortex Pharmaceuticals, TGBA01AD (a serotonin reuptake inhibitor, 5-HT2 agonist, 5-HT1A agonist, and 5-HT1D agonist) from Fabre-Kramer Pharmaceuticals, Inc., ORG 4420 (an NaSSA (noradrenergic/specific serotonergic antidepressant) from Organon, CP-316,311 (a CRF1 antagonist) from Pfizer, BMS-562086 (a CRF1 antagonist) from Bristol-Myers Squibb, GW876008 (a CRF1 antagonist) from Neurocrine/GlaxoSmithKline, ONO-2333Ms (a CRF1 antagonist) from Ono Pharmaceutical Co., Ltd., JNJ-19567470 or TS-041 (a CRF1 antagonist) from Janssen (Johnson & Johnson) and Taisho, SSR 125543 or SSR 126374 (a CRF1 antagonist) from Sanofi-Aventis, Lu AA21004 and Lu AA24530 (both from H. Lundbeck A/S), SEP-225289 from Sepracor Inc., ND7001 (a PDE2 inhibitor) from Neuro3d, SSR 411298 or SSR 101010 (a fatty acid amide hydrolase, or FAAH, inhibitor) from Sanofi-Aventis, 163090 (a mixed serotonin receptor inhibitor) from Glaxo- SmithKline, SSR 241586 (an NK2 and NK3 receptor antagonist) from Sanofi-Aventis, SAR 102279 (an NK2 receptor antagonist) from Sanofi-Aventis, YKP581 from SK Pharmaceuticals (Johnson & Johnson), R1576 (a GPCR modulator) from Roche, or ND1251 (a PDE4 inhibitor) from Neuro3d.

In other disclosed embodiments, a reported anti-psychotic agent may be used in combination with a 4-acylaminopyridine derivative such as MKC-231. Non-limiting examples of a reported anti-psychotic agent as a member of a combination include olanzapine, quetiapine (Seroquel), clozapine (CAS RN 5786-21-0) or its metabolite ACP-104 (N-desmethylclozapine or norclozapine, CAS RN 6104-71-8), reserpine, aripiprazole, risperidone, ziprasidone, sertindole, trazodone, paliperidone (CAS RN 144598-75-4), mifepristone (CAS RN 84371-65-3), bifeprunox or DU-127090 (CAS RN 350992-10-8), asenapine or ORG 5222 (CAS RN 65576-45-6), iloperidone (CAS RN 133454-47-4), ocaperidone (CAS RN 129029-23-8), SLV 308 (CAS RN 269718-83-4), licarbazepine or GP 47779 (CAS RN 29331-92-8), Org 34517 (CAS RN 189035-07-2), ORG 34850 (CAS RN 162607-84-3), Org 24448 (CAS RN 211735-76-1), lurasidone (CAS RN 367514-87-2), blonanserin or lonasen (CAS RN 132810-10-7), Talnetant or SB-223412 (CAS RN 174636-32-9), secretin (CAS RN 1393-25-5) or human secretin (CAS RN 108153-74-8) which are endogenous pancreatic hormones, ABT 089 (CAS RN 161417-03-4), SSR 504734 (see compound 13 in Hashimoto "Glycine Transporter Inhibitors as Therapeutic Agents for Schizophrenia." *Recent Patents on CNS Drug Discovery*, 2006 1:43-53), MEM 3454 (see Mazurov et al. "Selective alpha7 nicotinic acetylcholine receptor ligands." *Curr Med. Chem.* 2006 13(13):1567-84), a phosphodiesterase 10A (PDE10A) inhibitor such as papaverine (CAS RN 58-74-2) or papaverine hydrochloride (CAS RN 61-25-6), paliperidone (CAS RN 144598-75-4), trifluoperazine (CAS RN 117-89-5), or trifluoperazine hydrochloride (CAS RN 440-17-5).

Additional non-limiting examples of such agents include trifluoperazine, fluphenazine, chlorpromazine, perphenazine, thioridazine, haloperidol, loxapine, mesoridazine, molindone, pimoxide, or thiothixene, SSR 146977 (see Emonds-Alt et al. "Biochemical and pharmacological activities of SSR 146977, a new potent nonpeptide tachykinin NK3 receptor antagonist." *Can J Physiol Pharmacol.* 2002 80(5):482-8), SSR181507 ((3-exo)-8-benzoyl-N—[[(2 s)-7-chloro-2,3-dihydro-1,4-benzodioxin-1-yl]methyl]-8-azabicyclo[3.2.1]octane-3-methanamine monohydrochloride), or SLV313 (1-(2, 3-dihydro-benzo[1,4]dioxin-5-yl)-4-[5-(4-fluorophenyl)-pyridin-3-ylmethyl]-piperazine).

Further non-limiting examples of such agents include Lu-35-138 (a D4/5-HT antagonist) from Lundbeck, AVE 1625 (a CB1 antagonist) from Sanofi-Aventis, SLV 310,313 (a 5-HT2A antagonist) from Solvay, SSR 181507 (a D2/5-HT2 antagonist) from Sanofi-Aventis, GWO7034 (a 5-HT6 antagonist) or GW773812 (a D2,5-HT antagonist) from GlaxoSmithiKline, YKP 1538 from SK Pharmaceuticals, SSR 125047 (a sigma receptor antagonist) from Sanofi-Aventis, MEM 1003 (a L-type calcium channel modulator) from Memory Pharmaceuticals, JNJ-17305600 (a GLYT1 inhibitor) from Johnson & Johnson, XY 2401 (a glycine site specific NMDA modulator) from Xytis, PNU 170413 from Pfizer, RGH-188 (a D2, D3 antagonist) from Forrest, SSR 180711 (an alpha7 nicotinic acetylcholine receptor partial agonist) or SSR 103800 (a GLYT1 (Type 1 glycine transporter) inhibitor) or SSR 241586 (a NK3 antagonist) from Sanofi-Aventis.

In other disclosed embodiments, a reported anti-psychotic agent may be one used in treating schizophrenia. Non-limiting examples of a reported anti-schizophrenia agent as a member of a combination with a 4-acylaminopyridine derivative such as MKC-231 include molindone hydrochloride (MOBAN®) and TC-1827 (see Bohme et al. "In vitro and in vivo characterization of TC-1827, a novel brain α4β2 nicotinic receptor agonist with pro-cognitive activity." *Drug Development Research* 2004 62(1):26-40).

In light of the positive recitation (above and below) of combinations with alternative agents to treat conditions disclosed herein, the disclosure includes embodiments with the explicit exclusion of one or more of the alternative agents. As would be recognized by the skilled person, a description of the whole of a plurality of alternative agents necessarily includes and describes subsets of the possible alternatives, or the part remaining with the exclusion of one or more of the alternatives.

The combination therapy may be of one of the above with a 4-acylaminopyridine derivative such as MKC-231 as described herein to improve the condition of the subject or patient. Non-limiting examples of combination therapy include the use of lower dosages of the above which reduce side effects of the anti-depressant agent when used alone. For example, an anti-depressant agent like fluoxetine or paroxetine or sertraline may be administered at a reduced or limited dose, optionally also reduced in frequency of administration, in combination with a 4-acylaminopyridine derivative such as MKC-231 alone or in combination with another 4-acylaminopyridine derivative. The reduced dose or frequency mediates a sufficient anti-depressant effect so that the side effects of the anti-depressant agent alone are reduced or eliminated.

In additional embodiments, such as, but not limited to, treating weight gain, metabolic syndrome, or obesity, and/or to induce weight loss, a 4-acylaminopyridine derivative such as MKC-231 may be used in combination. Non-limiting examples of another agent include those reported for treating weight gain or metabolic syndrome and/or inducing weight loss such as various diet pills that are commercially or clinically available. In some embodiments, the reported agent for treating weight gain, metabolic syndrome, obesity, or for inducing weight loss is orlistat (CAS RN 96829-58-2), sibutramine (CAS RN 106650-56-0) or sibutramine hydrochloride (CAS RN 84485-00-7), phetermine (CAS RN 122-09-8) or phetermine hydrochloride (CAS RN 1197-21-3), diethylpropion or amfepramone (CAS RN 90-84-6) or diethylpropion hydrochloride, benzphetamine (CAS RN 156-08-1) or benzphetamine hydrochloride, phendimetrazine (CAS RN 634-03-7 or 21784-30-5) or phendimetrazine hydrochloride (CAS RN 17140-98-6) or phendimetrazine tartrate, rimonabant (CAS RN 168273-06-1), bupropion hydrochloride (CAS RN: 31677-93-7), topiramate (CAS RN 97240-79-4), zonisamide (CAS RN 68291-97-4), or APD-356 (CAS RN 846589-98-8).

In other non-limiting embodiments, the agent may be fenfluramine or Pondimin (CAS RN 458-24-2), dexfenfluramine or Redux (CAS RN 3239-44-9), or levofenfluramine (CAS RN 37577-24-5); or a combination thereof or a combination with phentermine. Non-limiting examples include a combination of fenfluramine and phentermine (or "fen-phen") and of dexfenfluramine and phentermine (or "dexfen-phen").

The combination therapy may be of one of the above with a 4-acylaminopyridine derivative in combination with one or more other neurogenic agents as described herein to improve the condition of the subject or patient. Non-limiting examples of combination therapy include the use of lower dosages of the above additional agents, or combinations thereof, which reduce side effects of the agent or combination when used alone. For example, a combination of fenfluramine and phentermine, or phentermine and dexfenfluramine, may be administered at a reduced or limited dose, optionally also reduced in frequency of administration, in combination with a 4-acylaminopyridine derivative in combination with one or more other neurogenic agents. The reduced dose or frequency may be that which reduces or eliminates the side effects of the combination.

As indicated herein, the disclosure includes combination therapy, where a 4-acylaminopyridine derivative in combination with one or more other neurogenic agents is used to produce neurogenesis. When administered as a combination, the therapeutic compounds can be formulated as separate compositions that are administered at the same time or sequentially at different times, or the therapeutic compounds can be given as a single composition. The methods of the disclosure are not limited in the sequence of administration.

Instead, the disclosure includes methods wherein treatment with a 4-acylaminopyridine derivative such as MKC-231 and another neurogenic agent occurs over a period of more than about 48 hours, more than about 72 hours, more than about 96 hours, more than about 120 hours, more than about 144 hours, more than about 7 days, more than about 9 days, more than about 11 days, more than about 14 days, more than about 21 days, more than about 28 days, more than about 35 days, more than about 42 days, more than about 49 days, more than about 56 days, more than about 63 days, more than about 70 days, more than about 77 days, more than about 12 weeks, more than about 16 weeks, more than about 20 weeks, or more than about 24 weeks or more. In some embodiments, treatment by administering a 4-acylaminopyridine derivative such as MKC-231, occurs at least about 12 hours, such as at least about 24, or at least about 36 hours, before administration of another neurogenic agent. Following administration of a 4-acylaminopyridine derivative such as MKC-231, further administrations may be of only the other neurogenic agent in some embodiments of the disclosure. In other embodiments, further administrations may be of only the a 4-acylaminopyridine derivative.

In some non-limiting embodiments, combination therapy with a 4-acylaminopyridine derivative such as MKC-231 and one or more additional agents results in a enhanced efficacy, safety, therapeutic index, and/or tolerability, and/or reduced side effects (frequency, severity, or other aspects), dosage levels, dosage frequency, and/or treatment duration. Examples of compounds useful in combinations provided herein are provided below, for which structures, synthetic processes, safety profiles, biological activity data, methods for determining biological activity, pharmaceutical preparations, and methods of administration are known in the art and/or provided in the cited references, all of which are herein incorporated by reference in their entirety. Dosages of compounds administered in combination with a a 4-acylaminopyridine derivative such as MKC-231 can be, e.g., a dosage within the range of pharmacological dosages established in humans, or a dosage that is a fraction of the established human dosage, e.g., 70%, 50%, 30%, 10%, or less than the establishes human dosage.

In other embodiments, the neurogenic agent combined with a 4-acylaminopyridine derivative such as MKC-231 may be a reported opioid or non-opioid (acts independently of an opioid receptor) agent. In some embodiments, the neurogenic agent is one reported as antagonizing one or more opioid receptors or as an inverse agonist of at least one opioid receptor. A opioid receptor antagonist or inverse agonist may be specific or selective (or alternatively non-specific or non-selective) for opioid receptor subtypes. So an antagonist may be non-specific or non-selective such that it antagonizes more than one of the three known opioid receptor subtypes, identified as $OP_1$, $OP_2$, and $OP_3$ (also know as delta, or δ, kappa, or κ, and mu, or μ, respectively). Thus an opioid that antagonizes any two, or all three, of these subtypes, or an inverse agonist that is specific or selective for any two or all three of these subtypes, may be used as the neurogenic agent in the practice. Alternatively, an antagonist or inverse agonist may be specific or selective for one of the three subtypes, such as the kappa subtype as a non-limiting example.

Non-limiting examples of reported opioid antagonists include naltrindol, naloxone, naloxene, naltrexone, JDTic (Registry Number 785835-79-2; also known as 3-isoquinolinecarboxamide, 1,2,3,4-tetrahydro-7-hydroxy-N-[(1S)-1-[[(3R,4R)-4-(3-hydroxyphenyl)-3,4-dimethyl-1-piperidinyl] methyl]-2-methylpropyl]-dihydrochloride, (3R)-(9CI)), norbinaltorphimine, and buprenorphine. In some embodiments, a reported selective kappa opioid receptor antagonist compound, as described in US 2002/0132828, U.S. Pat. No. 6,559,159, and/or WO 2002/053533, may be used. All three of these documents are herein incorporated by reference in their entireties as if fully set forth. Further non-limiting examples of such reported antagonists is a compound disclosed in U.S. Pat. No. 6,900,228 (herein incorporated by reference in its entirety), arodyn (Ac[Phe(1,2,3), Arg(4),d-Ala(8)]Dyn A-(1-11)NH(2), as described in Bennett, et al. (2002) *J. Med. Chem.* 45:5617-5619), and an active analog of arodyn as described in Bennett et al. (2005) J Pept Res. 65(3):322-32, alvimopan.

In some embodiments, the neurogenic agent used in the methods described herein has "selective" activity (such as in the case of an antagonist or inverse agonist) under certain conditions against one or more opioid receptor subtypes with respect to the degree and/or nature of activity against one or more other opioid receptor subtypes. For example, in some embodiments, the neurogenic agent has an antagonist effect against one or more subtypes, and a much weaker effect or substantially no effect against other subtypes. As another example, an additional neurogenic agent used in the methods described herein may act as an agonist at one or more opioid receptor subtypes and as antagonist at one or more other opioid receptor subtypes. In some embodiments, a neurogenic agent has activity against kappa opioid receptors, while having substantially lesser activity against one or both of the delta and mu receptor subtypes. In other embodiments, a neurogenic agent has activity against two opioid receptor subtypes, such as the kappa and delta subtypes. As non-limiting examples, the agents naloxone and naltrexone have nonselective antagonist activities against more than one opioid receptor subtypes. In certain embodiments, selective activity of one or more opioid antagonists results in enhanced efficacy, fewer side effects, lower effective dosages, less frequent dosing, or other desirable attributes.

An opioid receptor antagonist is an agent able to inhibit one or more characteristic responses of an opioid receptor or receptor subtype. As a non-limiting example, an antagonist may competitively or non-competitively bind to an opioid receptor, an agonist or partial agonist (or other ligand) of a receptor, and/or a downstream signaling molecule to inhibit a receptor's function.

An inverse agonist able to block or inhibit a constitutive activity of an opioid receptor may also be used. An inverse agonist may competitively or non-competitively bind to an opioid receptor and/or a downstream signaling molecule to inhibit a receptor's function. Non-limiting examples of inverse agonists for use in the disclosed methods include ICI-174864 (N,N-diallyl-Tyr-Aib-Aib-Phe-Leu), RTI-5989-

1, RTI-5989-23, and RTI-5989-25 (see Zaki et al. *J. Pharmacol. Exp. Therap.* 298(3): 1015-1020, 2001).

Additional embodiments of the disclosure include a combination of a 4-acylaminopyridine derivative such as MKC-231 with an additional agent such as acetylcholine or a reported modulator of an androgen receptor. Non-limiting examples include the androgen receptor agonists ehydroepiandrosterone (DHEA) and DHEA sulfate (DHEAS).

Alternatively, the neurogenic agent in combination with a 4-acylaminopyridine derivative such as MKC-231 may be an enzymatic inhibitor, such as a reported inhibitor of HMG CoA reductase. Non-limiting examples of such inhibitors include atorvastatin (CAS RN 134523-00-5), cerivastatin (CAS RN 145599-86-6), crilvastatin (CAS RN 120551-59-9), fluvastatin (CAS RN 93957-54-1) and fluvastatin sodium (CAS RN 93957-55-2), simvastatin (CAS RN 79902-63-9), lovastatin (CAS RN 75330-75-5), pravastatin (CAS RN 81093-37-0) or pravastatin sodium, rosuvastatin (CAS RN 287714-41-4), and simvastatin (CAS RN 79902-63-9). Formulations containing one or more of such inhibitors may also be used in a combination. Non-limiting examples include formulations comprising lovastatin such as Advicor® (an extended-release, niacin containing formulation) or Altocor® (an extended release formulation); and formulations comprising simvastatin such as Vytorin® (combination of simvastatin and ezetimibe).

In other non-limiting embodiments, the neurogenic agent in combination with a 4-acylaminopyridine derivative such as MKC-231 may be a reported Rho kinase inhibitor. Non-limiting examples of such an inhibitor include fasudil (CAS RN 103745-39-7); fasudil hydrochloride (CAS RN 105628-07-7); the metabolite of fasudil, which is hydroxyfasudil (see Shimokawa et al. "Rho-kinase-mediated pathway induces enhanced myosin light chain phosphorylations in a swine model of coronary artery spasm." *Cardiovasc Res.* 1999 43:1029-1039), Y 27632 (CAS RN 138381-45-0); a fasudil analog thereof such as (S)-Hexahydro-1-(4-ethenylisoquinoline-5-sulfonyl)-2-methyl-1H-1,4-diazepine, (S)-hexahydro-4-glycyl-2-methyl-1-(4-methylisoquinoline-5-sulfonyl)-1H-1,4-diazepine, or (S)-(+)-2-methyl-1-[(4-methyl-5-isoquinoline)sulfonyl]-homopiperazine (also known as H-1152P; see Sasaki et al. "The novel and specific Rho-kinase inhibitor (S)-(+)-2-methyl-1-[(4-methyl-5-isoquinoline)sulfonyl]-homopiperazine as a probing molecule for Rho-kinase-involved pathway." *Pharmacol Ther.* 2002 93(2-3):225-32); or a substituted isoquinolinesulfonamide compound as disclosed in U.S. Pat. No. 6,906,061.

Furthermore, the neurogenic agent in combination with a 4-acylaminopyridine derivative such as MKC-231 may be a reported GSK-3 inhibitor or modulator. In some non-limiting embodiments, the reported GSK3-beta modulator is a paullone, such as alsterpaullone, kenpaullone (9-bromo-7,12-dihydroindolo[3,2-d][1]benzazepin-6(5H)-one), gwennpaullone (see Knockaert et al. "Intracellular Targets of Paullones. Identification following affinity purification on immobilized inhibitor." *J Biol. Chem.* 2002 277(28):25493-501), azakenpaullone (see Kunick et al. "1-Azakenpaullone is a selective inhibitor of glycogen synthase kinase-3 beta." *Bioorg Med Chem. Lett.* 2004 14(2):413-6), or the compounds described in U.S. Publication No. 2003/0181439; International Publication No. WO 01/60374; Leost et al., *Eur. J. Biochem.* 267:5983-5994 (2000); Kunick et al., J Med. Chem.; 47(1): 22-36 (2004); or Shultz et al., J. Med. Chem. 42:2909-2919 (1999); an anticonvulsant, such as lithium or a derivative thereof (e.g., a compound described in U.S. Pat. Nos. 1,873,732; 3,814,812; and 4,301,176); valproic acid or a derivative thereof (e.g., valproate, or a compound described in Werstuck et al., Bioorg Med Chem. Lett., 14(22): 5465-7 (2004)); lamotrigine; SL 76002 (Progabide), Gabapentin; tiagabine; or vigabatrin; a maleimide or a related compound, such as Ro 31-8220, SB-216763, SB-410111, SB-495052, or SB-415286, or a compound described, e.g., in U.S. Pat. No. 6,719,520; U.S. Publication No. 2004/0010031; International Publication Nos. WO-2004072062; WO-03082859; WO-03104222; WO-03103663, WO-03095452, WO-2005000836; WO 0021927; WO-03076398; WO-00021927; WO-00038675; or WO-03076442; or Coghlan et al., Chemistry & Biology 7: 793 (2000); a pyridine or pyrimidine derivative, or a related compound (such as 5-iodotubercidin, GI 179186X, GW 784752× and GW 784775X, and compounds described, e.g., in U.S. Pat. Nos. 6,489,344; 6,417,185; and 6153618; U.S. Publication Nos. 2005/0171094; and 2003/0130289; European Patent Nos. EP-01454908, EP-01454910, EP-01295884, EP-01295885; and EP-01460076; EP-01454900; International Publication Nos. WO 01/70683; WO 01/70729; WO 01/70728; WO 01/70727; WO 01/70726; WO 01/70725; WO-00218385; WO-00218386; WO-03072579; WO-03072580; WO-03027115; WO-03027116; WO-2004078760; WO-2005037800, WO-2004026881, WO-03076437, WO-03029223; WO-2004098607; WO-2005026155; WO-2005026159; WO-2005025567; WO-03070730; WO-03070729; WO-2005019218; WO-2005019219; WO-2004013140; WO-2004080977; WO-2004026229, WO-2004022561; WO-03080616; WO-03080609; WO-03051847; WO-2004009602; WO-2004009596; WO-2004009597; WO-03045949; WO-03068773; WO-03080617; WO 99/65897; WO 00/18758; WO0307073; WO-00220495; WO-2004043953, WO-2004056368, WO-2005012298, WO-2005012262, WO-2005042525, WO-2005005438, WO-2004009562, WO-03037877; WO-03037869; WO-03037891; WO-05012307; WO-05012304 and WO 98/16528; and in Massillon et al., Biochem J 299:123-8 (1994)); a pyrazine derivative, such as Aloisine A (7-n-Butyl-6-(4-hydroxyphenyl)[5H]pyrrolo[2,3-b]pyrazine) or a compound described in International Publication Nos. WO-00144206; WO0144246; or WO-2005035532; a thiadiazole or thiazole, such as TDZD-8 (Benzyl-2-methyl-1,2,4-thiadiazolidine-3,5-dione); OTDZT (4-Dibenzyl-5-oxothiadiazolidine-3-thione); or a related compound described, e.g., in U.S. Pat. No. 6,645,990 or 6762179; U.S. Publication No. 2001/0039275; International Publication Nos. WO 01/56567, WO-03011843, WO-03004478, or WO-03089419; or Mettey, Y., et al., J. Med. Chem. 46, 222 (2003); TWS119 or a related compound, such as a compound described in Ding et al., Proc Natl Acad Sci USA., 100(13): 7632-7 (2003); an indole derivative, such as a compound described in International Publication Nos. WO-03053330, WO-03053444, WO-03055877, WO-03055492, WO-03082853, or WO-2005027823; a pyrazine or pyrazole derivative, such as a compound described in U.S. Pat. Nos. 6,727,251, 6,696,452, 6,664,247, 6,660,773, 6,656,939, 6,653,301, 6,653,300, 6,638,926, 6,613,776, or 6610677; or International Publication Nos. WO-2005002552, WO-2005002576, or WO-2005012256; a compound described in U.S. Pat. Nos. 6,719,520; 6,498,176; 6,800,632; or 6872737; U.S. Publication Nos. 2005/0137201; 2005/0176713; 2005/0004125; 2004/0010031; 2003/0105075; 2003/0008866; 2001/0044436; 2004/0138273; or 2004/0214928; International Publication Nos. WO 99/21859; WO-00210158; WO-05051919; WO-00232896; WO-2004046117; WO-2004106343; WO-00210141; WO-00218346; WO 00/21927; WO 01/81345; WO 01/74771; WO 05/028475; WO 01/09106;

WO 00/21927; WO01/41768; WO 00/17184; WO 04/037791; WO-04065370; WO 01/37819; WO 01/42224; WO 01/85685; WO 04/072063; WO-2004085439; WO-2005000303; WO-2005000304; or WO 99/47522; or Naerum, L., et al., Bioorg. Med. Chem. Lett. 12, 1525 (2002); CP-79049, G1179186X, GW 784752X, GW 784775X, AZD-1080, AR-014418, SN-8914, SN-3728, OTDZT, Aloisine A, TWS119, CHIR98023, CHIR99021, CHIR98014, CHIR98023, 5-iodotubercidin, Ro 31-8220, SB-216763, SB-410111, SB-495052, SB-415286, alsterpaullone, kenpaullone, gwennpaullone, LY294002, wortmanin, sildenafil, CT98014, CT-99025, flavoperidol, or L803-mts.

In yet further embodiments, the neurogenic agent used in combination with a 4-acylaminopyridine derivative such as MKC-231 may be a reported glutamate modulator or metabotropic glutamate (mGlu) receptor modulator. In some embodiments, the reported mGlu receptor modulator is a Group II modulator, having activity against one or more Group II receptors (mGlu$_2$ and/or mGlu$_3$). Embodiments include those where the Group II modulator is a Group II agonist. Non-limiting examples of Group II agonists include: (i) (1S,3R)-1-aminocyclopentane-1,3-dicarboxylic acid (ACPD), a broad spectrum mGlu agonist having substantial activity at Group I and II receptors; (ii) (−)-2-thia-4-aminobicyclo-hexane-4,6-dicarboxylate (LY389795), which is described in Monn et al., *J. Med. Chem.*, 42(6): 1027-40 (1999); (iii) compounds described in US App. No. 20040102521 and Pellicciari et al., *J. Med. Chem.*, 39, 2259-2269 (1996); and (iv) the Group II-specific modulators described below.

Non-limiting examples of reported Group II antagonists include: (i) phenylglycine analogues, such as (RS)-alpha-methyl-4-sulphonophenylglycine (MSPG), (RS)-alpha-methyl-4-phosphonophenylglycine (MPPG), and (RS)-alpha-methyl-4-tetrazolylphenylglycine (MTPG), described in Jane et al., *Neuropharmacology* 34: 851-856 (1995); (ii) LY366457, which is described in O'Neill et al., *Neuropharmacol.*, 45(5): 565-74 (2003); (iii) compounds described in US App Nos. 20050049243, 20050119345 and 20030157647; and (iv) the Group II-specific modulators described below.

In some non-limiting embodiments, the reported Group II modulator is a Group II-selective modulator, capable of modulating mGlu$_2$ and/or mGlu$_3$ under conditions where it is substantially inactive at other mGlu subtypes (of Groups I and III). Examples of Group II-selective modulators include compounds described in Monn, et al., *J. Med. Chem.*, 40, 528-537 (1997); Schoepp, et al., *Neuropharmacol.*, 36, 1-11 (1997) (e.g., 1S,2S,5R,6S-2-aminobicyclohexane-2,6-dicarboxylate); and Schoepp, Neurochem. Int., 24, 439 (1994).

Non-limiting examples of reported Group II-selective agonists include (i) (+)-2-aminobicyclohexane-2,6-dicarboxylic acid (LY354740), which is described in Johnson et al., *Drug Metab. Disposition*, 30(1): 27-33 (2002) and Bond et al., *NeuroReport* 8: 1463-1466 (1997), and is systemically active after oral administration (e.g., Grillon et al., *Psychopharmacol.* (Berl), 168: 446-454 (2003)); (ii) (−)-2-Oxa-4-aminobicyclohexane-4,6-dicarboxylic acid (LY379268), which is described in Monn et al., *J. Med. Chem.* 42: 1027-1040 (1999) and U.S. Pat. No. 5,688,826. LY379268 is readily permeable across the blood-brain barrier, and has EC$_{50}$ values in the low nanomolar range (e.g., below about 10 nM, or below about 5 nM) against human mGlu$_2$ and mGlu$_3$ receptors in vitro; (iii) (2R,4R)-4-aminopyrrolidine-2,4-dicarboxylate ((2R,4R)-APDC), which is described in Monn et al., *J. Med. Chem.* 39: 2990 (1996) and Schoepp et al., *Neuropharmacology*, 38: 1431 (1999); (iv) (1S,3S)-1-aminocyclopentane-1,3-dicarboxylic acid ((1S,3S)-ACPD), described in Schoepp, *Neurochem. Int.*, 24: 439 (1994); (v) (2R,4R)-4-aminopyrrolidine-2,4-dicarboxylic acid ((2R,4R)-APDC), described in Howson and Jane, *British Journal of Pharmacology*, 139, 147-155 (2003); (vi) (2S,1'S,2'S)-2-(carboxycyclopropyl)-glycine (L-CCG-I), described in Brabet et al., *Neuropharmacology* 37: 1043-1051 (1998); (vii) (2S,2'R,3'R)-2-(2',3'-dicarboxycyclopropyl)glycine (DCG-IV), described in Hayashi et al., *Nature*, 366, 687-690 (1993); (viii) 1S,2S,5R, 6S-2-aminobicyclohexane-2,6-dicarboxylate, described in Monn, et al., *J. Med. Chem.*, 40, 528 (1997) and Schoepp, et al., *Neuropharmacol.*, 36, 1 (1997); and (vii) compounds described in US App. No. 20040002478; U.S. Pat. Nos. 6,204,292, 6,333,428, 5,750,566 and 6,498,180; and Bond et al., *Neuroreport* 8: 1463-1466 (1997).

Non-limiting examples of reported Group II-selective antagonists useful in methods provided herein include the competitive antagonist (2S)-2-amino-2-(1S,2S-2-carboxycyclopropyl)-3-(xanth-9-yl) propanoic acid (LY341495), which is described, e.g., in Kingston et al., *Neuropharmacology* 37: 1-12 (1998) and Monn et al., *J Med Chem* 42: 1027-1040 (1999). LY341495 is readily permeably across the blood-brain barrier, and has IC$_{50}$ values in the low nanomolar range (e.g., below about 10 DM, or below about 5 nM) against cloned human mGlu$_2$ and mGlu$_3$ receptors. LY341495 has a high degree of selectivity for Group II receptors relative to Group I and Group III receptors at low concentrations (e.g., nanomolar range), whereas at higher concentrations (e.g., above 1 μM), LY341495 also has antagonist activity against mGlu$_7$ and mGlu$_8$, in addition to mGlu$_{2/3}$. LY341495 is substantially inactive against KA, AMPA, and NMDA iGlu receptors.

Additional non-limiting examples of reported Group II-selective antagonists include the following compounds, indicated by chemical name and/or described in the cited references: (i) α-methyl-L-(carboxycyclopropyl) glycine (CCG); (ii) (2S,3S,4S)-2-methyl-2-(carboxycyclopropyl) glycine (MCCG); (iii) (1R,2R,3R,5R,6R)-2-amino-3-(3,4-dichlorobenzyloxy)-6 fluorobicyclohexane-2,6-dicarboxylic acid (MGS0039), which is described in Nakazato et al., *J. Med. Chem.*, 47(18):4570-87 (2004); (iv) an n-hexyl, n-heptyl, n-octyl, 5-methylbutyl, or 6-methylpentyl ester prodrug of MGS0039; (v) MGS0210 (3-(3,4-dichlorobenzyloxy)-2-amino-6-fluorobicyclohexane-2,6-dicarboxylic acid n-heptyl ester); (vi) (RS)-1-amino-5-phosphonoindan-1-carboxylic acid (APICA), which is described in Ma et al., *Bioorg. Med. Chem. Lett.*, 7: 1195 (1997); (vii) (2S)-ethylglutamic acid (EGLU), which is described in Thomas et al., *Br. J. Pharmacol.* 117: 70P (1996); (viii) (2S,1'S,2'S,3'R)-2-(2'-carboxy-3'-phenylcyclopropyl)glycine (PCCG-IV); and (ix) compounds described in U.S. Pat. No. 6,107,342 and US App No. 20040006114. APICA has an IC$_{50}$ value of approximately 30 μM against mGluR$_2$ and mGluR$_3$, with no appreciable activity against Group I or Group III receptors at sub-mM concentrations.

In some non-limiting embodiments, a reported Group II-selective modulator is a subtype-selective modulator, capable of modulating the activity of mGlu$_2$ under conditions in which it is substantially inactive at mGlu$_3$ (mGlu$_2$-selective), or vice versa (mGlu$_3$-selective). Non-limiting examples of subtype-selective modulators include compounds described in U.S. Pat. No. 6,376,532 (mGlu$_2$-selective agonists) and US App No. 20040002478 (mGlu$_3$-selective agonists). Additional non-limiting examples of subtype-selective modulators include allosteric mGlu receptor modulators (mGlu$_2$ and mGlu$_3$) and NAAG-related compounds (mGlu$_3$), such as those described below.

In other non-limiting embodiments, a reported Group II modulator is a compound with activity at Group I and/or Group III receptors, in addition to Group II receptors, while having selectivity with respect to one or more mGlu receptor subtypes. Non-limiting examples of such compounds include: (i) (2S,3S,4S)-2-(carboxycyclopropyl)glycine (L-CCG-1) (Group I/Group II agonist), which is described in Nicoletti et al., *Trends Neurosci.* 19: 267-271 (1996), Nakagawa, et al., *Eur. J. Pharmacol.*, 184, 205 (1990), Hayashi, et al., *Br. J. Pharmacol.*, 107, 539 (1992), and Schoepp et al., *J. Neurochem.*, 63., page 769-772 (1994); (ii) (S)-4-carboxy-3-hydroxyphenylglycine (4C$_3$HPG) (Group II agonist/Group I competitive antagonist); (iii) gamma-carboxy-L-glutamic acid (GLA) (Group II antagonist/Group III partial agonist/antagonist); (iv) (2S,2'R,3'R)-2-(2,3-dicarboxycyclopropyl) glycine (DCG-IV) (Group II agonist/Group III antagonist), which is described in Ohfune et al, *Bioorg. Med. Chem. Lett.*, 3: 15 (1993); (v) (RS)-a-methyl-4-carboxyphenylglycine (MCPG) (Group I/Group II competitive antagonist), which is described in Eaton et al., *Eur. J. Pharmacol.*, 244: 195 (1993), Collingridge and Watkins, *TiPS*, 15: 333 (1994), and Joly et al., *J. Neurosci.*, 15: 3970 (1995); and (vi) the Group II/III modulators described in U.S. Pat. Nos. 5,916,920, 5,688,826, 5,945,417, 5,958,960, 6,143,783, 6,268,507, 6,284,785.

In some non-limiting embodiments, the reported mGlu receptor modulator comprises (S)-MCPG (the active isomer of the Group I/Group II competitive antagonist (RS)-MCPG) substantially free from (R)-MCPG. (S)-MCPG is described, e.g., in Sekiyama et al., *Br. J. Pharmacol.*, 117: 1493 (1996) and Collingridge and Watkins, TiPS, 15: 333 (1994).

Additional non-limiting examples of reported mGlu modulators useful in methods disclosed herein include compounds described in U.S. Pat. Nos. 6,956,049, 6,825,211, 5,473,077, 5,912,248, 6,054,448, and 5,500,420; US App Nos. 20040077599, 20040147482, 20040102521, 20030199533 and 20050234048; and Intl Pub/App Nos. WO 97/19049, WO 98/00391, and EP0870760.

In some non-limiting embodiments, the reported mGlu receptor modulator is a prodrug, metabolite, or other derivative of N-Acetylaspartylglutamate (NAAG), a peptide neurotransmitter in the mammalian CNS that is a highly selective agonist for mGluR$_3$ receptors, as described in Wroblewska et al., *J. Neurochem.*, 69(1): 174-181 (1997). In other embodiments, the mGlu modulator is a compound that modulates the levels of endogenous NAAG, such as an inhibitor of the enzyme N-acetylated-alpha-linked-acidic dipeptidase (NAALADase), which catalyzes the hydrolysis of NAAG to N-acetyl-aspartate and glutamate. Examples of NAALADase inhibitors include 2-PMPA (2-(phosphonomethyl)pentanedioic acid), which is described in Slusher et al., *Nat. Med.*, 5(12): 1396-402 (1999); and compounds described in *J. Med. Chem.* 39: 619 (1996), US Pub. No. 20040002478, and U.S. Pat. Nos. 6,313,159, 6,479,470, and 6,528,499. In some embodiments, the mGlu modulator is the mGlu$_3$-selective antagonist, beta-NAAG.

Additional non-limiting examples of reported glutamate modulators include memantine (CAS RN 19982-08-2), memantine hydrochloride (CAS RN 41100-52-1), and riluzole (CAS RN 1744-22-5).

In some non-limiting embodiments, a reported Group II modulator is administered in combination with one or more additional compounds reported as active against a Group I and/or a Group III mGlu receptor. For example, in some cases, methods comprise modulating the activity of at least one Group I receptor and at least one Group II mGlu receptor (e.g., with a compound described herein). Examples of compounds useful in modulating the activity of Group I receptors include Group I-selective agonists, such as (i) trans-azetidine-2,4,-dicarboxylic acid (tADA), which is described in Kozikowski et al., *J. Med. Chem.*, 36: 2706 (1993) and Manahan-Vaughan et al., *Neuroscience,* 72: 999 (1996); (ii) (RS)-3,5-Dihydroxyphenylglycine (DHPG), which is described in Ito et al., *NeuroReport* 3: 1013 (1992); or a composition comprising (S)-DHPG substantially free of (R)-DHPG, as described, e.g., in Baker et al., *Bioorg. Med. Chem. Lett.* 5: 223 (1995); (iii) (RS)-3-Hydroxyphenylglycine, which is described in Birse et al., *Neuroscience* 52: 481 (1993); or a composition comprising (S)-3-Hydroxyphenylglycine substantially free of (R)-3-Hydroxyphenylglycine, as described, e.g., in Hayashi et al., *J. Neurosci.,* 14: 3370 (1994); (iv) and (S)-Homoquisqualate, which is described in Porter et al., *Br. J. Pharmacol.*, 106: 509 (1992).

Additional non-limiting examples of reported Group I modulators include (i) Group I agonists, such as (RS)-3,5-dihydroxyphenylglycine, described in Brabet et al., *Neuropharmacology*, 34, 895-903, 1995; and compounds described in U.S. Pat. Nos. 6,399,641 and 6,589,978, and US Pub No. 20030212066; (ii) Group I antagonists, such as (S)-4-Carboxy-3-hydroxyphenylglycine; 7-(Hydroxyimino)cyclopropa-β-chromen-1α-carboxylate ethyl ester; (RS)-1-Aminoindan-1,5-dicarboxylic acid (AIDA); 2-Methyl-6 (phenylethynyl)pyridine (MPEP); 2-Methyl-6-(2-phenylethenyl)pyridine (SIB-1893); 6-Methyl-2-(phenylazo)-3-pyridinol (SIB-1757); (Sα-Amino-4-carboxy-2-methylbenzeneacetic acid; and compounds described in U.S. Pat. Nos. 6,586,422, 5,783,575, 5,843,988, 5,536,721, 6,429,207, 5,696,148, and 6,218,385, and US Pub Nos. 20030109504, 20030013715, 20050154027, 20050004130, 20050209273, 20050197361, and 20040082592; (iii) mGlu$_5$-selective agonists, such as (RS)-2-Chloro-5-hydroxyphenylglycine (CHPG); and (iv) mGlu$_5$-selective antagonists, such as 2-methyl-6-(phenylethynyl)-pyridine (MPEP); and compounds described in U.S. Pat. No. 6,660,753; and US Pub Nos. 20030195139, 20040229917, 20050153986, 20050085514, 20050065340, 20050026963, 20050020585, and 20040259917.

Non-limiting examples of compounds reported to modulate Group III receptors include (i) the Group III-selective agonists (L)-2-amino-4-phosphonobutyric acid (L-AP4), described in Knopfel et al., *J. Med. Chem.,* 38, 1417-1426 (1995); and (S)-2-Amino-2-methyl-4-phosphonobutanoic acid; (ii) the Group III-selective antagonists (RS)-α-Cyclopropyl-4-phosphonophenylglycine; (RS)-α-Methylserine-O-phosphate (MSOP); and compounds described in US App. No. 20030109504; and (iii) (1S,3R,4S)-1-aminocyclopentane-1,2,4-tricarboxylic acid (ACPT-I).

In additional embodiments, the neurogenic agent used in combination with a 4-acylaminopyridine derivative such as MKC-231 may be a reported AMPA modulator. Non-limiting examples include CX-516 or ampalex (CAS RN 154235-83-3), Org-24448 (CAS RN 211735-76-1), LY451395 (2-propanesulfonamide, N-[(2R)-2-[4'-[2-[methylsulfonyl)amino] ethyl][1,1'-biphenyl]-4-yl]propyl]-), LY-450108 (see Jhee et al. "Multiple-dose plasma pharmacokinetic and safety study of LY450108 and LY451395 (AMPA receptor potentiators) and their concentration in cerebrospinal fluid in healthy human subjects." *J Clin Pharmacol.* 2006 46(4):424-32), and CX717. Additional examples of reported antagonists include irampanel (CAS RN 206260-33-5) and E-2007.

Further non-limiting examples of reported AMPA receptor antagonists for use in combinations include YM90K (CAS RN 154164-30-4), YM872 or Zonampanel (CAS RN 210245-80-0), NBQX (or 2,3-Dioxo-6-nitro-7-sulfamoyl-benzo[f]quinoxaline; CAS RN 118876-58-7), PNQX (1,4,7,8,9,10-hexahydro-9-methyl-6-nitropyrido[3,4-f]quinoxaline-2,3-dione), and ZK200775 ([1,2,3,4-tetrahydro-7-morpholinyl-2,3-dioxo-6-(fluoromethyl) quinoxalin-1-yl] methylphosphonate).

In additional embodiments, a neurogenic agent used in combination with a 4-acylaminopyridine derivative such as MKC-231 may be a reported muscarinic agent. Non-limiting examples of a reported muscarinic agent include the muscarinic agonist milameline (CI-979), or a compound that is structurally or functionally related to milameline. Structures, biological activity data, methods for obtaining biological activity data, methods of synthesis, modes of administration and pharmaceutical formulations for milameline and related compounds are disclosed in U.S. Pat. Nos. 4,786,648, 5,362,860, 5,424,301, 5,650,174, 4,710,508, 5,314,901, 5,356,914, and 5,356,912, all of which are herein incorporated by reference in their entirety.

In other embodiments, the muscarinic agonist is xanomeline, or a compound that is structurally or functionally related to xanomeline. Structures, biological activity data, methods for obtaining biological activity data, methods of synthesis, modes of administration and pharmaceutical formulations for xanomeline and related compounds are disclosed in U.S. Pat. Nos. 5,041,455, 5,043,345, and 5,260,314, all of which are herein incorporated by reference in their entirety.

In further embodiments, the muscarinic agent is alvameline (LU 25-109), or a compound that is functionally or structurally related to alvameline. Structures, biological activity data, methods for obtaining biological activity data, methods of synthesis, modes of administration and pharmaceutical formulations for alvameline and related compounds are disclosed in U.S. Pat. Nos. 6,297,262, 4,866,077, RE36,374, 4,925,858, PCT Publication No. WO 97/17074, and in Moltzen et al., J Med. Chem. 1994 Nov. 25; 37(24):4085-99, all of which are herein incorporated by reference in their entirety.

In additional embodiments, the muscarinic agent is 2,8-dimethyl-3-methylene-1-oxa-8-azaspiro[4,5]decane (YM-796) or YM-954, or a functionally or structurally related compound. Structures, biological activity data, methods for obtaining biological activity data, methods of synthesis, modes of administration and pharmaceutical formulations for YM-796, YM-954, and related compounds are disclosed in U.S. Pat. No. 4,940,795, RE34,653, U.S. Pat. Nos. 4,996,210, 5,041,549, 5,403,931, and 5,412,096, and in Wanibuchi et al., Eur. J. Pharmacol., 187, 479-486 (1990), all of which are herein incorporated by reference in their entirety.

In yet further embodiments, the muscarinic agent is cevimeline (AF102B) or a compound that is functionally or structurally related to cevimeline. Cevimeline is approved by the FDA for the treatment of symptoms of dry mouth in patients with Sjorgren's Syndrome. Structures, biological activity data, methods for obtaining biological activity data, methods of synthesis, modes of administration and pharmaceutical formulations for cevimeline and related compounds are disclosed in U.S. Pat. Nos. 4,855,290, 5,340,821, 5,580,880 (American Home Products), and U.S. Pat. No. 4,981,858 (optical isomers of AF102B), all of which are herein incorporated by reference in their entirety.

In yet additional embodiments, the muscarinic agent is sabcomeline (SB 202026), or a compound that is functionally or structurally related to sabcomeline. Structures, biological activity data, methods for obtaining biological activity data, methods of synthesis, modes of administration and pharmaceutical formulations for sabcomeline and related compounds are described in U.S. Pat. No. 5,278,170, RE35,593, U.S. Pat. Nos. 6,468,560, 5,773,619, 5,808,075, 5,545,740, 5,534,522, and 6,596,869, U.S. Patent Publication Nos. 2002/0127271, 2003/0129246, 2002/0150618, 2001/0018074, 2003/0157169, and 2001/0003588, Bromidge et al., J Med. Chem. 19; 40(26):4265-80 (1997), and Harries et al., British J. Pharm., 124, 409-415 (1998), all of which are herein incorporated by reference in their entirety.

In other embodiments, the muscarinic agent is talsaclidine (WAL 2014 FU), or a compound that is functionally or structurally related to talsaclidine. Structures, biological activity data, methods for obtaining biological activity data, methods of synthesis, modes of administration and pharmaceutical formulations for talsaclidine and related compounds are disclosed in U.S. Pat. Nos. 5,451,587, 5,286,864, 5,508,405, 5,451,587, 5,286,864, 5,508,405, and 5,137,895, and in Pharmacol. Toxicol., 78, 59-68 (1996), all of which are herein incorporated by reference in their entirety.

In some embodiments, the muscarinic agent is a 1-methyl-1,2,5,6-tetrahydropyridyl-1,2,5-thiadiazole derivative, such as tetra(ethyleneglycol)(4-methoxy-1,2,5-thiadiazol-3-yl)[3-(1-methyl-1,2,5,6-tetrahydropyrid-3-yl)-1,2,5-thiadiazol-4-yl]ether, or a compound that is functionally or structurally related to a 1-methyl-1,2,5,6-tetrahydropyridyl-1,2,5-thiadiazole derivative. Structures, biological activity data, methods for obtaining biological activity data, methods of synthesis, and other information relating to using these derivatives and related compounds as pharmaceutical agents is provided by Cao et al. ("Synthesis and biological characterization of 1-methyl-1,2,5,6-tetrahydropyridyl-1,2,5-thiadiazole derivatives as muscarinic agonists for the treatment of neurological disorders." J. Med. Chem. 46(20):4273-4286, 2003), which is herein incorporated by reference in its entirety.

In further embodiments, the muscarinic agent is besipiridine, SR-46559, L-689,660, S-9977-2, AF-102, or thiopilocarpine. The structures, biological activity data, methods for obtaining biological activity data, methods of synthesis, modes of administration and pharmaceutical formulations for these and related compounds are known in the art and/or described in the publications referenced herein.

In yet further embodiments, the muscarinic agent is an analog of clozapine or a pharmaceutically acceptable salt, ester, amide, or prodrug form thereof. In some embodiments, the analog is a diaryl[a,d]cycloheptene, such as an amino substituted form thereof. A compound that is functionally or structurally related to such analogs of clozapine may also be used in the practice of the invention. In some embodiments, the compound is N-desmethylclozapine, which has been reported to be a metabolite of clozapine and discovered to be highly neurogenic in assays as disclosed herein. Structures, biological activity data, methods for obtaining biological activity data, methods of synthesis, modes of administration and pharmaceutical formulations for these analogs and related compounds are disclosed in US 2005/0192268 and WO 05/63254, both of which are hereby incorporated by reference as if fully set forth.

In other embodiments, the muscarinic agent is an $m_1$ receptor agonist selected from 55-LH-3B,55-LH-25A, 55-LH-30B, 55-LH-4-1A,40-LH-67,55-LH-15A, 55-LH-16B, 55-LH-11C, 55-LH-31A, 55-LH-46,55-LH-47,55-LH-4-3A, or a compound that is functionally or structurally related to one or more of these agonists. Structures, biological activity data, methods for obtaining biological activity data, methods of synthesis, modes of administration and pharmaceutical formulations for these agonists and related compounds are disclosed in US 2005/0130961 and WO 04/087158, both of which are hereby incorporated by reference as if fully set forth.

In additional embodiments, the muscarinic agent is a benzimidazolidinone derivative or a compound that is functionally or structurally related to a benzimidazolidinone derivative. The derivative or related compound may be selective for the $m_1$ and/or $m_4$ receptor subtypes. Structures, biological activity data, methods for obtaining biological activity data, methods of synthesis, modes of administration and pharmaceutical formulations for these derivatives and related compounds are disclosed in U.S. Pat. No. 6,951,849, US 2003/0100545, WO 04/089942, and WO 03/028650, all of which are hereby incorporated by reference as if fully set forth.

In yet additional embodiments, the muscarinic agent is a spiroazacyclic compound or a compound that is functionally or structurally related to a spiroazacyclic compound. In some embodiments, the compound is 1-oxa-3,8-diaza-spiro[4,5]decan-2-one. Structures, biological activity data, methods for obtaining biological activity data, methods of synthesis, modes of administration and pharmaceutical formulations for these spiroazacyclic compounds and related compounds are disclosed in U.S. Pat. No. 6,911,452 and WO 03/057698, both of which are hereby incorporated by reference as if fully set forth.

In other embodiments, the muscarinic agent is a tetrahydroquinoline analog or a compound that is functionally or structurally related to a tetrahydroquinoline analog. Structures, biological activity data, methods for obtaining biological activity data, methods of synthesis, modes of administration and pharmaceutical formulations for these spiroazacyclic compounds and related compounds are disclosed in US 2003/0176418, US 2005/0209226, and WO 03/057672, all of which are hereby incorporated by reference as if fully set forth.

In further embodiments, the agent is a muscarinic agonist or a compound that is functionally or structurally related to such an agonist. Structures, biological activity data, methods for obtaining biological activity data, methods of synthesis, modes of administration and pharmaceutical formulations for these agonists and related compounds are disclosed in U.S. Pat. No. 6,627,645, US 2005/0113357, and WO 01/83472, all of which are hereby incorporated by reference as if fully set forth.

In yet further embodiments, the agent is a muscarinic agonist or a compound that is functionally or structurally related to such an agonist. Structures, biological activity data, methods for obtaining biological activity data, methods of synthesis, modes of administration and pharmaceutical formulations for these agonists and related compounds are disclosed in U.S. Pat. Nos. 6,528,529, US 2003/0144285, WO 01/05763, and WO 99/50247, all of which are hereby incorporated by reference as if fully set forth.

Structures, biological activity data, methods for obtaining biological activity data, methods of synthesis, modes of administration and pharmaceutical formulations for other muscarinic agents are described in U.S. Pat. Nos., 5,675,007, 5,902,814, 6,051,581, 5,384,408, 5,468,875, 5,773,458, 5,512,574, 5,407,938, 5,668,174, 4,870,081, 4,968,691, 4,971,975, 5,110,828, 5,166,357, 5,124,460, 5,132,316, 5,262,427, 5,324,724, 5,534,520, 5,541,194, 5,599,937, 5,852,029, 5,981,545, 5,527,813, 5,571,826, 5,574,043, 5,578,602, 5,605,908, 5,641,791, 5,646,289, 5,665,745, 5,672,709, 6,911,477, 5,834,458, 5,756,501, 5,510,478, 5,093,333, 5,571,819, 4,992,457, and 5,362,739, Intl. Publication Nos. EP 384288, WO 9917771, JP 61280497, WO 9700894, WO 9847900, WO 9314089, EP 805153, WO 9422861, WO 9603377, EP 429344, EP 647642, WO 9626196, WO 9800412, WO 9531457, JP 61280497, JP 6298732, JP 6305967, WO 9640687, EP 311313, EP 370415, EP 709381, EP 723781, EP 727208, EP 727209, WO 9740044 and EP 384285, Ward et al., J. Med. Chem., 38, 3469 (1995), Wermuth et al., Farmaco., 48(2):253-74 (1993), Biorg. Med. Chem. Let., 2; 833-838 (1992), and Nordvall et al., J. Med. Chem., 35, 1541 (1992), all of which are herein incorporated by reference in their entirety.

Provided herein, are muscarinic agents such as AChE inhibitors, like metrifonate or echothiophate.

Metrifonate is also known as metriphonate or trichlorfon or its active metabolite, 2,2-dimethyldichlorovinyl phosphate (or dichlorvos or DDVP). Metrifonate is represented by the following formula:

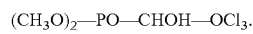

$(CH_3O)_2$—PO—CHOH—OCl$_3$.

Metrifonate has been used to treat Alzheimer's Disease (see the studies of Cummings et al. "The efficacy of Metrifonate in improving the behavioral disturbance of Alzheimer's disease patients.". Neurology 1998; 50:A251).

Echothiophate is also known as ecothiopate, echothiophate iodide, phospholine iodide, (2-Mercaptoethyl)trimethylammonium S-ester with O,O'-diethylphosphorothioate, BRN 1794025, ecothiopatum, or phospholine. Echothiophate is referenced by CAS Registry Number 6736-03-4.

In other embodiments, an AChE inhibitor is an aminoacridine such as tacrine or ipidacrine as non-limiting examples. Tacrine is also known as tetrahydroaminoacridine or THA. Tacrine is referenced by CAS Registry Number 321-64-2. Ipidacrine is also known as Amiridin.

In additional embodiments, an AChE inhibitor is a carbamate such as physostigmine, neostigmine, or rivastigmine as non-limiting examples.

Physostigmine, also known as 1,2,3,3a,8,8a-hexahydro-1,3a,8-trimethyl-, methylcarbamate (ester) or (3aS,8aR)-pyrrolo[2,3-b]indol-5-ol, is referenced by CAS number 57-47-6. It is a tertiary amine capable of crossing the blood-brain barrier.

Neostigmine, or m-hydroxyphenyl)trimethyl-dimethylcarbamate(ester) ammonium, is referenced by CAS number 59-99-4.

Rivastigmine is also known as rivastigmine tartrate or (S)—N-Ethyl-N-methyl-3-[1-(dimethylamino)ethyl]-phenyl carbamate hydrogen-(2R,3R)-tartrate or SDZ ENA 713 or ENA 713. The reference for rivastigmine is CAS Registry Number 123441-03-2.

In further embodiments, an AChE inhibitor is a carbamate phenanthrine derivative such as galantamine or its hydrogen bromide form as non-limiting examples.

Galantamine is also known as (4aS,6R,8aS)-4-a,5,9,10,11,12-hexahydro-3-methoxy-11-methyl-6H-benzofuro(3a,3,2-ef)(2)benzazepin-6-ol and is often used in its hydrogen bromide form. Galantamine is referenced by CAS number 357-70-0.

An AChE inhibitor may also be a piperidine derivative, such as donepezil as a non-limiting example. Donepezil is also known as 2,3-dihydro-5,6-dimethoxy-2-((1-(phenylmethyl)-4-piperidinyl)methyl)-1H-inden-1-one, and is referenced by CAS number 120014-06-4.

Itopride may also be an AChE inhibitor for use in embodiments disclosed herein. Itopride HCl is referenced by CAS Registry Number 122898-67-3. In one embodiment, a total daily dose range for itopride HCl is from about 25 mg to about 1000 mg, or between about 100 mg to about 300 mg. In some embodiments, the AChE inhibitor, or neurogenic agent, is the N-oxide derivative of itopride, which is the primary human metabolite of itopride HCl.

Another AChE inhibitor for use in the disclosed embodiments is (−)-huperzine A, which is also referred to as HupA and 1-amino-13-ethylidene-11-methyl-6-aza-tricyclo[7.3.1.02,7]trideca-2(7),3,10-trien-5-one. It is referenced by CAS number 102518-79-6.

A further embodiment of an AChE inhibitor is phenserine, the structure and synthesis of which is described in U.S. Pat. No. 6,495,700, which is hereby incorporated by reference as if fully set forth.

In yet additional embodiments, the neurogenic agent in combination with a 4-acylaminopyridine derivative such as MKC-231 is a reported HDAC inhibitor. The term "HDAC" refers to any one of a family of enzymes that remove acetyl groups from the epsilon-amino groups of lysine residues at the N-terminus of a histone. An HDAC inhibitor refers to compounds capable of inhibiting, reducing, or otherwise modulating the deacetylation of histones mediated by a histone deacetylase. Non-limiting examples of a reported HDAC inhibitor include a short-chain fatty acid, such as butyric acid, phenylbutyrate (PB), 4-phenylbutyrate (4-PBA), pivaloyloxymethyl butyrate (Pivanex, AN-9), isovalerate, valerate, valproate, valproic acid, propionate, butyramide, isobutyramide, phenylacetate, 3-bromopropionate, or tributyrin; a compound bearing a hydroxyamic acid group, such as suberoylanlide hydroxamic acid (SAHA), trichostatin A (TSA), trichostatin C (TSC), salicylhydroxamic acid, oxamflatin, suberic bishydroxamic acid (SBHA), m-carboxy-cinnamic acid bishydroxamic acid (CBHA), pyroxamide (CAS RN 382180-17-8), diethyl bis-(pentamethylene-N,N-dimethylcarboxamide) malonate (EMBA), azelaic bishydroxamic acid (ABHA), azelaic-1-hydroxamate-9-anilide (AAHA), 6-(3-Chlorophenylureido) carpoic hydroxamic acid, or A-161906; a cyclic tetrapeptide, such as Depsipeptide (FK228), FR225497, trapoxin A, apicidin, chlamydocin, or HC-toxin; a benzamide, such as MS-275; depudecin, a sulfonamide anilide (e.g., diallyl sulfide), BL1521, curcumin (diferuloylmethane), CI-994 (N-acetyldinaline), spiruchostatin A, Scriptaid, carbamazepine (CBZ), or a related compound; a compound comprising a cyclic tetrapeptide group and a hydroxamic acid group (examples of such compounds are described in U.S. Pat. Nos. 6,833,384 and 6,552,065); a compound comprising a benzamide group and a hydroxamic acid group (examples of such compounds are described in Ryu et al., Cancer Lett. 2005 Jul. 9 (epub), Plumb et al., Mol Cancer Ther., 2(8):721-8 (2003), Ragno et al., J Med Chem., 47(6):1351-9 (2004), Mai et al., J Med. Chem., 47(5):1098-109 (2004), Mai et al., J Med. Chem., 46(4):512-24 (2003), Mai et al., J Med. Chem., 45(9):1778-84 (2002), Massa et al., J Med Chem., 44(13):2069-72 (2001), Mai et al., J Med. Chem., 48(9):3344-53 (2005), and Mai et al., J Med. Chem., 46(23):4826-9 (2003)); a compound described in U.S. Pat. Nos. 6,897,220, 6,888,027, 5,369,108, 6,541,661, 6,720,445, 6,562,995, 6,777,217, or 6,387,673, or U.S. Patent Publication Nos. 2005/0171347, 2005/0165016, 2005/0159470, 2005/0143385, 2005/0137234, 2005/0137232, 2005/0119250, 2005/0113373, 2005/0107445, 2005/0107384, 2005/0096468, 2005/0085515, 2005/0032831, 2005/0014839, 2004/0266769, 2004/0254220, 2004/0229889, 2004/0198830, 2004/0142953, 2004/0106599, 2004/0092598, 2004/0077726, 2004/0077698, 2004/0053960, 2003/0187027, 2002/0177594, 2002/0161045, 2002/0119996, 2002/0115826, 2002/0103192, or 2002/0065282; FK228, AN-9, MS-275, CI-994, SAHA, G2M-777, PXD-101, LBH-589, MGCD-0103, MK0683, sodium phenylbutyrate, CRA-024781, and derivatives, salts, metabolites, prodrugs, and stereoisomers thereof; and a molecule that inhibits the transcription and/or translation of one or more HDACs.

Additional non-limiting examples include a reported HDac inhibitor selected from ONO-2506 or arundic acid (CAS RN 185517-21-9); MGCDO103 (see Gelmon et al. "Phase I trials of the oral histone deacetylase (HDAC) inhibitor MGCDO103 given either daily or 3× weekly for 14 days every 3 weeks in patients (pts) with advanced solid tumors."*Journal of Clinical Oncology,* 2005 ASCO Annual Meeting Proceedings. 23(16S, June 1 Supplement), 2005: 3147 and Kalita et al. "Pharmacodynamic effect of MGCD0103, an oral isotype-selective histone deacetylase (HDAC) inhibitor, on HDAC enzyme inhibition and histone acetylation induction in Phase I clinical trials in patients (pts) with advanced solid tumors or non-Hodgkin's lymphoma (NHL)" *Journal of Clinical Oncology,* 2005 ASCO Annual Meeting Proceedings. 23(16S, Part I of II, June 1 Supplement), 2005: 9631), a reported thiophenyl derivative of benzamide HDac inhibitor as presented at the 97th American Association for Cancer Research (AACR) Annual Meeting in Washington, D.C. in a poster titled "Enhanced Isotype-Selectivity and Antiproliferative Activity of Thiophenyl Derivatives of BenzamideHDAC Inhibitors In Human Cancer Cells," (abstract #4725), and a reported HDac inhibitor as described in U.S. Pat. No. 6,541,661; SAHA or Vorinostat (CAS RN 149647-78-9); PXD101 or PXD 101 or PX 105684 (CAS RN 414864-00-9), CI-994 or Tacedinaline (CAS RN 112522-64-2), MS-275 (CAS RN 209783-80-2), or an inhibitor reported in WO2005/108367.

In other embodiments, the neurogenic agent in combination with a 4-acylaminopyridine derivative such as MKC-231 is a reported GABA modulator which modulates GABA receptor activity at the receptor level (e.g., by binding directly to GABA receptors), at the transcriptional and/or translational level (e.g., by preventing GABA receptor gene expression), and/or by other modes (e.g., by binding to a ligand or effector of a GABA receptor, or by modulating the activity of an agent that directly or indirectly modulates GABA receptor activity). Non-limiting examples of GABA-A receptor modulators useful in methods described herein include triazolophthalazine derivatives, such as those disclosed in WO 99/25353, and WO/98/04560; tricyclic pyrazolo-pyridazinone analogues, such as those disclosed in WO 99/00391; fenamates, such as those disclosed in U.S. Pat. No. 5,637,617; triazolo-pyridazine derivatives, such as those disclosed in WO 99/37649, WO 99/37648, and WO 99/37644; pyrazolopyridine derivatives, such as those disclosed in WO 99/48892; nicotinic derivatives, such as those disclosed in WO 99/43661 and U.S. Pat. No. 5,723,462; muscimol, thiomuscimol, and compounds disclosed in U.S. Pat. No. 3,242,190; baclofen and compounds disclosed in U.S. Pat. No. 3,471,548; phaclofen; quisqualamine; ZAPA; zaleplon; THIP; imidazole-4-acetic acid (IMA); (+)-bicuculline; gabalinoleamide; isoguvicaine; 3-aminopropane sulphonic acid; piperidine-4-sulphonic acid; 4,5,6,7-tetrahydro-[5,4-c]-pyridin-3-ol; SR 95531; RU5315; CGP 55845; CGP 35348; FG 8094; SCH 50911; NG2-73; NGD-96-3; pricrotoxin and other bicyclophosphates disclosed in Bowery et al., Br. J. Pharmacol., 57; 435 (1976).

Additional non-limiting examples of GABA-A modulators include compounds described in U.S. Pat. Nos. 6,503,925; 6,218,547; 6,399,604; 6,646,124; 6,515,140; 6,451,809; 6,448,259; 6,448,246; 6,423,711; 6,414,147; 6,399,604; 6,380,209; 6,353,109; 6,297,256; 6,297,252; 6,268,496; 6,211,365; 6,166,203; 6,177,569; 6,194,427; 6,156,898; 6,143,760; 6,127,395; 6,103,903; 6,103,731; 6,723,735;

6,479,506; 6,476,030; 6,337,331; 6,730,676; 6,730,681; 6,828,322; 6,872,720; 6,699,859; 6,696,444; 6,617,326; 6,608,062; 6,579,875; 6,541,484; 6,500,828; 6,355,798; 6,333,336; 6,319,924; 6,303,605; 6,303,597; 6,291,460; 6,255,305; 6,133,255; 6,872,731; 6,900,215; 6,642,229; 6,593,325; 6,914,060; 6,914,063; 6,914,065; 6,936,608; 6,534,505; 6,426,343; 6,313,125; 6,310,203; 6,200,975; 6,071,909; 5,922,724; 6,096,887; 6,080,873; 6,013,799; 5,936,095; 5,925,770; 5,910,590; 5,908,932; 5,849,927; 5,840,888; 5,817,813; 5,804,686; 5,792,766; 5,750,702; 5,744,603; 5,744,602; 5,723,462; 5,696,260; 5,693,801; 5,677,309; 5,668,283; 5,637,725; 5,637,724; 5,625,063; 5,610,299; 5,608,079; 5,606,059; 5,604,235; 5,585,490; 5,510,480; 5,484,944; 5,473,073; 5,463,054; 5,451,585; 5,426,186; 5,367,077; 5,328,912 5,326,868; 5,312,822; 5,306,819; 5,286,860; 5,266,698; 5,243,049; 5,216,159; 5,212,310; 5,185,446; 5,185,446; 5,182,290; 5,130,430; 5,095,015; 20050014939; 20040171633; 20050165048; 20050165023; 20040259818; and 20040192692.

In some embodiments, the GABA-A modulator is a sub-unit-selective modulator. Non-limiting examples of GABA-A modulator having specificity for the alpha1 subunit include alpidem and zolpidem. Non-limiting examples of GABA-A modulator having specificity for the alpha2 and/or alpha3 subunits include compounds described in U.S. Pat. Nos. 6,730,681; 6,828,322; 6,872,720; 6,699,859; 6,696,444; 6,617,326; 6,608,062; 6,579,875; 6,541,484; 6,500,828; 6,355,798; 6,333,336; 6,319,924; 6,303,605; 6,303,597; 6,291,460; 6,255,305; 6,133,255; 6,900,215; 6,642,229; 6,593,325; and 6,914,063. Non-limiting examples of GABA-A modulator having specificity for the alpha2, alpha3 and/or alpha5 subunits include compounds described in U.S. Pat. Nos. 6,730,676 and 6,936,608. Non-limiting examples of GABA-A modulators having specificity for the alpha5 sub-unit include compounds described in U.S. Pat. Nos. 6,534,505; 6,426,343; 6,313,125; 6,310,203; 6,200,975 and 6,399,604. Additional non-limiting subunit selective GABA-A modulators include CL218,872 and related compounds disclosed in Squires et al., *Pharmacol. Biochem. Behav.*, 10: 825 (1979); and beta-carboline-3-carboxylic acid esters described in Nielsen et al., *Nature*, 286: 606 (1980).

In some embodiments, the GABA-A receptor modulator is a reported allosteric modulator. In various embodiments, allosteric modulators modulate one or more aspects of the activity of GABA at the target GABA receptor, such as potency, maximal effect, affinity, and/or responsiveness to other GABA modulators. In some embodiments, allosteric modulators potentiate the effect of GABA (e.g., positive allosteric modulators), and/or reduce the effect of GABA (e.g., inverse agonists). Non-limiting examples of benzodiazepine GABA-A modulators include aiprazolam, bentazepam, bretazenil, bromazepam, brotizolam, cannazepam, chlordiazepoxide, clobazam, clonazepam, cinolazepam, clotiazepam, cloxazolam, clozapin, delorazepam, diazepam, dibenzepin, dipotassium chlorazepat, divaplon, estazolam, ethylloflazepat, etizolam, fludiazepam, flumazenil, flunitrazepam, flurazepamI 1HCl, flutoprazepam, halazepam, haloxazolam, imidazenil, ketazolam, lorazepam, loprazolam, lormetazepam, medazepam, metaclazepam, mexozolam, midazolam-HCl, nabanezil, nimetazepam, nitrazepam, nordazepam, oxazepam-tazepam, oxazolam, pinazepam, prazepam, quazepam, sarmazenil, suriclone, temazepam, tetrazepam, tofisopam, triazolam, zaleplon, zolezepam, zolpidem, zopiclone, and zopielon.

Additional non-limiting examples of benzodiazepine GABA-A modulators include Ro15-4513, CL218872, CGS 8216, CGS 9895, PK 9084, U-93631, beta-CCM, beta-CCB, beta-CCP, Ro 19-8022, CGS 20625, NNC 14-0590, Ru 33-203,5-amino-1-bromouracil, GYKI-52322, FG 8205, Ro 19-4603, ZG-63, RWJ46771, SX-3228, and L-655,078; NNC 14-0578, NNC 14-8198, and additional compounds described in Wong et al., *Eur J Pharmacol* 209: 319-325 (1995); Y-23684 and additional compounds in Yasumatsu et al., *Br J Pharmacol* 111: 1170-1178 (1994); and compounds described in U.S. Pat. No. 4,513,135.

Non-limiting examples of barbiturate or barbituric acid derivative GABA-A modulators include phenobarbital, pentobarbital, pentobarbitone, primidone, barbexaclon, dipropyl barbituric acid, eunarcon, hexobarbital, mephobarbital, methohexital, Na-methohexital, 2,4,6(1H,3H,5)-pyrimidintrion, secbutabarbital and/or thiopental.

Non-limiting examples of neurosteroid GABA-A modulators include alphaxalone, allotetrahydrodeoxycorticosterone, tetrahydrodeoxycorticosterone, estrogen, progesterone 3-beta-hydroxyandrost-5-en-17-on-3-sulfate, dehydroepianrosterone, eltanolone, ethinylestradiol, 5-pregnen-3-beta-ol-20 on-sulfate, 5a-pregnan-3α-ol-20-one (5PG), allopregnanolone, pregnanolone, and steroid derivatives and metabolites described in U.S. Pat. Nos. 5,939,545, 5,925,630, 6,277,838, 6,143,736, RE35,517, U.S. Pat. Nos. 5,925,630, 5,591,733, 5,232,917, 20050176976, WO 96116076, WO 98/05337, WO 95/21617, WO 94/27608, WO 93/18053, WO 93/05786, WO 93/03732, WO 91116897, EP01038880, and Han et al., *J. Med. Chem.*, 36, 3956-3967 (1993), Anderson et al., *J. Med. Chem.*, 40, 1668-1681 (1997), Hogenkamp et al., *J. Med. Chem.*, 40, 61-72 (1997), Upasani et al., *J. Med. Chem.*, 40, 73-84 (1997), Majewska et al., *Science* 232:1004-1007 (1986), Harrison et al., *J. Pharmacol. Exp. Ther.* 241: 346-353 (1987), Gee et al., *Eur. J. Pharmacol.*, 136:419-423 (1987) and Birtran et al., *Brain Res.*, 561, 157-161 (1991).

Non-limiting examples of beta-carboline GABA-A modulators include abecarnil, 3,4-dihydro-beta-carboline, gedocarnil, 1-methyl-1-vinyl-2,3,4-trihydro-beta-carboline-3-carboxylic acid, 6-methoxy-1,2,3,4-tetrahydro-beta-carboline, N—BOC-L-1,2,3,4-tetrahydro-beta-carboline-3-carboxylic acid, tryptoline, pinoline, methoxyharmalan, tetrahydro-beta-carboline (THBC), 1-methyl-THBC, 6-methoxy-THBC$_{1-6}$-hydroxy-THBC, 6-methoxyharmalan, norharman, 3,4-dihydro-beta-carboline, and compounds described in Nielsen et al., Nature, 286: 606 (1980).

In some embodiments, the GABA modulator modulates GABA-B receptor activity. Non-limiting examples of reported GABA-B receptor modulators useful in methods described herein include CGP36742; CGP-64213; CGP 56999A; CGP 54433A; CGP 36742; SCH 50911; CGP 7930; CGP 13501; baclofen and compounds disclosed in U.S. Pat. No. 3,471,548; saclofen; phaclofen; 2-hydroxysaclofen; SKF 97541; CGP 35348 and related compounds described in Olpe, et al, *Eur. J. Pharmacol.*, 187, 27 (1990); phosphinic acid derivatives described in Hills, et al, *Br. J. Pharmacol.*, 102, pp. 5-6 (1991); and compounds described in 4,656,298, 5,929,236, EP0463969, EP 0356128, Kaupmann et al., *Nature* 368: 239 (1997), Karla et al., *J Med Chem.*, 42(11): 2053-9 (1992), Ansar et al., *Therapie*, 54(5):651-8 (1999), and Castelli et al., *Eur J Pharmacol.*, 446(1-3):1-5 (2002).

In some embodiments, the GABA modulator modulates GABA-C receptor activity. Non-limiting examples of reported GABA-C receptor modulators useful in methods described herein include cis-aminocrotonic acid (CACA); 1,2,5,6-tetrahydropyridine-4-yl methyl phosphinic acid (TP-MPA) and related compounds such as P4MPA, PPA and SEPI; 2-methyl-TACA; (+/−)-TAMP; muscimol and compounds disclosed in U.S. Pat. No. 3,242,190; ZAPA; THIP and related analogues, such as aza-THIP; pricotroxin; imidazole-4-acetic acid (IMA); and CGP36742.

In some embodiments, the GABA modulator modulates the activity of glutamic acid decarboxylase (GAD).

In some embodiments, the GABA modulator modulates GABA transaminase (GTA). Non-limiting examples of GTA modulators include the GABA analogue vigabatrin and compounds disclosed in U.S. Pat. No. 3,960,927.

In some embodiments, the GABA modulator modulates the reuptake and/or transport of GABA from extracellular regions. In other embodiments, the GABA modulator modulates the activity of the GABA transporters, GAT-1, GAT-2, GAT-3 and/or BGT-1. Non-limiting examples of GABA reuptake and/or transport modulators include nipecotic acid and related derivatives, such as CI-966; SKF 89976A; TACA; stiripentol; tiagabine and GAT-1 inhibitors disclosed in U.S. Pat. No. 5,010,090; (R)-1-(4,4-diphenyl-3-butenyl)-3-piperidinecarboxylic acid and related compounds disclosed in U.S. Pat. No. 4,383,999; (R)-1-[4,4-bis(3-methyl-2-thienyl)-3-butenyl]-3-piperidinecarboxylic acid and related compounds disclosed in Anderson et al., *J. Med. Chem.* 36, (1993) 1716-1725; guvacine and related compounds disclosed in Krogsgaard-Larsen, *Molecular & Cellular Biochemistry* 31, 105-121 (1980); GAT-4 inhibitors disclosed in U.S. Pat. No. 6,071,932; and compounds disclosed in U.S. Pat. No. 6,906, 177 and Ali, F. E., et al. *J. Med. Chem.* 1985, 28, 653-660. Methods for detecting GABA reuptake inhibitors are known in the art, and are described, e.g., in U.S. Pat. Nos. 6,906,177; 6,225,115; 4,383,999; Ali, F. E., et al. *J. Med. Chem.* 1985, 28, 653-660.

In some embodiments, the GABA modulator is the benzodiazepine Clonazepam, which is described, e.g., in U.S. Pat. No. 3,121,076 and U.S. Pat. No. 3,116,203; the benzodiazepine Diazepam, which is described, e.g., in U.S. Pat. Nos. 3,371,085; 3,109,843; and 3,136,815; the short-acting diazepam derivative Midazolam, which is a described, e.g., in U.S. Pat. No. 4,280,957; the imidazodiazepine Flumazenil, which is described, e.g., in U.S. Pat. No. 4,316,839; the benzodiazepine Lorazepam is described, e.g., in U.S. Pat. No. 3,296,249; the benzodiazepine L-655708, which is described, e.g., in Quirk et al. *Neuropharmacology* 1996, 35, 1331; Sur et al. *Mol. Pharmacol.* 1998, 54, 928; and Sur et al. *Brain Res.* 1999, 822, 265; the benzodiazepine Gabitril; Zopiclone, which binds the benzodiazepine site on GABA-A receptors, and is disclosed, e.g., in U.S. Pat. Nos. 3,862,149 and 4,220,646; the GABA-A potentiator Indiplon as described, e.g., in Foster et al., *J Pharmacol Exp Ther.*, 311 (2):547-59 (2004), U.S. Pat. Nos. 4,521,422 and 4,900,836; Zolpidem, described, e.g., in U.S. Pat. No. 4,794,185 and EP50563; Zaleplon, described, e.g., in U.S. Pat. No. 4,626, 538; Abecarnil, described, e.g., in Stephens et al., *J Pharmacol Exp Ther.*, 253(1):334-43 (1990); the GABA-A agonist Isoguvacine, which is described, e.g., in Chebib et al., *Clin. Exp. Pharmacol. Physiol.* 1999, 26, 937-940; Leinekugel et al. *J. Physiol.* 1995, 487, 319-29; and White et al., *J. Neurochem.* 1983, 40(6), 1701-8; the GABA-A agonist Gaboxadol (THIP), which is described, e.g., in U.S. Pat. No. 4,278,676 and Krogsgaard-Larsen, *Acta. Chem. Scand.* 1977, 31, 584; the GABA-A agonist Muscimol, which is described, e.g., in U.S. Pat. Nos. 3,242,190 and 3,397,209; the inverse GABA-A agonist beta-CCP, which is described, e.g., in Nielsen et al., *J. Neurochem.*, 36(1):276-85 (1981); the GABA-A potentiator Riluzole, which is described, e.g., in U.S. Pat. No. 4,370,338 and EP 50,551; the GABA-B agonist and GABA-C antagonist SKF 97541, which is described, e.g., in Froestl et al., *J. Med. Chem.* 38 3297 (1995); Hoskison et al., *Neurosci. Lett.* 2004, 365(1), 48-53 and Hue et al., *J. Insect Physiol.* 1997, 43(12), 1125-1131; the GABA-B agonist Baclofen, which is described, e.g., in U.S. Pat. No. 3,471,548; the GABA-C agonist cis-4-aminocrotonic acid (CACA), which is described, e.g., in Ulloor et al. *J. Neurophysiol.* 2004, 91(4), 1822-31; the GABA-A antagonist Phaclofen, which is described, e.g., in Kerr et al. *Brain Res.* 1987, 405, 150; Karlsson et al. *Eur. J. Pharmacol.* 1988, 148, 485; and Hasuo, Gallagher *Neurosci. Lett.* 1988, 86, 77; the GABA-A antagonist SR 95531, which is described, e.g., in Stell et al. *J. Neurosci.* 2002, 22(10), RC223; Wermuth et al., *J. Med. Chem.* 30 239 (1987); and Luddens and Korpi, *J. Neurosci.* 15: 6957 (1995); the GABA-A antagonist Bicuculline, which is a described, e.g., in Groenewoud, *J. Chem. Soc.* 1936, 199; Olsen et al., *Brain Res.* 102: 283 (1976) and Haworth et al. *Nature* 1950, 165, 529; the selective GABA-B antagonist CGP 35348, which is described, e.g., in Olpe et al. *Eur. J. Pharmacol.* 1990, 187, 27; Hao et al. *Neurosci. Lett.* 1994, 182, 299; and Froestl et al. *Pharmacol. Rev. Comm.* 1996, 8, 127; the selective GABA-B antagonist CGP 46381, which is described, e.g., in Lingenhoehl, *Pharmacol. Comm.* 1993, 3, 49; the selective GABA-B antagonist CGP 52432, which is described, e.g., in Lanza et al. *Eur. J. Pharmacol.* 1993, 237, 191; Froestl et al. *Pharmacol. Rev. Comm.* 1996, 8, 127; Bonanno et al. *Eur. J. Pharmacol.* 1998, 362, 143; and Libri et al. *Naunyn-Schmied. Arch. Pharmacol.* 1998, 358, 168; the selective GABA-B antagonist CGP 54626, which is described, e.g., in Brugger et al. *Eur. J. Pharmacol.* 1993, 235, 153; Froestl et al. *Pharmacol. Rev. Comm.* 1996, 8, 127; and Kaupmann et al. *Nature* 1998, 396, 683; the selective GABA-B antagonist CGP 55845, which is a GABA-receptor antagonist described, e.g., in Davies et al. *Neuropharmacology* 1993, 32, 1071; Froestl et al. *Pharmacol. Rev. Comm.* 1996, 8, 127; and Deisz *Neuroscience* 1999, 93, 1241; the selective GABA-B antagonist Saclofen, which is described, e.g., in Bowery, *TiPS,* 1989, 10, 401; and Kerr et al. *Neurosci Lett.* 1988; 92(1):92-6; the GABA-B antagonist 2-Hydroxysaclofen, which is described, e.g., in Kerr et al. *Neurosci. Lett.* 1988, 92, 92; and Curtis et al. *Neurosci. Lett.* 1988, 92, 97; the GABA-B antagonist SCH 50,911, which is described, e.g., in Carruthers et al., *Bioorg Med Chem Lett* 8: 3059-3064 (1998); Bolser et al. *J. Pharmacol. Exp. Ther.* 1996, 274, 1393; Hosford et al. *J. Pharmacol. Exp. Ther.* 1996, 274, 1399; and Ong et al. *Eur. J. Pharmacol.* 1998, 362, 35; the selective GABA-C antagonist TPMPA, which is described, e.g., in Schlicker et al., *Brain Res. Bull.* 2004, 63(2), 91-7; Murata et al., *Bioorg. Med. Chem. Lett.* 6: 2073 (1996); and Ragozzino et al., *Mol. Pharmacol.* 50: 1024 (1996); a GABA derivative, such as Pregabalin [(S)-(+)-3-isobutylgaba] or gabapentin [1-(aminomethyl)cyclohexane acetic acid]. Gabapentin is described, e.g., in U.S. Pat. No. 4,024,175; the lipid-soluble GABA agonist Progabide, which is metabolized in vivo into GABA and/or pharmaceutically active GABA derivatives in vivo. Progabide is described, e.g., in U.S. Pat. Nos. 4,094,992 and 4,361,583; the GAT1 inhibitor Tiagabine, which is described, e.g., in U.S. Pat. No. 5,010,090 and Andersen et al. *J. Med. Chem.* 1993, 36, 1716; the GABA transaminase inhibitor Valproic Acid (2-propylpentanoic acid or dispropylacetic acid), which is described, e.g., in U.S. Pat. No. 4,699,927 and Carraz et al., *Therapie,* 1965, 20, 419; the GABA transaminase inhibitor Vigabatrin, which is described, e.g., in U.S. Pat. No. 3,960,927; or Topiramate, which is described, e.g., in U.S. Pat. No. 4,513,006.

Additionally, the neurogenic agent in combination with a 4-acylaminopyridine derivative such as MKC-231 may be a neurogenic sensitizing agent is a reported anti-epileptic agent. Non-limiting examples of such agents include carbamazepine or tegretol (CAS RN 298-46-4), clonazepam (CAS RN 1622-61-3), BPA or 3-(p-Boronophenyl)alanine (CAS RN 90580-64-6), gabapentin or neurontin (CAS RN 60142-96-3), phenyloin (CAS RN 57-41-0), topiramate, lamotrigine or lamictal (CAS RN 84057-84-1), phenobarbital (CAS RN 50-06-6), oxcarbazepine (CAS RN 28721-07-5), primidone (CAS RN 125-33-7), ethosuximide (CAS RN 77-67-8), levetiracetam (CAS RN 102767-28-2), zonisamide, tiagabine (CAS RN 115103-54-3), depakote or divalproex sodium (CAS RN 76584-70-8), Felbamate (Na-channel and NMDA receptor antagonist), or pregabalin (CAS RN 148553-50-8).

In further embodiments, the neurogenic sensitizing agent may be a reported direct or indirect modulator of dopamine receptors. Non-limiting examples of such agents include the indirect dopamine agonists methylphenidate (CAS RN 113-45-1) or Methylphenidate hydrochloride (also known as ritalin CAS RN 298-59-9), amphetamine (CAS RN 300-62-9) and methamphetamine (CAS RN 537-46-2), and the direct dopamine agonists sumanirole (CAS RN 179386-43-7), roprinirole (CAS RN 91374-21-9), and rotigotine (CAS RN 99755-59-6). Additional non-limiting examples include 7-OH-DPAT, quinpirole, haloperidole, or clozapine.

Additional non-limiting examples include bromocriptine (CAS RN 25614-03-3), adrogolide (CAS RN 171752-56-0), pramipexole (CAS RN 104632-26-0), Ropinirole (CAS RN 91374-21-9), apomorphine (CAS RN 58-00-4) or apomorphine hydrochloride (CAS RN 314-19-2), lisuride (CAS RN 18016-80-3), Sibenadet hydrochloride or Viozan (CAS RN 154189-24-9), L-DOPA or Levodopa (CAS RN 59-92-7), Melevodopa (CAS RN 7101-51-1), etilevodopa (CAS RN 37178-37-3), Talipexole hydrochloride (CAS RN 36085-73-1) or Talipexole (CAS RN 101626-70-4), Nolomirole (CAS RN 90060-42-7), quinelorane (CAS RN 97466-90-5), pergolide (CAS RN 66104-22-1), fenoldopam (CAS RN 67227-56-9), Carmoxirole (CAS RN 98323-83-2), terguride (CAS RN 37686-84-3), cabergoline (CAS RN 81409-90-7), quinagolide (CAS RN 87056-78-8) or quinagolide hydrochloride (CAS RN 94424-50-7), sumanirole, docarpamine (CAS RN 74639-40-0), SLV-308 or 2(3H)-Benzoxazolone, 7-(4-methyl-1-piperazinyl)-monohydrochloride (CAS RN 269718-83-4), aripiprazole (CAS RN 129722-12-9), bifeprunox, lisdexamfetamine dimesylate (CAS RN 608137-33-3), safinamide (CAS RN 133865-89-1), or Adderall or Amfetamine (CAS RN 300-62-9).

In further embodiments, the neurogenic agent used in combination with a 4-acylaminopyridine derivative such as MKC-231 may be a reported dual sodium and calcium channel modulator. Non-limiting examples of such agents include safinamide and zonisamide. Additional non-limiting examples include enecadin (CAS RN 259525-01-4), Levosemotiadil (CAS RN 116476-16-5), bisaramil (CAS RN 89194-77-4), SL-34.0829 (see U.S. Pat. No. 6,897,305), lifarizine (CAS RN 119514-66-8), JTV-519 (4-[3-(4-benzylpiperidin-1-yl)propionyl]-7-methoxy-2,3,4,5-tetrahydro-1,4-benzothiazepine monohydrochloride), and delapril.

In further embodiments, the neurogenic agent in used in combination with a 4-acylaminopyridine derivative such as MKC-231 may be a reported calcium channel antagonist such as amlodipine (CAS RN 88150-42-9) or amlodipine maleate (CAS RN 88150-47-4), nifedipine (CAS RN 21829-25-4), MEM-1003 (CAS RN see Rose et al. "Efficacy of MEM 1003, a novel calcium channel blocker, in delay and trace eyeblink conditioning in older rabbits." Neurobiol Aging. 2006 Apr. 16; [Epub ahead of print]), isradipine (CAS RN 75695-93-1), felodipine (CAS RN 72509-76-3; 3,5-Pyridinedicarboxylic acid, 1,4-dihydro-4-(2,3-dichlorophenyl)-2,6-dimethyl-, ethyl methyl ester) or felodipine (CAS RN 86189-69-7; 3,5-Pyridinedicarboxylic acid, 4-(2,3-dichlorophenyl)-1,4-dihydro-2,6-dimethyl-, ethyl methyl ester, (+-)-), lemildipine (CAS RN 125729-29-5 or 94739-29-4), clevidipine (CAS RN 166432-28-6 or 167221-71-8), verapamil (CAS RN 52-53-9), ziconotide (CAS RN 107452-89-1), monatepil maleate (CAS RN 132046-06-1), manidipine (CAS RN 89226-50-6), Furnidipine (CAS RN 138661-03-7), Nitrendipine (CAS RN 39562-70-4), Loperamide (CAS RN 53179-11-6), Amiodarone (CAS RN 1951-25-3), Bepridil (CAS RN 64706-54-3), diltiazem (CAS RN 42399-41-7), Nimodipine (CAS RN 66085-59-4), Lamotrigine, Cinnarizine (CAS RN 298-57-7), lacipidine (CAS RN 103890-78-4), nilvadipine (CAS RN 75530-68-6), dotarizine (CAS RN 84625-59-2), cilnidipine (CAS RN 132203-70-4), Oxodipine (CAS RN 90729-41-2), aranidipine (CAS RN 86780-90-7), anipamil (CAS RN 83200-10-6), ipenoxazone (CAS RN 104454-71-9), Efonidipine hydrochloride or NZ 105 (CAS RN 111011-53-1) or Efonidipine (CAS RN 111011-63-3), temiverine (CAS RN 173324-94-2), pranidipine (CAS RN 99522-79-9), dopropidil (CAS RN 79700-61-1), lercanidipine (CAS RN 100427-26-7), terodiline (CAS RN 15793-40-5), fantofarone (CAS RN 114432-13-2), azelnidipine (CAS RN 123524-52-7), mibefradil (CAS RN 116644-53-2) or mibefradil dihydrochloride (CAS RN 116666-63-8), SB-237376 (see Xu et al. "Electrophysiologic effects of SB-237376: a new antiarrhythmic compound with dual potassium and calcium channel blocking action." J Cardiovasc Pharmacol. 2003 41(3):414-21), BRL-32872 (CAS RN 113241-47-7), S-2150 (see Ishibashi et al. "Pharmacodynamics of S-2150, a simultaneous calcium-blocking and alpha1-inhibiting antihypertensive drug, in rats." J Pharm Pharmacol. 2000 52(3):273-80), nisoldipine (CAS RN 63675-72-9), semotiadil (CAS RN 116476-13-2), palonidipine (CAS RN 96515-73-0) or palonidipine hydrochloride (CAS RN 96515-74-1), SL-87.0495 (see U.S. Pat. No. 6,897,305), YM430 (4(((S)-2-hydroxy-3-phenoxypropyl)amino)butyl methyl 2,6-dimethyl-((S)-4-(m-nitrophenyl))-1,4-dihydropyridine-3,5-dicarboxylate), barnidipine (CAS RN 104713-75-9), and AM336 or CVID (see Adams et al. "Omega-Conotoxin CVID Inhibits a Pharmacologically Distinct Voltage-sensitive Calcium Channel Associated with Transmitter Release from Preganglionic Nerve Terminals" J. Biol. Chem., 278(6): 4057-4062, 2003). An additional non-limiting example is NMED-160.

In other embodiments, the neurogenic agent used in combination with a 4-acylaminopyridine derivative such as MKC-231 may be a reported modulator of a melatonin receptor. Non-limiting examples of such modulators include the melatonin receptor agonists melatonin, LY-156735 (CAS RN 118702-11-7), agomelatine (CAS RN 138112-76-2), 6-chloromelatonin (CAS RN 63762-74-3), Ramelteon (CAS RN 196597-26-9), 2-Methyl-6,7-dichloromelatonin (CAS RN 104513-29-3), and ML 23 (CAS RN 108929-03-9).

In yet further embodiments, the neurogenic agent in combination with a 4-acylaminopyridine derivative such as MKC-231 may be a reported modulator of a melanocortin receptor. Non-limiting examples of such agents include a melanocortin receptor agonists selected from melanotan II (CAS RN 121062-08-6), PT-141 or Bremelanotide (CAS RN 189691-06-3), HP-228 (see Getting et al. "The melanocortin peptide HP228 displays protective effects in acute models of inflammation and organ damage." Eur J. Pharmacol. 2006 Jan. 24), or AP214 from Action Pharma A/S.

Additional embodiments include a combination of a 4-acylaminopyridine derivative such as MKC-231 and a reported modulator of angiotensin II function, such as at an angiotensin II receptor. In some embodiments, the neurogenic sensitizing agent used with a 4-acylaminopyridine derivative such as MKC-231 may be a reported inhibitor of an angiotensin converting enzyme (ACE). Non-limiting examples of such reported inhibitors include a sulflhydryl-containing (or mercapto-containing) agent, such as Alacepril, captopril (Capoten®), fentiapril, pivopril, pivalopril, or zofenopril; a dicarboxylate-containing agent, such as enalapril (Vasotec® or Renitec®) or enalaprilat, ramipril (Altace® or Tritace® or Ramace®), quinapril (Accupril®) or quinapril hydrochloride, perindopril (Coversyl®) or perindopril erbumine (Aceon®), lisinopril (Lisodur® or Prinivil® or Zestril®); a phosphonate-containing (or phosphate-containing) agent, such as fosinopril (Monopril®), fosinoprilat, fosinopril sodium (CAS RN 88889-14-9), benazepril (Lotensin®) or benazepril hydrochloride, imidapril or imidapril hydrochloride, moexipril (Univasc®), or trandolapril (Mavik®). In other embodiments, a modulator is administered in the form of an ester that increases biovavailability upon oral administration with subsequent conversion into metabolites with greater activity.

Further embodiments include reported angiotensin II modulating entities that are naturally occurring, such as casokinins and lactokinins (breakdown products of casein and whey) which may be administered as such to obviate the need for their formation during digestion. Additional non-limiting embodiments of reported angiotensin receptor antagonists include candesartan (Atacand® or Ratacand®, 139481-59-7) or candesartan cilexetil; eprosartan (Teveten®) or eprosartan mesylate; irbesartan (Aprovel® or Karvea® or Avapro®); losartan (Cozaarg or Hyzaar®); olmesartan (Benicar®, CAS RN 144689-24-7) or olmesartan medoxomil (CAS RN 144689-63-4); telmisartan (Micardis® or Pritor®); or valsartan (Diovan®).

Additional non-limiting examples of a reported angiotensin modulator that may be used in a combination include nateglinide or starlix (CAS RN 105816-04-4); tasosartan or its metabolite enoltasosartan; omapatrilat (CAS RN 167305-00-2); or a a combination of nateglinide and valsartan, amoldipine and benazepril (Lotrel 10-40 or Lotrel 5-40), or delapril and manidipine (CHF 1521).

Additionally, the agent used with a 4-acylaminopyridine derivative such as MKC-231 may be a reported 5HT1a receptor agonist (or partial agonist) such as buspirone (buspar). In some embodiments, a reported 5HT1a receptor agonist is an azapirone, such as, but not limited to, tandospirone, gepirone and ipsapirone. Non-limiting examples of additional reported 5HT1a receptor agonists include flesinoxan (CAS RN 98206-10-1), MDL 72832 hydrochloride, U-92016A, (+)-UH 301, F 13714, F 13640,6-hydroxy-buspirone (see US 2005/0137206), S-6-hydroxy-buspirone (see US 2003/0022899), R-6-hydroxy-buspirone (see US 2003/0009851), adatanserin, buspirone-saccharide (see WO 00/12067) or 8-hydroxy-2-dipropylaminotetralin (8-OHDPAT).

Additional non-limiting examples of reported 5HT1a receptor agonists include OPC-14523 (1-[3-[4-(3-chlorophenyl)-1-piperazinyl]propyl]-5-methoxy-3,4-dihydro-2[1H]-quinolinone monomethanesulfonate); BMS-181100 or BMY 14802 (CAS RN 105565-56-8); flibanserin (CAS RN 167933-07-5); repinotan (CAS RN 144980-29-0); lesopitron (CAS RN 132449-46-8); piclozotan (CAS RN 182415-09-4); Aripiprazole, Org-13011 (1-(4-trifluoromethyl-2-pyridinyl)-4-[4-[2-oxo-1-pyrrolidinyl]butyl]piperazine (E)-2-butenedioate); SDZ-MAR 327 (see Christian et al. "Positron emission tomographic analysis of central dopamine D1 receptor binding in normal subjects treated with the atypical neuroleptic, SDZ MAR 327." Int J Mol. Med. 1998 1(1):243-7); MKC-242 ((S)-5-[3-[(1,4-benzodioxan-2-ylmethyl)amino]propoxy]-1,3-benzodioxole HCl); vilazodone; sarizotan (CAS RN 177975-08-5); roxindole (CAS RN 112192-04-8) or roxindole methanesulfonate (CAS RN 119742-13-1); alnespirone (CAS RN 138298-79-0); bromerguride (CAS RN 83455-48-5); xaliproden (CAS RN 135354-02-8); mazapertine succinate (CAS RN 134208-18-7) or mazapertine (CAS RN 134208-17-6); PRX-00023; F-13640 ((3-chloro-4-fluoro-phenyl)-[4-fluoro-4-[[(5-methyl-pyridin-2-ylm-ethyl)-amino]methyl]piperidin-1-yl]methanone, fumaric acid salt); eptapirone (CAS RN 179756-85-5); Ziprasidone (CAS RN 146939-27-7); Sunepitron (see Becker et al. "G protein-coupled receptors: In silico drug discovery in 3D" PNAS 2004 101(31):11304-11309); umespirone (CAS RN 107736-98-1); SLV-308; bifeprunox; and zalospirone (CAS RN 114298-18-9).

Yet further non-limiting examples include AP-521 (partial agonist from AsahiKasei) and Du-123015 (from Solvay).

Alternatively, the agent used with a 4-acylaminopyridine derivative such as MKC-231 may be a reported 5HT4 receptor agonist (or partial agonist). In some embodiments, a reported 5HT4 receptor agonist or partial agonist is a substituted benzamide, such as cisapride; individual, or a combination of, cisapride enantiomers ((+) cisapride and (−) cisapride); mosapride; and renzapride as non-limiting examples. In other embodiments, the chemical entity is a benzofuran derivative, such as prucalopride. Additional embodiments include indoles, such as tegaserod, or benzimidazolones. Other non-limiting chemical entities reported as a 5HT4 receptor agonist or partial agonist include zacopride (CAS RN 90182-92-6), SC-53116 (CAS RN 141196-99-8) and its racemate SC-49518 (CAS RN 146388-57-0), BIMU1 (CAS RN 127595-43-1), TS-951 (CAS RN 174486-39-6), or ML10302 CAS RN 148868-55-7). Additional non-limiting chemical entities include metoclopramide, 5-methoxytryptamine, RS67506, 2-[1-(4-piperonyl)piperazinyl]benzothiazole, RS66331, BIMU8, SB 205149 (the n-butyl quaternary analog of renzapride), or an indole carbazimidamide as described by Buchheit et al. ("The serotonin 5-HT4 receptor. 2. Structure-activity studies of the indole carbazimidamide class of agonists." J Med. Chem. (1995) 38(13):2331-8).

Yet additional non-limiting examples include norcisapride (CAS RN 102671-04-5) which is the metabolite of cisapride; mosapride citrate; the maleate form of tegaserod (CAS RN 189188-57-6); zacopride hydrochloride (CAS RN 99617-34-2); mezacopride (CAS RN 89613-77-4); SK-951 ((+-)-4-amino-N-(2-(1-azabicyclo(3.3.0)octan-5-yl)ethyl)-5-chloro-2,3-dihydro-2-methylbenzo[b]furan-7-carboxamide hemifumarate); ATI-7505, a cisapride analog from ARYx Therapeutics; SDZ-216-454, a selective 5HT4 receptor agonist that stimulates cAMP formation in a concentration dependent manner (see Markstein et al. "Pharmacological characterisation of 5-HT receptors positively coupled to adenylyl cyclase in the rat hippocampus." Naunyn Schmiedebergs Arch Pharmacol. (1999) 359(6):454-9); SC-54750, or Aminomethylazaadamantane; Y-36912, or 4-amino-N-[1-[3-(benzylsulfonyl)propyl]piperidin-4-ylmethyl]-5-chloro-2-methoxybenzamide as disclosed by Sonda et al. ("Synthesis and pharmacological properties of benzamide derivatives as selective serotonin 4 receptor agonists." Bioorg Med. Chem. (2004) 12(10):2737-47); TKS159, or 4-amino-5-chloro-2-methoxy-N-[(2S,4S)-1-ethyl-2-hydroxymethyl-4-pyrrolidinyl] benzamide, as reported by Haga et al. ("Effect of TKS159, a novel 5-hydroxytryptamine-4 agonist, on gastric contractile activity in conscious dogs."; RS67333, or 1-(4-amino-5-chloro-2-methoxyphenyl)-3-(1-n-butyl-4-piperidinyl)-1-propanone; KDR-5169, or 4-amino-5-chloro-N-[1-(3-fluoro-4-methoxybenzyl)piperidin-4-yl]-2-(2-hydroxyethoxy)benzamide hydrochloride dihydrate as reported by Tazawa, et al. (2002) "KDR-5169, a new gastrointestinal prokinetic agent, enhances gastric contractile and emptying activities in dogs and rats." *Eur J Pharmacol* 434(3):169-76); SL65.0155, or 5-(8-amino-7-chloro-2,3-dihydro-1,4-benzodioxin-5-yl)-3-[1-(2-phenyl ethyl)-4-piperidinyl]-1,3,4-oxadiazol-2(3H)-one monohydrochloride; and Y-34959, or 4-Amino-5-chloro-2-methoxy-N-[1-[5-(1-methylindol-3-ylcarbonylamino)pentyl]piperidin-4-ylmethyl]benzamide.

Other non-limiting reported 5HT4 receptor agonists and partial agonists for use in combination with a 4-acylaminopyridine derivative such as MKC-231 include metoclopramide (CAS RN 364-62-5), 5-methoxytryptamine (CAS RN 608-07-1), RS67506 (CAS RN 168986-61-6), 2-[1-(4-piperonyl)piperazinyl]benzothiazole (CAS RN 155106-73-3), RS66331 (see Buccafusco et al. "Multiple Central Nervous System Targets for Eliciting Beneficial Effects on Memory and Cognition." (2000) Pharmacology 295(2):438-446), BIMU8 (endo-N-8-methyl-8-azabicyclo[3.2.1]oct-3-yl)-2,3-dehydro-2-oxo-3-(prop-2-yl)-1H-benzimid-azole-1-carboxamide), or SB 205149 (the n-butyl quaternary analog of renzapride. Compounds related to metoclopramide, such as metoclopramide dihydrochloride (CAS RN 2576-84-3) or metoclopramide dihydrochloride (CAS RN 5581-45-3) or metoclopramide hydrochloride (CAS RN 7232-21-5 or 54143-57-6) may also be used in a combination or method as described herein.

Additionally, the agent used with a 4-acylaminopyridine derivative such as MKC-231 may be a reported 5HT3 receptor antagonist such as azasetron (CAS RN 123039-99-6); Ondansetron (CAS RN 99614-02-5) or Ondansetron hydrochloride (CAS RN 99614-01-4); Cilansetron (CAS RN 120635-74-7); Aloxi or Palonosetron Hydrochloride (CAS RN 135729-62-3); Palenosetron (CAS RN 135729-61-2 or 135729-56-5); Cisplatin (CAS RN 15663-27-1); Lotronex or Alosetron hydrochloride (CAS RN 122852-69-1); Anzemet or Dolasetron mesylate (CAS RN 115956-13-3); zacopride or R-Zacopride; E-3620 ([3(S)-endo]-4-amino-5-chloro-N-(8-methyl—8-azabicyclo[3.2.1-]oct-3-yl-2-[(1-methyl-2-butynyl)oxy]benzamide) or E-3620HCl (3(S)-endo-4-amino-5-chloro-N-(8-methyl-8-azabicyclo[3.2.1] oct-3-yl)-2-(1-methyl-2-butinyl)oxy)-benzamide-HCl); YM 060 or Ramosetron hydrochloride (CAS RN 132907-72-3); a thieno [2,3-d]pyrimidine derivative antagonist described in U.S. Pat. No. 6,846,823, such as DDP 225 or MC1-225 (CAS RN 135991-48-9); Marinol or Dronabinol (CAS RN 1972-08-3); or Lac Hydrin or Ammonium lactate (CAS RN 515-98-0); Kytril or Granisetron hydrochloride (CAS RN 107007-99-8); Bemesetron (CAS RN 40796-97-2); Tropisetron (CAS RN 89565-68-4); Zatosetron (CAS RN 123482-22-4); Mirisetron (CAS RN 135905-89-4) or Mirisetron maleate (CAS RN 148611-75-0); or renzapride (CAS RN 112727-80-7).

Additionally, the agent used with a 4-acylaminopyridine derivative such as MKC-231 may be a reported 5HT2A/2C receptor antagonist such as Ketanserin (CAS RN 74050-98-9) or ketanserin tartrate; risperidone; olanzapine; adatanserin (CAS RN 127266-56-2); Ritanserin (CAS RN 87051-43-2); etoperidone; nefazodone; deramciclane (CAS RN 120444-71-5); Geoden or Ziprasidone hydrochloride (CAS RN 138982-67-9); Zeldox or Ziprasidone or Ziprasidone hydrochloride; EMD 281014 (7-[4-[2-(4-fluoro-phenyl)-ethyl]-piperazine-1-carbonyl]-1H-indole-3-carbonitrile HCl); MDL 100907 or M100907 (CAS RN 139290-65-6); Effexor XR (Venlafaxine formulation); Zomaril or Iloperidone; quetiapine (CAS RN 111974-69-7) or Quetiapine fumarate (CAS RN 111974-72-2) or Seroquel; SB 228357 or SB 243213 (see Bromidge et al. "Biarylcarbamoylindolines are novel and selective 5-HT(2C) receptor inverse agonists: identification of 5-methyl-1-[[2-[(2-methyl-3-pyridyl)oxy]-5-pyridyl]carbamoyl]-6-trifluoromethylindoline (SB-243213) as a potential antidepressant/anxiolytic agent." J Med. Chem. 2000 43(6):1123-34; SB 220453 or Tonabersat (CAS RN 175013-84-0); Sertindole (CAS RN 106516-24-9); Eplivanserin (CAS RN 130579-75-8) or Eplivanserin fumarate (CAS RN 130580-02-8); Lubazodone hydrochloride (CAS RN 161178-10-5); Cyproheptadine (CAS RN 129-03-3); Pizotyline or pizotifen (CAS RN 15574-96-6); Mesulergine (CAS RN 64795-35-3); Irindalone (CAS RN 96478-43-2); MDL 11939 (CAS RN 107703-78-6); or pruvanserin (CAS RN 443144-26-1).

Additional non-limiting examples of modulators include reported 5-HT2C agonists or partial agonists, such as m-chlorophenylpiperazine; or 5-HT2A receptor inverse agonists, such as ACP 103 (CAS RN: 868855-07-6), APD125 (from Arena Pharmaceuticals), AVE 8488 (from Sanofi-Aventis) or TGWOOAD/AA (from Fabre Kramer Pharmaceuticals).

Additionally, the agent used with a 4-acylaminopyridine derivative such as MKC-231 may be a reported 5HT6 receptor antagonist such as SB-357134 (N-(2,5-Dibromo-3-fluorophenyl)-4-methoxy-3-piperazin-1-ylbenzenesulfonamide); SB-271046 (5-chloro-N-(4-methoxy-3-(piperazin-1-yl)phenyl)-3-methylbenzo[b]thiophene-2-sulfonamide); Ro 04-06790 (N-(2,6-bis(methylamino)pyrimidin-4-yl)-4-aminobenzenesulfonamide); Ro 63-0563 (4-amino-N-(2,6 bis-methylamino-pyridin-4-yl)-benzene sulfonamide); clozapine or its metabolite N-desmethylclozapine; olanzapine (CAS RN 132539-06-1); fluperlapine (CAS RN 67121-76-0); seroquel (quetiapine or quetiapine fumarate); clomipramine (CAS RN 303-49-1); amitriptyline (CAS RN50-48-6); doxepin (CAS RN 1668-19-5); nortryptyline (CAS RN 72-69-5); 5-methoxytryptamine (CAS RN 608-07-1); bromocryptine (CAS RN 25614-03-3); octoclothepin (CAS RN 13448-22-1); chlorpromazine (CAS RN 50-53-3); loxapine (CAS RN 1977-10-2); fluphenazine (CAS RN 69-23-8); or GSK 742457 (presented by David Witty, "Early Optimisation of in vivo Activity: the discovery of 5-HT6 Receptor Antagonist 742457" GlaxoSmithKline at SCIpharm 2006, International Pharmaceutical Industry Conference in Edinburgh, 16 May 2006).

As an additional non-limiting example, the reported 5HT6 modulator may be SB-258585 (4-Iodo-N-[4-methoxy-3-(4-methyl-piperazin-1-yl)-phenyl]-benzen esulphonamide); PRX 07034 (from Predix Pharmaceuticals) or a partial agonist, such as E-6801 (6-chloro-N-(3-(2-(dimethylamino)ethyl)-1H-indol-5-yl)imidazo[2,1-b]thiazole-5-sulfonamide) or E-6837 (5-chloro-N-(3-(2-(dimethylamino)ethyl)-1H-indol-5-yl)naphthalene-2-sulfonamide).

Additionally, the agent used in combination with a 4-acylaminopyridine derivative such as MKC-231 may be a reported compound (or "monoamine modulator") that modulates neurotransmission mediated by one or more monoamine neurotransmitters (referred to herein as "monoamines") or other biogenic amines, such as trace amines (TAs) as a non-limiting example. TAs are endogenous, CNS-active amines that are structurally related to classical biogenic amines (e.g., norepinephrine, dopamine (4-(2-aminoethyl)benzene-1,2-diol), and/or serotonin (5-hydroxytryptamine (5-HT), or a metabolite, precursor, prodrug, or analogue thereof. The methods of the disclosure thus include administration of one or more reported TAs in a combination with a 4-acylaminopyridine derivative such as MKC-231. Additional CNS-active monoamine receptor modulators are well known in the art, and are described, e.g., in the Merck Index, 12th Ed. (1996).

Certain food products, e.g., chocolates, cheeses, and wines, can also provide a significant dietary source of TAs and/or TA-related compounds. Non-limiting examples of mammalian TAs useful as constitutive factors include, but are not limited to, tryptamine, ρ-tyramine, m-tyramine, octopamine, synephrine or β-phenylethylamine (β-PEA). Additional useful TA-related compounds include, but are not limited to, 5-hydroxytryptamine, amphetamine, bufotenin, 5-methoxytryptamine, dihydromethoxytryptamine, phenylephrine, or a metabolite, precursor, prodrug, or analogue thereof.

In some embodiments, the constitutive factor is a biogenic amine or a ligand of a trace amine-associated receptor (TAAR), and/or an agent that mediates one or more biological effects of a TA. TAs have been shown to bind to and activate a number of unique receptors, termed TAARs, which comprise a family of G-protein coupled receptors (TAAR1-TAAR9) with homology to classical biogenic amine receptors. For example, TAAR1 is activated by both tyramine and β-PEA.

Thus non-limiting embodiments include methods and combination compositions wherein the constitutive factor is β-PEA, which has been indicated as having a significant neuromodulatory role in the mammalian CNS and is found at relatively high levels in the hippocampus (e.g., Taga et al., Biomed Chromatogr., 3(3): 118-20 (1989)); a metabolite, prodrug, precursor, or other analogue of β-PEA, such as the β-PEA precursor L-phenylalanine, the β-PEA metabolite β-phenylacetic acid (β-PAA), or the β-PEA analogues methylphenidate, amphetamine, and related compounds.

Most TAs and monoamines have a short half-life (e.g., less than about 30 s) due, e.g., to their rapid extracellular metabolism. Thus embodiments of the disclosure include use of a monoamine "metabolic modulator," which increases the extracellular concentration of one or more monoamines by inhibiting monoamine metabolism. In some embodiments, the metabolic modulator is an inhibitor of the enzyme monoamine oxidase (MAO), which catalyzes the extracellular breakdown of monoamines into inactive species. Isoforms MAO-A and/or MAO-B provide the major pathway for TA metabolism. Thus, in some embodiments, TA levels are regulated by modulating the activity of MAO-A and/or MAO-B. For example, in some embodiments, endogenous TA levels are increased (and TA signaling is enhanced) by administering an inhibitor of MAO-A and/or MAO-B, in combination with a 4-acylaminopyridine derivative such as MKC-231 as described herein.

Non-limiting examples of inhibitors of monoamine oxidase (MAO) include reported inhibitors of the MAO-A isoform, which preferentially deaminates 5-hydroxytryptamine (serotonin) (5-HT) and norepinephrine (NE), and/or the MAO-β isoform, which preferentially deaminates phenylethylamine (PEA) and benzylamine (both MAO-A and MAO-B metabolize Dopamine (DA)). In various embodiments, MAO inhibitors may be irreversible or reversible (e.g., reversible inhibitors of MAO-A (RIMA)), and may have varying potencies against MAO-A and/or MAO-B (e.g., non-selective dual inhibitors or isoform-selective inhibitors). Non-limiting examples of MAO inhibitors useful in methods described herein include clorgyline, L-deprenyl, isocarboxazid (Marplan), ayahuasca, nialamide, iproniazide, iproclozide, moclobemide (Aurorix), phenelzine (Nardil), tranylcypromine (Parnate) (the congeneric of phenylzine), toloxatone, levo-deprenyl (Selegiline), harmala, RIMAs (e.g., moclobemide, described in Da Prada et al., J Pharmacol Exp Ther 248: 400-414 (1989); brofaromine; and befloxatone, described in Curet et al., J Affect Disord 51: 287-303 (1998)), lazabemide (Ro 19 6327), described in Ann. Neurol., 40(1): 99-107 (1996), and SL25.1131, described in Aubin et al., J. Pharmacol. Exp. Ther., 310: 1171-1182 (2004).

In additional embodiments, the monoamine modulator is an "uptake inhibitor," which increases extracellular monoamine levels by inhibiting the transport of monoamines away from the synaptic cleft and/or other extracellular regions. In some embodiments, the monoamine modulator is a monoamine uptake inhibitor, which may selectively/preferentially inhibit uptake of one or more monoamines relative to one or more other monoamines. The term "uptake inhibitors" includes compounds that inhibit the transport of monoamines (e.g., uptake inhibitors) and/or the binding of monoamine substrates (e.g., uptake blockers) by transporter proteins (e.g., the dopamine transporter (DAT), the NE transporter (NET), the 5-HT transporter (SERT), and/or the extraneuronal monoamine transporter (EMT)) and/or other molecules that mediate the removal of extracellular monoamines. Monoamine uptake inhibitors are generally classified according to their potencies with respect to particular monoamines, as described, e.g., in Koe, J. Pharmacol. Exp. Ther. 199: 649-661 (1976). However, references to compounds as being active against one or more monoamines are not intended to be exhaustive or inclusive of the monoamines modulated in vivo, but rather as general guidance for the skilled practitioner in selecting compounds for use in therapeutic methods provided herein.

In embodiments relating to a biogenic amine modulator used in a combination or method with a 4-acylaminopyridine derivative such as MKC-231 as disclosed herein, the modulator may be (i) a norepinephrine and dopamine reuptake inhibitor, such as bupropion (described, e.g., in U.S. Pat. Nos. 3,819,706 and 3,885,046), or (S,S)-hydroxybupropion (described, e.g., in U.S. Pat. No. 6,342,496); (ii) selective dopamine reuptake inhibitors, such as medifoxamine, aminepetine (described, e.g., in U.S. Pat. Nos. 3,758,528 and 3,821,249), GBR12909, GBR12783 and GBR13069, described in Andersen, Eur J Pharmacol, 166:493-504 (1989); or (iii) a monoamine "releaser" which stimulates the release of monoamines, such as biogenic amines from presynaptic sites, e.g., by modulating presynaptic receptors (e.g., autoreceptors, heteroreceptors), modulating the packaging (e.g., vesicular formation) and/or release (e.g., vesicular fusion and release) of monoamines, and/or otherwise modulating monoamine release. Advantageously, monoamine releasers provide a method for increasing levels of one or more monoamines within the synaptic cleft or other extracellular region independently of the activity of the presynaptic neuron.

Monoamine releasers useful in combinations provided herein include fenfluramine or p-chloroamphetamine (PCA) or the dopamine, norepinephrine, and serotonin releasing compound aminepetine (described, e.g., in U.S. Pat. Nos. 3,758,528 and 3,821,249).

The agent used with a 4-acylaminopyridine derivative such as MKC-231 may be a reported phosphodiesterase (PDE) inhibitor. In some embodiments, a reported inhibitor of PDE activity include an inhibitor of a cAMP-specific PDE. Non-limiting examples of cAMP specific PDE inhibitors useful in the methods described herein include a pyrrolidinone, such as a compound disclosed in U.S. Pat. No. 5,665,754, US20040152754 or US20040023945; a quinazolineone, such as a compound disclosed in U.S. Pat. No. 6,747,035 or 6,828,315, WO 97/49702 or WO 97/42174; a xanthine derivative; a phenylpyridine, such as a compound disclosed in U.S. Pat. No. 6,410,547 or 6,090,817, or WO 97/22585; a diazepine derivative, such as a compound disclosed in WO 97/36905; an oxime derivative, such as a compound disclosed in U.S. Pat. No. 5,693,659 or WO 96/00215; a naphthyridine, such as a compound described in U.S. Pat. Nos. 5,817,670, 6,740,662, 6,136,821, 6,331,548, 6,297,248, 6,541,480, 6,642,250, or 6,900,205, or Trifilieff et al., *Pharmacology*, 301(1): 241-248 (2002), or Hersperger et al., *J Med Chem.*, 43(4):675-82 (2000); a benzofuran, such as a compound disclosed in U.S. Pat. Nos. 5,902,824, 6,211,203, 6,514,996, 6,716,987, 6,376,535, 6,080,782, or 6,054,475, or EP 819688, EP685479, or Perrier et al., *Bioorg. Med. Chem. Lett.* 9:323-326 (1999); a phenanthridine, such as that disclosed in U.S. Pat. Nos. 6,191,138, 6,121,279, or 6,127,378; a benzoxazole, such as that disclosed in U.S. Pat. No. 6,166,041 or 6,376,485; a purine derivative, such as a compound disclosed in U.S. Pat. No. 6,228,859; a benzamide, such as a compound described in U.S. Pat. No. 5,981,527 or 5,712,298, or WO95/01338, WO 97/48697 or Ashton et al., *J. Med Chem* 37: 1696-1703 (1994); a substituted phenyl compound, such as a compound disclosed in U.S. Pat. Nos. 6,297,264, 5,866,593, 65 5,859,034, 6,245,774, 6,197,792, 6,080,790, 6,077,854, 5,962,483, 5,674,880, 5,786,354, 5,739,144, 5,776,958, 5,798,373, 5,891,896, 5,849,770, 5,550,137, 5,340,827, 5,780,478, 5,780,477, or 5,633,257 or WO 95/35283; a substituted biphenyl compound, such as that disclosed in U.S. Pat. No. 5,877,190; or a quinilinone, such as a compound described in U.S. Pat. No. 6,800,625 or WO 98/14432.

Additional non-limiting examples of reported cAMP-specific PDE inhibitors useful in methods disclosed herein include a compound disclosed in U.S. Pat. Nos. 6,818,651, 6,737,436, 6,613,778, 6,617,357, 6,146,876, 6,838,559, 6,884,800, 6,716,987, 6,514,996, 6,376,535, 6,740,655, 6,559,168, 6,069,151, 6,365,585, 6,313,116, 6,245,774, 6,011,037, 6,127,363, 6,303,789, 6,316,472, 6,348,602, 6,331,543, 6,333,354, 5,491,147, 5,608,070, 5,622,977, 5,580,888, 6,680,336, 6,569,890, 6,569,885, 6,500,856, 6,486,186, 6,458,787, 6,455,562, 6,444,671, 6,423,710, 6,376,489, 6,372,777, 6,362,213, 6,313,156, 6,294,561, 6,258,843, 6,258,833, 6,121,279, 6,043,263, RE38,624, U.S. Pat. Nos. 6,297,257, 6,251,923, 6,613,794, 6,407,108, 6,107,295, 6,103,718, 6,479,494, 6,602,890, 6,545,158, 6,545,025, 6,498,160, 6,743,802, 6,787,554, 6,828,333, 6,869,945, 6,894,041, 6,924,292, 6,949,573, 6,953,810, 6,156,753, 5,972,927, 5,962,492, 5,814,651, 5,723,460, 5,716,967, 5,686,434, 5,502,072, 5,116,837, 5,091,431; 4,670,434; 4,490,371; 5,710,160, 5,710,170, 6,384,236, or 3,941,785, or US20050119225, US20050026913, US20050059686, US20040138279, US20050222138, US20040214843, US20040106631, US 20030045557, US 20020198198, US20030162802, US20030092908, US 20030104974, US20030100571, 20030092721, US20050148604, WO 99/65880, WO 00/26201, WO 98/06704, WO 00/59890, WO9907704, WO9422852, WO 98/20007, WO 02/096423, WO 98/18796, WO 98/02440, WO 02/096463, WO 97/44337, WO 97/44036, WO 97/44322, EP 0763534, Aoki et al., *J Pharmacol Exp Ther.*, 295(1):255-60 (2000), Del Piaz et al., *Eur. J. Med. Chem.*, 35; 463-480 (2000), or Barnette et al., *Pharmacol. Rev. Commun.* 8: 65-73 (1997).

In some embodiments, the reported cAMP-specific PDE inhibitor is Cilomilast (SB-207499); Filaminast; Tibenelast (LY-186655); Ibudilast; Piclamilast (RP 73401); Doxofylline; Cipamfylline (HEP-688); atizoram (CP-80633); theophylline; isobutylmethylxanthine; Mesopram (ZK-117137); Zardaverine; vinpocetine; Rolipram (ZK-62711); Arofylline (LAS-31025); roflumilast (BY-217); Pumafentrin (BY-343); Denbufylline; EHNA; milrinone; Siguazodan; Zaprinast; Tolafentrine; Isbufylline; IBMX; 1C-485; dyphylline; verolylline; bamifylline; pentoxyfilline; enprofilline; lirimilast (BAY 19-8004); filaminast (WAY-PDA-641); benafentrine; trequinsin; nitroquazone; cilostamide; vesnarinone; piroximone; enoximone; aminone; olprinone; imazodan or 5-methyl-imazodan; indolidan; anagrelide; carbazeran; ampizone; emoradan; motapizone; phthalazinol; lixazinone (RS 82856); quazinone; bemorandan (RWJ 22867); adibendan (BM 14,478); Pimobendan (MC1-154); Saterinone (BDF 8634); Tetomilast (OPC-6535); benzafentrine; sulmazole (ARL 115); Revizinone; 349-U-85; AH-21-132; ATZ-1993; AWD-12-343; AWD-12-281; AWD-12-232; BRL 50481; CC-7085; CDC-801; CDC-998; CDP-840; CH-422; CH-673; CH-928; CH-3697; CH-3442; CH-2874; CH-4139; Chiroscience 245412; CI-930; CI-1018; CI-1044; CI-1118; CP-353164; CP-77059; CP-146523; CP-293321; CP-220629; CT-2450; CT-2820; CT-3883; CT-5210; D-4418; D-22888; E-4021; EMD 54622; EMD-53998; EMD-57033; GF-248; GW-3600; IC-485; ICI-63197; ICI 153,110; IPL-4088; KF-19514; KW-4490; L-787258; L-826141; L-791943; LY181512; NCS-613; NM-702; NSP-153; NSP-306; NSP-307; Org-30029; Org-20241; Org-9731; ORG 9935; PD-168787; PD-190749; PD-190036; PDB-093; PLX650; PLX369; PLX371; PLX788; PLX939; Ro-20-1724; RPR-132294; RPR-117658A; RPR-114597; RPR-122818; RPR-132703; RS-17597; RS-25344; RS-14203; SCA 40; Sch-351591; SDZ-ISQ-844; SDZ-MKS-492; SKF 94120; SKF-95654; SKF-107806; SKF 96231; T-440; T-2585; WAY-126120; WAY-122331; WAY-127093B; WIN-63291; WIN-62582; V-11294A; VMX 554; VMX 565; XT-044; XT-611; Y-590; YM-58897; YM-976; ZK-62711; methyl 3-[6-(2H-3, 4,5,6-tetrahydropyran-2-yloxy)-2-(3-thienylcarbonyl)benzo [b]furan-3-yl]propanoate; 4-[4-methoxy-3-(5-phenylpentyloxy)phenyl]-2-methylbenzoic acid; methyl 3-{2-[(4-chlorophenyl)carbonyl]-6-hydroxybenzo[b]furan-3-yl}propanoate; (R*,R*)-(±)-methyl 3-acetyl-4-[3-(cyclopentyloxy)-4-methoxyphenyl]-3-methyl-1-pyrrolidinecarboxylate; or 4-(3-bromophenyl)-1-ethyl-7-methylhydropyridino[2,3-b]pyridin-2-one.

In some embodiments, the reported PDE inhibitor inhibits a cGMP-specific PDE. Non-limiting examples of a cGMP specific PDE inhibitor for use in the combinations and methods described herein include a pyrimidine or pyrimidinone derivative, such as a compound described in U.S. Pat. Nos. 6,677,335, 6,458,951, 6,251,904, 6,787,548, 5,294,612, 5,250,534, or 6,469,012, WO 94/28902, WO96/16657, EP0702555, and Eddahibi, *Br. J. Pharmacol.*, 125(4): 681-688 (1988); a griseolic acid derivative, such as a compound disclosed in U.S. Pat. No. 4,460,765; a 1-arylnaphthalene lignan, such as that described in Ukita, *J. Med. Chem.* 42(7): 1293-1305 (1999); a quinazoline derivative, such as 4-[[3',4'-(methylenedioxy)benzyl]amino]-6-methoxyquinazoline) or a compound described in U.S. Pat. No. 3,932,407 or 4,146, 718, or RE31,617; a pyrroloquinolone or pyrrolopyridinone, such as that described in U.S. Pat. Nos. 6,686,349, 6,635,638, 6,818,646, US20050113402; a carboline derivative, such a compound described in U.S. Pat. Nos. 6,492,358, 6,462,047, 6,821,975, 6,306,870, 6,117,881, 6,043,252, or 3,819,631, US20030166641, WO 97/43287, Daugan et al., *J Med. Chem.*, 46(21):4533-42 (2003), or Daugan et al., *J Med. Chem.*, 9; 46(21):4525-32 (2003); an imidazo derivative, such as a compound disclosed in U.S. Pat. Nos. 6,130,333, 6,566,360, 6,362,178, or 6,582,351, US20050070541, or US20040067945; or a compound described in U.S. Pat. Nos. 6,825,197, 5,719,283, 6,943,166, 5,981,527, 6,576,644, 5,859,009, 6,943,253, 6,864,253, 5,869,516, 5,488,055, 6,140,329, 5,859,006, or 6,143,777, WO 96/16644, WO 01/19802, WO 96/26940, Dunn, *Org. Proc. Res. Dev.,* 9: 88-97 (2005), or Bi et al., *Bioorg Med Chem. Lett.,* 11(18): 2461-4 (2001).

In some embodiments, the PDE inhibitor used in a combination or method disclosed herein is caffeine. In some embodiments, the caffeine is administered in a formulation comprising a 4-acylaminopyridine derivative such as MKC-231. In other embodiments, the caffeine is administered simultaneously with a 4-acylaminopyridine derivative. In alternative embodiments, the caffeine is administered in a formulation, dosage, or concentration lower or higher than that of a caffeinated beverage such as coffee, tea, or soft drinks. In further embodiments, the caffeine is administered by a non-oral means, including, but not limited to, parenteral (e.g., intravenous, intradermal, subcutaneous, inhalation), transdermal (topical), transmucosal, rectal, or intranasal (including, but not limited to, inhalation of aerosol suspensions for delivery of compositions to the nasal mucosa, trachea and bronchioli) administration. The disclosure includes embodiments with the explicit exclusion of caffeine or another one or more of the described agents for use in combination with a 4-acylaminopyridine derivative such as MKC-231.

In further alternative embodiments, the caffeine is in an isolated form, such as that which is separated from one or more molecules or macromolecules normally found with caffeine before use in a combination or method as disclosed herein. In other embodiments, the caffeine is completely or partially purified from one or more molecules or macromolecules normally found with the caffeine. Exemplary cases of molecules or macromolecules found with caffeine include a plant or plant part, an animal or animal part, and a food or beverage product.

Non-limiting examples of a reported PDE1 inhibitor include IBMX; vinpocetine; MMPX; KS-505a; SCH-51866; W-7; PLX650; PLX371; PLX788; a phenothiazines; or a compound described in U.S. Pat. No. 4,861,891.

Non-limiting examples of a PDE2 inhibitor include EHNA; PLX650; PLX369; PLX788; PLX 939; Bay 60-7550 or a related compound described in Boess et al., *Neuropharmacology,* 47(7): 1081-92 (2004); or a compound described in US20020132754.

Non-limiting examples of reported PDE3 inhibitors include a dihydroquinolinone compound such as cilostamide, cilostazol, vesnarinone, or OPC 3911; an imidazolone such as piroximone or enoximone; a bipyridine such as milrinone, aminone or olprinone; an imidazoline such as imazodan or 5-methyl-imazodan; a pyridazinone such as indolidan; LY181512 (see Komas et al. "Differential sensitivity to cardiotonic drugs of cyclic AMP phosphodiesterases isolated from canine ventricular and sinoatrial-enriched tissues." *J Cardiovasc Pharmacol.* 1989 14(2):213-20); ibudilast; isomazole; motapizone; phthalazinol; trequinsin; lixazinone (RS 82856); Y-590; SKF 94120; quazinone; ICI 153,110; bemorandan (RWJ 22867); siguazodan (SK&F 94836); adibendan (BM 14,478); Pimobendan (UD-CG 115, MC1-154); Saterinone (BDF 8634); NSP-153; zardaverine; a quinazoline; benzafentrine; sulmazole (ARL 115); ORG 9935; CI-930; SKF-95654; SDZ-MKS-492; 349-U-85; EMD-53998; EMD-57033; NSP-306; NSP-307; Revizinone; NM-702; WIN-62582; ATZ-1993; WIN-63291; ZK-62711; PLX650; PLX369; PLX788; PLX939; anagrelide; carbazeran; ampizone; emoradan; or a compound disclosed in U.S. Pat. No. 6,156,753.

Non-limiting examples of reported PDE4 inhibitors include a pyrrolidinone, such as a compound disclosed in U.S. Pat. No. 5,665,754, US20040152754 or US20040023945; a quinazolineone, such as a compound disclosed in U.S. Pat. No. 6,747,035 or 6,828,315, WO 97/49702 or WO 97/42174; a xanthine derivative; a phenylpyridine, such as a compound disclosed in U.S. Pat. No. 6,410,547 or 6,090,817 or WO 97/22585; a diazepine derivative, such as a compound disclosed in WO 97/36905; an oxime derivative, such as a compound disclosed in U.S. Pat. No. 5,693,659 or WO 96/00215; a naphthyridine, such as a compound described in U.S. Pat. Nos. 5,817,670, 6,740,662, 6,136,821, 6,331,548, 6,297,248, 6,541,480, 6,642,250, or 6,900,205, Trifilieff et al., *Pharmacology,* 301(1): 241-248 (2002) or Hersperger et al., *J Med. Chem.,* 43(4):675-82 (2000); a benzofuran, such as a compound disclosed in U.S. Pat. Nos. 5,902,824, 6,211,203, 6,514,996, 6,716,987, 6,376,535, 6,080,782, or 6,054,475, EP 819688, EP685479, or Perrier et al., *Bioorg. Med. Chem. Lett.* 9:323-326 (1999); a phenanthridine, such as that disclosed in U.S. Pat. Nos. 6,191,138, 6,121,279, or 6,127,378; a benzoxazole, such as that disclosed in U.S. Pat. No. 6,166,041 or 6,376,485; a purine derivative, such as a compound disclosed in U.S. Pat. No. 6,228,859; a benzamide, such as a compound described in U.S. Pat. No. 5,981,527 or 5,712,298, WO95/01338, WO 97/48697, or Ashton et al., *J. Med Chem* 37: 1696-1703 (1994); a substituted phenyl compound, such as a compound disclosed in U.S. Pat. Nos. 6,297,264, 5,866,593,65 5,859, 034, 6,245,774, 6,197,792, 6,080,790, 6,077,854, 5,962,483, 5,674,880, 5,786,354, 5,739,144, 5,776,958, 5,798,373, 5,891,896, 5,849,770, 5,550,137, 5,340,827, 5,780,478, 5,780,477, or 5,633,257, or WO 95/35283; a substituted biphenyl compound, such as that disclosed in U.S. Pat. No. 5,877,190; or a quinolinone, such as a compound described in U.S. Pat. No. 6,800,625 or WO 98/14432.

Additional examples of reported PDE4 inhibitors useful in methods provided herein include a compound disclosed in U.S. Pat. Nos. 6,716,987, 6,514,996, 6,376,535, 6,740,655, 6,559,168, 6,069,151, 6,365,585, 6,313,116, 6,245,774, 6,011,037, 6,127,363, 6,303,789, 6,316,472, 6,348,602, 6,331,543, 6,333,354, 5,491,147, 5,608,070, 5,622,977, 5,580,888, 6,680,336, 6,569,890, 6,569,885, 6,500,856, 6,486,186, 6,458,787, 6,455,562, 6,444,671, 6,423,710, 6,376,489, 6,372,777, 6,362,213, 6,313,156, 6,294,561, 6,258,843, 6,258,833, 6,121,279, 6,043,263, RE38,624, U.S. Pat. No. 6,297,257, 6,251,923, 6,613,794, 6,407,108, 6,107, 295, 6,103,718, 6,479,494, 6,602,890, 6,545,158, 6,545,025, 6,498,160, 6,743,802, 6,787,554, 6,828,333, 6,869,945, 6,894,041, 6,924,292, 6,949,573, 6,953,810, 5,972,927, 5,962,492, 5,814,651, 5,723,460, 5,716,967, 5,686,434, 5,502,072, 5,116,837, 5,091,431; 4,670,434; 4,490,371; 5,710,160, 5,710,170, 6,384,236, or 3,941,785, US20050119225, US20050026913, WO 99/65880, WO 00/26201, WO 98/06704, WO 00/59890, WO9907704, WO9422852, WO 98/20007, WO 02/096423, WO 98/18796, WO 98/02440, WO 02/096463, WO 97/44337, WO 97/44036, WO 97/44322, EP 0763534, Aoki et al., *J Pharmacol Exp Ther.,* 295(1):255-60 (2000), Del Piaz et al., *Eur. J. Med. Chem.,* 35; 463-480 (2000), or Barnette et al., *Pharmacol. Rev. Commun.* 8: 65-73 (1997).

In some embodiments, the reported PDE4 inhibitor is Cilomilast (SB-207499); Filaminast; Tibenelast (LY-186655); Ibudilast; Piclamilast (RP 73401); Doxofylline; Cipamfylline (HEP-688); atizoram (CP-80633); theophylline; isobutylmethylxanthine; Mesopram (ZK-117137); Zardaverine; vinpocetine; Rolipram (ZK-62711); Arofylline (LAS-31025); roflumilast (BY-217); Pumafentrin (BY-343); Denbufylline; EHNA; milrinone; Siguazodan; Zaprinast; Tolafentrine; Isbufylline; IBMX; 1C-485; dyphylline; verolylline; bamifylline; pentoxyfilline; enprofilline; lirimilast (BAY 19-8004); filaminast (WAY-PDA-641); benafentrine;

trequinsin; nitroquazone; Tetomilast (OPC-6535); AH-21-132; AWD-12-343; AWD-12-281; AWD-12-232; CC-7085; CDC-801; CDC-998; CDP-840; CH-422; CH-673; CH-928; CH-3697; CH-3442; CH-2874; CH-4139; Chiroscience 245412; CI-1018; CI-1044; CI-1118; CP-353164; CP-77059; CP-146523; CP-293321; CP-220629; CT-2450; CT-2820; CT-3883; CT-5210; D-4418; D-22888; E-4021; EMD 54622; GF-248; GW-3600; IC-485; ICI-63197; IPL-4088; KF-19514; KW-4490; L-787258; L-826141; L-791943; NCS-613; Org-30029; Org-20241; Org-9731; PD-168787; PD-190749; PD-190036; PDB-093; PLX650; PLX369; PLX371; PLX788; PLX939; Ro-20-1724; RPR-132294; RPR-117658A; RPR-114597; RPR-122818; RPR-132703; RS-17597; RS-25344; RS-14203; SCA 40; Sch-351591; SDZ-ISQ-844; SKF-107806; SKF 96231; T-440; T-2585; WAY-126120; WAY-122331; WAY-127093B; V-11294A; VMX 554; VMX 565; XT-044; XT-611; YM-58897; YM-976; methyl 3-[6-(2H-3,4,5,6-tetrahydropyran-2-yloxy)-2-(3-thienylcarbonyl)benzo[b]furan-3-yl]propanoate; 4-[4-methoxy-3-(5-phenylpentyloxy)phenyl]-2-methylbenzoic acid; methyl 3-{2-[(4-chlorophenyl)carbonyl]-6-hydroxybenzo[b]furan-3-yl}propanoate; (R*,R*)-(±)-methyl 3-acetyl-4-[3-(cyclopentyloxy)-4-methoxyphenyl]-3-methyl-1-pyrrolidinecarboxylate; or 4-(3-bromophenyl)-1-ethyl-7-methylhydropyridino[2,3-b]pyridin-2-one.

Non-limiting examples of a reported PDE5 inhibitor useful in a combination or method described herein include a pyrimidine or pyrimidinone derivative, such as a compound described in U.S. Pat. Nos. 6,677,335, 6,458,951, 6,251,904, 6,787,548, 5,294,612, 5,250,534, or 6,469,012, WO 94/28902, WO96/16657, EP0702555, or Eddahibi, *Br. J. Pharmacol.*, 125(4): 681-688 (1988); a griseolic acid derivative, such as a compound disclosed in U.S. Pat. No. 4,460,765; a 1-arylnaphthalene lignan, such as that described in Ukita, *J. Med. Chem.* 42(7): 1293-1305 (1999); a quinazoline derivative, such as 4-[[3',4'-(methylenedioxy)benzyl]amino]-6-methoxyquinazoline) or a compound described in U.S. Pat. No. 3,932,407 or 4,146,718, or RE31,617; a pyrroloquinolones orpyrrolopyridinone, such as that described in U.S. Pat. Nos. 6,686,349, 6,635,638, or 6,818,646, US20050113402; a carboline derivative, such a compound described in U.S. Pat. Nos. 6,492,358, 6,462,047, 6,821,975, 6,306,870, 6,117,881, 6,043,252, or 3,819,631, US20030166641, WO 97/43287, Daugan et al., *J Med. Chem.*, 46(21):4533-42 (2003), and Daugan et al., *J Med. Chem.*, 9; 46(21):4525-32 (2003); an imidazo derivative, such as a compound disclosed in U.S. Pat. Nos. 6,130,333, 6,566,360, 6,362,178, or 6,582,351, US20050070541, or US20040067945; or a compound described in U.S. Pat. Nos. 6,825,197, 6,943,166, 5,981,527, 6,576,644, 5,859,009, 6,943,253, 6,864,253, 5,869,516, 5,488,055, 6,140,329, 5,859,006, or 6,143,777, WO 96/16644, WO 01/19802, WO 96/26940, Dunn, *Org. Proc. Res. Dev.*, 9: 88-97 (2005), or Bi et al., *Bioorg Med Chem. Lett.*, 11(18):2461-4 (2001).

In some embodiments, a reported PDE5 inhibitor is zaprinast; MY-5445; dipyridamole; vinpocetine; FR229934; 1-methyl-3-isobutyl-8-(methylamino)xanthine; furazlocillin; Sch-51866; E4021; GF-196960; IC-351; T-1032; sildenafil; tadalafil; vardenafil; DMPPO; RX-RA-69; KT-734; SKF-96231; ER-21355; BF/GP-385; NM-702; PLX650; PLX134; PLX369; PLX788; orvesnarinone.

In some embodiments, the reported PDE5 inhibitor is sildenafil or a related compound disclosed in U.S. Pat. Nos. 5,346,901, 5,250,534, or 6,469,012; tadalafil or a related compound disclosed in U.S. Pat. Nos. 5,859,006, 6,140,329, 6,821,975, or 6,943,166; or vardenafil or a related compound disclosed in U.S. Pat. No. 6,362,178.

Non-limiting examples of a reported PDE6 inhibitor useful in a combination or method described herein include dipyridamole or zaprinast.

Non-limiting examples of a reported PDE7 inhibitor for use in the combinations and methods described herein include BRL 50481; PLX369; PLX788; or a compound described in U.S. Pat. Nos. 6,818,651; 6,737,436, 6,613,778, 6,617,357; 6,146,876, 6,838,559, or 6,884,800, US20050059686; US20040138279; US20050222138; US20040214843; US20040106631; US 20030045557; US 20020198198; US20030162802, US20030092908, US 20030104974; US20030100571; 20030092721; or US20050148604.

A non-limiting examples of a reported inhibitor of PDE8 activity is dipyridamole.

Non-limiting examples of a reported PDE9 inhibitor useful in a combination or method described herein include SCH-51866; IBMX; or BAY 73-6691.

Non-limiting examples of a PDE 10 inhibitor include sildenafil; SCH-51866; papaverine; Zaprinast; Dipyridamole; E4021; Vinpocetine; EHNA; Milrinone; Rolipram; PLX107; or a compound described in U.S. Pat. No. 6,930,114, US20040138249, or US20040249148.

Non-limiting examples of a PDE11 inhibitor includes IC-351 or a related compound described in WO 9519978; E4021 or a related compound described in WO 9307124; UK-235,187 or a related compound described in EP 579496; PLX788; Zaprinast; Dipyridamole; or a compound described in US20040106631 or Maw et al., *Bioorg Med Chem. Lett.* 2003 Apr. 17; 13(8):1425-8.

In some embodiments, the reported PDE inhibitor is a compound described in U.S. Pat. Nos. 5,091,431, 5,081,242, 5,066,653, 5,010,086, 4,971,972, 4,963,561, 4,943,573, 4,906,628, 4,861,891, 4,775,674, 4,766,118, 4,761,416, 4,739,056, 4,721,784, 4,701,459, 4,670,434, 4,663,320, 4,642,345, 4,593,029, 4,564,619, 4,490,371, 4,489,078, 4,404,380, 4,370,328, 4,366,156, 4,298,734, 4,289,772, RE30,511, U.S. Pat. Nos. 4,188,391, 4,123,534, 4,107,309, 4,107,307, 4,096,257, 4,093,617, 4,051,236, or 4,036,840.

In some embodiments, the reported PDE inhibitor inhibits dual-specificity PDE. Non-limiting examples of a dual-specificity PDE inhibitor useful in a combination or method described herein include a cAMP-specific or cGMP-specific PDE inhibitor described herein; MMPX; KS-505a; W-7; a phenothiazine; Bay 60-7550 or a related compound described in Boess et al., *Neuropharmacology,* 47(7):1081-92 (2004); UK-235,187 or a related compound described in EP 579496; or a compound described in U.S. Pat. No. 6,930,114 or 4,861,891, US20020132754, US20040138249, US20040249148, US20040106631, WO 951997, or Maw et al., *Bioorg Med Chem. Lett.* 2003 Apr. 17; 13(8):1425-8.

In some embodiments, a reported PDE inhibitor exhibits dual-selectivity, being substantially more active against two PDE isozymes relative to other PDE isozymes. For example, in some embodiments, a reported PDE inhibitor is a dual PDE4/PDE7 inhibitor, such as a compound described in US20030104974; a dual PDE3/PDE4 inhibitor, such as zardaverine, tolafentrine, benafentrine, trequinsine, Org-30029, L-686398, SDZ-ISQ-844, Org-20241, EMD-54622, or a compound described in U.S. Pat. Nos. 5,521,187, or 6,306,869; or a dual PDE1/PDE4 inhibitor, such as KF19514 (5-phenyl-3-(3-pyridyl)methyl-3H-imidazo[4,5-c][1,8] naphthyridin-4(5H)-one).

Furthermore, the neurogenic agent in combination with a 4-acylaminopyridine derivative such as MKC-231 may be a reported neurosteroid. Non-limiting examples of such a neurosteroid include pregnenolone and allopregnenalone.

Alternatively, the neurogenic sensitizing agent may be a reported non-steroidal anti-inflammatory drug (NSAID) or an anti-inflammatory mechanism targeting agent in general. Non-limiting examples of a reported NSAID include a cyclooxygenase inhibitor, such as indomethacin, ibuprofen, celecoxib, cofecoxib, naproxen, or aspirin. Additional non-limiting examples for use in combination with a 4-acylaminopyridine derivative such as MKC-231 include rofecoxib, meloxicam, piroxicam, valdecoxib, parecoxib, etoricoxib, etodolac, nimesulide, acemetacin, bufexamac, diflunisal, ethenzamide, etofenamate, flobufen, isoxicam, kebuzone, lonazolac, meclofenamic acid, metamizol, mofebutazone, niflumic acid, oxyphenbutazone, paracetamol, phenidine, propacetamol, propyphenazone, salicylamide, tenoxicam, tiaprofenic acid, oxaprozin, lornoxicam, nabumetone, minocycline, benorylate, aloxiprin, salsalate, flurbiprofen, ketoprofen, fenoprofen, fenbufen, benoxaprofen, suprofen, piroxicam, meloxicam, diclofenac, ketorolac, fenclofenac, sulindac, tolmetin, xyphenbutazone, phenylbutazone, feprazone, azapropazone, flufenamic acid or mefenamic acid.

In additional embodiments, the neurogenic agent in combination with a 4-acylaminopyridine derivative such as MKC-231 may be a reported agent for treating migraines. Non-limiting examples of such an agent include a triptan, such as almotriptan or almotriptan malate; naratriptan or naratriptan hydrochloride; rizatriptan or rizatriptan benzoate; sumatriptan or sumatriptan succinate; zolmatriptan or zolmitriptan, frovatriptan or frovatriptan succinate; or eletriptan or eletriptan hydrobromide. Embodiments of the disclosure may exclude combinations of triptans and an SSRI or SNRI that result in life threatening serotonin syndrome.

Other non-limiting examples include an ergot derivative, such as dihydroergotamine or dihydroergotamine mesylate, ergotamine or ergotamine tartrate; diclofenac or diclofenac potassium or diclofenac sodium; flurbiprofen; amitriptyline; nortriptyline; divalproex or divalproex sodium; propranolol or propranolol hydrochloride; verapamil; methysergide (CAS RN 361-37-5); metoclopramide; prochlorperazine (CAS RN 58-38-8); acetaminophen; topiramate; GW274150 ([2-[(1-iminoethyl)amino]ethyl]-L-homocysteine); or ganaxalone (CAS RN 38398-32-2).

Additional non-limiting examples include a COX-2 inhibitor, such as Celecoxib.

In other embodiments, the neurogenic agent in combination with a 4-acylaminopyridine derivative such as MKC-231 may be a reported modulator of a nuclear hormone receptor. Nuclear hormone receptors are activated via ligand interactions to regulate gene expression, in some cases as part of cell signaling pathways. Non-limiting examples of a reported modulator include a dihydrotestosterone agonist such as dihydrotestosterone; a 2-quinolone like LG121071 (4-ethyl-1,2,3,4-tetrahydro-6-(trifluoromethyl)-8-pyridono[5,6-g]-quinoline); a non-steroidal agonist or partial agonist compound described in U.S. Pat. No. 6,017,924; LGD2226 (see WO 01/16108, WO 01/16133, WO 01/16139, and Rosen et al. "Novel, non-steroidal, selective androgen receptor modulators (SARMs) with anabolic activity in bone and muscle and improved safety profile." *J Musculoskelet Neuronal Interact.* 2002 2(3):222-4); or LGD2941 (from collaboration between Ligand Pharmaceuticals Inc. and TAP Pharmaceutical Products Inc.).

Additional non-limiting examples of a reported modulator include a selective androgen receptor modulator (SARM) such as andarine, ostarine, prostarin, or andromustine (all from GTx, Inc.); bicalutamide or a bicalutamide derivative such as GTx-007 (U.S. Pat. No. 6,492,554); or a SARM as described in U.S. Pat. No. 6,492,554.

Further non-limiting examples of a reported modulator include an androgen receptor antagonist such as cyproterone, bicalutamide, flutamide, or nilutamide; a 2-quinolone such as LG120907, represented by the following structure:

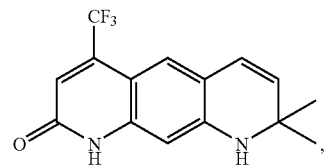

or a derivative compound represented by the following structure:

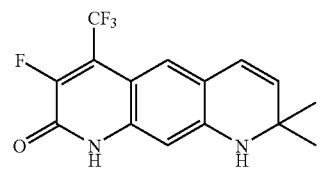

(see Allan et al. "Therapeutic androgen receptor ligands" *Nucl Recept Signal* 2003; 1: e009); a phthalamide, such as a modulator as described by Miyachi et al. ("Potent novel non-steroidal androgen antagonists with a phthalimide skeleton." *Bioorg. Med. Chem. Lett.* 1997 7:1483-1488); osaterone or osaterone acetate; hydroxyflutamide; or a non-steroidal antagonist described in U.S. Pat. No. 6,017,924.

Other non-limiting examples of a reported modulator include a retinoic acid receptor agonist such as all-trans retinoic acid (Tretinoin); isotretinoin (13-cis-retinoic acid); 9-cis retinoic acid; bexarotene; TAC-101 (4-[3,5-bis(trimethylsilyl)benzamide] benzoic acid); AC-261066 (see Lund et al. "Discovery of a potent, orally available, and isoform-selective retinoic acid beta2 receptor agonist." *J Med. Chem.* 2005 48(24):7517-9); LGD1550 ((2E,4E,6E)-3-methyl-7-(3,5-di-ter-butylphen-yl)octatrienoic acid); E6060 (E6060 [4-{5-[7-fluoro-4-(trifluoromethyl)benzo[b]furan-2-yl]-1H-2-pyrrolyl}benzoic acid]; agonist 1 or 2 as described by Schapira et al. ("In silico discovery of novel Retinoic Acid Receptor agonist structures." *BMC Struct Biol.* 2001; 1:1 (published online 2001 Jun. 4) where "Agonist 1 was purchased from Bionet Research (catalog number 1G-433S). Agonist 2 was purchased from Sigma-Aldrich (Sigma Aldrich library of rare chemicals. Catalog number S08503-1"); a synthetic acetylenic retinoic acid, such as AGN 190121 (CAS RN: 132032-67-8), AGN 190168 (or Tazarotene or CAS RN 118292-40-3), or its metabolite AGN 190299 (CAS RN 118292-41-4); Etretinate; acitretin; an acetylenic retinoate, such as AGN 190073 (CAS 132032-68-9), or AGN 190089 (or 3-Pyridinecarboxylic acid, 6-(4-(2,6,6-trimethyl-1-cyclohexen-1-yl)-3-buten-1-ynyl)-, ethyl ester or CAS RN 116627-73-7).

In further embodiments, the additional agent for use in combination with a 4-acylaminopyridine derivative such as MKC-231 may be a reported modulator selected from thyroxin, tri-iodothyronine, or levothyroxine.

Alternatively, the additional agent is a vitamin D (1,25-dihydroxyvitamine $D_3$) receptor modulator, such as calcitriol or a compound described in Ma et al. ("Identification and characterization of noncalcemic, tissue-selective, nonsecosteroidal vitamin D receptor modulators." *J Clin Invest.* 2006 116(4):892-904) or Molnar et al. ("Vitamin D receptor agonists specifically modulate the volume of the ligand-binding pocket." *J Biol. Chem.* 2006 281(15):10516-26) or Milliken et al. ("EB1089, a vitamin D receptor agonist, reduces proliferation and decreases tumor growth rate in a mouse model of hormone-induced mammary cancer." *Cancer Lett.* 2005 229(2):205-15) or Yee et al. ("Vitamin D receptor modulators for inflammation and cancer." *Mini Rev Med. Chem.* 2005 5(8):761-78) or Adachi et al. "Selective activation of vitamin D receptor by lithocholic acid acetate, a bile acid derivative." *J Lipid Res.* 2005 46(1):46-57).

Furthermore, the additional agent may be a reported cortisol receptor modulator, such as methylprednisolone or its prodrug methylprednisolone suleptanate; PI-1020 (NCX-1020 or budesonide-21-nitrooxymethylbenzoate); fluticasone furoate; GW-215864; betamethasone valerate; beclomethasone; prednisolone; or BVT-3498 (AMG-311).

Alternatively, the additional agent may be a reported aldosterone (or mineralocorticoid) receptor modulator, such as spironolactone or eplerenone.

In other embodiments, the additional agent may be a reported progesterone receptor modulator such as Asoprisnil (CAS RN 199396-76-4); mesoprogestin or J1042; J956; medroxyprogesterone acetate (MPA); R5020; tanaproget; trimegestone; progesterone; norgestomet; melengestrol acetate; mifepristone; onapristone; ZK137316; ZK230211 (see Fuhrrmann et al. "Synthesis and biological activity of a novel, highly potent progesterone receptor antagonist." *J Med. Chem.* 2000 43(26):5010-6); or a compound described in Spitz "Progesterone antagonists and progesterone receptor modulators: an overview." *Steroids* 2003 68(10-13):981-93.

In further embodiments, the additional agent may be a reported i) peroxisome proliferator-activated receptor agonist such as muraglitazar; tesaglitazar; reglitazar; GW-409544 (see Xu et al. "Structural determinants of ligand binding selectivity between the peroxisome proliferator-activated receptors." *Proc Natl Acad Sci USA.* 2001 98(24):13919-24); or DRL 11605 (Dr. Reddy's Laboratories); ii) a peroxisome proliferator-activated receptor alpha agonist like clofibrate; ciprofibrate; fenofibrate; gemfibrozil; DRF-10945 (Dr. Reddy's Laboratories); iii) a peroxisome proliferator-activated receptor delta agonist such as GW501516 (CAS RN 317318-70-0); or iv) a peroxisome proliferator-activated gamma receptor agonist like a hydroxyoctadecadienoic acid (HODE); a prostaglandin derivatives, such as 15-deoxy-Delta12,14-prostaglandin J2; a thiazolidinedione (glitazone), such as pioglitazone, troglitazone; rosiglitazone or rosiglitazone maleate; ciglitazone; Balaglitazone or DRF-2593; AMG 131 (from Amgen); or G1262570 (from GlaxoWellcome). In additional embodiments, a PPAR ligand is a PPARγ antagonist such as T0070907 (CAS RN 313516-66-4) or GW9662 (CAS RN 22978-25-2).

In additional embodiments, the additional agent may be a reported modulator of an "orphan" nuclear hormone receptor. Embodiments include a reported modulator of a liver X receptor, such as a compound described in U.S. Pat. No. 6,924,311; a farnesoid X receptor, such as GW4064 as described by Maloney et al. ("Identification of a chemical tool for the orphan nuclear receptor FXR." *J Med. Chem.* 2000 43(16):2971-4); a RXR receptor; a CAR receptor, such as 1,4-bis[2-(3,5-dichloropyridyloxy)] benzene (TCPOBOP); or a PXR receptor, such as SR-12813 (tetra-ethyl 2-(3,5-ditert-butyl-4-hydroxyphenyl)ethenyl-1,1-bisphosphonate).

In additional embodiments, the agent in combination with a 4-acylaminopyridine derivative such as MKC-231 is ethyl eicosapentaenoate or ethyl-EPA (also known as 5,8,11,14,17-eicosapentaenoic acid ethyl ester or miraxion, CAS RN 86227-47-6), docosahexaenoic acid (DHA), or a retinoid acid drug. As an additional non-limiting example, the agent may be Omacor, a combination of DHA and EPA, or idebenone (CAS RN 58186-27-9).

In further embodiments, a reported nootropic compound may be used as an agent in combination with a 4-acylaminopyridine derivative such as MKC-231. Non-limiting examples of such a compound include Piracetam (Nootropil), Aniracetam, Oxiracetam, Pramiracetam, Pyritinol (Enerbol), Ergoloid mesylates (Hydergine), Galantamine or Galantamine hydrobromide, Selegiline, Centrophenoxine (Lucidril), Desmopressin (DDAVP), Nicergoline, Vinpocetine, Picamilon, Vasopressin, Milacemide, FK-960, FK-962, levetiracetam, nefiracetam, or hyperzine A (CAS RN: 102518-79-6).

Additional non-limiting examples of such a compound include anapsos (CAS RN 75919-65-2), nebracetam (CAS RN 97205-34-0 or 116041-13-5), metrifonate, ensaculin (or CAS RN 155773-59-4 or KA-672) or ensaculin HCl, Rokan (CAS RN 122933-57-7 or EGb 761), AC-3933 (5-(3-methoxyphenyl)-3-(5-methyl-1,2,4-oxadiazol-3-yl)-2-oxo-1,2-dihydro-1,6-naphthyridine) or its hydroxylated metabolite SX-5745 (3-(5-hydroxymethyl-1,2,4-oxadiazol-3-yl)-5-(3-methoxyphenyl)-2-oxo-1,2-dihydro-1,6-naphthyridine), JTP-2942 (CAS RN 148152-77-6), sabeluzole (CAS RN 104383-17-7), ladostigil (CAS RN 209394-27-4), choline alphoscerate (CAS RN 28319-77-9 or Gliatilin), Dimebon (CAS RN 3613-73-8), tramiprosate (CAS RN 3687-18-1), omigapil (CAS RN 181296-84-4), cebaracetam (CAS RN 113957-09-8), fasoracetam (CAS RN 110958-19-5), PD-151832 (see Jaen et al. "In vitro and in vivo evaluation of the subtype-selective muscarinic agonist PD 151832." *Life Sci.* 1995 56(11-12):845-52), Vinconate (CAS RN 70704-03-9), PYM-50028 PYM-50028 (Cogane) or PYM-50018 (Myogane) as described by Harvey ("Natural Products in Drug Discovery and Development. 27-28 Jun. 2005, London, UK." IDrugs. 2005 8(9):719-21), SR-46559A (3-[N-(2 diethyl-amino-2-methylpropyl)-6-phenyl-5-propyl), dihydroergocristine (CAS RN 17479-19-5), dabelotine (CAS RN 118976-38-8), zanapezil (CAS RN 142852-50-4).

Further non-limiting examples include NBI-113 (from Neurocrine Biosciences, Inc.), NDD-094 (from Novartis), P-58 or P58 (from Pfizer), or SR-57667 (from Sanofi-Synthelabo).

In additional embodiments, the neurogenic agent used in combination with a 4-acylaminopyridine agent may be a reported AMPA modulator. Non-limiting examples include CX-516 or ampalex (CAS RN 154235-83-3), Org-24448 (CAS RN 211735-76-1), LY451395 (2-propanesulfonamide, N-[(2R)-2-[4'-[2-[methylsulfonyl)amino]ethyl][1,1'-biphenyl]-4-yl]propyl]-), LY-450108 (see Jhee et al. "Multiple-dose plasma pharmacokinetic and safety study of LY450108 and LY451395 (AMPA receptor potentiators) and their concentration in cerebrospinal fluid in healthy human subjects." *J Clin Pharmacol.* 2006 46(4):424-32), and CX717. Additional examples of reported antagonists include irampanel (CAS RN 206260-33-5) and E-2007.

Moreover, an agent in combination with a 4-acylaminopyridine derivative such as MKC-231 may be a reported modulator of the nicotinic receptor. Non-limiting examples of such a modulator include nicotine, acetylcholine, carbamylcholine, epibatidine, ABT-418 (structurally similar to nicotine, with an ixoxazole moiety replacing the pyridyl group of nicotine), epiboxidine (a structural analogue with elements of both epibatidine and ABT-418), ABT-594 (azetidine analogue of epibatidine), lobeline, SSR-591813, represented by the following formula:

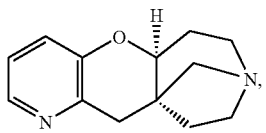

or SIB-1508 (altinicline).

In additional embodiments, an agent used in combination with a 4-acylaminopyridine derivative such as MKC-231 is a reported aromatase inhibitor. Reported aromatase inhibitors include, but are not limited to, nonsteroidal or steroidal agents. Non-limiting examples of the former, which inhibit aromatase via the heme prosthetic group, include anastrozole (Arimidex®), letrozole (Femara®), or vorozole (Rivisor). Non-limiting examples of steroidal aromatase inhibitors AIs, which inactivate aromatase, include, but are not limited to, exemestane (Aromasin(g), androstenedione, or formestane (lentaron).

Additional non-limiting examples of a reported aromatase for use in a combination or method as disclosed herein include aminoglutethimide, 4-androstene-3,6,17-trione (or "6-OXO"), or zoledronic acid or Zometa (CAS RN 118072-93-8).

Further embodiments include a combination of a 4-acylaminopyridine derivative such as MKC-231 and a reported selective estrogen receptor modulator (SERM) may be used as described herein. Non-limiting examples include estradiol, tamoxifen, raloxifene, toremifene, clomifene, bazedoxifene, arzoxifene, or lasofoxifene. Additional non-limiting examples include a steroid antagonist or partial agonist, such as centchroman, clomiphene, or droloxifene.

In other embodiments, a combination of a 4-acylaminopyridine derivative such as MKC-231 and a reported cannabinoid receptor modulator may be used as described herein. Non-limiting examples include synthetic cannabinoids, endogenous cannabinoids, or natural cannabinoids. In some embodiments, the reported cannabinoid receptor modulator is rimonabant (SR141716 or Acomplia), nabilone, levonantradol, marinol, or sativex (an extract containing both THC and CBD). Non-limiting examples of endogenous cannabinoids include arachidonyl ethanolamine (anandamide); analogs of anandamide, such as docosatetraenylethanolamide or homo-γ-linoenylethanolamide; N-acyl ethanolamine signalling lipids, such as the noncannabimimetic palmitoylethanolamine or oleoylethanolamine; or 2-arachidonyl glycerol. Non-limiting examples of natural cannabinoids include tetrahydrocannabinol (THC), cannabidiol (CBD), cannabinol (CBN), cannabigerol (CBG), cannabichromene (CBC), cannabicyclol (CBL), cannabivarol (CBV), tetrahydrocannabivarin (THCV), cannabidivarin (CBDV), cannabichromevarin (CBCV), cannabigerovarin (CBGV), or cannabigerol monoethyl ether (CBGM).

In yet further embodiments, an agent used in combination with a 4-acylaminopyridine derivative such as MKC-231 is a reported FAAH (fatty acid amide hydrolase) inhibitor. Non-limiting examples of reported inhibitor agents include URB597 (3'-carbamoyl-biphenyl-3-yl-cyclohexylcarbamate); CAY10401 (1-oxazolo[4,5-b]pyridin-2-yl-9-octadecyn-1-one); OL-135 (1-oxo-1 [5-(2-pyridyl)-2-yl]-7-phenyl-heptane); anandamide (CAS RN 94421-68-8); AA-5-HT (see Bisogno et al. "Arachidonoylserotonin and other novel inhibitors of fatty acid amide hydrolase." *Biochem Biophys Res Commun.* 1998 248(3):515-22); 1-Octanesulfonyl fluoride; or O-2142 or another arvanil derivative FAAH inhibitor as described by Di Marzo et al. ("A structure/activity relationship study on arvanil, an endocannabinoid and vanilloid hybrid." *J Pharmacol Exp Ther.* 2002 300(3):984-91).

Further non-limiting examples include SSR 411298 (from Sanofi-Aventis), JNJ28614118 (from Johnson & Johnson), or SSR 101010 (from Sanofi-Aventis)

In additional embodiments, an agent in combination with a 4-acylaminopyridine derivative such as MKC-231 may be a reported modulator of nitric oxide function. One non-limiting example is sildenafil (Viagra®).

In additional embodiments, an agent in combination with a 4-acylaminopyridine derivative such as MKC-231 may be a reported modulator of prolactin or a prolactin modulator.

In additional embodiments, an agent in combination with a 4-acylaminopyridine derivative such as MKC-231 is a reported anti-viral agent, with ribavirin and amantadine as non-limiting examples.

In additional embodiments, an agent in combination with a 4-acylaminopyridine derivative such as MKC-231 may be a component of a natural product or a derivative of such a component. In some embodiments, the component or derivative thereof is in an isolated form, such as that which is separated from one or more molecules or macromolecules normally found with the component or derivative before use in a combination or method as disclosed herein. In other embodiments, the component or derivative is completely or partially purified from one or more molecules or macromolecules normally found with the component or derivative. Exemplary cases of molecules or macromolecules found with a component or derivative as described herein include a plant or plant part, an animal or animal part, and a food or beverage product.

Non-limiting examples such a component include folic acid, folate, methylfolate; a flavinoid, such as a citrus flavonoid; a flavonol, such as Quercetin, Kaempferol, Myricetin, or Isorhamnetin; a flavone, such as Luteolin or Apigenin; a flavanone, such as Hesperetin, Naringenin, or Eriodictyol; a flavan-3-ol (including a monomeric, dimeric, or polymeric flavanol), such as (+)-Catechin, (+)-Gallocatechin, (−)-Epicatechin, (−)-Epigallocatechin, (−)-Epicatechin 3-gallate, (−)-Epigallocatechin 3-gallate, Theaflavin, Theaflavin 3-gallate, Theaflavin 3'-gallate, Theaflavin 3,3' digallate, a Thearubigin, or Proanthocyanidin; an anthocyanidin, such as Cyanidin, Delphinidin, Malvidin, Pelargonidin, Peonidin, or Petunidin; an isoflavone, such as daidzein, genistein, or glycitein; flavopiridol; a prenylated chalcone, such as Xanthohumol; a prenylated flavanone, such as Isoxanthohumol; a non-prenylated chalcone, such as Chalconaringenin; a non-prenylated flavanone, such as Naringenin; Resveratrol; or an anti-oxidant neutraceutical (such as any present in chocolate, like dark chocolate or unprocessed or unrefined chocolate).

Additional non-limiting examples include a component of Gingko biloba, such as a flavo glycoside or a terpene. In some embodiments, the component is a flavanoid, such as a flavonol or flavone glycoside, or a quercetin or kaempferol glycoside, or rutin; or a terpenoid, such as ginkgolides A, B, C, or M, or bilobalide.

Further non-limiting examples include a component that is a flavanol, or a related oligomer, or a polyphenol as described in US2005/245601AA, US2002/018807AA, US2003/180406AA, US2002/086833AA, US2004/0236123, WO9809533, or WO9945788; a procyanidin or derivative thereof or polyphenol as described in US2005/171029AA; a procyanidin, optionally in combination with L-arginine as described in US2003/104075AA; a low fat cocoa extract as described in US2005/031762AA; lipophilic bioactive compound containing composition as described in US2002/107292AA; a cocoa extract, such as those containing one or more polyphenols or procyanidins as described in US2002/004523AA; an extract of oxidized tea leaves as described in U.S. Pat. No. 5,139,802 or 5,130,154; a food supplement as described in WO 2002/024002.

Of course a composition comprising any of the above components, alone or in combination with a 4-acylaminopyridine derivative as described herein is included within the disclosure.

In additional embodiments, an agent in combination with a 4-acylaminopyridine derivative such as MKC-231 may be a reported calcitonin receptor agonist such as calcitonin or the 'orphan peptide' PHM-27 (see Ma et al. "Discovery of novel peptide/receptor interactions: identification of PHM-27 as a potent agonist of the human calcitonin receptor." *Biochem Pharmacol.* 2004 67(7):1279-84). A further non-limiting example is the agonist from Kemia, Inc.

In an alternative embodiment, the agent may be a reported modulator of parathyroid hormone activity, such as parathyroid hormone, or a modulator of the parathyroid hormone receptor.

In additional embodiments, an agent in combination with a 4-acylaminopyridine derivative such as MKC-231 may a reported antioxidant, such as N-acetylcysteine or acetylcysteine; disufenton sodium (or CAS RN 168021-79-2 or Cerovive); activin (CAS RN 104625-48-1); selenium; L-methionine; an alpha, gamma, beta, or delta, or mixed, tocopherol; alpha lipoic acid; Coenzyme Q; Benzimidazole; benzoic acid; dipyridamole; glucosamine; IRFI-016 (2(2,3-dihydro-5-acetoxy-4,6,7-trimethylbenzofuranyl)acetic acid); L-carnosine; L-Histidine; glycine; flavocoxid (or LIMBREL); baicalin, optionally with catechin (3,3',4',5,7-pentahydroxyflavan (2R,3S form)), and/or its stereo-isomer; masoprocol (CAS RN 27686-84-6); mesna (CAS RN 19767-45-4); probucol (CAS RN 23288-49-5); silibinin (CAS RN 22888-70-6); sorbinil (CAS RN 68367-52-2); spermine; tangeretin (CAS RN 481-53-8); butylated hydroxyanisole (BHA); butylated hydroxytoluene (BHT); propyl gallate (PG); tertiary-butyl-hydroquinone (TBHQ); nordihydroguaiaretic acid (CAS RN 500-38-9); astaxanthin (CAS RN 472-61-7); or an antioxidant flavonoid.

Additional non-limiting examples include a vitamin, such as vitamin A (Retinol) or C (Ascorbic acid) or E (including Tocotrienol and/or Tocopherol); a vitamin cofactors or mineral, such as Coenzyme Q10 (CoQ 10), Manganese, or Melatonin; a carotenoid terpenoid, such as Lycopene, Lutein, Alpha-carotene, Beta-carotene, Zeaxanthin, Astaxanthin, or Canthaxantin; a non-carotenoid terpenoid, such as Eugenol; a flavonoid polyphenolic (or bioflavonoid); a flavonol, such as Resveratrol, Pterostilbene (methoxylated analogue of resveratrol), Kaempferol, Myricetin, Isorhamnetin, a Proanthocyanidin, or a tannin; a flavone, such as Quercetin, rutin, Luteolin, Apigenin, or Tangeritin; a flavanone, such as Hesperetin or its metabolite hesperidin, naringenin or its precursor naringin, or Eriodictyol; a flavan-3-ols (anthocyanidins), such as Catechin, Gallocatechin, Epicatechin or a gallate form thereof, Epigallocatechin or a gallate form thereof, Theaflavin or a gallate form thereof, or a Thearubigin; an isoflavone phytoestrogens, such as Genistein, Daidzein, or Glycitein; an anthocyanins, such as Cyanidin, Delphinidin, Malvidin, Pelargonidin, Peonidin, or Petunidin; a phenolic acid or ester thereof, such as Ellagic acid, Gallic acid, Salicylic acid, Rosmarinic acid, Cinnamic acid or a derivative thereof like ferulic acid, Chlorogenic acid, Chicoric acid, a Gallotannin, or an Ellagitannin; a nonflavonoid phenolic, such as Curcumin; an anthoxanthin, betacyanin, Citric acid, Uric acid, R-α-lipoic acid, or Silymarin.

Further non-limiting examples include 1-(carboxymethylthio)tetradecane; 2,2,5,7,8-pentamethyl-1-hydroxychroman; 2,2,6,6-tetramethyl-4-piperidinol-N-oxyl; 2,5-di-tert-butylhydroquinone; 2-tert-butylhydroquinone; 3,4-dihydroxyphenylethanol; 3-hydroxypyridine; 3-hydroxytamoxifen; 4-coumaric acid; 4-hydroxyanisole; 4-hydroxyphenylethanol; 4-methylcatechol; 5,6,7,8-tetrahydrobiopterin; 6,6'-methylenebis(2,2-dimethyl-4-methanesulfonic acid-1,2-dihydroquinoline); 6-hydroxy-2,5,7,8-tetramethylchroman-2-carboxylic acid; 6-methyl-2-ethyl-3-hydroxypyridine; 6-O-palmitoylascorbic acid; acetovanillone; acteoside; Actovegin; allicin; allyl sulfide; alpha-pentyl-3-(2-quinolinylmethoxy)benzenemethanol; alpha-tocopherol acetate; apolipoprotein A-IV; bemethyl; boldine; bucillamine; Calcium Citrate; Canthaxantin; crocetin; diallyl trisulfide; dicarbine; dihydrolipoic acid; dimephosphon; ebselen; Efamol; enkephalin-Leu,Ala(2)-Arg(6)-; Ergothioneine; esculetin; essential 303 forte; Ethonium; etofyllinclofibrate; fenozan; glaucine; H290-51; histidyl-proline diketopiperazine; hydroquinone; hypotaurine; idebenone; indole-3-carbinol; isoascorbic acid; kojic acid, lacidipine, lodoxamide tromethamine; mexidol; morin; N,N'-diphenyl-4-phenylenediamine; N-isopropyl-N-phenyl-4-phenylenediamine; N-monoacetylcystine; nicaraven, nicotinoyl-GABA; nitecapone; nitroxyl; nobiletin; oxymethacil; p-tert-butyl catechol; phenidone; pramipexol; proanthocyanidin; procyanidin; prolinedithiocarbamate; Propyl Gallate; purpurogallin; pyrrolidine dithiocarbamic acid; rebamipide; retinol palmitate; salvin; Selenious Acid; sesamin; sesamol; sodium selenate; sodium thiosulfate; theaflavin; thiazolidine-4-carboxylic acid; tirilazad; tocopherylquinone; tocotrienol, alpha; a Tocotrienol; tricyclodecane-9-yl-xanthogenate; turmeric extract; U 74389F; U 74500A; U 78517F; ubiquinone 9; vanillin; vinpocetine; xylometazoline; zeta Carotene; zilascorb; zinc thionein; or zonisamide.

In additional embodiments, an agent in combination with a 4-acylaminopyridine derivative such as MKC-231 may be a reported modulator of a norepinephrine receptor. Non-limiting examples include Atomoxetine (Strattera); a norepinephrine reuptake inhibitor, such as talsupram, tomoxetine, nortriptyline, nisoxetine, reboxetine (described, e.g., in U.S. Pat. No. 4,229,449), or tomoxetine (described, e.g., in U.S. Pat. No. 4,314,081); or a direct agonist, such as a beta adrenergic agonist.

Additional non-limiting examples include an alpha adrenergic agonist such as etilefrine or a reported agonist of the α2-adrenergic receptor (or α2 adrenoceptor) like clonidine (CAS RN 4205-90-7), yohimbine, mirtazepine, atipamezole, carvedilol; dexmedetomidine or dexmedetomidine hydrochloride; ephedrine, epinephrine; etilefrine; lidamidine; tetramethylpyrazine; tizanidine or tizanidine hydrochloride; apraclonidine; bitolterol mesylate; brimonidine or brimonidine tartrate; dipivefrin (which is converted to epinephrine in vivo); guanabenz; guanfacine; methyldopa; alphamethylnoradrenaline; mivazerol; natural ephedrine or D(−)ephedrine; any one or any mixture of two, three, or four of the optically active forms of ephedrine; CHF1035 or nolomirole hydrochloride (CAS RN 138531-51-8); or lofexidine (CAS RN 31036-80-3).

Alternative non-limiting examples include an adrenergic antagonist such as a reported antagonist of the α2-adrenergic receptor like yohimbine (CAS RN 146-48-5) or yohimbine hydrochloride, idazoxan, fluparoxan, mirtazepine, atipamezole, or RX781094 (see Elliott et al. "Peripheral pre and postjunctional alpha 2-adrenoceptors in man: studies with RX781094, a selective alpha 2 antagonist." J Hypertens Suppl. 1983 1(2):109-11).

Other non-limiting embodiments include a reported modulator of an α1-adrenergic receptor such as cirazoline; modafinil; ergotamine; metaraminol; methoxamine; midodrine (a prodrug which is metabolized to the major metabolite desglymidodrine formed by deglycination of midodrine); oxymetazoline; phenylephrine; phenylpropanolamine; or pseudoephedrine.

Further non-limiting embodiments include a reported modulator of a beta adrenergic receptor such as arbutamine, befunolol, cimaterol, higenamine, isoxsuprine, methoxyphenamine, oxyfedrine, ractopamine, tretoquinol, or TQ-1016 (from TheraQuest Biosciences, LLC), or a reported β1-adrenergic receptor modulator such as prenalterol, Ro 363, or xamoterol or a reported β1-adrenergic receptor agonist like dobutamine.

Alternatively, the reported modulator may be of a β2-adrenergic receptor such as levosalbutamol (CAS RN 34391-04-3), metaproterenol, MN-221 or KUR-1246 ((−)-bis(2-{[(2S)-2-({(2R)-2-hydroxy-2-[4-hydroxy-3-(2-hydroxyethyl) phenyl]ethyl}amino)-1,2,3,4-tetrahydronaphthalen-7-yl] oxy}-N,N-dimethylacetamide)monosulfate or bis(2-[[(2S)-2-([(2R)-2-hydroxy-2-[4-hydroxy-3-(2-hydroxyethyl)-phenyl]ethyl]amino)-1,2,3,4-tetrahydronaphthalen-7-yl] oxy]-N,N-dimethylacetamide) sulfate or CAS RN 194785-31-4), nylidrin, orciprenaline, pirbuterol, procaterol, reproterol, ritodrine, salmeterol, salmeterol xinafoate, terbutaline, tulobuterol, zinterol or bromoacetylalprenololmenthane, or a reported β2-adrenergic receptor agonist like albuterol, albuterol sulfate, salbutamol (CAS RN 35763-26-9), clenbuterol, broxaterol, dopexamine, formoterol, formoterol fumarate, isoetharine, levalbuterol tartrate hydrofluoroalkane, or mabuterol.

Additional non-limiting embodiments include a reported modulator of a β3-adrenergic receptor such as AJ-9677 or TAK677 ([3-[(2R)-[[(2R)-(3-chlorophenyl)-2-hydroxyethyl]amino]propyl]-1H-indol-7-yloxy]acetic acid), or a reported β3-adrenergic receptor agonist like SR58611A (described in Simiand et al., Eur J Pharmacol, 219:193-201 (1992), BRL 26830A, BRL 35135, BRL 37344, CL 316243 or ICI D7114.

Further alternative embodiments include a reported nonselective alpha and beta adrenergic receptor agonist such as epinephrine or ephedrine; a reported nonselective alpha and beta adrenergic receptor antagonist such as carvedilol; a β1 and β2 adrenergic receptor agonist such as isopreoterenol; or a β1 and β2 adrenergic receptor antagonist such as CGP 12177, fenoterol, or hexoprenaline.

Non-limiting examples of reported adrenergic agonists include albuterol, albuterol sulfate, salbutamol (CAS RN 35763-26-9), clenbuterol, adrafinil, and SR58611A (described in Simiand et al., Eur J Pharmacol, 219:193-201 (1992)), clonidine (CAS RN 4205-90-7), yohimbine (CAS RN 146-48-5) or yohimbine hydrochloride, arbutamine; befunolol; BRL 26830A; BRL 35135; BRL 37344; bromoacetylalprenololmenthane; broxaterol; carvedilol; CGP 12177; cimaterol; cirazoline; CL 316243; Clenbuterol; denopamine; dexmedetomidine or dexmedetomidine hydrochloride; Dobutamine, dopexamine, Ephedrine, Epinephrine, Etilefrine; Fenoterol; formoterol; formoterol fumarate; Hexoprenaline; higenamine; ICI D7114; Isoetharine; Isoproterenol; Isoxsuprine; levalbuterol tartrate hydrofluoroalkane; lidamidine; mabuterol; methoxyphenamine; modafinil; Nylidrin; Orciprenaline; Oxyfedrine; pirbuterol; Prenalterol; Procaterol; ractopamine; reproterol; Ritodrine; Ro 363; salmeterol; salmeterol xinafoate; Terbutaline; tetramethylpyrazine; tizanidine or tizanidine hydrochloride; Tretoquinol; tulobuterol; Xamoterol; or zinterol. Additional non-limiting examples include Apraclonidine, Bitolterol Mesylate, Brimonidine or Brimonidine tartrate, Dipivefrin (which is converted to epinephrine in vivo), Epinephrine, Ergotamine, Guanabenz, guanfacine, Metaproterenol, Metaraminol, Methoxamine, Methyldopa, Midodrine (a prodrug which is metabolized to the major metabolite desglymidodrine formed by deglycination of midodrine), Oxymetazoline, Phenylephrine, Phenylpropanolamine, Pseudoephedrine, alphamethylnoradrenaline, mivazerol, natural ephedrine or D(−)ephedrine, any one or any mixture of two, three, or four of the optically active forms of ephedrine, CHF1035 or nolomirole hydrochloride (CAS RN 138531-51-8), AJ-9677 or TAK677 ([3-[(2R)-[[(2R)-(3-chlorophenyl)-2-hydroxyethyl]amino] propyl]-1H-indol-7-yloxy]acetic acid), MN-221 or KUR-1246 ((−)-bis(2-{[(2S)-2-({(2R)-2-hydroxy-2-[4-hydroxy-3-(2-hydroxyethyl)phenyl]ethyl}amino)-1,2,3,4-tetrahydronaphthalen-7-yl]oxy}-N,N-dimethylacetamide) monosulfate or bis(2-[[(2S)-2-([(2R)-2-hydroxy-2-[4-hydroxy-3-(2-hydroxyethyl)-phenyl]ethyl]amino)-1,2,3,4-tetrahydronaphthalen-7-yl]oxy]-N,N-dimethylacetamide) sulfate or CAS RN 194785-31-4), levosalbutamol (CAS RN 34391-04-3), lofexidine (CAS RN 31036-80-3) or TQ-1016 (from TheraQuest Biosciences, LLC).

In further embodiments, a reported adrenergic antagonist, such as idazoxan or fluparoxan, may be used as an agent in combination with a 4-acylaminopyridine derivative as described herein.

In further embodiments, an agent in combination with a 4-acylaminopyridine derivative such as MKC-231 may be a reported modulator of carbonic anhydrase. Non-limiting examples of such an agent include acetazolamide, benzenesulfonamide, benzolamide, brinzolamide, dichlorphenamide, dorzolamide or dorzolamide HCl, ethoxzolamide, flurbiprofen, mafenide, methazolamide, sezolamide, zonisamide, bendroflumethiazide, benzthiazide, chlorothiazide, cyclothiazide, dansylamide, diazoxide, ethinamate, furosemide, hydrochlorothiazide, hydroflumethiazide, mercuribenzoic acid, methyclothiazide, trichloromethazide, amlodipine, cyanamide, or a benzenesulfonamide. Additional non-limitinge examples of such an agent include (4s-Trans)-4-(Ethylamino)-5,6-Dihydro-6-Methyl-4h-Thieno(2,3-B)Thiopyran-2-Sulfonamide-7,7-Dioxide; (4s-Trans)-4-(Methylamino)-5,6-Dihydro-6-Methyl-4h-Thieno(2,3-B) Thiopyran-2-Sulfonamide-7,7-Dioxide; (R)—N-(3-Indol-1-yl-2-Methyl-Propyl)-4-Sulfamoyl-Benzamide; (S)—N-(3-Indol-1-yl-2-Methyl-Propyl)-4-Sulfamoyl-Benzamide; 1,2,4-Triazole; 1-Methyl-3-Oxo-1,3-Dihydro-Benzo[α] Isothiazole-5-Sulfonic Acid Amide; 2,6-Difluorobenzenesulfonamide; 3,5-Difluorobenzenesulfonamide; 3-Mercuri-4-Aminobenzenesulfonamide; 3-Nitro-4-(2-Oxo-Pyrrolidin-1-yl)-Benzenesulfonamide; 4-(Aminosulfonyl)-N-[(2,3,4-Trifluorophenyl)Methyl]-Benzamide; 4-(Aminosulfonyl)-N-[(2,4,6-Trifluorophenyl)Methyl]-Benzamide; 4-(Aminosulfonyl)-N-[(2,4-Difluorophenyl)Methyl]-Benzamide; 4-(Aminosulfonyl)-N-[(2,5-Difluorophenyl)Methyl]-Benzamide; 4-(Aminosulfonyl)-N-[(3,4,5-Trifluorophenyl)Methyl]-Benzamide; 4-(Aminosulfonyl)-N-[(4-Fluorophenyl)Methyl]-Benzamide; 4-(Hydroxymercury) Benzoic Acid; 4-Fluorobenzenesulfonamide; 4-Methylimidazole; 4-Sulfonamide-[1-(4-Aminobutane)] Benzamide; 4-Sulfonamide-[4-(Thiomethylaminobutane)] Benzamide; 5-Acetamido-1,3,4-Thiadiazole-2-Sulfonamide; 6-Oxo-8,9, 10,11-Tetrahydro-7h-Cyclohepta[α][1]Benzopyran-3-O-Sulfamate; (4-sulfamoyl-phenyl)-thiocarbamic acid O-(2-thiophen-3-yl-ethyl) ester; (R)-4-ethylamino-3,4-dihydro-2-(2-methoylethyl)-2H-thieno[3,2-E]-1,2-thiazine-6-sulfonamide-1,1-dioxide; 3,4-dihydro-4-hydroxy-2-(2-thienymethyl)-2H-thieno[3,2-E]-1,2-thiazine-6-sulfonamide-1,1-dioxide; 3,4-dihydro-4-hydroxy-2-(4-methoxyphenyl)-2H-thieno[3,2-E]-1,2-thiazine-6-sulfonamide-1,1-dioxide; N-[(4-methoxyphenyl)methyl]2,5-thiophenedesulfonamide; 2-(3-methoxyphenyl)-2H-thieno-[3,2-E]-1,2-thiazine-6-sulfinamide-1,1-dioxide; (R)-3,4-didhydro-2-(3-methoxyphenyl)-4-methylamino-2H-thieno[3,2-E]-1,2-thiazine-6-sulfonamide-1,1-dioxide; (S)-3,4-dihydro-2-(3-methoxyphenyl)-4-methylamino-2H-thieno[3,2-E]-1,2-thiazine-6-sulfonamide-1,1-dioxide; 3,4-dihydro-2-(3-methoxyphenyl)-2H-thieno-[3,2-E]-1,2-thiazine-6-sulfonamide-1,1-dioxide; [2h-Thieno[3,2-E]-1,2-Thiazine-6-Sulfonamide,2-(3-Hydroxyphenyl)-3-(4-Morpholinyl)-, 1,1-Dioxide]; [2h-Thieno[3,2-E]-1,2-Thiazine-6-Sulfonamide,2-(3-Methoxyphenyl)-3-(4-Morpholinyl)-, 1,1-Dioxide]; Aminodi(Ethyloxy)Ethylaminocarbonylbenzenesulfonamide; N-(2,3,4,5,6-Pentafluoro-Benzyl)-4-Sulfamoyl-Benzamide; N-(2,6-Difluoro-Benzyl)-4-Sulfamoyl-Benzamide; N-(2-Fluoro-Benzyl)-4-Sulfamoyl-Benzamide; N-(2-Thienylmethyl)-2,5-Thiophenedisulfonamide; N-[2-(1H-Indol-5-yl)-Butyl]-4-Sulfamoyl-Benzamide; N-Benzyl-4-Sulfamoyl-Benzamide; or Sulfamic Acid 2,3-O-(1-Methylethylidene)-4,5-O-Sulfonyl-Beta-Fructopyranose Ester.

In yet additional embodiments, an agent in combination with a 4-acylaminopyridine derivative such as MKC-231 may be a reported modulator of a catechol-O-methyltransferase (COMT), such as floproprion, or a COMT inhibitor, such as tolcapone (CAS RN 134308-13-7), nitecapone (CAS RN 116313-94-1), or entacapone (CAS RN 116314-67-1 or 130929-57-6).

In yet further embodiments, an agent in combination with a 4-acylaminopyridine derivative such as MKC-231 may be a reported modulator of hedgehog pathway or signaling activity such as cyclopamine, jervine, ezetimibe, regadenoson (CAS RN 313348-27-5, or CVT-3146), a compound described in U.S. Pat. No. 6,683,192 or identified as described in U.S. Pat. No. 7,060,450, or CUR-61414 or another compound described in U.S. Pat. No. 6,552,016.

In other embodiments, an agent in combination with a 4-acylaminopyridine derivative such as MKC-231 may be a reported modulator of IMPDH, such as mycophenolic acid or mycophenolate mofetil (CAS RN 128794-94-5).

In yet additional embodiments, an agent in combination with a 4-acylaminopyridine derivative such as MKC-231 may be a reported modulator of a sigma receptor, including sigma-1 and sigma-2. Non-limiting examples of such a modulator include an agonist of sigma-1 and/or sigma-2 receptor, such as (+)-pentazocine, SKF 10,047 (N-allyl-normetazocine), or 1,3-di-o-tolylguanidine (DTG). Additional non-limiting examples include SPD-473 (from Shire Pharmaceuticals); a molecule with sigma modulatory activity as known in the field (see e.g., Bowen et al., *Pharmaceutica Acta Helvetiae* 74: 211-218 (2000)); a guanidine derivative such as those described in U.S. Pat. Nos. 5,489,709; 6,147,063; 5,298,657; 6,087,346; 5,574,070; 5,502,255; 4,709,094; 5,478,863; 5,385,946; 5,312,840; or 5,093,525; WO9014067; an antipsychotic with activity at one or more sigma receptors, such as haloperidol, rimcazole, perphenazine, fluphenazine, (-)-butaclamol, acetophenazine, trifluoperazine, molindone, pimozide, thioridazine, chlorpromazine and triflupromazine, BMY 14802, BMY 13980, remoxipride, tiospirone, cinuperone (HR 375), or WY47384.

Additional non-limiting examples include igmesine; BD1008 and related compounds disclosed in U.S. Publication No. 2003/0171347; cis-isomers of U50488 and related compounds described in de Costa et al, *J. Med. Chem.*, 32(8): 1996-2002 (1989); U101958; SKF10,047; apomorphine; OPC-14523 and related compounds described in Oshiro et al., *J Med Chem.;* 43(2): 177-89 (2000); arylcyclohexamines such as PCP; (+)-morphinans such as dextrallorphan; phenylpiperidines such as (+)-3-PPP and OHBQs; neurosteroids such as progesterone and desoxycorticosterone; butryophenones; BD614; or PRX-00023. Yet additional non-limiting examples include a compound described in U.S. Pat. Nos. 6,908,914; 6,872,716; 5,169,855; 5,561,135; 5,395,841; 4,929,734; 5,061,728; 5,731,307; 5,086,054; 5,158,947; 5,116,995; 5,149,817; 5,109,002; 5,162,341; 4,956,368; 4,831,031; or 4,957,916; U.S. Publication Nos. 2005/0132429; 2005/0107432; 2005/0038011, 2003/0105079; 2003/0171355; 2003/0212094; or 2004/0019060; European Patent Nos. EP 503 411; EP 362 001-A1; or EP 461 986; International Publication Nos. WO 92/14464; WO 93/09094; WO 92/22554; WO 95/15948; WO 92/18127; 91/06297; WO01/02380; WO91/18868; or WO 93/00313; or in Russell et al., *J Med Chem.;* 35(11): 2025-33 (1992) or Chambers et al., *J. Med Chem.;* 35(11): 2033-9 (1992).

Further non-limiting examples include a sigma-1 agonist, such as IPAG (1-(4-iodophenyl)-3-(2-adamantyl)guanidine); pre-084; carbetapentane; 4-IBP; L-687,384 and related compounds described in Middlemiss et al., *Br. J. Phamm.*, 102: 153 (1991); BD 737 and related compounds described in Bowen et al., *J Pharmacol Exp Ther.*, 262(1): 32-40 (1992)); OPC-14523 or a related compound described in Oshiro et al., *J Med Chem.;* 43(2): 177-89 (2000); a sigma-1 selective agonist, such as igmesine; (+)-benzomorphans, such as (+)-pentazocine and (+)-ethylketocyclazocine; SA-4503 or a related compound described in U.S. Pat. No. 5,736,546 or by Matsuno et al., *Eur J Pharmacol.*, 306(1-3): 271-9 (1996); SK&F 10047; or ifenprodil; a sigma-2 agonist, such as haloperidol, (+)-5,8-disubstituted morphan-7-ones, including CB 64D, CB 184, or a related compound described in Bowen et al., *Eur. J. Parmacol.* 278:257-260 (1995) or Bertha et al., *J. Med. Chem.* 38:4776-4785 (1995); or a sigma-2 selective agonist, such as 1-(4-fluorophenyl)-3-[4-[3-(4-fluorophenyl)-8-azabicyclo[3.2.1]oct-2-en-8-yl]-1-butyl]-1H-indole, Lu 28-179, Lu 29-253 or a related compound disclosed in U.S. Pat. No. 5,665,725 or 6,844,352, U.S. Publication No. 2005/0171135, International Patent Publication Nos. WO 92/22554 or WO 99/24436, Moltzen et al., *J. Med. Chem.*, 26; 38(11): 2009-17 (1995) or Perregaard et al., *J Med. Chem.*, 26; 38(11): 1998-2008 (1995).

Alternative non-limiting examples include a sigma-1 antagonist such as BD-1047 (N(-)[2-(3,4-dichlorophenyl)ethyl]-N-methyl-2-(dimethylamin-o)ethylamine), BD-1063 (1 (-) [2-(3,4-dichlorophenyl)ethyl]-4-methylpiperazine, rimcazole, haloperidol, BD-1047, BD-1063, BMY 14802, DuP 734, NE-100, AC915, or R-(+)-3-PPP. Particular non-limiting examples include fluoxetine, fluvoxamine, citalopram, sertaline, clorgyline, imipramine, igmesine, opipramol, siramesine, SL 82.0715, imcazole, DuP 734, BMY 14802, SA 4503, OPC 14523, panamasine, or PRX-00023.

Other non-limiting examples of an agent in combination with a 4-acylaminopyridine derivative such as MKC-231 include acamprosate (CAS RN 77337-76-9); a growth factor, like LIF, EGF, FGF, bFGF or VEGF as non-limiting examples; octreotide (CAS RN 83150-76-9); an NMDA modulator like DTG, (+)-pentazocine, DHEA, Lu 28-179 (1'-[4-[1-(4-fluorophenyl)-1H-indol-3-yl]-1-butyl]-spiro [isobenzofuran-1(3H), 4'piperidine]), BD 1008 (CAS RN 138356-08-8), ACEA1021 (Licostinel or CAS RN 153504-81-5), GV150526A (Gavestinel or CAS RN 153436-22-7), sertraline, clorgyline, or memantine as non-limiting examples; or metformin.

Of course a further combination therapy may also be that of a 4-acylaminopyridine derivative in combination with one or more other neurogenic agents with a non-chemical based therapy. Non-limiting examples include the use of psychotherapy for the treatment of many conditions described herein, such as the psychiatric conditions, as well as behavior modification therapy such as that use in connection with a weight loss program.

Having now generally described the invention, the same will be more readily understood through reference to the following examples which are provided by way of illustration, and are not intended to be limiting of the disclosed invention, unless specified.

EXAMPLES

Example 1

Effect of Combining MKC-231 and an AMPA Agonist on Neuronal Differentiation of Human Neural Stem Cells Human neural stem cells (hNSCs) were isolated and grown in monolayer culture, plated, treated with varying concentrations of MKC-231 in the presence or absence of the AMPA agonist AMPA, and stained with TUJ-1 antibody, as described in U.S. Published Application No. 2007/0015138. Mitogen-free test media with a positive control for neuronal differentiation was used along with basal media without growth factors as a negative control.

Results are shown in FIG. 1, which shows concentration response curves of neuronal differentiation after background media values are subtracted. The concentration response curve of the combination of MKC-231 with AMPA is shown with the concentration response curves of MKC-231 alone. The data is presented as a percent of neuronal positive control. The data indicate that the combination of MKC-231 with a fixed concentration of 0.316 μM AMPA resulted in superior promotion of neuronal differentiation than MKC-231 alone.

Example 2

Effects of Estrogen Receptor Modulators in Combination with the MKC-231 on Differentiation of Human Neural Stem Cells Human neural stem cells (hNSCs) were isolated and grown in monolayer culture, plated, treated with varying concentrations of MKC-231 in the presence or absence of the estrogen receptor agonist estradiol or the selective estrogen receptor modulator tamoxifen, and stained with TUJ-1 antibody for the detection of neuronal differentiation as described above. Mitogen-free test media with a positive control for neuronal differentiation was used along with basal media without growth factors as a negative control.

Results are shown in FIGS. 2 (estradiol) and 3 (tamoxifen), which show concentration response curves of neuronal differentiation after background media values are subtracted. The concentration response curves of the combination of estradiol or tamoxifen with MKC-231 are shown with the concentration response curves each agent alone. The data is presented as a percent of neuronal positive control. The data indicate that the combination of an estrogen modulator with MKC-231 resulted in synergistically enhanced neuronal differentiation relative to that that produced by each agent alone.

Example 3

Effect of Combining Azakenpaullone and MKC-231 on Neuronal Differentiation of Human Neural Stem Cells Human neural stem cells (hNSCs) were isolated and grown in monolayer culture, plated, treated with varying concentrations of azakenpaullone and/or MKC-231 (test compounds), and stained with TUJ-1 antibody for the detection of neuronal differentiation as described above. Mitogen-free test media with a positive control for neuronal differentiation was used along with basal media without growth factors as a negative control.

Results are shown in FIG. 4, which shows concentration response curves of neuronal differentiation after background media values are subtracted. The concentration response curve of the combination of azakenpaullone and MKC-231 is shown with the concentration response curves of azakenpaullone or MKC-231 alone. The data is presented as a percent of neuronal positive control. The data indicate that the combination of azakenpaullone and MKC-231 resulted in superior promotion of neuronal differentiation than either agent alone.

Example 4

Effects of the Mixed Opioid Antagonist Naltrexone in Combination with the MKC-231 on Differentiation of Human Neural Stem Cells Human neural stem cells (hNSCs) were isolated and grown in monolayer culture, plated, treated with varying concentrations of MKC-231 in the presence or absence of naltrexone, and stained with TUJ-1 antibody for the detection of neuronal differentiation as described above. Mitogen-free test media with a positive control for neuronal differentiation was used along with basal media without growth factors as a negative control.

Results are shown in FIG. 5, which shows concentration response curves of neuronal differentiation after background media values are subtracted. The concentration response curves of the combination of MKC-231 with naltrexone are shown with the concentration response curves either agent alone. The data is presented as a percent of neuronal positive control. The data indicate that the combination of MKC-231 with naltrexone resulted in synergistically enhanced neuronal differentiation relative to that that produced by either agent alone.

Example 5

Effects of Methylfolate in Combination with the MKC-231 on Differentiation of Human Neural Stem Cells Human neural stem cells (hNSCs) were isolated and grown in monolayer culture, plated, treated with varying concentrations of MKC-231 in the presence or absence of methylfolate, and stained with TUJ-1 antibody for the detection of neuronal differentiation as described above. Mitogen-free test media with a positive control for neuronal differentiation was used along with basal media without growth factors as a negative control.

Results are shown in FIG. 6, which shows concentration response curves of neuronal differentiation after background media values are subtracted. The concentration response curves of the combination of MKC-231 with methylfolate are shown with the concentration response curves either agent alone. The data is presented as a percent of neuronal positive control. The data indicate that the combination of MKC-231 with methylfolate resulted in synergistically enhanced neuronal differentiation relative to that that produced by either agent alone.

Example 6

Effects of the Carbonic Anhydrase Inhibitor Acetazolamide in Combination with the MKC-231 on Differentiation of Human Neural Stem Cells Human neural stem cells (hNSCs) were isolated and grown in monolayer culture, plated, treated with varying concentrations of MKC-231 in the presence or absence of acetazolamide, and stained with TUJ-1 antibody for the detection of neuronal differentiation as described above. Mitogen-free test media with a positive control for neuronal differentiation was used along with basal media without growth factors as a negative control.

Results are shown in FIG. 7, which shows concentration response curves of neuronal differentiation after background media values are subtracted. The concentration response curves of the combination of MKC-231 with acetazolamide are shown with the concentration response curves either agent alone. The data is presented as a percent of neuronal positive control. The data indicate that the combination of MKC-231 with acetazolamide resulted in synergistically enhanced neuronal differentiation relative to that that produced by either agent alone.

Example 7

Effects of the HMGCR Inhibitor Atorvastatin in Combination with the MKC-231 on Differentiation of Human Neural Stem Cells Human neural stem cells (hNSCs) were isolated and grown in monolayer culture, plated, treated with varying concentrations of MKC-231 in the presence or absence of atorvastatin, and stained with TUJ-1 antibody for the detection of neuronal differentiation as described above. Mitogen-free test media with a positive control for neuronal differentiation was used along with basal media without growth factors as a negative control.

Results are shown in FIG. 8, which shows concentration response curves of neuronal differentiation after background media values are subtracted. The concentration response curves of the combination of MKC-231 with atorvastatin are shown with the concentration response curves either agent alone. The data is presented as a percent of neuronal positive control. The data indicate that the combination of MKC-231 with atorvastatin resulted in synergistically enhanced neuronal differentiation relative to that that produced by either agent alone.

Example 8

Effects of Modafinil in Combination with the MKC-231 on Differentiation of Human Neural Stem Cells Human neural stem cells (hNSCs) were isolated and grown in monolayer culture, plated, treated with varying concentrations of MKC-231 in the presence or absence of modafinil, and stained with TUJ-1 antibody for the detection of neuronal differentiation as described in above. Mitogen-free test media with a positive control for neuronal differentiation was used along with basal media without growth factors as a negative control.

Results are shown in FIG. 9, which shows concentration response curves of neuronal differentiation after background media values are subtracted. The concentration response curves of the combination of MKC-231 with modafinil are shown with the concentration response curves either agent alone. The data is presented as a percent of neuronal positive control. The data indicate that the combination of MKC-231 with modafinil resulted in synergistically enhanced neuronal differentiation relative to that that produced by either agent alone.

Example 9

Effects of the PPAR Gamma Agonist Rosiglitazone in Combination with the MKC-231 on Differentiation of Human Neural Stem Cells Human neural stem cells (hNSCs) were isolated and grown in monolayer culture, plated, treated with varying concentrations of MKC-231 in the presence or absence of rosiglitazone, and stained with TUJ-1 antibody for the detection of neuronal differentiation as described above. Mitogen-free test media with a positive control for neuronal differentiation was used along with basal media without growth factors as a negative control.

Results are shown in FIG. 10, which shows concentration response curves of neuronal differentiation after background media values are subtracted. The concentration response curves of the combination of MKC-231 with rosiglitazone are shown with the concentration response curves either agent alone. The data is presented as a percent of neuronal positive control. The data indicate that the combination of MKC-231 with rosiglitazone resulted in synergistically enhanced neuronal differentiation relative to that that produced by either agent alone.

Example 10

Determination of Synergy

The presence of synergy was determined by use of a combination index (CI). The CI based on the $EC_{50}$ was used to determine whether a pair of compounds had an additive, synergistic (greater than additive), or antagonistic effect when run in combination. The CI is a quantitative measure of the nature of drug interactions, comparing the $EC_{50}$'s of two compounds, when each is assayed alone, to the $EC_{50}$ of each compound when assayed in combination. The combination index (CI) is equal to the following formula:

$$\frac{C1}{IC1} + \frac{C2}{IC2} + \frac{(C1*C2)}{(IC1*IC2)}$$

wherein C1 and C2 are the concentrations of a first and a second compound, respectively, resulting in 50% activity in neuronal differentiation when assayed in combination; and IC1 and IC2 are the concentrations of each compound resulting in 50% activity when assayed independently. A CI of less than 1 indicates the presence of synergy; a CI euql to 1 indicates an additive effect; and a CI greater than 1 indicates antagonism between the two compounds.

Non-limiting examples of combinations of MKC-231 and an additional agent as described herein were observed to result in synergistic activity. The exemplary results are shown in the following table:

| Combination | CI |
|---|---|
| MKC-231 + AMPA | 0.04 |
| MKC-231 + Estradiol | 0.03 |
| MKC-231 + Tamoxifen | 0.3 |
| MKC-231 + Methylfolate | 0.82 |
| MKC-231 + Naltrexone | 0.25 |
| MKC-231 + Acetazolamide | 0.12 |
| MKC-231 + Atorvastatin | 0.5 |
| MKC-231 + Modafinil | 0.14 |
| MKC-231 + Rosiglitazone | 0.21 |

Combination Index <1 indicates synergy

AS the CI is less than 1 for each of these combinations, the two compounds have a synergistic effect in neuronal differentiation.

The above is based on the selection of $EC_{50}$ as the point of comparison for the two compounds. The comparison is not limited by the point used, but rather the same comparison may be made at another point, such as $EC_{20}$, $EC_{30}$, $EC_{40}$, $EC_{60}$, $EC_{70}$, $EC_{80}$, or any other EC value above, below, or between any of those points.

All references cited herein, including patents, patent applications, and publications, are hereby incorporated by reference in their entireties, whether previously specifically incorporated or not.

Having now fully provided the instant disclosure, it will be appreciated by those skilled in the art that the same can be performed within a wide range of equivalent parameters, concentrations, and conditions without departing from the spirit and scope of the disclosure and without undue experimentation.

While the disclosure has been described in connection with specific embodiments thereof, it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth.

What is claimed is:

1. A composition comprising a 4-acylaminopyridine compound in synergistic combination with an active agent, wherein the 4-acylaminopyridine compound is 2-(2-oxopyrrolidin-1-yl)-N-(2,3-dimethyl-5,6,7,8-tetrahydrofuro[2,3-b]quinolin-4-yl)acetoamide (MKC-231), or an isomer thereof and the active agent is modafinil, or an isomer thereof.

2. The composition of claim 1, wherein the effective dosage of the 4-acylaminopyridine compound and the active agent in combination is synergistic when compared to the effective dosage of the compound or active agent when used alone.

3. The composition of claim 1, wherein the combination is in a single formulation.

4. The composition of claim 1 wherein the 4-acylaminopyridine compound and the active agent are contained in the same unit dosage form.

5. A method of treating depression in a subject in need thereof comprising administering the composition of claim 1 to said subject.

* * * * *